(12) United States Patent
Yeung et al.

(10) Patent No.: US 10,590,105 B2
(45) Date of Patent: Mar. 17, 2020

(54) 1,3-DIHYDROXY-PHENYL DERIVATIVES USEFUL AS IMMUNOMODULATORS

(71) Applicant: BRISTOL-MYERS SQUIBB COMPANY, Princeton, NJ (US)

(72) Inventors: Kap-Sun Yeung, Madison, CT (US); Katharine A. Grant-Young, Vieques, PR (US); Juliang Zhu, North Haven, CT (US); Mark G. Saulnier, Higganum, CT (US); David B. Frennesson, Naugatuck, CT (US); Zhaoxing Meng, Pennington, NJ (US); Paul Michael Scola, Glastonbury, CT (US)

(73) Assignee: Bristol-Meyers Squibb Company, Princeton, NJ (US)

( * ) Notice: Subject to any disclaimer, the term of this patent is extended or adjusted under 35 U.S.C. 154(b) by 0 days.

(21) Appl. No.: 16/315,800

(22) PCT Filed: Jul. 5, 2017

(86) PCT No.: PCT/US2017/040663
§ 371 (c)(1),
(2) Date: Jan. 7, 2019

(87) PCT Pub. No.: WO2018/009505
PCT Pub. Date: Jan. 11, 2018

(65) Prior Publication Data
US 2019/0185450 A1  Jun. 20, 2019

Related U.S. Application Data

(60) Provisional application No. 62/359,971, filed on Jul. 8, 2016.

(51) Int. Cl.
| | | |
|---|---|---|
| *C07D 401/10* | (2006.01) |
| *C07D 413/14* | (2006.01) |
| *C07D 417/12* | (2006.01) |
| *C07D 405/12* | (2006.01) |
| *C07D 401/14* | (2006.01) |
| *C07D 413/12* | (2006.01) |
| *C07D 401/12* | (2006.01) |
| *A61K 31/4439* | (2006.01) |
| *A61K 31/4545* | (2006.01) |
| *A61K 31/498* | (2006.01) |
| *A61K 45/06* | (2006.01) |
| *C07D 405/14* | (2006.01) |
| *C07D 417/14* | (2006.01) |

(52) U.S. Cl.
CPC ........ *C07D 401/10* (2013.01); *A61K 31/4439* (2013.01); *A61K 31/4545* (2013.01); *A61K 31/498* (2013.01); *A61K 45/06* (2013.01); *C07D 401/12* (2013.01); *C07D 401/14* (2013.01); *C07D 405/12* (2013.01); *C07D 405/14* (2013.01); *C07D 413/12* (2013.01); *C07D 413/14* (2013.01); *C07D 417/12* (2013.01); *C07D 417/14* (2013.01)

(58) Field of Classification Search
None
See application file for complete search history.

(56) References Cited

U.S. PATENT DOCUMENTS 6,124,343 A * 9/2000 Smith .................. C07C 255/54
514/438

FOREIGN PATENT DOCUMENTS

| EP | 2 011 788 A1 | 1/2009 |
| WO | WO 2015/034820 A1 | 3/2015 |
| WO | WO 2015/160641 A2 | 10/2015 |
| WO | WO 2017/066227 A1 | 4/2017 |

OTHER PUBLICATIONS

Katarzyna, Guzik, et al., "Small-Molecule Inhibitors of the Programmed Cell Death-1/Programmed Death-Ligand 1 (PD-1/PD-L1) Interaction via Transiently Induced Protein States and Dimerization of PD-L1", Journal of Medicinal Chemistry, 2017, vol. 60, No. 13, pp. 5857-5867.

* cited by examiner

*Primary Examiner* — Zinna Northington Davis
(74) *Attorney, Agent, or Firm* — Sterne, Kessler, Goldstein & Fox P.L.L.C.

(57) ABSTRACT

The present disclosure generally relates to compounds of formula (I), wherein R2 is a phenyl or pyridinyl moiety, useful as immunomodulators. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

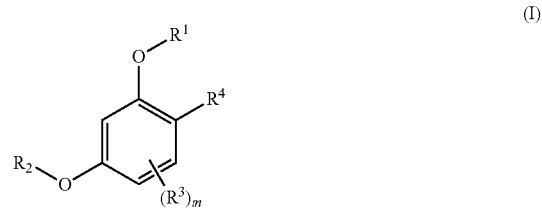

(I)

8 Claims, No Drawings
Specification includes a Sequence Listing.

SEQUENCE LISTING

<160> NUMBER OF SEQ ID NOS: 2

<210> SEQ ID NO 1
<211> LENGTH: 384
<212> TYPE: PRT
<213> ORGANISM: Homo sapiens

<400> SEQUENCE: 1

```
Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Gly
    130                 135                 140

Ser Pro Gly Gly Gly Gly Arg Glu Pro Lys Ser Ser Asp Lys Thr
145                 150                 155                 160

His Thr Ser Pro Pro Ser Pro Ala Pro Glu Leu Leu Gly Gly Ser Ser
                165                 170                 175

Val Phe Leu Phe Pro Pro Lys Pro Lys Asp Thr Leu Met Ile Ser Arg
```

```
                180              185              190
Thr Pro Glu Val Thr Cys Val Val Asp Val Ser His Glu Asp Pro
            195                  200              205

Glu Val Lys Phe Asn Trp Tyr Val Asp Gly Val Glu Val His Asn Ala
        210                  215              220

Lys Thr Lys Pro Arg Glu Glu Gln Tyr Asn Ser Thr Tyr Arg Val Val
225                  230                  235              240

Ser Val Leu Thr Val Leu His Gln Asp Trp Leu Asn Gly Lys Glu Tyr
                245                  250                  255

Lys Cys Lys Val Ser Asn Lys Ala Leu Pro Ala Pro Ile Glu Lys Thr
            260                  265                  270

Ile Ser Lys Ala Lys Gly Gln Pro Arg Glu Pro Gln Val Tyr Thr Leu
        275                  280                  285

Pro Pro Ser Arg Asp Glu Leu Thr Lys Asn Gln Val Ser Leu Thr Cys
        290                  295                  300

Leu Val Lys Gly Phe Tyr Pro Ser Asp Ile Ala Val Glu Trp Glu Ser
305                  310                  315                  320

Asn Gly Gln Pro Glu Asn Asn Tyr Lys Thr Thr Pro Pro Val Leu Asp
                325                  330                  335

Ser Asp Gly Ser Phe Phe Leu Tyr Ser Lys Leu Thr Val Asp Lys Ser
            340                  345                  350

Arg Trp Gln Gln Gly Asn Val Phe Ser Cys Ser Val Met His Glu Ala
        355                  360                  365

Leu His Asn His Tyr Thr Gln Lys Ser Leu Ser Leu Ser Pro Gly Lys
        370                  375                  380

<210> SEQ ID NO 2
<211> LENGTH: 237
<212> TYPE: PRT
<213> ORGANISM: Homo sapiens

<400> SEQUENCE: 2

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175
```

```
Ser Thr Leu Arg Ile Asn Thr Thr Thr Asn Glu Ile Phe Tyr Cys Thr
            180                 185                 190
Phe Arg Arg Leu Asp Pro Glu Glu Asn His Thr Ala Glu Leu Val Ile
            195                 200                 205
Pro Glu Leu Pro Leu Ala His Pro Pro Asn Glu Arg Thr Gly Ser Ser
            210                 215                 220
Glu Thr Val Arg Phe Gln Gly His His His His His His
225                 230                 235
```

1,3-DIHYDROXY-PHENYL DERIVATIVES USEFUL AS IMMUNOMODULATORS

CROSS REFERENCE TO RELATED APPLICATION

This application claims the priority of U.S. Provisional Application Ser. No. 62/359,971 filed Jul. 8, 2016 which is herein incorporated by reference.

The present disclosure generally relates to compounds useful as inhibitors of the PD-1/PD-L1 protein/protein and CD80/PD-L1 protein/protein interactions. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

Programmed death-1 (CD279) is a receptor on T cells that has been shown to suppress activating signals from the T cell receptor when bound by either of its ligands, Programmed death-ligand 1 (PD-L1, CD274, B7-H1) or PD-L2 (CD273, B7-DC) (Sharpe et al., Nat. Imm. 2007). When PD-1 expressing T cells contact cells expressing its ligands, functional activities in response to antigenic stimuli, including proliferation, cytokine secretion, and cytolytic activity are reduced. PD-1/PD-Ligand interactions down regulate immune responses during resolution of an infection or tumor, or during the development of self tolerance (Keir Me, Butte M J, Freeman G J, et al. PD-1 and its ligands in tolerance and immunity. Annu. Rev. Immunol. 2008; 26: Epub). Chronic antigen stimulation, such as that which occurs during tumor disease or chronic infections, results in T cells that express elevated levels of PD-1 and are dysfunctional with respect to activity towards the chronic antigen (reviewed in Kim and Ahmed, Curr Opin Imm, 2010). This is termed "T cell exhaustion". B cells also display PD-1/PD-ligand suppression and "exhaustion".

PD-L1 has also been shown to interact with CD80 (Butte M J et al, Immunity; 27:111-122 (2007)). The interaction of PD-L1/CD80 on expressing immune cells has been shown to be an inhibitory one. Blockade of this interaction has been shown to abrogate this inhibitory interaction (Paterson A M, et al., J Immunol., 187:1097-1105 (2011); Yang J, et al. J Immunol. August 1; 187(3):1113-9 (2011)).

Blockade of the PD-1/PD-L1 interaction using antibodies to PD-L1 has been shown to restore and augment T cell activation in many systems. Patients with advanced cancer benefit from therapy with a monoclonal antibody to PD-L1 (Brahmer et al., New Engl J Med 2012). Preclinical animal models of tumors have shown that blockade of the PD-1/PD-L1 pathway by monoclonal antibodies can enhance the immune response and result in the immune response to a number of histologically distinct tumors (Dong H, Chen L. B7-H1 pathway and its role in the Evasion of tumor immunity. J Mol Med. 2003; 81(5):281-287; Dong H, Strome S E, Salamoa D R, et al. Tumor-associated B7-H1 promotes T-cell apoptosis: a potential mechanism of immune evasion. Nat Med. 2002; 8(8):793-800).

Interference with the PD-1/PD-L1 interaction has also shown enhanced T cell activity in chronic infection systems. Chronic lymphocytic chorio meningitis virus infection of mice also exhibits improved virus clearance and restored immunity with blockade of PD-L1 (Barber D L, Wherry E J, Masopust D, et al. Restoring function in exhausted CD8 T cells during chronic viral infection. Nature. 2006; 439 (7077):682-687). Humanized mice infected with HIV-1 show enhanced protection against viremia and reduced viral depletion of CD4+ T cells (Palmer et al., J. Immunol 2013). Blockade of PD-1/PD-L1 through monoclonal antibodies to PD-L1 can restore in vitro antigen-specific functionality to T cells from HIV patients (Day, Nature 2006; Petrovas, J. Exp. Med. 2006; Trautman, Nature Med. 2006; D'Souza, J. Immunol. 2007; Zhang, Blood 2007; Kaufmann, Nature Imm. 2007; Kasu, J. Immunol. 2010; Porichis, Blood 2011), HCV patients [Golden-Mason, J. Virol. 2007; Jeung, J. Leuk. Biol. 2007; Urbani, J. Hepatol. 2008; Nakamoto, PLoS Path. 2009; Nakamoto, Gastroenterology 2008] or HBV patients (Boni, J. Virol. 2007; Fisicaro, Gastro. 2010; Fisicaro et al., Gastroenterology, 2012; Boni et al., Gastro., 2012; Penna et al., JHep, 2012; Raziorrough, Hepatology 2009; Liang, World J Gastro. 2010; Zhang, Gastro. 2008).

Blockade of the PD-L1/CD80 interaction has also been shown to stimulate immunity (Yang J., et al., J Immunol. August 1; 187(3):1113-9 (2011)). The immune stimulation resulting from blockade of the PD-L1/CD80 interaction has been shown to be enhanced through combination with blockade of further PD-1/PD-L1 or PD-1/PD-L2 interactions.

Alterations in immune cell phenotypes are hypothesized to be an important factor in septic shock (Hotchkiss, et al., Nat Rev Immunol (2013)). These include increased levels of PD-1 and PD-L1 and T cell apoptosis (Guignant, et al, Crit. Care (2011)). Antibodies directed to PD-L1 can reduce the level of Immune cell apoptosis (Zhang et al, Crit. Care (2011)). Furthermore, mice lacking PD-1 expression are more resistant to septic shock symptoms than wildtype mice (Yang J., et al. J Immunol. August 1; 187(3):1113-9 (2011)). Studies have revealed that blockade of the interactions of PD-L1 using antibodies can suppress inappropriate immune responses and ameliorate disease symptoms.

In addition to enhancing immunologic responses to chronic antigens, blockade of the PD-1/PD-L1 pathway has also been shown to enhance responses to vaccination, including therapeutic vaccination in the context of chronic infection (S. J. Ha, S. N. Mueller, E. J. Wherry et al., "Enhancing therapeutic vaccination by blocking PD-1-mediated inhibitory signals during chronic infection," The Journal of Experimental Medicine, vol. 205, no. 3, pp. 543-555, 2008; A. C. Finnefrock, A. Tang, F. Li et al., "PD-1 blockade in rhesus macaques: impact on chronic infection and prophylactic vaccination," The Journal of Immunology, vol. 182, no. 2, pp. 980-987, 2009; M.-Y. Song, S.-H. Park, H. J. Nam, D.-H. Choi, and Y.-C. Sung, "Enhancement of vaccine-induced primary and memory CD8+t-cell responses by soluble PD-1," The Journal of Immunotherapy, vol. 34, no. 3, pp. 297-306, 2011).

The PD-1 pathway is a key inhibitory molecule in T cell exhaustion that arises from chronic antigen stimulation during chronic infections and tumor disease. Blockade of the PD-1/PD-L1 interaction through targeting the PD-L1 protein has been shown to restore antigen-specific T cell immune functions in vitro and in vivo, including enhanced responses to vaccination in the setting of tumor or chronic infection.

Accordingly, agents that block the interaction of PD-L1 with either PD-1 or CD80 are desired.

Applicants found potent compounds that have activity as inhibitors of the interaction of PD-L1 with PD-1 and CD80, and thus may be useful for therapeutic administration to enhance immunity in cancer or infections, including therapeutic vaccine. These compounds are provided to be useful as pharmaceuticals with desirable stability, bioavailability, therapeutic index, and toxicity values that are important to their drugability.

The present disclosure also provides pharmaceutical compositions comprising a compound of formula (I) and/or a pharmaceutically acceptable salt thereof; and a pharmaceutically acceptable carrier.

The present disclosure also provides a method of treating a disease or disorder associated with the activity of PD-L1 including its interaction with other proteins such as PD-1 and B7-1(CD80), the method comprising administering to a patient in need thereof a compound of formula (I) and/or a pharmaceutically acceptable salt thereof.

The present disclosure also provides processes and intermediates for making the compounds of formula (I) and/or salts thereof.

The present disclosure also provides a compound of formula (I) and/or a pharmaceutically acceptable salt thereof, for use in therapy.

The present disclosure also provides the use of the compounds of formula (I) and/or pharmaceutically acceptable salts thereof, for the manufacture of a medicament for the treatment or prophylaxis of PD-L1 related conditions, such as cancer and infectious diseases.

The compounds of formula (I) and compositions comprising the compounds of formula (I) may be used in treating, preventing, or curing various infectious diseases and cancer. Pharmaceutical compositions comprising these compounds are useful in treating, preventing, or slowing the progression of diseases or disorders in a variety of therapeutic areas, such as cancer and infectious diseases.

These and other features of the disclosure will be set forth in expanded form as the disclosure continues.

In a first aspect the present disclosure provides a compound of formula (I):

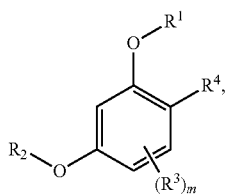

(I)

or a pharmaceutically acceptable salt thereof, wherein:
m is 0, 1, or 2;
$R^1$ is selected from hydrogen, haloC$_1$-C$_4$alkyl, hydroxyC$_1$-C$_4$alkyl, —(CH$_2$)$_n$X, and —(CH$_2$)$_n$Ar; wherein n is 1, 2, 3, or 4;
X is selected from hydrogen, —CH$_3$, —CF$_3$, C$_1$-C$_4$alkoxy, —N(CH$_3$)$_2$, C$_3$-C$_6$cycloalkyl, CN, —CO$_2$R$^g$, —C(O)NH$_2$,

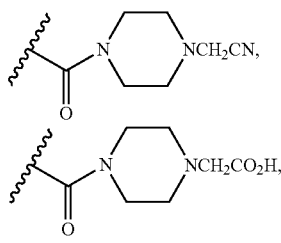

morpholinyl, tetrahydropyranyl, pyrrolidonyl optionally substituted with a hydroxy group, and piperidinyl optionally substituted with one or two groups independently selected from C$_1$-C$_4$alkyl, carboxy, hydroxy, and C$_1$-C$_4$alkoxycarbonyl; wherein R$^g$ is selected from hydrogen and C$_1$-C$_4$alkyl;

Ar is selected from benzodioxanyl, indazolyl, isoquinolinyl, isoxazolyl, naphthyl, oxadiazolyl, phenyl, pyridinyl, pyrimidinyl, and quinolinyl; wherein each ring is optionally substituted with 1, 2, 3, or 4 substituents independently selected from C$_1$-C$_4$alkoxy, C$_1$-C$_4$alkoxycarbonyl, C$_1$-C$_4$alkoxycarbonylamino, C$_1$-C$_4$alkyl, C$_1$-C$_4$alkylcarbonyl, C$_1$-C$_4$alkylsulfonyl, amido, amidoC$_1$-C$_4$alkyl, —(CH$_2$)$_q$CO$_2$C$_1$-C$_4$alkyl, —(CH$_2$)$_q$OH, carboxy, cyano, formyl, halo, haloC$_1$-C$_4$alkyl, haloC$_1$-C$_4$alkoxy, nitro, phenyl optionally substituted with one cyano group, phenyloxy optionally substituted with one halo group, phenylcarbonyl, pyrrole, and tetrahydropyran, wherein q is 0, 1, 2, 3, or 4;

$R^2$ is selected from

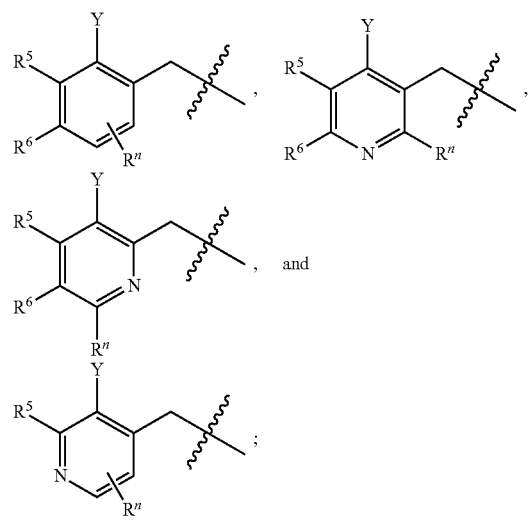

wherein $R^n$ is selected from hydrogen, C$_1$-C$_3$alkyl, halo, and haloC$_1$-C$_3$alkyl;

Y is selected from hydrogen, C$_1$-C$_3$alkoxy, C$_1$-C$_3$alkyl, cyano, and halo;

$R^5$ is phenyl or a monocyclic or bicyclic unsaturated heterocycle containing five to ten atoms wherein one to four of those atoms are independently selected from nitrogen, oxygen and sulfur; and wherein the phenyl and the monocyclic or bicyclic group is optionally substituted with one, two, three, four, or five substituents independently selected from C$_1$-C$_3$alkyl, cyano, formyl, halo, haloC$_1$-C$_3$alkoxy, haloC$_1$-C$_3$alkyl, hydroxy, oxo, -L-(CH$_2$)$_m$NR$^c$R$^d$, -L-(CH$_2$)$_m$OH,

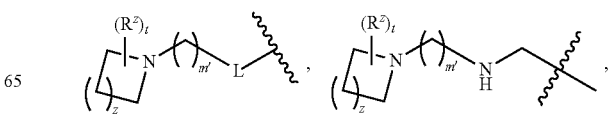

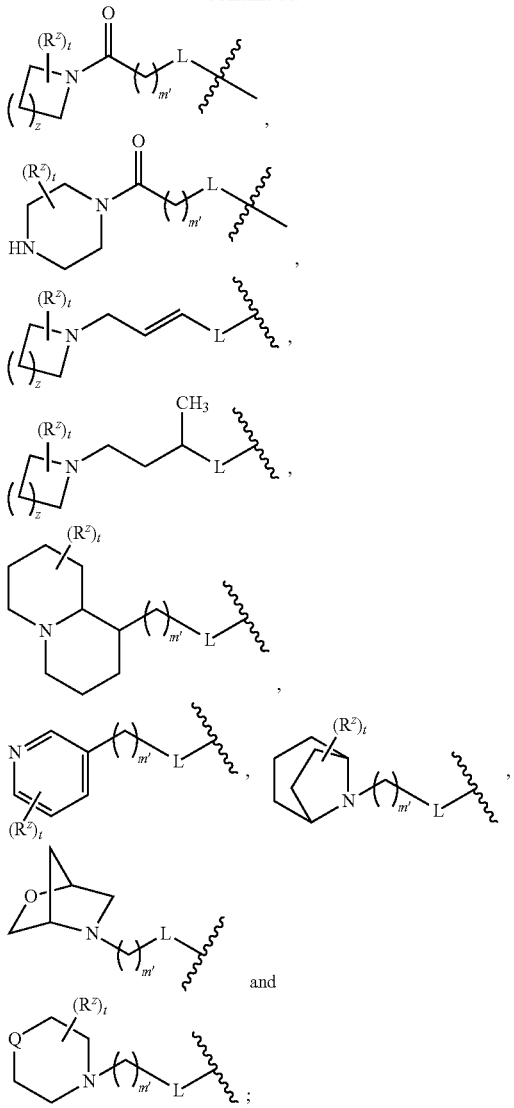

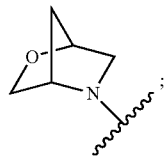 [SMILES: *N1CC2CC1CO2]

wherein
- L is selected from a bond, —CH$_2$, —NHC(O)—, —C(O)NH—, and —O—; provided that L is —CH$_2$— when it is attached to the parent molecular moiety through a nitrogen atom in the heterocycle;
- m' is 1, 2, 3, or 4; provided that when m' is 1, L is a bond that is attached to the parent molecular moiety through a carbon atom;
- t is 0, 1, 2, or 3;
- z is 1, 2, or 3;
- each R$^z$ is independently selected from C$_1$-C$_4$alkoxy, C$_1$-C$_4$alkoxycarbonyl, C$_1$-C$_4$alkoxycarbonylC$_1$-C$_4$alkyl, C$_1$-C$_4$alkyl, C$_1$-C$_4$alkylamido, C$_1$-C$_4$alkylamino, C$_1$-C$_4$alkylcarbonyl, amido, carboxy, carboxyC$_1$-C$_4$alkyl, cyano, di(C$_1$-C$_4$alkyl)amido, di(C$_1$-C$_4$alkyl)amino, halo, haloC$_1$-C$_4$alkoxy, haloC$_1$-C$_4$alkyl, hydroxy, hydroxyC$_1$-C$_4$alkyl, —NR$^c$R$^d$, (NR$^c$R$^d$)C$_1$-C$_4$alkyl, —NR$^e$R$^f$, (NR$^e$R$^f$)C$_1$-C$_4$alkyl, phenyl, and phenylC$_1$-C$_4$alkyl; wherein R$^e$ and R$^f$, together with the atom to which they are attached, form a ring selected from morpholine and

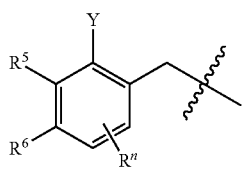

- R$^c$ and R$^d$ are independently selected from hydrogen, C$_2$-C$_4$alkenylcarbonyl, C$_1$-C$_4$alkoxycarbonyl, C$_1$-C$_6$alkyl, C$_1$-C$_4$alkylcarbonyl, amidoC$_1$-C$_4$alkyl, aminoC$_1$-C$_4$alkyl, arylC$_1$-C$_4$alkyl, C$_3$-C$_{10}$cycloalkyl, (C$_3$-C$_{10}$cycloalkyl)C$_1$-C$_4$alkyl, haloC$_1$-C$_4$alkylcarbonyl, heteroarylC$_1$-C$_4$alkyl, and hydroxyC$_1$-C$_4$alkyl; wherein the alkyl part of the amidoC$_1$-C$_4$alkyl, the aminoC$_1$-C$_4$alkyl, the arylC$_1$-C$_4$alkyl, the (C$_3$-C$_{10}$cycloalkyl)C$_1$-C$_4$alkyl, and the heteroarylC$_1$-C$_4$alkyl is optionally substituted with one or two groups independently selected from carboxy and hydroxy; wherein the alkyl part of the hydroxyC$_1$-C$_4$alkyl is optionally substituted with one or two groups independently selected from carboxy and hydroxy; and wherein the aryl part of the arylC$_1$-C$_4$alkyl, the C$_3$-C$_{10}$cycloalkyl, the cycloalkyl part of the (C$_3$-C$_{10}$cycloalkyl)C$_1$-C$_4$alkyl and the heteroaryl part of the heteroarylC$_1$-C$_4$alkyl are each optionally substituted with one, two, or three groups independently selected from C$_1$-C$_4$alkoxycarbonyl, C$_1$-C$_4$alkyl, and halo;
- Q is selected from S, O, and —NR$^p$; wherein R$^p$ is selected from hydrogen, C$_1$-C$_4$alkyl, C$_1$-C$_4$alkylamidoC$_1$-C$_4$alkyl, C$_1$-C$_4$alkylaminoC$_1$-C$_4$alkyl, amidoC$_1$-C$_4$alkyl, aminoC$_1$-C$_4$alkyl, di(C$_1$-C$_4$alkyl)amidoC$_1$-C$_4$alkyl, di(C$_1$-C$_4$alkyl)aminoC$_1$-C$_3$alkyl, hydroxyC$_1$-C$_4$alkyl, pyridinyl, and phenyl optionally substituted with methoxy;

provided that when R$^2$ is then R$^5$ is other than phenyl; and
- R$^6$ is hydrogen, or, R$^5$ and R$^6$, together with the atoms to which they are attached, form a five- or six-membered unsaturated ring containing one or two heteroatoms independently selected from nitrogen, oxygen, and sulfur; wherein the ring is optionally substituted with one or two substituents independently selected from C$_1$-C$_3$alkyl, cyano, formyl, halo, haloC$_1$-C$_3$alkyl, hydroxy, oxo, -L-(CH$_2$)$_n$NR$^c$R$^d$, -L-(CH$_2$)$_n$OH;
- each R$^3$ is independently selected from C$_2$-C$_4$alkenyl, C$_1$-C$_4$alkoxy, C$_1$-C$_4$alkyl, cyano, halo, and haloC$_1$-C$_4$alkyl; and
- R$^4$ is selected from —(CH$_2$)$_p$CHO, —(CH$_2$)$_n$OH, and —(CH$_2$)$_n$NR$^q$R$^8$, wherein
  - p is 0, 1, 2, or 3;
  - n' is 1, 2, 3, or 4;
- R$^q$ is selected from hydrogen, C$_1$-C$_4$alkyl, and benzyl; and $R^8$ is selected from

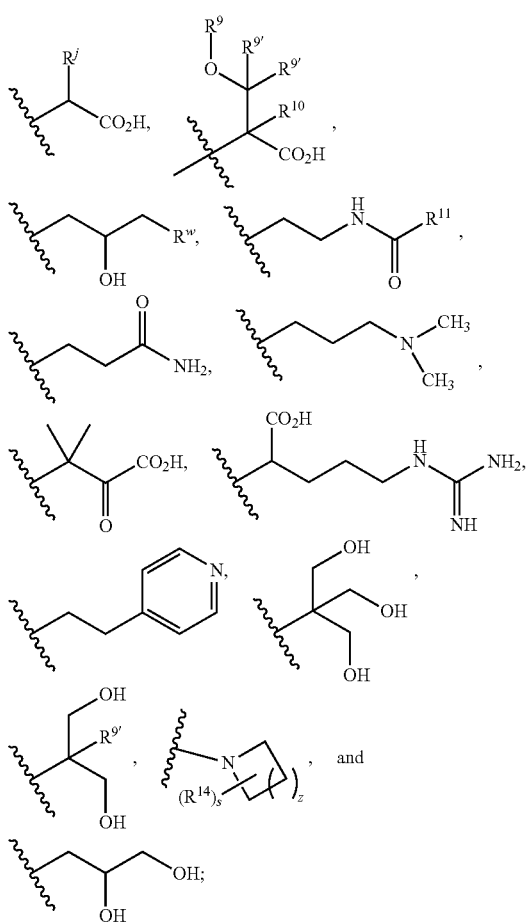

wherein
s is 0, 1, or 2;
z is 1, 2, or 3;
$R^j$ is selected from $C_1$-$C_3$alkyl, $C_1$-$C_3$alkylsulfonyl$C_1$-$C_3$alkyl, $C_1$-$C_3$alkylsulfoxyl$C_1$-$C_3$alkyl, and $C_1$-$C_3$alkylsulfanyl$C_1$-$C_3$alkyl;
$R^w$ is —$CO_2H$ or —$CONH_2$,
$R^9$ is selected from hydrogen, benzyl, and methyl;
each $R^{9'}$ is independently selected from hydrogen, ethyl, and methyl;
$R^{10}$ is selected from hydrogen, $C_1$-$C_3$alkyl, and benzyl; and
$R^{11}$ is selected from $C_2$-$C_4$alkenyl and $C_1$-$C_4$alkyl;
or
$R^8$ and $R^q$, together with the nitrogen atom to which they are attached, form a ring selected from

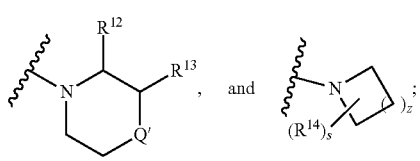

wherein
s is 0, 1, or 2;
z is 1, 2, or 3;
$Q'$ is selected from $CHR^{13'}$, S, O, —$N(CH_2)_2OH$, and $NCH_3$;
$R^{12}$ is selected from hydrogen, —$CO_2H$, hydroxy$C_1$-$C_4$alkyl, and —$C(O)NHSO_2R^{16}$; wherein $R^{16}$ is selected from trifluoromethyl, cyclopropyl, $C_1$-$C_4$alkyl, dimethylamino, 4-methylpiperazinyl, and imidazolyl substituted with a methyl group;
$R^{13}$ is selected from hydrogen, hydroxy$C_1$-$C_4$alkyl, and —$CO_2H$;
$R^{13'}$ is selected from hydrogen, hydroxy$C_1$-$C_3$alkyl, and —$CO_2H$; and
$R^{14}$ is selected from $C_1$-$C_4$alkoxycarbonyl, $C_1$-$C_3$alkyl, carboxy, halo, hydroxy, hydroxy$C_1$-$C_4$alkyl, and —$NR^{c'}R^{d'}$; wherein $R^{c'}$ and $R^{d'}$ are independently selected from hydrogen, $C_1$-$C_4$alkoxycarbonyl, and $C_1$-$C_4$alkylcarbonyl.

In a first embodiment of the first aspect the present disclosure provides a compound of formula (I), or a pharmaceutically acceptable salt thereof, wherein $R^1$ is —$(CH_2)_nAr$ wherein n is 1 and Ar is pyridinyl optionally substituted with cyano.

In a second embodiment of the first aspect the present disclosure provides a compound of formula (I), or a pharmaceutically acceptable salt thereof, wherein $R^1$ is —$(CH_2)_nAr$ wherein n is 1 and Ar is pyridinyl optionally substituted with cyano; m is 1; and $R^3$ is halo.

In a third embodiment, the present disclosure provides a compound of formula (I), or a pharmaceutically acceptable salt thereof, wherein $R^1$ is —$(CH_2)_nAr$ wherein n is 1 and Ar is pyridinyl optionally substituted with cyano; m is 1; and $R^3$ is halo and wherein $R^2$ is selected from

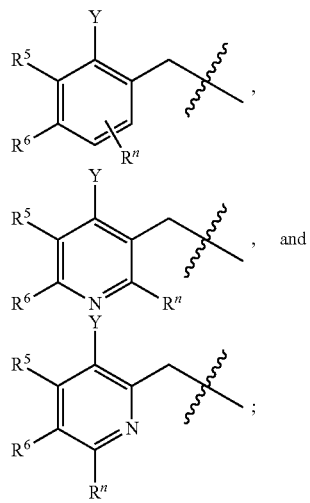

wherein
$R^n$ is hydrogen;
Y is methyl;
$R^5$ is phenyl or a monocyclic or bicyclic unsaturated heterocycle containing five to ten atoms wherein one to four of those atoms are independently selected from nitrogen, oxygen and sulfur; and wherein the phenyl and the monocyclic or bicyclic group is optionally substituted with one, two, or three substituents independently selected from $C_1$-$C_3$alkyl, cyano, formyl, halo, halo$C_1$-$C_3$alkoxy, halo$C_1$-$C_3$alkyl, hydroxy, oxo, -L-$(CH_2)_mNR^cR^d$, -L-$(CH_2)_mOH$,

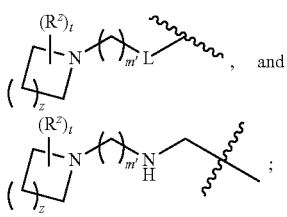, and wherein L is selected from a bond, —CH$_2$—, and —O—;
m' is 1, 2, 3, or 4; provided that when m' is 1, L is a bond that is attached to the parent molecular moiety through a carbon atom;
t is 0 or 1;
z is 2 or 3;
R$^z$ is hydroxy;
R$^c$ and R$^d$ are each methyl; and
R$^6$ is hydrogen.

In a fourth embodiment of the first aspect the present disclosure provides a compound of formula (I), or a pharmaceutically acceptable salt thereof, wherein R$^1$ is —(CH$_2$)$_n$Ar wherein n is 1 and Ar is pyridinyl optionally substituted with cyano; m is 1; and R$^3$ is halo; R$^4$ is selected from —(CH$_2$)$_p$CHO, —(CH$_2$)$_{n'}$OH, and —(CH$_2$)$_{n'}$NR$^q$R$^8$, wherein
p is 0;
n' is 1;
R$^q$ is hydrogen; and
R$^8$ is selected from

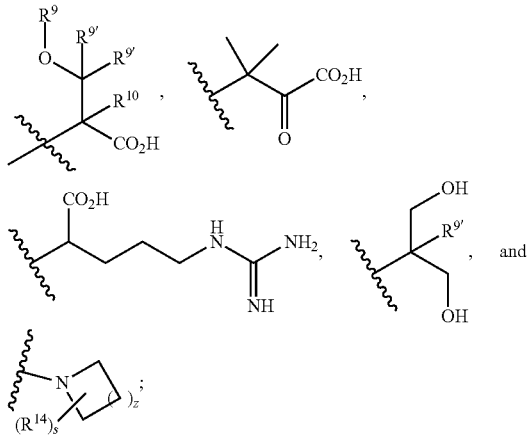

s is 1;
z is 2;
R$^9$ is selected from hydrogen, benzyl, and methyl;
each R$^{9'}$ is independently selected from hydrogen, ethyl, and methyl; and
R$^{10}$ is selected from hydrogen, C$_1$-C$_3$alkyl, and benzyl; or R$^8$ and R$^q$, together with the nitrogen atom to which they are attached, form a ring which is:

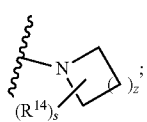

wherein
s is 0, 1, or 2;
z is 1, 2, or 3; and
R$^{14}$ is selected from C$_1$-C$_4$alkoxycarbonyl, C$_1$-C$_3$alkyl, carboxy, and hydroxy.

In a second aspect the present disclosure provides a compound of formula (I),

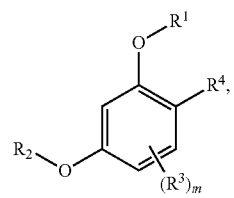

or a pharmaceutically acceptable salt thereof, wherein:
m is 1;
R$^1$ is —(CH$_2$)$_n$Ar; wherein
n is 1,
Ar is pyridinyl optionally substituted with cyano;
R$^2$ is selected from

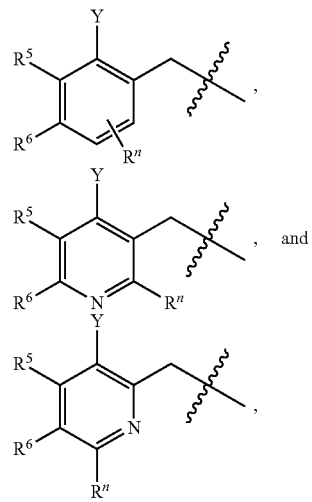

wherein
R$^n$ is hydrogen;
Y is C$_1$-C$_3$alkyl;
R$^5$ is phenyl or a monocyclic or bicyclic unsaturated heterocycle containing five to ten atoms wherein one to four of those atoms are independently selected from nitrogen, oxygen and sulfur; and wherein the phenyl and the monocyclic or bicyclic group is optionally substituted with one, two, three, four, or five substituents independently selected from C$_1$-C$_3$alkyl, cyano, formyl, halo, haloC$_1$-C$_3$alkoxy, haloC$_1$-C$_3$alkyl, hydroxy, oxo, -L-(CH$_2$)$_m$NR$^c$R$^d$, -L-(CH$_2$)$_m$OH,

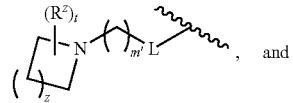, and

-continued

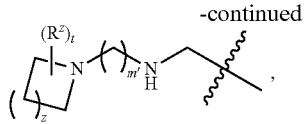

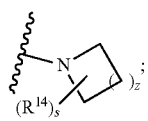

wherein
  s is 1 or 2;
  z is 2 or 3; and
  $R^{14}$ is selected from $C_1$-$C_4$alkoxycarbonyl, $C_1$-$C_3$alkyl, carboxy, halo, and hydroxy.

wherein
  L is selected from a bond, —$CH_2$—, and —O—; provided that L is —$CH_2$— when it is attached to the parent molecular moiety through a nitrogen atom in the heterocycle;
  m' is 1, 2, 3, or 4; provided that when m' is 1, L is a bond that is attached to the parent molecular moiety through a carbon atom;
  t is 0, 1, 2, or 3;
  z is 1, 2, or 3;
  $R^z$ is hydroxy;
  $R^c$ and $R^d$ are $C_1$-$C_6$alkyl;
provided that when $R^2$ is

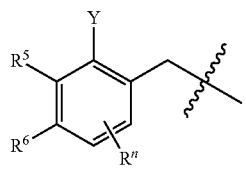

then $R^5$ is other than phenyl;
  $R^6$ is hydrogen,
  $R^3$ is halo; and
  $R^4$ is selected from —$(CH_2)_p$CHO, —$(CH_2)_n$OH, and —$(CH_2)_n$NR$^q$R$^8$, wherein
  p is 0;
  n' is 1;
  $R^q$ is hydrogen; and
  $R^8$ is selected from

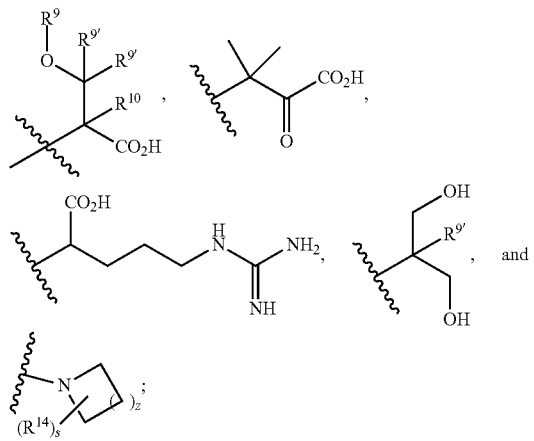

s is 1;
z is 2;
$R^9$ is selected from hydrogen, benzyl, and methyl;
each $R^{9'}$ is independently selected from hydrogen, ethyl, and methyl; and
$R^{10}$ is selected from hydrogen, $C_1$-$C_3$alkyl, and benzyl; or
$R^8$ and $R^q$, together with the nitrogen atom to which they are attached, form a ring which is In a third aspect the present disclosure provides a pharmaceutical composition comprising a compound of formula (I), or a pharmaceutically acceptable salt thereof, and a pharmaceutically acceptable carrier.

In a fourth aspect the present disclosure provides a method of enhancing, stimulating, modulating and/or increasing the immune response in a subject in need thereof, said method comprising administering to the subject a therapeutically effective amount of a compound of formula (I), or a pharmaceutically acceptable salt thereof. In a first embodiment of the fourth aspect the method further comprises administering an additional agent prior to, after, or simultaneously with the compound of formula (I), or the pharmaceutically acceptable salt thereof. In a second embodiment of the fourth aspect the additional agent is an antimicrobial agent, an antiviral agent, an agent that modifies gene expression, a cytotoxic agent, and/or an immune response modifier.

In a fifth aspect the present disclosure provides a method of inhibiting growth, proliferation, or metastasis of cancer cells in a subject in need thereof, said method comprising administering to the subject a therapeutically effective amount of a compound of formula (I), or a pharmaceutically acceptable salt. In a first embodiment of the fifth aspect the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and a hematological malignancy.

In a sixth aspect the present disclosure provides a method of treating an infectious disease in a subject in need thereof, the method comprising administering to the subject a therapeutically effective amount of a compound of formula (I), or a pharmaceutically acceptable salt thereof. In a first embodiment of the sixth aspect the infectious disease is caused by a virus. In a second embodiment of the sixth aspect the virus is selected from HIV, Hepatitis A, Hepatitis B, Hepatitis C, Hepatitis D, herpes viruses, papillomaviruses and influenza.

In a seventh aspect the present disclosure provides a method of treating septic shock in a subject in need thereof, the method comprising administering to the subject a therapeutically effective amount of a compound of formula (I), or a pharmaceutically acceptable salt thereof.

In an eighth aspect the present disclosure provides a method blocking the interaction of PD-L1 with PD-1 and/or CD80 in a subject, said method comprising administering to the subject a therapeutically effective amount of a compound of formula (I), or a pharmaceutically acceptable salt thereof.

The features and advantages of the disclosure may be more readily understood by those of ordinary skill in the art upon reading the following detailed description. It is to be appreciated that certain features of the disclosure that are, for clarity reasons, described above and below in the context of separate embodiments, may also be combined to form a single embodiment. Conversely, various features of the disclosure that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compound(s) or pharmaceutically acceptable salts thereof" refers to at least one compound, at least one salt of the compounds, or a combination thereof. For example, compounds of formula (I) or pharmaceutically acceptable salts thereof includes a compound of formula (I); two compounds of formula (I); a salt of a compound of formula (I); a compound of formula (I) and one or more salts of the compound of formula (I); and two or more salts of a compound of formula (I).

Unless otherwise indicated, any atom with unsatisfied valences is assumed to have hydrogen atoms sufficient to satisfy the valences.

Throughout the specification, groups and substituents thereof may be chosen by one skilled in the field to provide stable moieties and compounds.

Listed below are definitions of various terms used to describe the present disclosure. These definitions apply to the terms as they are used throughout the specification (unless they are otherwise limited in specific instances) either individually or as part of a larger group. The definitions set forth herein take precedence over definitions set forth in any patent, patent application, and/or patent application publication incorporated herein by reference.

The term "$C_2$-$C_4$alkenyl," as used herein, refers to a group derived from a straight or branched chain hydrocarbon containing from one to four carbon atoms and one or two double bonds.

The term "$C_2$-$C_4$alkenylcarbonyl," as used herein, refers to a $C_2$-$C_4$alkenyl group attached to the parent molecular moiety through a carbonyl group.

The term "$C_1$-$C_4$alkoxy," as used herein, refers to a $C_1$-$C_4$alkyl group attached to the parent molecular moiety through an oxygen atom.

The term "$C_1$-$C_4$alkoxycarbonyl," as used herein, refers to a $C_1$-$C_4$alkoxy group attached to the parent molecular moiety through a carbonyl group.

The term "$C_1$-$C_4$alkoxycarbonyl$C_1$-$C_4$alkyl," as used herein, refers to a $C_1$-$C_4$alkoxycarbonyl group attached to the parent molecular moiety through a $C_1$-$C_4$alkyl group.

The term "$C_1$-$C_4$alkoxycarbonylamino," as used herein, refers to a $C_1$-$C_4$alkoxycarbonyl group attached to the parent molecular moiety through an —NH group.

The term "$C_1$-$C_3$alkyl," as used herein, refers to a group derived from a straight or branched chain saturated hydrocarbon containing from one to three carbon atoms.

The term "$C_1$-$C_4$alkyl," as used herein, refers to a group derived from a straight or branched chain saturated hydrocarbon containing from one to four carbon atoms.

The term "$C_1$-$C_6$alkyl," as used herein, refers to a group derived from a straight or branched chain saturated hydrocarbon containing from one to six carbon atoms.

The term "$C_1$-$C_4$alkylamido," as used herein, refers to —C(O)NHR, wherein R is a $C_1$-$C_4$alkyl group.

The term "$C_1$-$C_4$alkylamido$C_{1-4}$alkyl," as used herein, refers to a $C_1$-$C_4$alkylamido group attached to the parent molecular moiety through a $C_1$-$C_4$alkyl group.

The term "$C_1$-$C_4$alkylamino," as used herein, refers to —NHR, wherein R is a $C_1$-$C_4$alkyl group.

The term "$C_1$-$C_4$alkylamino$C_{1-4}$alkyl," as used herein, refers to a $C_1$-$C_4$alkylamino group attached to the parent molecular moiety through a $C_1$-$C_4$alkyl group.

The term "$C_1$-$C_4$alkylcarbonyl," as used herein, refers to a $C_1$-$C_4$alkyl group attached to the parent molecular moiety through a carbonyl group.

The term "$C_1$-$C_3$alkylsulfanyl," as used herein, refers to a $C_1$-$C_3$alkyl group attached to the parent molecular moiety through a sulfur atom.

The term "$C_1$-$C_3$alkylsulfanyl$C_1$-$C_3$alkyl," as used herein, refers to a $C_1$-$C_3$alkylsulfanyl attached to the parent molecular moiety through a $C_1$-$C_3$alkyl group.

The term "$C_1$-$C_3$alkylsulfonyl," as used herein, refers to a $C_1$-$C_4$alkyl group attached to the parent molecular moiety through a sulfonyl group.

The term "$C_1$-$C_4$alkylsulfonyl," as used herein, refers to a $C_1$-$C_4$alkyl group attached to the parent molecular moiety through a sulfonyl group.

The term "$C_1$-$C_3$alkylsulfonyl$C_1$-$C_3$alkyl," as used herein, refers to a $C_1$-$C_3$alkylsulfonyl group attached to the parent molecular moiety through a $C_1$-$C_3$alkyl group.

The term "$C_1$-$C_3$alkylsulfoxyl," as used herein, refers to a $C_1$-$C_3$alkyl group attached to the parent molecular moiety through a sulfoxyl group.

The term "$C_1$-$C_3$alkylsulfoxyl$C_1$-$C_3$alkyl," as used herein, refers to a $C_1$-$C_3$alkylsulfoxyl group attached to the parent molecular moiety through a $C_1$-$C_3$alkyl group.

The term "amido," as used herein, refers to —C(O)NH$_2$.

The term "amido$C_1$-$C_4$alkyl," as used herein, refers to an amido group attached to the parent molecular moiety through a $C_1$-$C_4$alkyl group.

The term "amino$C_1$-$C_4$alkyl," as used herein, refers to an amino group attached to the parent molecular moiety through a $C_1$-$C_4$alkyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present invention can be attached to the parent molecular moiety through any substitutable carbon atom in the group. Representative examples of aryl groups include, but are not limited to, indanyl, indenyl, naphthyl, phenyl, and tetrahydronaphthyl.

The term "aryl$C_1$-$C_4$alkyl," as used herein, refers to an aryl group attached to the parent molecular moiety through a $C_1$-$C_4$alkyl group.

The term "carbonyl," as used herein, refers to —C(O)—.

The term "carboxy," as used herein, refers to —CO$_2$H.

The term "carboxy$C_1$-$C_4$alkyl," as used herein, refers to a carboxy group attached to the parent molecular moiety through a $C_1$-$C_4$alkyl group.

The term "cyano," as used herein, refers to —CN.

The term "$C_3$-$C_6$cycloalkyl," as used herein, refers to a saturated monocyclic, hydrocarbon ring system having three to six carbon atoms and zero heteroatoms.

The term "$C_3$-$C_{10}$cycloalkyl," as used herein, refers to a saturated monocyclic, hydrocarbon ring system having three to ten carbon atoms and zero heteroatoms.

The term "($C_3$-$C_{10}$cycloalkyl)$C_1$-$C_4$alkyl," as used herein, refers to a $C_3$-$C_{10}$cycloalkyl group attached to the parent molecular moiety through a $C_1$-$C_4$alkyl group.

The term "di($C_1$-$C_4$alkyl)amido," as used herein, refers to —C(O)$NR_2$, wherein R is a $C_1$-$C_4$alkyl group. The two R groups may be the same or different.

The term "di($C_1$-$C_4$alkyl)amido$C_1$-$C_4$alkyl," as used herein, refers to a di($C_1$-$C_4$alkyl)amido group attached to the parent molecular moiety through a $C_1$-$C_4$alkyl group.

The term "di($C_1$-$C_4$alkyl)amino," as used herein, refers to —$NR_2$, wherein R is a $C_1$-$C_4$alkyl group. The two R groups may be the same or different.

The term "di($C_1$-$C_4$alkyl)amino$C_1$-$C_4$alkyl," as used herein, refers to a group di($C_1$-$C_4$alkyl)amino attached to the parent molecular moiety through a $C_1$-$C_4$alkyl group.

The term "dimethylamino," as used herein, refers to —N($CH_3$)$_2$.

The term "formyl," as used herein, refers to —C(O)H.

The terms "halo" and "halogen," as used herein, refer to F, Cl, Br, or I.

The term "halo$C_1$-$C_3$alkyl," as used herein, refers to a $C_1$-$C_3$alkyl group substituted with one, two, or three halogen atoms.

The term "halo$C_1$-$C_4$alkoxy," as used herein, refers to a halo$C_1$-$C_4$alkyl group attached to the parent molecular moiety through an oxygen atom.

The term "halo$C_1$-$C_4$alkyl," as used herein, refers to a $C_1$-$C_4$alkyl group substituted with one, two, or three halogen atoms.

The term "halo$C_1$-$C_4$alkylcarbonyl," as used herein, refers to a halo$C_1$-$C_4$alkyl group attached to the parent molecular moiety through a carbonyl group.

The term "heteroaryl," as used herein, refers to a five- or six-membered aromatic ring containing one, two, or three heteroatoms independently selected from nitrogen, oxygen, and sulfur. The term "heteroaryl" also includes bicyclic groups in which the heteroaryl ring is fused to another monocyclic heteroaryl group or a phenyl group.

The term "heteroaryl$C_1$-$C_4$alkyl," as used herein, refers to a heteroaryl group attached to the parent molecular moiety through a $C_1$-$C_4$alkyl group.

The term "hydroxy," as used herein, refers to —OH.

The term "hydroxy$C_1$-$C_4$alkyl," as used herein, refers to a hydroxy group attached to the parent molecular moiety through a $C_1$-$C_4$alkyl group.

The term "(NR$^c$R$^d$)$C_1$-$C_4$alkyl," as used herein, refers to an NR$^c$R$^d$ group attached to the parent molecular moiety through a $C_1$-$C_4$alkyl group.

The term "(NR$^e$R$^f$)$C_1$-$C_4$alkyl," as used herein, refers to an NR$^c$R$^d$ group attached to the parent molecular moiety through a $C_1$-$C_4$alkyl group.

The term "nitro," as used herein, refers to —$NO_2$.

The term "oxo," as used herein, refers to =O.

The term "phenyl$C_1$-$C_4$alkyl," as used herein, refers to a phenyl group attached to the parent molecular moiety through a $C_1$-$C_4$alkyl group.

The term "phenylcarbonyl," as used herein, refers to a phenyl group attached to the parent molecular moiety through a carbonyl group.

The term "phenyloxy," as used herein, refers to a phenyl group attached to the parent molecular moiety through an oxygen atom.

The term "sulfonyl," as used herein, refers to —$SO_2$—.

The term "sulfoxyl," as used herein, refers to —SO—.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of formula (I) can form salts which are also within the scope of this disclosure. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the disclosure. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of formula (I), subsequent to their preparation, can be isolated and purified to obtain a composition containing an amount by weight equal to or greater than 99% of a compound of formula (I) ("substantially pure"), which is then used or formulated as described herein. Such "substantially pure" compounds of formula (I) are also contemplated herein as part of the present disclosure.

"Stable compound" and "stable structure" are meant to indicate a compound that is sufficiently robust to survive isolation to a useful degree of purity from a reaction mixture, and formulation into an efficacious therapeutic agent. The present disclosure is intended to embody stable compounds.

"Therapeutically effective amount" is intended to include an amount of a compound of the present disclosure alone or an amount of the combination of compounds claimed or an amount of a compound of the present disclosure in combination with other active ingredients effective to inhibit PD-1/PD-L1 protein/protein and/or CD80/PD-L1 protein/protein interactions, or effective to treat or prevent cancer or infectious disease, such as HIV or hepatitis B, hepatitis C, and hepatitis D.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present disclosure are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Compounds in accordance with formula (I) and/or pharmaceutically acceptable salts thereof can be administered by any means suitable for the condition to be treated, which can depend on the need for site-specific treatment or quantity of formula (I) compound to be delivered. Also embraced within this disclosure is a class of pharmaceutical compositions comprising a compound of formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of formula (I) may be administered by any suitable route, preferably in the form of a pharmaceutical composition adapted to such a route, and in a dose effective for the treatment intended. The compounds and compositions of the present disclosure may, for example, be administered orally, mucosally, rectally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the disclosure can contain at least one agent selected from sweetening agents, flavoring agents, coloring agents, demulcents, antioxidants, and preserving agents.

A tablet can, for example, be prepared by admixing at least one compound of formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of formula (I) and/or at least one salt thereof with at least one inert solid diluent, such as, for example, calcium carbonate; calcium phosphate; and kaolin.

Soft gelatin capsules can, for example, be prepared by mixing at least one compound of formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of formula (I) and/or at least one pharmaceutically acceptable salt thereof in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of formula (I) and/or at least one pharmaceutically acceptable salt thereof can, for example, be prepared as an oil-in-water emulsion. The oily phase of the emulsions comprising compounds of formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present disclosure include Tween 60, Span 80, cetostearyl alcohol, myristyl alcohol, glyceryl monostearate, sodium lauryl sulfate, glyceryl distearate alone or with a wax, or other materials well known in the art.

The compounds of formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of formula (I) in an oily phase, such as, for example, a mixture of soybean oil and lecithin; 2) combining the formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this disclosure include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this disclosure can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this disclosure depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this disclosure are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this disclosure comprise at least one compound of formula (I) and/or at least one pharmaceutically acceptable salt thereof, and optionally an additional agent selected from any pharmaceutically acceptable carrier, adjuvant, and vehicle. Alternate compositions of this disclosure comprise a compound of the formula (I) described herein, or a prodrug thereof, and a pharmaceutically acceptable carrier, adjuvant, or vehicle.

The compounds of the disclosure inhibit the PD-1/PD-L1 protein/protein resulting in a PD-L1 blockade. The blockade of PD-L1 can enhance the immune response to cancerous cells and infectious diseases in mammals, including humans.

In one aspect, the present disclosure relates to treatment of a subject in vivo using a compound of formula (I) or a salt thereof such that growth of cancerous tumors is inhibited. A compound of formula (I) or a salt thereof may be used alone to inhibit the growth of cancerous tumors. Alternatively, a compound of formula (I) or a salt thereof may be used in conjunction with other immunogenic agents or standard cancer treatments, as described below.

In one embodiment, the disclosure provides a method of inhibiting growth of tumor cells in a subject, comprising administering to the subject a therapeutically effective amount of a compound of formula (I) or a salt thereof.

In one embodiment, a method is provided for treating cancer comprising administering to a patient in need thereof, a therapeutically effective amount of a compound of formula (I) or a salt thereof. Examples of cancers include those whose growth may be inhibited using compounds of the disclosure include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the disclosure includes refractory or recurrent malignancies whose growth may be inhibited using the compounds of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al. (2005) Int. Immunol. 17:133-144).

Optionally, the compounds of formula (I) or salts thereof can be combined with another immunogenic agent, such as cancerous cells, purified tumor antigens (including recombinant proteins, peptides, and carbohydrate molecules), cells, and cells transfected with genes encoding immune stimulating cytokines (He et al (2004) J. Immunol. 173: 4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. In humans, some tumors have been shown to be immunogenic such as melanomas. It is anticipated that by raising the threshold of T cell activation by PD-L1 blockade, tumor responses are expected to be activated in the host.

The PD-L1 blockade can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogenenic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-L1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (ie. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV, HDV and HCV) and Kaposi's Herpes Sarcoma Virus (KHSV). Another form of tumor specific antigen which may be used in conjunction with PD-L1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269:1585-1588; Tamura, Y. et al. (1997) Science 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) Nature Medicine 4: 328-332). DCs may also be transduced by genetic means to express these tumor antigens as well. DCs have also been fused directly to tumor cells for the purposes of immunization (Kugler, A. et al. (2000) Nature Medicine 6:332-336). As a method of vaccination, DC immunization may be effectively combined with PD-L1 blockade to activate more potent anti-tumor responses.

PD-L1 blockade may also be combined with standard cancer treatments. PD-L1 blockade may be effectively combined with chemotherapeutic regimes. In these instances, it may be possible to reduce the dose of chemotherapeutic reagent administered (Mokyr, M. et al. (1998) Cancer Research 58: 5301-5304). An example of such a combination is a compound of this disclosure in combination with dacarbazine for the treatment of melanoma. Another example of such a combination is a compound of this disclosure in combination with interleukin-2 (IL-2) for the treatment of melanoma. The scientific rationale behind the combined use of PD-L1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade. Inhibition of angiogenesis leads to tumor cell death which may feed tumor antigen into host antigen presentation pathways.

The compounds of this disclosure can also be used in combination with bispecific compounds that target Fc alpha or Fc gamma receptor-expressing effectors cells to tumor cells (see, e.g., U.S. Pat. Nos. 5,922,845 and 5,837,243). Bispecific compounds can be used to target two separate antigens. For example anti-Fc receptor/anti tumor antigen (e.g., Her-2/neu) bispecific compounds have been used to target macrophages to sites of tumor. This targeting may more effectively activate tumor specific responses. The T cell arm of these responses would be augmented by the use of PD-L1 blockade. Alternatively, antigen may be delivered directly to DCs by the use of bispecific compounds which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) J. Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). Inhibitors that bind to and block each of these entities may be used in combination with the compounds of this disclosure to counteract the effects of the immunosuppressive agent and favor tumor immune responses by the host.

Compounds that activate host immune responsiveness can be used in combination with PD-L1 blockade. These include molecules on the surface of dendritic cells which activate DC function and antigen presentation. Anti-CD40 compounds are able to substitute effectively for T cell helper activity (Ridge, J. et al. (1998) Nature 393: 474-478) and can be used in conjunction with PD-L1 blockade (Ito, N. et al. (2000) Immunobiology 201 (5) 527-40). Activating compounds to T cell costimulatory molecules such as CTLA-4 (e.g., U.S. Pat. No. 5,811,097), OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blockade can be used to increase the effectiveness of the donor engrafted tumor specific T cells.

Other methods of the disclosure are used to treat patients who have been exposed to particular toxins or pathogens. Accordingly, another aspect of the disclosure provides a method of treating an infectious disease in a subject comprising administering to the subject a therapeutically effective amount of a compound of formula (I) or salts thereof.

Similar to its application to tumors as discussed above, the compound of formula (I) or salts thereof can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, C or D), Influenza, Herpes, *Giardia*, Malaria, *Leishmania, Staphylococcus aureus, Pseudomonas Aeruginosa*. PD-L1 blockade is particularly useful against established infections by agents such as HIV that present altered antigens over the course of the infections. These novel epitopes are recognized as foreign at the time of administration, thus provoking a strong T cell response that is not dampened by negative signals through PD-1.

Some examples of pathogenic viruses causing infections treatable by methods of the disclosure include HIV, hepatitis (A, B, C, or D), herpes viruses (e.g., VZV, HSV-1, HAV-6, HHv-7, HHV-8, HSV-2, CMV, and Epstein Barr virus), adenovirus, influenza virus, flaviviruses, echovirus, rhinovirus, coxsackie virus, comovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include *Chlamydia*, rickettsial bacteria, mycobacteria, staphylococci, streptococci, pneumonococci, meningococci and conococci, *Klebsiella, Proteus, Serratia, Pseudomonas, Legionella*, diphtheria, *Salmonella*, bacilli, cholera, tetanus, botulism, anthrax, plague, leptospirosis, and Lymes disease bacteria.

Some examples of pathogenic fungi causing infections treatable by methods of the disclosure include *Candida* (*albicans, krusei, glabrata, tropicalis*, etc.), *Cryptococcus neoformans, Aspergillus (fumigatus, niger*, etc.), Genus *Mucorales* (*mucor, absidia, rhizophus*), *Sporothrix schenkii*, *Blastomyces dermatitidis, Paracoccidioides brasiliensis, Coccidioides immitis* and *Histoplasma capsulatum*.

Some examples of pathogenic parasites causing infections treatable by methods of the disclosure include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*. In all of the above methods, PD-L1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) Proc. Natl. Acad. Sci. USA 90:6444-6448; Poljak (1994) Structure 2:1121-1123), vaccines, or agents that modify gene expression.

The compounds of this disclosure may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B 16 melanoma in van Elsas et al. supra; depigmentation in Trp-2 vaccinated mice (Overwijk, W. et al. (1999) Proc. Natl. Acad. Sci. U.S.A. 96: 2982-2987); autoimmune prostatitis evoked by TRAMP tumor cell vaccines (Hurwitz, A. (2000) supra), melanoma peptide antigen vaccination and vitilago observed in human clinical trials (Rosenberg, S A and White, D E (1996) J. Immunother Emphasis Tumor Immunol 19 (1): 81-4).

Therefore, it is possible to consider using anti-PD-L1 blockade in conjunction with various self proteins in order to devise vaccination protocols to efficiently generate immune responses against these self proteins for disease treatment. For example, Alzheimer's disease involves inappropriate accumulation of A.beta. peptide in amyloid deposits in the brain; antibody responses against amyloid are able to clear these amyloid deposits (Schenk et al., (1999) Nature 400: 173-177).

Other self proteins may also be used as targets such as IgE for the treatment of allergy and asthma, and TNF.alpha. for rheumatoid arthritis. Finally, antibody responses to various hormones may be induced by the use of a compound of formula (I) or salts thereof. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-L1 antibody can be used for induction of therapeutic autoimmune responses to treat patients having an inappropriate accumulation of other self-antigens, such as amyloid deposits, including A.beta. in Alzheimer's disease, cytokines such as TNF alpha, and IgE.

The compounds of this disclosure may be used to stimulate antigen-specific immune responses by co-administration of a compound of formula (I) or salts thereof with an antigen of interest (e.g., a vaccine). Accordingly, in another aspect the disclosure provides a method of enhancing an immune response to an antigen in a subject, comprising administering to the subject: (i) the antigen; and (ii) a compound of formula (I) or salts thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

As previously described, the compounds of the disclosure can be co-administered with one or more other therapeutic agents, e.g., a cytotoxic agent, a radiotoxic agent or an immunosuppressive agent. The compounds of the disclosure can be administered before, after or concurrently with the other therapeutic agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/mL dose once every 21 days. Co-administration of a compound of formula (I) or salts thereof, with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present disclosure are kits comprising a compound of formula (I) or salts thereof and instructions for use. The kit can further contain at least one additional reagent. Kits typically include a label indicating the intended use of the contents of the kit. The term label includes any writing, or recorded material supplied on or with the kit, or which otherwise accompanies the kit.

The above other therapeutic agents, when employed in combination with the compounds of the present disclosure, may be used, for example, in those amounts indicated in the Physicians' Desk Reference (PDR) or as otherwise determined by one of ordinary skill in the art. In the methods of the present disclosure, such other therapeutic agent(s) may be administered prior to, simultaneously with, or following the administration of the inventive compounds.

In one embodiment, the compounds of formula (I) inhibit the PD-1/PD-L1 interaction with $IC_{50}$ values of 10 μM or less, for example, from 0.01 to 10 μM, as measured by the PD-1/PD-L1 Homogenous Time-Resolved Fluorescence (HTRF) binding assay. Preferably, the compounds of formula (I) inhibit the PD-1/PD-L1 interaction with $IC_{50}$ values of 1 μM or less, for example, from 0.01 to 1 μM.

EXAMPLES

The disclosure is further defined in the following Examples. It should be understood that the Examples are given by way of illustration only. From the above discussion and the Examples, one skilled in the art can ascertain the essential characteristics of the disclosure, and without departing from the spirit and scope thereof, can make various changes and modifications to adapt the disclosure to various uses and conditions. As a result, the disclosure is not limited by the illustrative examples set forth herein below, but rather is defined by the claims appended hereto.

Abbreviations used herein will be known to those of skill in the art. Examples are: THF for tetrahydrofuran; DCM for dichloromethane; DMF for N,N-dimethylformamide; DMSO for dimethylsulfoxide; TFA for trifluoracetic acid; AcOH for acetic acid; ACN or MeCN for acetonitrile; MeOH for methanol; $NH_4OAc$ for ammonium acetate; DIAD for diisopropyl azodicarboxylate; h for hours; min for minutes; DCE for 1,2-dichloroethane; EtOH for ethanol; rt or RT for retention time or room temperature (context will dictate); and DIPEA for diisopropylethylamine.

General Schemes 1, 2 and 3 represent some methods that may be employed for the preparation of the Examples. It is understanding that the cross-coupling partners, bromide and boronic acid (or boronic esters) are interchangable.

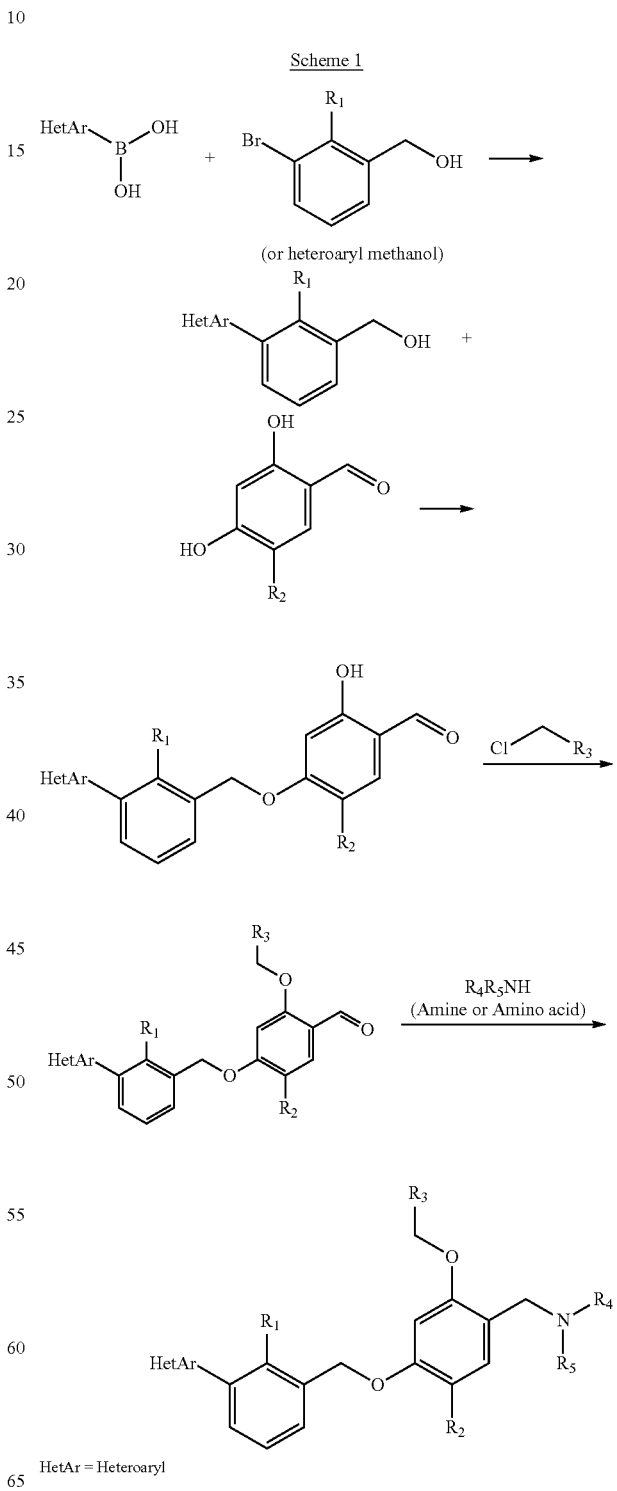

HetAr = Heteroaryl

Scheme 2

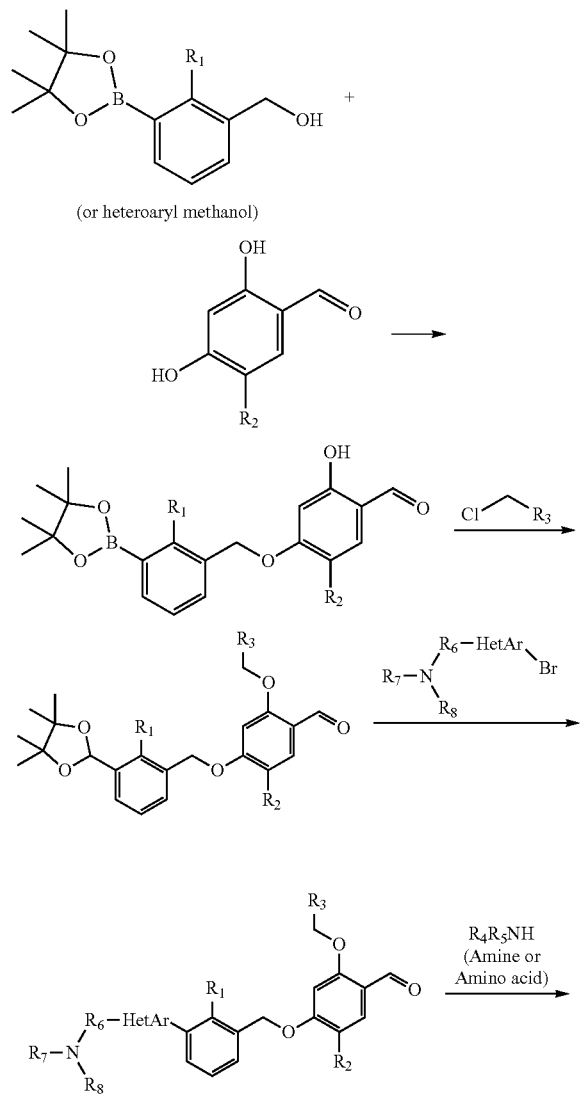

Scheme 3

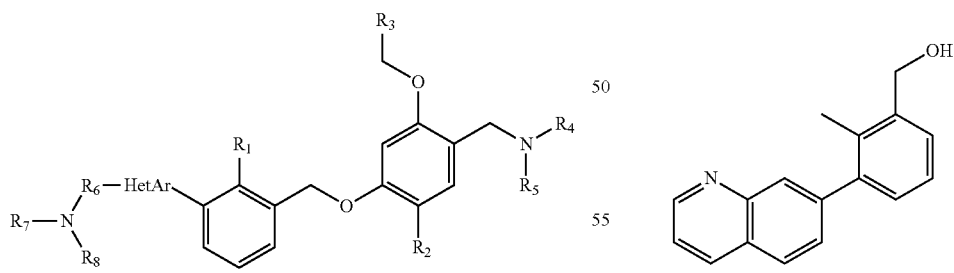

(X = leaving group)

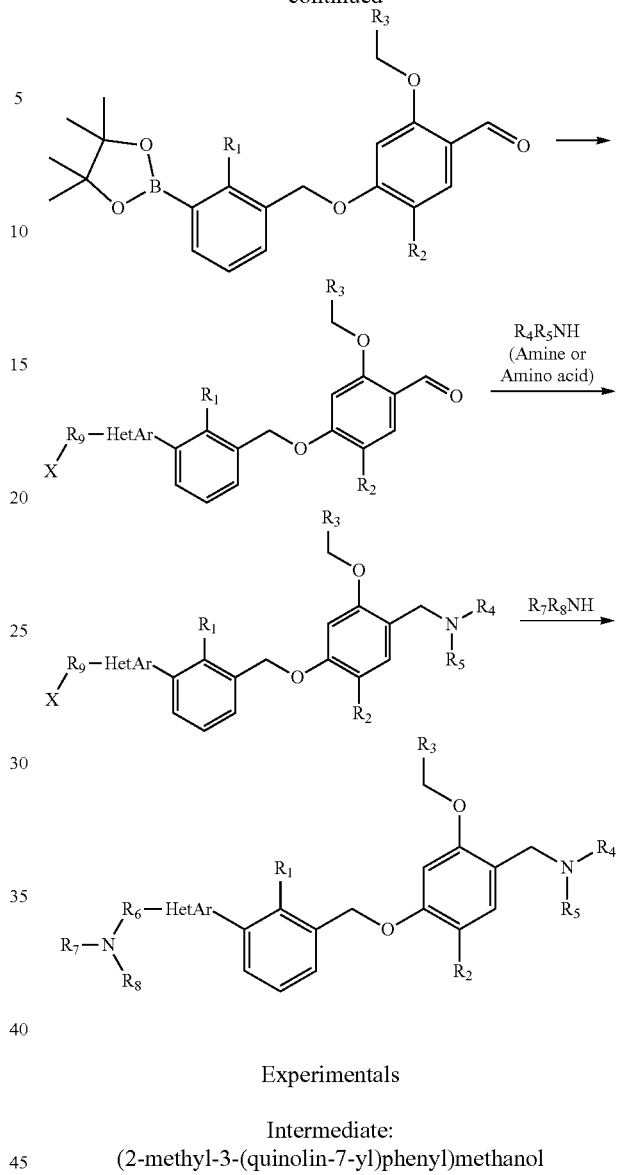

Experimentals

Intermediate: (2-methyl-3-(quinolin-7-yl)phenyl)methanol

To a sealed tube was added THF (75 mL), water (18 mL), quinoline-7-boronic acid (500 mg, 2.89 mmol), (3-bromo-2-methylphenyl)methanol (0.581 g, 2.89 mmol), potassium phosphate tribasic (1.53 g, 7.23 mmol), and 2nd generation XPhos precatalyst (0.068 g, 0.087 mmol). The mixture was de-gassed/flushed with nitrogen ×3 then stirred at room temperature for 2 days. The crude reaction mixture was diluted with DCM, washed with water, brine, dried over magnesium sulfate, filtered and evaporated. The crude product was purified on silica gel using 25-80% ethyl acetate/hexane to give 0.42 g of (2-methyl-3-(quinolin-7-yl)phenyl)methanol (57% yield) as a yellow solid. $^1$H NMR (400 MHz, DMSO-d$_6$) δ 8.94 (dd, J=4.2, 1.7 Hz, 1H), 8.42 (d, J=8.3 Hz, 1H), 8.04 (d, J=8.3 Hz, 1H), 7.88 (s, 1H), 7.62-7.51 (m, 2H), 7.47 (d, J=7.1 Hz, 1H), 7.33-7.26 (m, 1H), 7.25-7.19 (m, 1H), 5.15 (t, J=5.1 Hz, 1H), 4.59 (d, J=4.6 Hz, 2H), 2.17 (s, 3H).

Intermediate: 5-chloro-2-hydroxy-4-((2-methyl-3-(quinolin-7-yl)benzyl)oxy)benzaldehyde

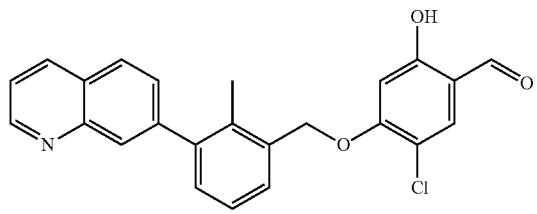 [SMILES: Cc1c(COc2cc(O)c(C=O)cc2Cl)cccc1-c1ccc2cccnc2c1]

Diisopropyl azodicarboxylate (184 mg, 0.911 mmol) in THF (12 mL) was added dropwise to a solution of (2-methyl-3-(quinolin-7-yl)phenyl)methanol (206.5 mg, 0.828 mmol), 5-chloro-2,4-dihydroxybenzaldehyde (157 mg, 0.911 mmol), and triphenylphosphine (239 mg, 0.911 mmol) in THF (12 mL) at 0° C. The resulting mixture was stirred and allowed to reach room temperature overnight. The reaction mixture was concentrated, then purified on silica gel using 10-80% ethylacetate/hexane to give 280 mgs (71% yield) of 5-chloro-2-hydroxy-4-((2-methyl-3-(quinolin-7-yl)benzyl)oxy)benzaldehyde as a yellow solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute. LCMS Rt (Retention time)=1.059 min., m/z 404.2 (M+H).

$^1$H NMR (500 MHz, DMSO-d$_6$) δ 10.06 (s, 1H), 8.96 (dd, J=4.3, 1.7 Hz, 1H), 8.88 (m, 2H), 8.45 (dd, J=8.4, 0.8 Hz, 1H), 8.08 (d, J=8.4 Hz, 1H), 7.95-7.89 (m, 1H), 7.73 (s, 1H), 7.63-7.56 (m, 2H), 7.43-7.34 (m, 1H), 6.90 (s, 1H), 5.38 (s, 2H), 2.29 (s, 3H).

Intermediate: 5-((4-chloro-2-formyl-5-((2-methyl-3-(quinolin-7-yl)benzyl)oxy)phenoxy)methyl)nicotinonitrile

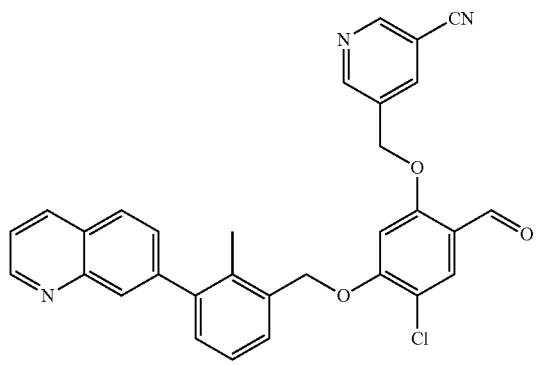 [SMILES: Cc1c(COc2cc(OCc3cncc(C#N)c3)c(C=O)cc2Cl)cccc1-c1ccc2cccnc2c1]

To a small round-bottomed flask (RBF) was added cesium carbonate (452 mg, 1.387 mmol), 5-(chloromethyl) nicotinonitrile (212 mg, 1.387 mmol), 5-chloro-2-hydroxy-4-((2-methyl-3-(quinolin-7-yl) benzyl)oxy)benzaldehyde (280 mg, 0.693 mmol), and DMF (10 mL). The mixture was stirred at room temperature overnight. The crude mixture was diluted with 10 mL DCM, neutralized with 4 drops of aq 0.1M HCl, extracted, washed with water, brine, dried over sodium sulfate, filtered and evaporated. The resulting solid was triturated with cold (0° C.) diethyl ether to give 179 mgs (37% yield) of 5-((4-chloro-2-formyl-5-((2-methyl-3-(quinolin-7-yl)benzyl)oxy)phenoxy)methyl)nicotinonitrile as a yellow solid. The LC/MS data was obtained on a Shimadzu analytical LC/Micromass Platform LC (ESI+) at 220 nm using the following set of conditions: Waters BEH 1.7 μm C18, 2×50 mm column, with a gradient of 0-100% B (B=95% HPLC grade acetonitrile/10 mM ammonium acetate/5% HPLC grade water), (A=95% HPLC grade water/10 mM ammonium acetate/5% HPLC grade acetonitrile), in 3 minutes with a 0.5 minute hold at a rate of 1 mL/minute. LCMS Rt=2.07 min., m/z 520.3 (M+H). $^1$H NMR (500 MHz, DMSO-d$_6$) δ 10.23 (s, 1H), 9.03 (d, J=2.6 Hz, 2H), 8.95 (d, J=2.9 Hz, 1H), 8.54 (s, 1H), 8.44 (d, J=8.1 Hz, 1H), 8.08 (d, J=8.1 Hz, 1H), 7.97-7.88 (m, 1H), 7.74 (s, 1H), 7.63-7.54 (m, 3H), 7.38 (d, J=4.0 Hz, 2H), 7.28 (s, 1H), 5.50 (s, 1H), 5.46 (s, 1H), 2.30 (s, 3H).

Example 1001: (R)-2-((5-chloro-2-((5-cyanopyridin-3-yl)methoxy)-4-((2-methyl-3-(quinolin-7-yl)benzyl)oxy)benzyl)amino)-3-hydroxy-2-methylpropanoic acid

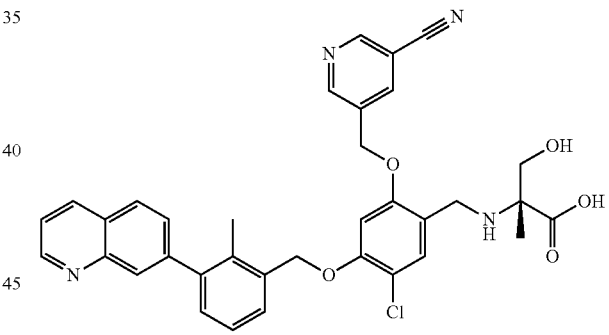

To a screw capped vial was added 5-((4-chloro-2-formyl-5-((2-methyl-3-(quinolin-7-yl)benzyl)oxy)phenoxy)methyl) nicotinonitrile (40 mg, 0.077 mmol), (R)-2-amino-3-hydroxy-2-methylpropanoic acid (27.5 mg, 0.231 mmol), sodium triacetoxyhydroborate (48.9 mg, 0.231 mmol) and DMF (3 mL). The vial was capped and the mixture was shaken at room temperature overnight. The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 20-85% B over 35 minutes with a 5-minute hold at 100% B at a flow rate of 20 mL/minute. Fractions containing the desired product were combined and dried via centrifugal evaporation. The yield of the product was 4.5 mg (10% yield), and its estimated purity by LCMS analysis was 99%.
$^1$H NMR (500 MHz, DMSO-d$_6$) δ 9.03 (s, 1H), 8.98 (s, 1H), 8.93 (d, J=4.0 Hz, 1H), 8.49 (s, 1H), 8.44 (d, J=8.4 Hz, 1H), 8.07 (d, J=8.4 Hz, 1H), 7.91 (s, 1H), 7.62-7.55 (m, 3H), 7.52 (m, 1H), 7.39-7.32 (m, 2H), 7.13 (s, 1H), 5.37 (s, 2H), 5.33 (s, 2H), 4.04 (m, 2H), 3.75-3.69 (m, 1H), 3.60-3.52 (m, 1H), 2.28 (s, 3H), 1.26 (s, 3H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.58 min; ESI-MS (+) m/z=623.4 (M+H), ESI-MS(−) m/z=621.3 (M−H).

Analysis condition 2: Retention time=2.66 min; ESI-MS (+) m/z=623.5 (M+H), ESI-MS(−) m/z=621.5 (M−H).

The following Examples were prepared in a similar manner as Example 1001:

Intermediate: (2-methyl-3-(quinolin-3-yl)phenyl)methanol

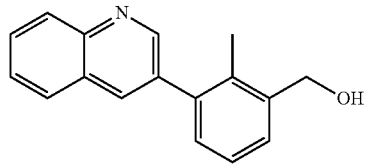 [SMILES: Cc1c(CO)cccc1-c1cnc2ccccc2c1]

The crude product was purified on silica gel using 25-80% ethylacetate/hexane to give 0.48 g of (2-methyl-3-(quinolin-3-yl)phenyl)methanol (99% yield) as a yellow solid.

$^1$H NMR (400 MHz, DMSO-$d_6$) δ 8.85 (d, J=2.2 Hz, 1H), 8.30 (d, J=2.0 Hz, 1H), 8.06 (dd, J=14.2, 8.3 Hz, 2H), 7.83-7.76 (m, 1H), 7.70-7.62 (m, 1H), 7.50 (d, J=7.6 Hz, 1H), 7.36-7.30 (m, 1H), 7.29-7.21 (m, 1H), 5.17 (t, J=5.4 Hz, 1H), 4.60 (d, J=5.4 Hz, 2H), 2.18 (s, 3H).

Intermediate: 5-chloro-2-hydroxy-4-((2-methyl-3-(quinolin-3-yl)benzyl)oxy)benzaldehyde

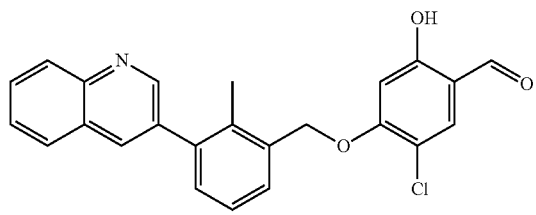 [SMILES: Cc1c(COc2cc(O)c(C=O)cc2Cl)cccc1-c1cnc2ccccc2c1]

The crude product was purified on silica gel using 10-80% ethylacetate/hexane to give 0.21 g of 5-chloro-2-hydroxy-4-((2-methyl-3-(quinolin-3-yl)benzyl)oxy)benzaldehyde (74% yield) as a yellow solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/ 0.05% trifluoroacetic acid), (A=100% HPLC grade water/ 0.05% trifluoroacetic acid), in 1.5 minutes with a 0.5 minute hold at a rate of 0.8 mL/minute. LCMS Rt (Retention time)=1.125 min., m/z 403.9 (M+H). $^1$H NMR (400 MHz, CDCl$_3$) δ 11.44 (s, 1H), 9.72 (s, 1H), 8.93 (d, J=2.2 Hz, 1H), 8.18 (d, J=8.6 Hz, 1H), 8.12 (d, J=2.0 Hz, 1H), 7.88 (d, J=8.3 Hz, 1H), 7.77 (m, 1H), 7.65-7.55 (m, 3H), 7.40-7.36 (m, 1H), 6.66 (s, 1H), 5.26 (s, 2H), 2.33 (s, 3H).

Intermediate: 5-((4-chloro-2-formyl-5-((2-methyl-3-(quinolin-3-yl)benzyl)oxy)phenoxy)methyl)nicotinonitrile

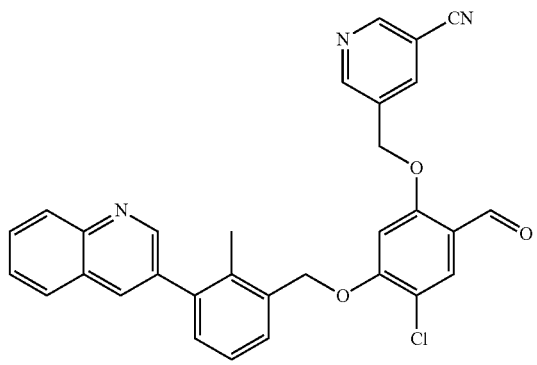

115 mgs of 5-((4-chloro-2-formyl-5-((2-methyl-3-(quinolin-3-yl)benzyl)oxy)phenoxy)methyl) nicotinonitrile was obtained (38% yield) as a yellow solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/ 0.05% trifluoroacetic acid), (A=100% HPLC grade water/ 0.05% trifluoroacetic acid), in 1.5 minutes with a 0.5 minute hold at a rate of 0.8 mL/minute. LCMS Rt=1.140 min., m/z 520.1 (M+H).

Example 1002: (R)-2-((5-chloro-2-((5-cyanopyridin-3-yl)methoxy)-4-((2-methyl-3-(quinolin-3-yl)benzyl) oxy)benzyl)amino)-3-hydroxy-2-methylpropanoic acid

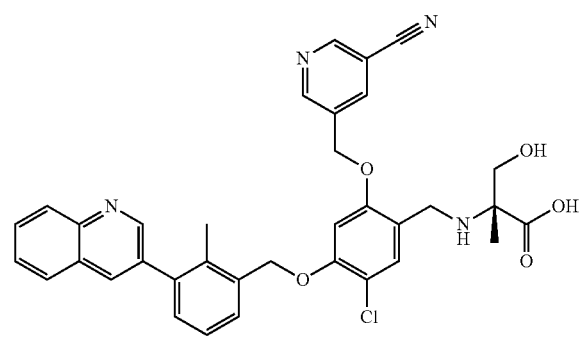 [SMILES: Cc1c(COc2cc(OCc3cncc(C#N)c3)c(CN[C@](C)(CO)C(=O)O)cc2Cl)cccc1-c1cnc2ccccc2c1]

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 40-80% B over 15 minutes with a 5-minute hold at 100% B at a flow rate of 20 mL/minute. Fractions containing the desired product were combined and dried via centrifugal evaporation. The yield of the product was 7.8 mg (16% yield), and its estimated purity by LCMS analysis was 99%. $^1$H NMR (500 MHz, DMSO-$d_6$) δ 9.02 (s, 1H), 8.98 (s, 1H), 8.86 (s, 1H), 8.48 (s, 1H), 8.34 (s, 1H), 8.12-8.03 (m, 2H), 7.82 (t, J=7.7 Hz, 1H), 7.67 (t, J=7.7 Hz, 1H), 7.60-7.52 (m, 2H), 7.42-7.33 (m, 2H), 7.12 (s, 1H), 5.35 (m, 4H), 4.03 (s, 2H), 3.71-3.69 (m, 1H), 3.59-3.53 (m, 1H), 2.29 (s, 3H), 1.25 (s, 3H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.60 min; ESI-MS (+) m/z=623.4 (M+H), ESI-MS(−) m/z=621.4 (M−H).

Analysis condition 2: Retention time=2.71 min; ESI-MS (+) m/z=623.4 (M+H), ESI-MS(−) m/z=621.3 (M−H).

Example 1003: (S)-1-(5-chloro-2-((5-cyanopyridin-3-yl)methoxy)-4-((2-methyl-3-(quinolin-3-yl)benzyl)oxy)benzyl) piperidine-2-carboxylic acid

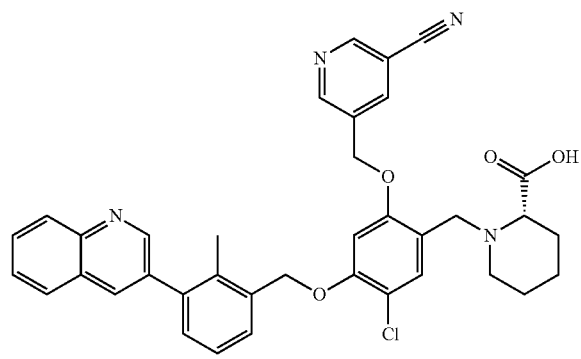 [SMILES: Cc1c(COc2cc(OCc3cncc(C#N)c3)c(CN3CCCC[C@H]3C(=O)O)cc2Cl)cccc1-c1cnc2ccccc2c1]

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 25-85% B over 30 minutes with a 5-minute hold at 100% B at a flow rate of 20 mL/minute. Fractions containing the desired product were combined and dried via centrifugal evaporation. The yield of the product was 4.8 mg (10% yield), and its estimated purity by LCMS analysis was 99%. $^1$H NMR (500 MHz, DMSO-$d_6$) δ 8.99 (d, J=5.1 Hz, 2H), 8.86 (s, 1H), 8.46 (s, 1H), 8.35 (s, 1H), 8.12-8.03 (m, 2H), 7.82 (t, J=7.7 Hz, 1H), 7.67 (t, J=7.3 Hz, 1H), 7.61-7.55 (m, 1H), 7.53 (s, 1H), 7.43-7.35 (m, 2H), 7.14 (s, 1H), 5.36 (s, 2H), 5.32 (s, 2H), 4.04 (d, J=12.8 Hz, 1H), 3.88 (t, J=6.4 Hz, 1H), 3.26-3.17 (m, 1H), 2.99 (m, 1H), 2.25 (m, 1H), 2.29 (s, 3H), 1.96-1.87 (m, 1H), 1.68 (d, J=9.9 Hz, 1H), 1.54 (m, 3H), 1.36 (m, 1H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.69 min; ESI-MS (+) m/z=633.5 (M+H), ESI-MS(−) m/z=631.4 (M−H).

Analysis condition 2: Retention time=2.75 min; ESI-MS (+) m/z=633.5 (M+H), ESI-MS(−) m/z=631.4 (M−H).

Intermediate:
(2-methyl-3-(quinolin-2-yl)phenyl)methanol

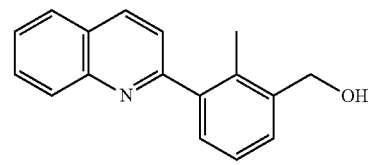 [SMILES: Cc1c(CO)cccc1-c1ccc2ccccc2n1]

The crude product was purified on silica gel using 25-80% ethylacetate/hexane to give 0.77 g of (2-methyl-3-(quinolin-2-yl)phenyl)methanol (85% yield) as a yellow solid.

$^1$H NMR (400 MHz, CDCl$_3$) δ 8.23 (d, J=8.3 Hz, 1H), 8.18 (d, J=8.6 Hz, 1H), 7.89 (d, J=8.1 Hz, 1H), 7.76 (m, 1H), 7.71-7.64 (m, 1H), 7.62-7.54 (m, 1H), 7.48 (m, 1H), 7.46-7.41 (m, 1H), 7.39-7.31 (m, 1H), 4.80 (d, J=5.6 Hz, 2H), 2.34 (s, 3H).

5-chloro-2-hydroxy-4-((2-methyl-3-(quinolin-2-yl)benzyl)ox benzaldehyde

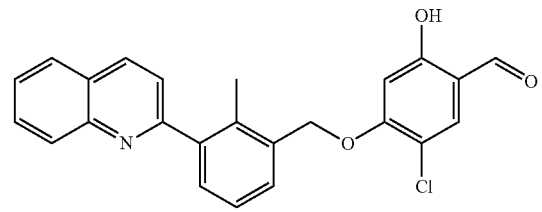 [SMILES: Cc1c(COc2cc(O)c(C=O)cc2Cl)cccc1-c1ccc2ccccc2n1]

The crude product was purified on silica gel using 10-70% ethylacetate/hexane to give 0.14 g of 5-chloro-2-hydroxy-4-((2-methyl-3-(quinolin-2-yl)benzyl)oxy)benzaldehyde (25% yield) as a yellow solid. $^1$H NMR (500 MHz, DMSO-$d_6$) δ 10.05 (s, 1H), 8.48 (d, J=8.4 Hz, 1H), 8.09-8.02 (m, 2H), 7.82 (m, 1H), 7.73 (s, 1H), 7.68-7.64 (m, 2H), 7.62-7.61 (m, 1H), 7.49 (dd, J=7.6, 1.1 Hz, 1H), 7.45-7.38 (m, 1H), 6.90 (s, 1H), 5.39 (s, 2H), 2.33 (s, 3H).

Intermediate: 5-((4-chloro-2-formyl-5-((2-methyl-3-(quinolin-2-yl)benzyl)oxy)phenoxy)methyl)nicotinonitrile

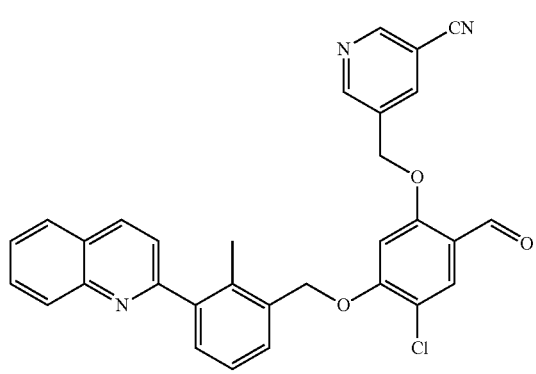 [SMILES: Cc1c(COc2cc(OCc3cncc(C#N)c3)c(C=O)cc2Cl)cccc1-c1ccc2ccccc2n1]

82 mgs of 5-((4-chloro-2-formyl-5-((2-methyl-3-(quinolin-3-yl)benzyl)oxy)phenoxy) methyl) nicotinonitrile was obtained (46% yield) as a beige solid. The LC/MS data was obtained on a Shimadzu analytical LC/Micromass Platform LC (ESI+) at 220 nm using the following set of conditions: Waters Aquity BEH 1.7 µm C18, 2.1×50 mm column, with a gradient of 2-98% B (B=100% HPLC grade acetonitrile/ 0.05% trifluoroacetic acid), (A=100% HPLC grade water/ 0.05% trifluoroacetic acid), in 1.5 minutes with a 0.5 minute hold at a rate of 0.8 mL/minute. LCMS Rt=1.134 min., m/z 520.0 (M+H). $^1$H NMR (500 MHz, DMSO-$d_6$) δ 10.25 (s, 1H), 9.05 (d, J=1.7 Hz, 2H), 8.57 (m, 1H), 8.48 (d, J=8.4 Hz, 1H), 8.10-8.02 (m, 2H), 7.82 (m, 1H), 7.78-7.73 (m, 1H), 7.71-7.62 (m, 3H), 7.51 (dd, J=7.6, 1.1 Hz, 1H), 7.44-7.37 (m, 1H), 7.32 (s, 1H), 5.55-5.46 (m, 4H), 2.40-2.33 (m, 3H).

Example 1004: (R)-2-((5-chloro-2-((5-cyanopyridin-3-yl)methoxy)-4-((2-methyl-3-(quinolin-2-yl)benzyl)oxy)benzyl)amino)-3-hydroxy-2-methylpropanoic acid

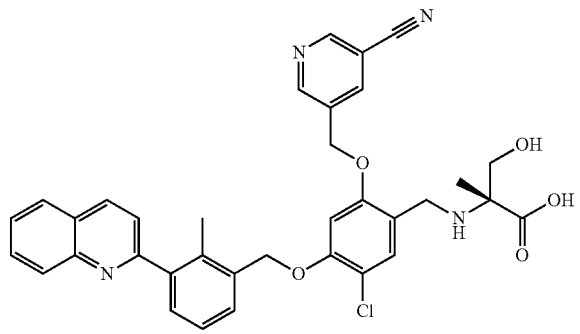

The crude material was purified via preparative LC/MS using the following conditions: Waters XBridge 5 µm C18, 19×200 mm where mobile phase A was 5:95 acetonitrile: water with 10 mM ammonium acetate and mobile phase B was 95:5 acetonitrile: water with 10 mM ammonium acetate at a gradient of 30-80% B over 15 minutes with a 5-minute hold at 100% B at a flow rate of 20 mL/minute. Fractions containing the desired product were combined and dried via centrifugal evaporation. The yield of the product was 16.1 mg (60% yield), and its estimated purity by LCMS analysis was 98%. $^1$H NMR (500 MHz, DMSO-$d_6$) δ 9.03 (d, J=14.3 Hz, 2H), 8.52 (s, 1H), 8.47 (d, J=8.4 Hz, 1H), 8.05 (t, J=7.3 Hz, 2H), 7.81 (t, J=7.5 Hz, 1H), 7.70-7.63 (m, 2H), 7.61-7.55 (m, 2H), 7.48 (d, J=7.3 Hz, 1H), 7.40-7.33 (m, 1H), 7.16 (s, 1H), 5.37 (m, 4H), 3.96 (s, 2H), 3.62 (m, 1H), 3.53 (m, 1H), 2.34 (s, 3H), 1.24 (s, 3H).

Two analytical LC/MS injections were used to determine the final purity.

Injection 1 conditions: Waters Acquity UPLC BEH 1.7 µm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 µm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.60 min; ESI-MS (+) m/z=623.5 (M+H), ESI-MS(−) m/z=621.4 (M−H).

Analysis condition 2: Retention time=2.82 min; ESI-MS (+) m/z=623.4 (M+H), ESI-MS(−) m/z=621.4 (M−H).

Intermediate: (2-methyl-3-(quinolin-6-yl)phenyl)methanol

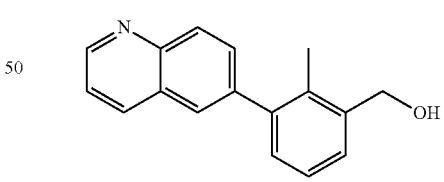

The crude product was purified on silica gel using 10-70% ethylacetate/hexane to give 0.28 g of (2-methyl-3-(quinolin-6-yl)phenyl)methanol (39% yield) as a yellow solid.

$^1$H NMR (400 MHz, CDCl$_3$) δ 8.96 (dd, J=4.3, 1.6 Hz, 1H), 8.23-8.12 (m, 2H), 7.74 (d, J=2.0 Hz, 1H), 7.69 (dd, J=8.8, 2.0 Hz, 1H), 7.46 (dt, J=8.1, 3.9 Hz, 2H), 7.36-7.29 (m, 2H), 4.82 (d, J=5.6 Hz, 2H), 2.29 (s, 3H).

Intermediate: 5-chloro-2-hydroxy-4-((2-methyl-3-(quinolin-6-yl)benzyl)oxy)benzaldehyde

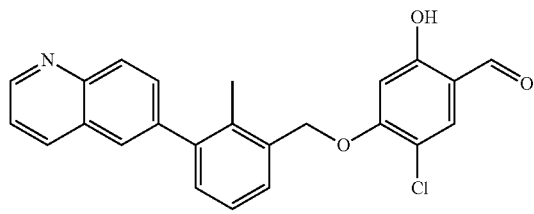 [SMILES: Cc1c(COc2cc(O)c(C=O)cc2Cl)cccc1-c1ccc2ncccc2c1]

The crude product was purified on silica gel using 10-70% ethylacetate/hexane to give 0.160 g of 5-chloro-2-hydroxy-4-((2-methyl-3-(quinolin-6-yl)benzyl)oxy)benzaldehyde (45% yield) as a yellow solid. $^1$H NMR (500 MHz, DMSO-$d_6$) δ 10.05 (s, 1H), 8.95 (dd, J=4.3, 1.7 Hz, 1H), 8.44 (dd, J=8.6, 1.0 Hz, 1H), 8.10 (d, J=8.7 Hz, 1H), 7.95 (d, J=2.0 Hz, 1H), 7.77-7.68 (m, 2H), 7.62-7.55 (m, 2H), 7.42-7.36 (m, 2H), 6.90 (s, 1H), 5.37 (s, 2H), 2.27 (s, 3H).

Intermediate: 5-((4-chloro-2-formyl-5-((2-methyl-3-(quinolin-6-yl)benzyl)oxy)phenoxy)methyl)nicotinonitrile

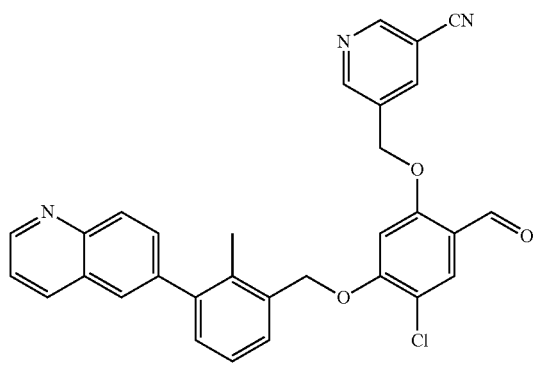 [SMILES: Cc1c(COc2cc(OCc3cncc(C#N)c3)c(C=O)cc2Cl)cccc1-c1ccc2ncccc2c1]

165 mgs of 5-((4-chloro-2-formyl-5-((2-methyl-3-(quinolin-6-yl)benzyl)oxy)phenoxy)methyl) nicotinonitrile was obtained (65% yield) as an orange solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute. LCMS Rt=1.090 min., m/z 520.0 (M+H). $^1$H NMR (500 MHz, DMSO-$d_6$) δ 10.25 (s, 1H), 9.05 (m, 2H), 8.95 (dd, J=4.2, 1.7 Hz, 1H), 8.57 (t, J=2.0 Hz, 1H), 8.48-8.41 (m, 1H), 8.11 (d, J=8.7 Hz, 1H), 7.96 (d, J=1.9 Hz, 1H), 7.79-7.72 (m, 2H), 7.63-7.56 (m, 2H), 7.42-7.36 (m, 2H), 7.32 (s, 1H), 5.52 (s, 2H), 5.47 (s, 2H), 2.30 (s, 3H).

Example 1005: (R)-2-((5-chloro-2-((5-cyanopyridin-3-yl)methoxy)-4-((2-methyl-3-(quinolin-6-yl)benzyl)oxy)benzyl) amino)-3-hydroxy-2-methylpropanoic acid

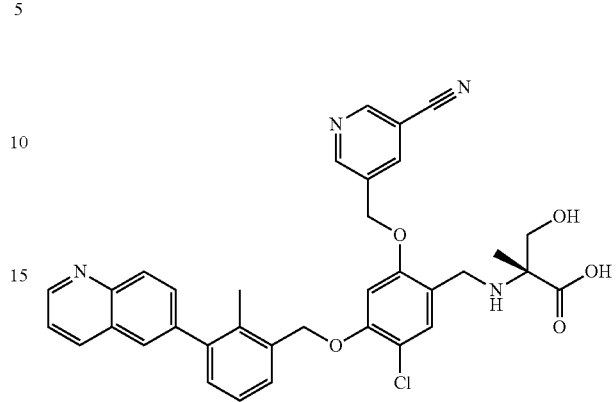

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 25-65% B over 15 minutes with a 5-minute hold at 100% B at a flow rate of 20 mL/minute. Fractions containing the desired product were combined and dried via centrifugal evaporation. The yield of the product was 16.0 mg (33% yield), and its estimated purity by LCMS analysis was 99%. $^1$H NMR (500 MHz, DMSO-$d_6$) δ 9.03 (d, J=15.4 Hz, 2H), 8.94 (d, J=4.0 Hz, 1H), 8.51 (s, 1H), 8.43 (d, J=8.4 Hz, 1H), 8.10 (d, J=8.4 Hz, 1H), 7.98-7.90 (m, 1H), 7.74 (d, J=8.4 Hz, 1H), 7.63-7.51 (m, 3H), 7.40-7.29 (m, 2H), 7.15 (s, 1H), 5.36 (m, 4H), 3.97 (s, 2H), 3.66-3.50 (m, 2H), 2.29 (s, 3H), 1.24 (s, 3H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.54 min; ESI-MS (+) m/z=623.4 (M+H), ESI-MS(−) m/z=621.4 (M−H).

Analysis condition 2: Retention time=2.82 min; ESI-MS (+) m/z=623.4 (M+H), ESI-MS(−) m/z=621.4 (M−H).

Intermediate: (2-methyl-3-(quinoxalin-2-yl)phenyl)methanol

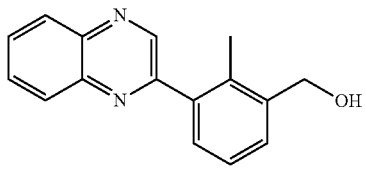 [SMILES: Cc1c(CO)cccc1-c1cnc2ccccc2n1]

The crude product was purified on silica gel using 20-80% ethylacetate/hexane to give 0.69 g of (2-methyl-3-(quinoxalin-2-yl)phenyl)methanol (79% yield) as a yellow solid. $^1$H NMR (500 MHz, DMSO-d$_6$) δ 9.08 (s, 1H), 8.21-8.10 (m, 2H), 7.95-7.85 (m, 2H), 7.61-7.57 (m, 1H), 7.47 (dd, J=7.6, 1.1 Hz, 1H), 7.42-7.35 (m, 1H), 5.24 (t, J=5.4 Hz, 1H), 4.63 (d, J=5.4 Hz, 2H), 2.28 (s, 3H).

Intermediate: 5-chloro-2-hydroxy-4-((2-methyl-3-(quinoxalin-2-yl)benzyl)oxy)benzaldehyde

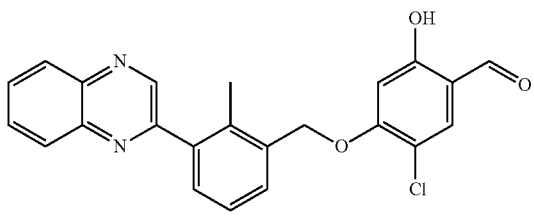

The crude product was purified on silica gel using 10-70% ethylacetate/hexane to give 0.360 g of 5-chloro-2-hydroxy-4-((2-methyl-3-(quinoxalin-2-yl)benzyl)oxy)benzaldehyde (17% yield) as a yellow solid. $^1$H NMR (500 MHz, DMSO-d$_6$) δ 10.05 (s, 1H), 9.12 (s, 1H), 8.15 (m, 2H), 7.92 (m, 2H), 7.71 (m, 2H), 7.47 (m, 2H), 6.87 (s, 1H), 5.40 (s, 2H), 2.38 (s, 3H).

Intermediate: 5-((4-chloro-2-formyl-5-((2-methyl-3-(quinoxalin-2-yl)benzyl)oxy)phenoxy)methyl)nicotinonitrile

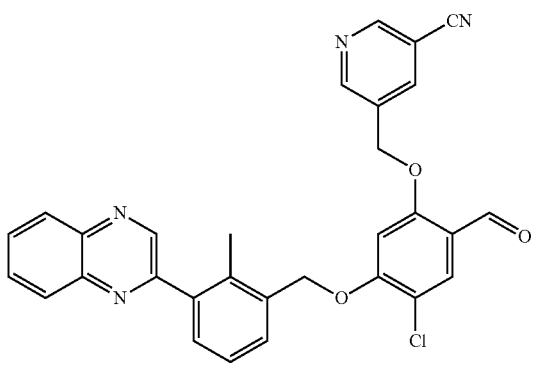 [SMILES: Cc1c(COc2cc(OCc3cncc(C#N)c3)c(C=O)cc2Cl)cccc1-c1cnc2ccccc2n1]

341 mgs of 5-((4-chloro-2-formyl-5-((2-methyl-3-(quinoxalin-2-yl)benzyl)oxy)phenoxy)methyl) nicotinonitrile was obtained (99% yield) as a yellow solid. The LC/MS data was obtained on a Shimadzu analytical LC/Micromass Platform LC (ESI+) at 220 nm using the following set of conditions: Waters Aquity BEH 1.7 µm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute. LCMS Rt=1.384 min., m/z 521.0 (M+H). $^1$H NMR (500 MHz, DMSO-d$_6$) δ 10.25 (s, 1H), 9.14 (s, 1H), 9.05 (dd, J=9.7, 2.0 Hz, 2H), 8.62-8.55 (m, 1H), 8.22-8.13 (m, 2H), 7.96-7.90 (m, 2H), 7.75 (s, 1H), 7.71 (d, J=7.3 Hz, 1H), 7.58-7.57 (m, 1H), 7.46 (t, J=7.6 Hz, 1H), 7.37 (s, 1H), 5.55 (m, 4H), 2.41 (s, 3H).

Example 1006: (R)-2-((5-chloro-2-((5-cyanopyridin-3-yl)methoxy)-4-((2-methyl-3-(quinoxalin-2-yl)benzyl)oxy) benzyl)amino)-3-hydroxy-2-methylpropanoic acid

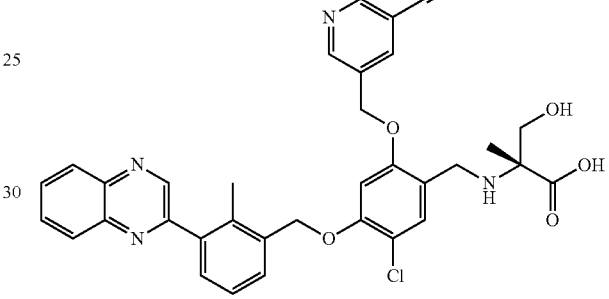

The crude material was purified via preparative LC/MS using the following conditions: Waters XBridge 5 µm C18, 19×200 mm where mobile phase A was 5:95 acetonitrile: water with 10 mM ammonium acetate and mobile phase B was 95:5 acetonitrile: water with 10 mM ammonium acetate at a gradient of 25-65% B over 15 minutes with a 5-minute hold at 100% B at a flow rate of 20 mL/minute. Fractions containing the desired product were combined and dried via centrifugal evaporation. The yield of the product was 4.3 mg (9.4% yield), and its estimated purity by LCMS analysis was 95%. $^1$H NMR (500 MHz, DMSO-d$_6$) δ 9.11 (s, 1H), 9.02 (d, J=15.8 Hz, 2H), 8.51 (s, 1H), 8.22-8.11 (m, 2H), 7.99-7.87 (m, 2H), 7.65 (d, J=7.7 Hz, 1H), 7.59 (d, J=7.3 Hz, 1H), 7.56 (s, 1H), 7.42 (t, J=7.7 Hz, 1H), 7.14 (s, 1H), 5.37 (m, 4H), 3.94 (s, 2H), 3.65-3.49 (m, 2H), 2.39 (s, 3H), 1.22 (s, 3H).

Two analytical LC/MS injections were used to determine the final purity.

Injection 1 conditions: Waters Acquity UPLC BEH 1.7 µm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 µm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.50 min; ESI-MS (+) m/z=624.5 (M+H), ESI-MS(−) m/z=622.4 (M−H).
Analysis condition 2: Retention time=2.77 min; ESI-MS (+) m/z=624.4 (M+H), ESI-MS(−) m/z=622.4 (M−H).

Intermediate: (3-(isoquinolin-3-yl)-2-methylphenyl)methanol

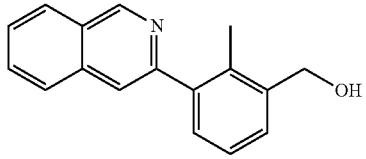 [SMILES: Cc1c(CO)cccc1-c1cc2ccccc2cn1]

The crude product was purified on silica gel using 25-80% ethylacetate/hexane to give 0.69 g of (3-(isoquinolin-3-yl)-2-methylphenyl)methanol (99% yield) as a yellow solid.
$^1$H NMR (400 MHz, DMSO-$d_6$) δ 9.40 (s, 1H), 8.17 (d, J=7.8 Hz, 1H), 8.02 (d, J=7.8 Hz, 1H), 7.89 (s, 1H), 7.82 (m, 1H), 7.75-7.68 (m, 1H), 7.52-7.44 (m, 1H), 7.37-7.25 (m, 2H), 5.18 (t, J=5.4 Hz, 1H), 4.60 (d, J=5.4 Hz, 2H), 2.22 (s, 3H).

Intermediate: 5-chloro-2-hydroxy-4-((3-(isoquinolin-3-yl)-2-methylbenzyl)oxy)benzaldehyde

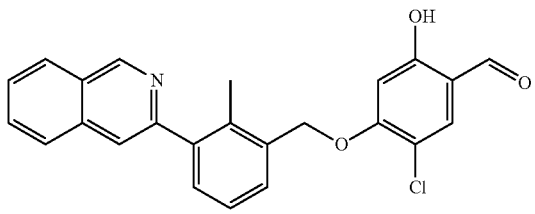 [SMILES: Cc1c(COc2cc(O)c(C=O)cc2Cl)cccc1-c1cc2ccccc2cn1]

The crude product was purified on silica gel using 10-70% ethylacetate/hexane to give 0.407 g of 5-chloro-2-hydroxy-4-((3-(isoquinolin-3-yl)-2-methylbenzyl)oxy)benzaldehyde (33% yield) as a yellow solid. $^1$H NMR (400 MHz, DMSO-$d_6$) δ 10.05 (s, 1H), 9.41 (s, 1H), 8.50 (br. s., 1H), 8.18 (d, J=8.3 Hz, 1H), 8.04 (d, J=8.5 Hz, 1H), 7.93 (s, 1H), 7.83 (t, J=7.4 Hz, 1H), 7.76-7.69 (m, 1H), 7.57 (d, J=6.8 Hz, 1H), 7.48 (d, J=6.8 Hz, 1H), 7.41-7.35 (m, 1H), 6.89 (s, 1H), 5.37 (s, 2H), 2.31 (s, 3H).

Intermediate: 5-((4-chloro-2-formyl-5-((3-(isoquinolin-3-yl)-2-methylbenzyl)oxy)phenoxy)methyl)nicotinonitrile

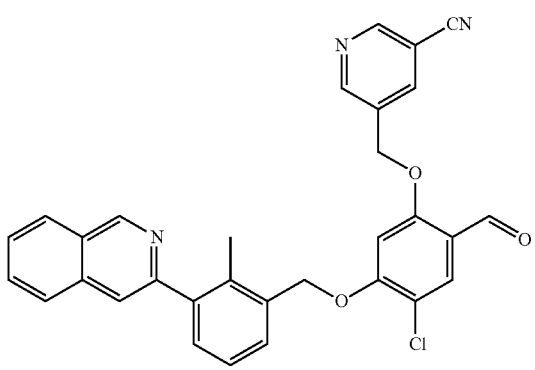 [SMILES: Cc1c(COc2cc(OCc3cncc(C#N)c3)c(C=O)cc2Cl)cccc1-c1cc2ccccc2cn1]

86 mgs of 5-((4-chloro-2-formyl-5-((3-(isoquinolin-3-yl)-2-methylbenzyl)oxy)phenoxy) methyl)nicotinonitrile was obtained (25% yield) as a tan solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/ 0.05% trifluoroacetic acid), (A=100% HPLC grade water/ 0.05% trifluoroacetic acid), in 1.5 minutes with a 0.5 minute hold at a rate of 0.8 mL/minute. LCMS Rt=1.109 min., m/z 520.1 (M+H).

Example 1007: (R)-2-((5-chloro-2-((5-cyanopyridin-3-yl)methoxy)-4-((3-(isoquinolin-3-yl)-2-methylbenzyl)oxy) benzyl)amino)-3-hydroxy-2-methylpropanoic acid

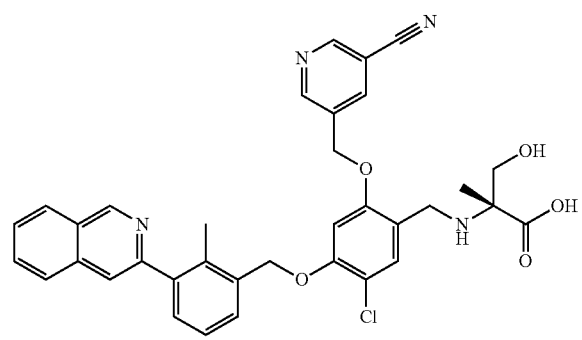 [SMILES: Cc1c(COc2cc(OCc3cncc(C#N)c3)c(CN[C@](C)(CO)C(=O)O)cc2Cl)cccc1-c1cc2ccccc2cn1]

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 20-100% B over 20 minutes with a 5-minute hold at 100% B at a flow rate of 20 mL/minute. Fractions containing the desired product were combined and dried via centrifugal evaporation. The yield of the product was 7.2 mg (17% yield), and its estimated purity by LCMS analysis was 100%. $^1$H NMR (500 MHz, DMSO-$d_6$) δ 9.41 (s, 1H), 9.05 (s, 1H), 9.02 (s, 1H), 8.52 (s, 1H), 8.19 (d, J=8.1 Hz, 1H), 8.04 (d, J=8.1 Hz, 1H), 7.93 (s, 1H), 7.83 (t, J=7.5 Hz, 1H), 7.73 (t, J=7.5 Hz, 1H), 7.60-7.54 (m, 2H), 7.47 (d, J=7.7 Hz, 1H), 7.35 (t, J=7.5 Hz, 1H), 7.16 (s, 1H), 5.36 (m, 4H), 3.98 (s, 2H), 3.66-3.60 (m, 1H), 3.55 (m, 1H), 2.34 (s, 3H), 1.24 (s, 3H).

Two analytical LC/MS injections were used to determine the final purity.
Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.59 min; ESI-MS (+) m/z=623.5 (M+H), ESI-MS(−) m/z=621.4 (M−H).
Analysis condition 2: Retention time=2.84 min; ESI-MS (+) m/z=623.5 (M+H), ESI-MS(−) m/z=621.5 (M−H).

Intermediate: (3-(isoquinolin-7-yl)-2-methylphenyl)methanol

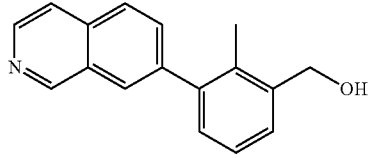 [SMILES: Cc1c(CO)cccc1-c1ccc2ccncc2c1]

The crude product was purified on silica gel using 25-80% ethylacetate/hexane to give 0.51 g of (3-(isoquinolin-7-yl)-2-methylphenyl)methanol (72% yield) as a yellow solid. $^1$H NMR (400 MHz, DMSO-d$_6$) δ 9.36 (s, 1H), 8.54 (d, J=5.9 Hz, 1H), 8.04 (m, 2H), 7.89 (d, J=5.9 Hz, 1H), 7.75 (dd, J=8.6, 1.7 Hz, 1H), 7.48 (d, J=7.3 Hz, 1H), 7.31 (t, J=7.5 Hz, 1H), 7.27-7.15 (m, 1H), 4.59 (m, 2H), 2.16 (s, 3H).

Intermediate: 5-chloro-2-hydroxy-4-((3-(isoquinolin-7-yl)-2-methylbenzyl)oxy)benzaldehyde

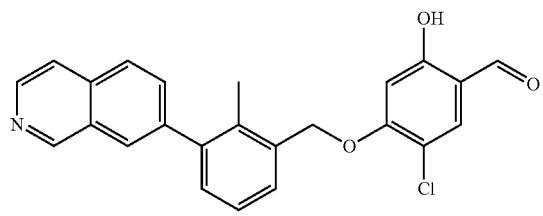 [SMILES: Cc1c(COc2cc(O)c(C=O)cc2Cl)cccc1-c1ccc2ccncc2c1]

The crude product was purified on silica gel using 10-80% ethylacetate/hexane to give 0.299 g of 5-chloro-2-hydroxy-4-((3-(isoquinolin-7-yl)-2-methylbenzyl)oxy)benzaldehyde (41% yield) as a yellow solid.
$^1$H NMR (400 MHz, DMSO-d$_6$) δ 10.04 (s, 1H), 9.38 (s, 1H), 8.54 (d, J=5.8 Hz, 1H), 8.11-8.03 (m, 2H), 7.90 (d, J=5.5 Hz, 1H), 7.76 (d, J=7.5 Hz, 1H), 7.71 (m, 1H), 7.57 (d, J=7.0 Hz, 1H), 7.42-7.32 (m, 2H), 6.87 (s, 1H), 5.36 (s, 2H), 2.26 (s, 3H).

Intermediate: 5-((4-chloro-2-formyl-5-((3-(isoquinolin-7-yl)-2-methylbenzyl)oxy)phenoxy)methyl)nicotinonitrile

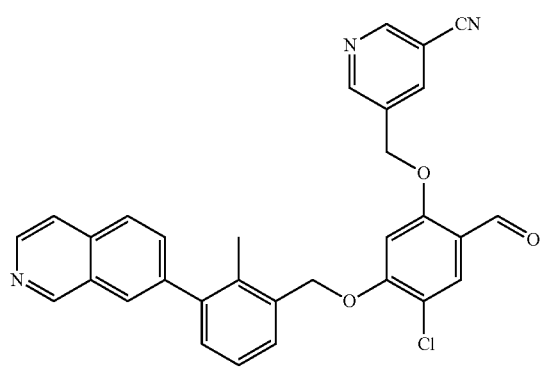 [SMILES: Cc1c(COc2cc(OCc3cncc(C#N)c3)c(C=O)cc2Cl)cccc1-c1ccc2ccncc2c1]

319 mgs of 5-((4-chloro-2-formyl-5-((3-(isoquinolin-7-yl)-2-methylbenzyl)oxy)phenoxy)methyl)nicotinonitrile was obtained (83% yield) as a tan solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute. LCMS Rt=1.065 min., m/z 520.2 (M+H).

Example 1008: (R)-2-((5-chloro-2-((5-cyanopyridin-3-yl)methoxy)-4-((3-(isoquinolin-7-yl)-2-methylbenzyl)oxy) benzyl)amino)-3-hydroxy-2-methylpropanoic acid

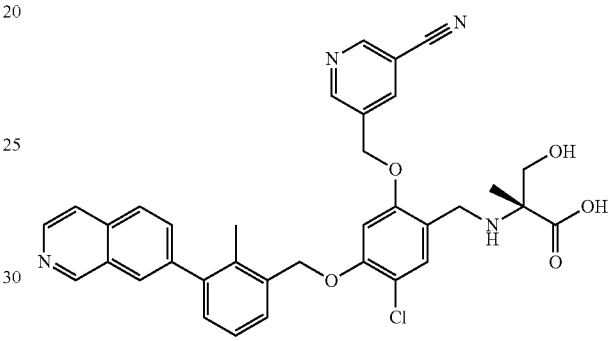

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile: water with 10 mM ammonium acetate at a gradient of 20-70% B over 20 minutes with a 5-minute hold at 100% B at a flow rate of 20 mL/minute. Fractions containing the desired product were combined and dried via centrifugal evaporation. The yield of the product was 2 mg (10% yield), and its estimated purity by LCMS analysis was 99%. $^1$H NMR (500 MHz, DMSO-d$_6$) δ 9.38 (s, 1H), 9.02 (m, 2H), 8.59-8.47 (m, 2H), 8.12-8.01 (m, 2H), 7.90 (d, J=5.5 Hz, 1H), 7.76 (d, J=7.7 Hz, 1H), 7.62-7.48 (m, 2H), 7.35 (m, 2H), 7.15 (s, 1H), 5.37 (s, 2H), 5.34 (s, 2H), 3.98 (br. s., 2H), 3.63 (m, 2H), 2.28 (s, 3H), 1.24 (s, 3H).
Two analytical LC/MS injections were used to determine the final purity.
Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Analysis condition 1: Retention time=1.53 min; ESI-MS (+) m/z=623.5 (M+H), ESI-MS(−) m/z=621.5 (M−H).

Analysis condition 2: Retention time=2.68 min; ESI-MS (+) m/z=623.5 (M+H), ESI-MS(-) m/z=621.5 (M-H).

Intermediate: (3-(isoquinolin-6-yl)-2-methylphenyl)methanol

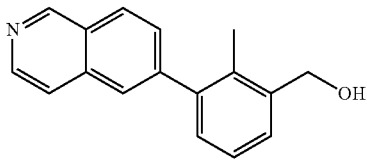 [SMILES: Cc1c(CO)cccc1-c1ccc2cnccc2c1]

The crude product was purified on silica gel using 10-80% ethylacetate/hexane to give 0.333 g of (3-(isoquinolin-6-yl)-2-methylphenyl)methanol (42% yield) as a yellow solid. $^1$H NMR (500 MHz, DMSO-$d_6$) δ 9.37 (s, 1H), 8.54 (d, J=5.7 Hz, 1H), 8.19 (d, J=8.4 Hz, 1H), 7.91-7.83 (m, 2H), 7.64 (dd, J=8.4, 1.4 Hz, 1H), 7.48 (d, J=7.4 Hz, 1H), 7.31 (t, J=7.6 Hz, 1H), 7.22 (d, J=7.4 Hz, 1H), 5.20 (t, J=5.3 Hz, 1H), 4.59 (d, J=5.0 Hz, 2H), 2.16 (s, 3H).

Intermediate: 5-chloro-2-hydroxy-4-((3-(isoquinolin-6-yl)-2-methylbenzyl)oxy)benzaldehyde

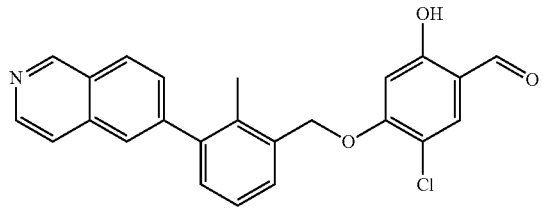 [SMILES: Cc1c(COc2cc(O)c(C=O)cc2Cl)cccc1-c1ccc2cnccc2c1]

The crude product was purified on silica gel using 10-80% ethylacetate/hexane to give 0.158 g of 5-chloro-2-hydroxy-4-((3-(isoquinolin-6-yl)-2-methylbenzyl)oxy)benzaldehyde (31% yield) as a yellow solid. $^1$H NMR (400 MHz, DMSO-$d_6$) δ 10.04 (s, 1H), 9.38 (s, 1H), 8.55 (d, J=5.8 Hz, 1H), 8.21 (d, J=8.8 Hz, 1H), 7.92 (s, 1H), 7.89 (d, J=6.0 Hz, 1H), 7.72 (s, 1H), 7.66 (d, J=7.0 Hz, 1H), 7.58 (d, J=7.3 Hz, 1H), 7.43-7.32 (m, 2H), 6.89 (s, 1H), 5.36 (s, 2H), 2.25 (s, 3H).

Intermediate: 5-((4-chloro-2-formyl-5-((3-(isoquinolin-6-yl)-2-methylbenzyl)oxy)phenoxy)methyl)nicotinonitrile

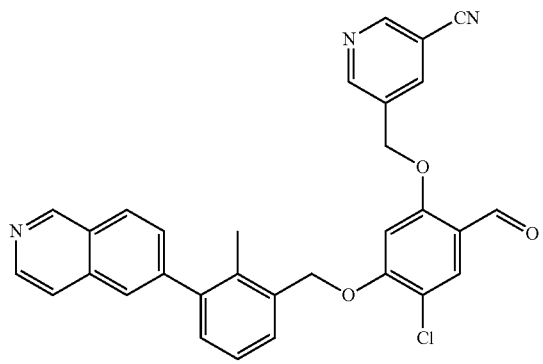 [SMILES: Cc1c(COc2cc(OCc3cncc(C#N)c3)c(C=O)cc2Cl)cccc1-c1ccc2cnccc2c1]

136 mgs of 5-((4-chloro-2-formyl-5-((3-(isoquinolin-6-yl)-2-methylbenzyl)oxy)phenoxy) methyl)nicotinonitrile was obtained (67% yield) as an orange solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute. LCMS Rt=1.065 min., m/z 520.0 (M+H).

Example 1009: (R)-2-((5-chloro-2-((5-cyanopyridin-3-yl)methoxy)-4-((3-(isoquinolin-6-yl)-2-methylbenzyl)oxy) benzyl)amino)-3-hydroxy-2-methylpropanoic acid

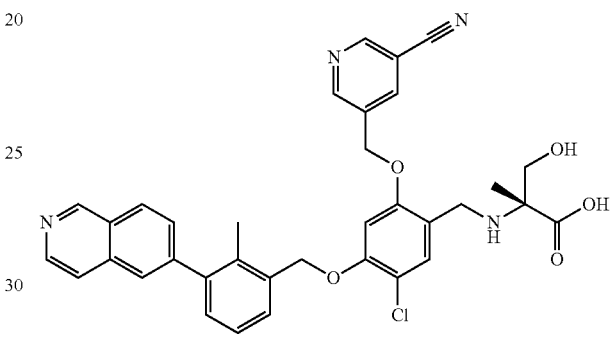

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 20-70% B over 20 minutes with a 5-minute hold at 100% B at a flow rate of 20 mL/minute. The material was further purified via preparative LC/MS using the following conditions: Waters XBridge 5 μm C18, 19×200 mm where mobile phase A was 5:95 methanol: water with 10 mM ammonium acetate and mobile phase B was 95:5 methanol: water with 10 mM ammonium acetate at a gradient of 45-85% B over 15 minutes with a 5-minute hold at 100% B at a flow rate of 20 mL/minute. Fractions containing the desired product were combined and dried via centrifugal evaporation. The yield of the product was 1.3 mg (3% yield), and its estimated purity by LCMS analysis was 100%. $^1$H NMR (500 MHz, DMSO-$d_6$) δ 9.37 (s, 1H), 9.01 (m, 2H), 8.55 (d, J=5.9 Hz, 1H), 8.50 (s, 1H), 8.21 (d, J=8.4 Hz, 1H), 7.93-7.86 (m, 2H), 7.66 (d, J=7.7 Hz, 1H), 7.56 (d, J=6.2 Hz, 1H), 7.49 (s, 1H), 7.37-7.30 (m, 2H), 7.13 (s, 1H), 5.36 (s, 2H), 5.31 (s, 2H), 3.94-3.86 (m, 2H), 3.53-3.46 (m, 2H), 2.27 (s, 3H), 1.17 (s, 3H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.52 min; ESI-MS (+) m/z=623.5 (M+H), ESI-MS(−) m/z=621.5 (M−H).

Analysis condition 2: Retention time=2.64 min; ESI-MS (+) m/z=623.1 (M+H), ESI-MS(−) m/z=621.5 (M−H).

Intermediate: 7-bromo-2-chloroquinoxaline

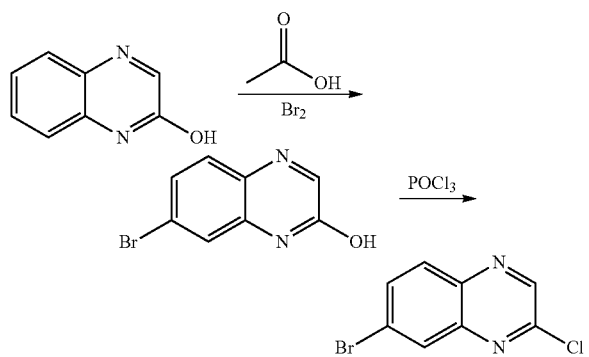

To a round bottomed flask (RBF) containing quinoxalin-2-ol (10 g, 68.4 mmol) and acetic acid (500 mL, 68.4 mmol) was slowly added, under nitrogen, dropwise, bromine (3.60 mL, 69.9 mmol). When the addition was complete, the red mixture was stirred for 1.5 hours at room temperature. The resulting crude product was filtered, the solid washed with 1 L of water and allowed to air dry for 1 hour. The solid was taken up in 10 mL of DMSO, and 100 mL of water was added. The resulting pale yellow solid was filtered and dried under vacuum to give 12.69 g of 7-bromoquinoxalin-2-ol (74%). The LC/MS data was obtained on a Shimadzu analytical LC/Micromass Platform LC (ESI+) at 220 nm using the following set of conditions: Waters Aquity BEH 1.7 μm C18, 2×50 mm column, with a gradient of 2-98% B (B=1000% HPLC grade acetonitrile/0.05% trifluoroacetic acid), (A=100% HPLC grade water/0.05% trifluoroacetic acid), in 1.5 minutes with a 1 minute hold at a rate of 0.8 mL/minute. LCMS Rt=0.859 min., m/z 226.9 (M+H). $^1$H NMR (500 MHz, DMSO-$d_6$) δ 12.39 (br.s., 1H), 8.19 (s, 1H), 7.74-7.68 (m, 1H), 7.46 (m, 2H).

To a RBF was added 7-bromoquinoxalin-2-ol (7.3 g, 32.4 mmol) and phosphoryl trichloride (36.3 mL, 389 mmol). The reaction mixture was stirred at 90° C. for 2.5 hours. The crude product was cooled to 0° C., then slowly dripped into 500 mL of ice water over 60 minutes. The resulting mixture was diluted with ethyl acetate and extracted. The organic layer was washed with brine, dried over magnesium sulfate, filtered and concentrated. The crude product was purified on silica gel using 30-90% DCM/hexanes to give 5.4 g (66.4%) of 7-bromo-2-chloroquinoxaline as a white solid.

The LC/MS data was obtained on a Shimadzu analytical LC/Micromass Platform LC (ESI+) at 220 nm using the following set of conditions: Waters Aquity BEH 1.7 μm C18, 2×50 mm column, with a gradient of 2-98% B (B=1000% HPLC grade acetonitrile/0.05% trifluoroacetic acid), (A=100% HPLC grade water/0.05% trifluoroacetic acid), in 1.5 minutes with a 1 minute hold at a rate of 0.8 mL/minute. LCMS Rt=1.275 min., m/z 244.8 (M+H). $^1$H NMR (400 MHz, DMSO-$d_6$) δ 9.06 (s, 1H), 8.35 (d, J=2.3 Hz, 1H), 8.14-8.09 (m, 1H), 8.09-8.04 (m, 1H).

Intermediate: (3-(7-bromoquinoxalin-2-yl)-2-methylphenyl)methanol

The crude product was purified by prep HPLC using the following method: a Shimadzu preparative HPLC employing methanol/water/trifluoroacetic acid where solvent A was 10% methanol/90% water/0.1% trifluoroacetic acid and solvent B was 10% water/90% methanol/0.1% trifluoroacetic acid with a Waters Sunfire 5 μm C18 19×100 mm column at a gradient of 30-100% B and a flow rate of 30 mL/min. over 15 minutes with a 7 minute hold to give 0.204 g (73% yield) of (3-(7-bromoquinoxalin-2-yl)-2-methylphenyl)methanol as a white solid. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2.0 minutes with a 1 minute hold at a rate of 1 mL/minute. LCMS Rt=1.593 min., m/z 329.2 (M+H); $^1$H NMR (500 MHz, DMSO-$d_6$) δ 9.12 (d, J=2.4 Hz, 1H), 8.36 (d, J=2.4 Hz, 1H), 8.11 (dd, J=8.9, 2.4 Hz, 1H), 8.06-8.00 (m, 1H), 7.59 (d, J=7.4 Hz, 1H), 7.47 (d, J=7.6 Hz, 1H), 7.43-7.35 (m, 1H), 5.26 (m, 1H), 4.62 (d, J=5.4 Hz, 2H), 2.27 (s, 3H).

Intermediate: 4-((3-(7-bromoquinoxalin-2-yl)-2-methylbenzyl)oxy)-5-chloro-2-hydroxybenzaldehyde

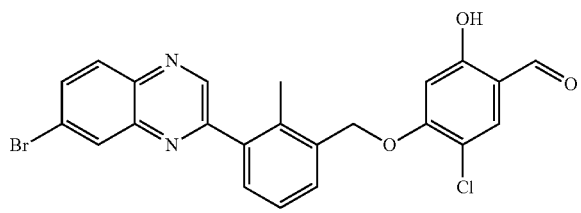 [SMILES: Cc1c(COc2cc(O)c(C=O)cc2Cl)cccc1-c1cnc2ccc(Br)cc2n1]

The crude product was triturated with 10 mL of ethanol, then filtered to give 160 mgs (38% yield) of 4-((3-(7-bromoquinoxalin-2-yl)-2-methylbenzyl)oxy)-5-chloro-2-hydroxybenzaldehyde as a light tan solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute.

LCMS Rt=1.562 min., m/z 484.8 (M+H).

Intermediate: 5-((5-((3-(7-bromoquinoxalin-2-yl)-2-methylbenzyl)oxy)-4-chloro-2-formylphenoxy)methyl)nicotinonitrile

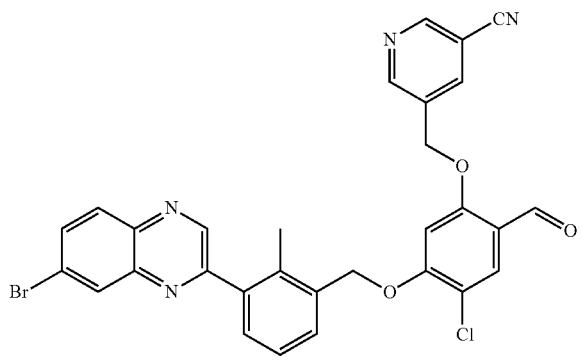 [SMILES: Cc1c(COc2cc(OCc3cncc(C#N)c3)c(C=O)cc2Cl)cccc1-c1cnc2ccc(Br)cc2n1]

115 mgs of 5-((5-((3-(7-bromoquinoxalin-2-yl)-2-methylbenzyl)oxy)-4-chloro-2-formylphenoxy) methyl) nicotinonitrile was obtained (41% yield) as an orange solid. The LC/MS data was obtained on a Shimadzu analytical LC/Micromass Platform LC (ESI+) at 220 nm using the following set of conditions: Waters Aquity BEH 1.7 ™ C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute.
LCMS Rt=1.529 min., m/z 600.9 (M+H).

Example 1010: (R)-2-((4-((3-(7-bromoquinoxalin-2-yl)-2-methylbenzyl)oxy)-5-chloro-2-((5-cyanopyridin-3-yl) methoxy)benzyl)amino)-3-hydroxy-2-methylpropanoic acid

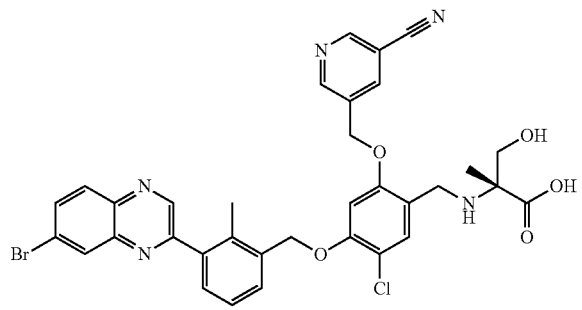 [SMILES: Cc1c(COc2cc(OCc3cncc(C#N)c3)c(CN[C@](C)(CO)C(=O)O)cc2Cl)cccc1-c1cnc2ccc(Br)cc2n1]

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 40-80% B over 15 minutes with a 5-minute hold at 100% B at a flow rate of 20 mL/minute. The material was further purified via preparative LC/MS using the following conditions: Waters XBridge 5 μm C18, 19×200 mm where mobile phase A was 5:95 methanol: water with 10 mM ammonium acetate and mobile phase B was 95:5 methanol: water with 10 mM ammonium acetate at a gradient of 50-90% B over 20 minutes with a 5-minute hold at 100% B at a flow rate of 20 mL/minute. Fractions containing the desired product were combined and dried via centrifugal evaporation. The yield of the product was 3.4 mg (7% yield), and its estimated purity by LCMS analysis was 97%. $^1$H NMR (500 MHz, DMSO-d$_6$) δ 9.16 (s, 1H), 9.02 (m, 2H), 8.51 (s, 1H), 8.38 (s, 1H), 8.17-8.10 (m, 1H), 8.05 (d, J=9.2 Hz, 1H), 7.66 (d, J=7.3 Hz, 1H), 7.60 (d, J=7.7 Hz, 1H), 7.56 (s, 1H), 7.43 (t, J=7.7 Hz, 1H), 7.15 (s, 1H), 5.37 (s, 4H), 4.03-3.86 (m, 3H), 3.65-3.50 (m, 2H), 2.40 (s, 3H), 1.23 (s, 3H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.76 min; ESI-MS (+) m/z=702.4 (M+H), ESI-MS(−) m/z=700.4 (M−H).

Analysis condition 2: Retention time=2.88 min; ESI-MS (+) m/z=702.4 (M+H), ESI-MS(−) m/z=700.4 (M−H).

Intermediate: (3-(benzo[d]thiazol-6-yl)-2-methylphenyl)methanol

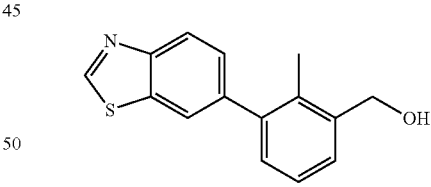

The crude product was purified on silica gel using 10-60% ethylacetate/hexane to give 0.577 g of (3-(benzo[d]thiazol-6-yl)-2-methylphenyl)methanol (95% yield) as a yellow solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute. LCMS Rt=1.044 min., m/z 256.5 (M+H). $^1$H NMR (400 MHz, CDCl$_3$) δ 9.03 (s, 1H), 8.18 (d, J=8.6 Hz, 1H), 7.88 (d, J=1.2 Hz, 1H), 7.51-7.41 (m, 2H), 7.33-7.28 (m, 1H), 7.25 (m, 1H), 4.81 (d, J=5.6 Hz, 2H), 2.27 (s, 3H).

Intermediate: 4-((3-(benzo[d]thiazol-6-yl)-2-methyl-benzyl)oxy)-5-chloro-2-hydroxybenzaldehyde

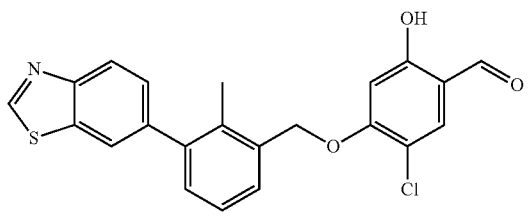

The crude product was purified on silica gel using 10-80% ethylacetate/hexane to give 0.500 g of 4-((3-(benzo[d]thiazol-6-yl)-2-methylbenzyl)oxy)-5-chloro-2-hydroxybenzaldehyde (32% yield) as a white solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute. LCMS Rt=1.439 min., m/z 409.9 (M+H). $^1$H NMR (400 MHz, CDCl$_3$) δ 11.46 (s, 1H), 9.74-9.68 (m, 1H), 9.05 (s, 1H), 8.20 (d, J=8.3 Hz, 1H), 7.91 (d, J=1.5 Hz, 1H), 7.59-7.47 (m, 3H), 7.36-7.30 (m, 2H), 5.24 (s, 2H), 2.28 (s, 3H).

Intermediate: 5-((5-((3-(benzo[d]thiazol-6-yl)-2-methylbenzyl)oxy)-4-chloro-2-formylphenoxy) methyl)nicotinonitrile

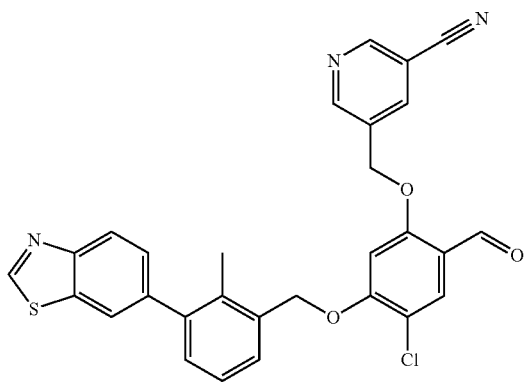

260 mgs of 5-((5-((3-(7-bromoquinoxalin-2-yl)-2-methylbenzyl)oxy)-4-chloro-2-formylphenoxy) methyl) nicotinonitrile was obtained (61% yield) as an orange solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute. LCMS Rt=1.405 min., m/z 526.0 (M+H). $^1$H NMR (500 MHz, DMSO-d$_6$) δ 10.25 (s, 1H), 9.44 (s, 1H), 9.05 (m, 2H), 8.60-8.53 (m, 1H), 8.17 (dd, J=4.9, 3.3 Hz, 2H), 7.75 (s, 1H), 7.58 (dd, J=6.9, 2.1 Hz, 1H), 7.50 (dd, J=8.4, 1.7 Hz, 1H), 7.39-7.34 (m, 2H), 7.31 (s, 1H), 5.51 (s, 2H), 5.46 (s, 2H), 2.28 (s, 3H).

Example 1011: (R)-2-((4-((3-(benzo[d]thiazol-6-yl)-2-methylbenzyl)oxy)-5-chloro-2-((5-cyanopyridin-3-yl)methoxy) benzyl)amino)-3-hydroxy-2-methylpropanoic acid

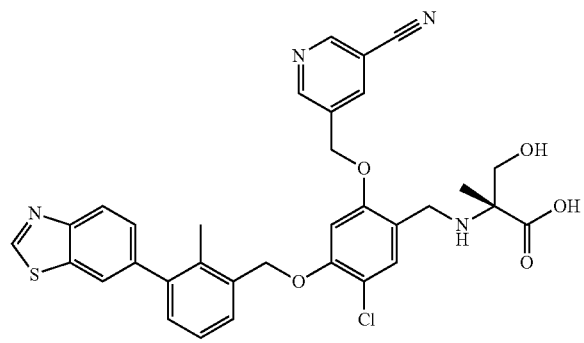 [SMILES: Cc1c(COc2cc(OCc3cncc(C#N)c3)c(CN[C@](C)(CO)C(=O)O)cc2Cl)cccc1-c1ccc2ncsc2c1]

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 20-60% B over 25 minutes with a 7-minute hold at 100% B at a flow rate of 20 mL/minute. Fractions containing the desired product were combined and dried via centrifugal evaporation. The yield of the product was 16 mg (35% yield), and its estimated purity by LCMS analysis was 100%. $^1$H NMR (500 MHz, DMSO-d$_6$) δ 9.43 (s, 1H), 9.03 (m, 2H), 8.51 (s, 1H), 8.21-8.10 (m, 2H), 7.57 (s, 1H), 7.55-7.45 (m, 2H), 7.35-7.27 (m, 2H), 7.15 (s, 1H), 5.43-5.25 (m, 4H), 3.98 (s, 2H), 3.68-3.54 (m, 2H), 2.26 (s, 3H), 1.24 (s, 3H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.59 min; ESI-MS (+) m/z=629.5 (M+H), ESI-MS(−) m/z=627.7 (M−H).

Analysis condition 2: Retention time=2.68 min; ESI-MS (+) m/z=629.5 (M+H), ESI-MS(−) m/z=627.7 (M−H).

Intermediate: (3-(benzo[d]oxazol-5-yl)-2-methylphenyl)methanol

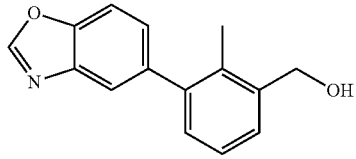 [SMILES: Cc1c(CO)cccc1-c1ccc2ocnc2c1]

The crude product was purified on silica gel using 10-60% ethylacetate/hexane to give 0.461 g of (3-(benzo[d]oxazol-5-yl)-2-methylphenyl)methanol (74% yield) as a yellow solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute. LCMS Rt=1.005 min., m/z 240.1 (M+H); $^1$H NMR (400 MHz, CDCl$_3$) δ 8.16 (s, 1H), 7.71 (d, J=1.5 Hz, 1H), 7.63 (d, J=8.3 Hz, 1H), 7.44 (d, J=7.3 Hz, 1H), 7.33 (dd, J=8.4, 1.6 Hz, 1H), 7.30 (m, 1H), 7.24 (m, 1H), 4.80 (d, J=5.4 Hz, 2H), 2.25 (s, 3H).

Intermediate: 4-((3-(benzo[d]oxazol-5-yl)-2-methylbenzyl)oxy)-5-chloro-2-hydroxybenzaldehyde

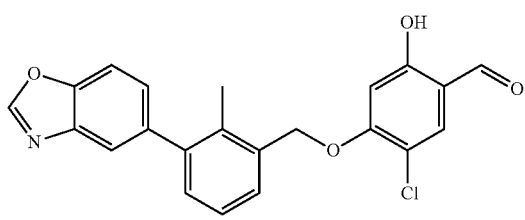

The crude product was purified on silica gel using 0-70% ethylacetate/hexane to give 0.320 g of 4-((3-(benzo[d]oxazol-5-yl)-2-methylbenzyl)oxy)-5-chloro-2-hydroxybenzaldehyde (40% yield) as a white solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute. LCMS Rt=1.400 min., m/z 394.3 (M+H). $^1$H NMR (400 MHz, CDCl$_3$) δ 11.45 (s, 1H), 9.72 (s, 1H), 8.17 (s, 1H), 7.75 (d, J=1.5 Hz, 1H), 7.65 (d, J=8.8 Hz, 1H), 7.57 (s, 1H), 7.54-7.48 (m, 1H), 7.40-7.29 (m, 3H), 5.24 (s, 2H), 2.26 (s, 3H).

Intermediate: 5-((5-((3-(benzo[d]oxazol-5-yl)-2-methylbenzyl)oxy)-4-chloro-2-formylphenoxy)methyl)nicotinonitrile 412 mgs of 5-((5-((3-(benzo[d]oxazol-5-yl)-2-methylbenzyl)oxy)-4-chloro-2-formylphenoxy) methyl)nicotinonitrile was obtained (80% yield) as an orange solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute. LCMS Rt=1.387 min., m/z 510.2 (M+H). $^1$H NMR (500 MHz, DMSO-d$_6$) δ 10.25 (s, 1H), 9.05 (m, 2H), 8.82 (s, 1H), 8.57 (s, 1H), 7.86 (d, J=8.4 Hz, 1H), 7.75 (m, 2H), 7.56 (d, J=6.1 Hz, 1H), 7.42-7.28 (m, 4H), 5.51 (s, 2H), 5.45 (s, 2H), 2.26 (s, 3H).

Example 1012: (R)-2-((4-((3-(benzo[d]oxazol-5-yl)-2-methylbenzyl)oxy)-5-chloro-2-((5-cyanopyridin-3-yl)methoxy) benzyl)amino)-3-hydroxy-2-methylpropanoic acid

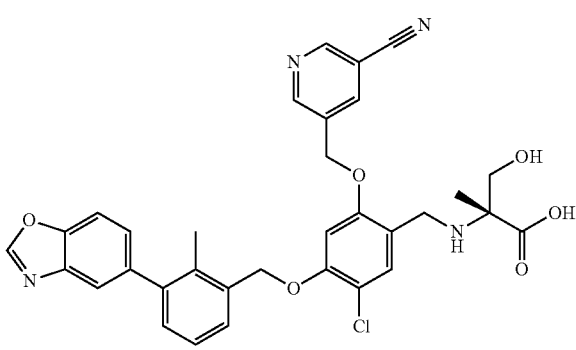 [SMILES: Cc1c(COc2cc(OCc3cncc(C#N)c3)c(CN[C@](C)(CO)C(=O)O)cc2Cl)cccc1-c1ccc2ocnc2c1]

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 20-80% B over 25 minutes with a 5-minute hold at 100% B at a flow rate of 20 mL/minute. Fractions containing the desired product were combined and dried via centrifugal evaporation. The yield of the product was 16 mg (33% yield), and its estimated purity by LCMS analysis was 100%. $^1$H NMR (500 MHz, DMSO-$d_6$) δ 9.02 (m, 2H), 8.81 (s, 1H), 8.51 (s, 1H), 7.85 (d, J=8.4 Hz, 1H), 7.72 (s, 1H), 7.57 (s, 1H), 7.51 (d, J=7.0 Hz, 1H), 7.38 (d, J=8.8 Hz, 1H), 7.30 (q, J=7.9 Hz, 2H), 7.14 (s, 1H), 5.37 (s, 2H), 5.32 (s, 2H), 3.98 (s, 2H), 3.67-3.60 (m, 1H), 3.55 (m, 1H), 2.24 (s, 3H), 1.25 (s, 3H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.55 min; ESI-MS (+) m/z=613.1 (M+H), ESI-MS(−) m/z=611.2 (M−H).

Analysis condition 2: Retention time=2.61 min; ESI-MS (+) m/z=613.0 (M+H), ESI-MS(−) m/z=611.1 (M−H).

Intermediate: (3-(benzofuran-5-yl)-2-methylphenyl)methanol

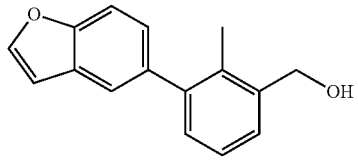 [SMILES: Cc1c(CO)cccc1-c1ccc2occc2c1]

The crude product was purified on silica gel using 10-60% ethylacetate/hexane to give 1.03 g of (3-(benzofuran-5-yl)-2-methylphenyl)methanol (55% yield) as a yellow solid. $^1$H NMR (400 MHz, CDCl$_3$) δ 7.68 (d, J=2.2 Hz, 1H), 7.55 (d, J=8.6 Hz, 1H), 7.51 (d, J=1.5 Hz, 1H), 7.44-7.40 (dd, J=1.5, 8.6 Hz, 1H), 7.33-7.28 (m, 1H), 7.28-7.25 (m, 1H), 7.24-7.21 (m, 1H), 6.83 (dd, J=2.1, 0.9 Hz, 1H), 4.80 (br. s., 2H), 2.27 (s, 3H).

Intermediate: 4-((3-(benzofuran-5-yl)-2-methylbenzyl)oxy)-5-chloro-2-hydroxybenzaldehyde

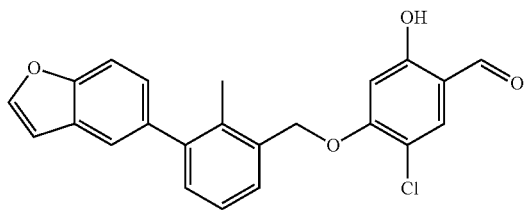 [SMILES: Cc1c(COc2cc(O)c(C=O)cc2Cl)cccc1-c1ccc2occc2c1]

The crude product was purified on silica gel using 0-50% ethylacetate/hexane to give 0.215 g of 4-((3-(benzo[d]ox-azol-5-yl)-2-methylbenzyl)oxy)-5-chloro-2-hydroxybenzaldehyde (41% yield) as a white solid. The LC/MS data was obtained on a Shimadzu analytical LC/Micromass Platform LC (ESI+/−) at 220 nm using the following set of conditions: Phenomenex Luna 3 μm C18, 2×30 mm column, with a gradient of 0-100% B (B=95% HPLC grade acetonitrile/10 mM ammonium acetate/5% HPLC grade water), (A=95% HPLC grade water/10 mM ammonium acetate/5% HPLC grade acetonitrile), in 2 minutes with a 1 minute hold at a rate of 1 mL/minute.

LCMS Rt=2.17 min., m/z 391.31 (M−H). $^1$H NMR (400 MHz, DMSO-$d_6$) δ 11.18 (s, 1H), 10.05 (s, 1H), 8.06 (d, J=2.0 Hz, 1H), 7.72 (s, 1H), 7.68 (d, J=8.3 Hz, 1H), 7.58 (d, J=1.7 Hz, 1H), 7.52 (d, J=7.1 Hz, 1H), 7.37-7.21 (m, 2H), 7.04-6.99 (m, 1H), 6.88 (s, 1H), 5.34 (s, 2H), 2.23 (s, 3H).

Intermediate: 5-((5-((3-(benzofuran-5-yl)-2-methylbenzyl)oxy)-4-chloro-2-formylphenoxy)methyl) nicotinonitrile

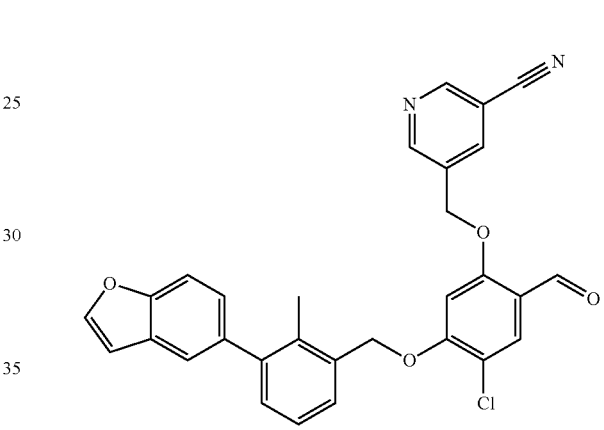

The crude material was purified via preparative LC/MS employing the following conditions: Waters XBridge 5 μm C18, 19×200 mm column with Mobile Phase A, 5:95 acetonitrile/water with 10 mM ammonium acetate and Mobile Phase B, 95:5 acetonitrile/water with 10 mM ammonium acetate at a gradient of 55-95% B over 15 minutes with a 5-minute hold at 100% B at a flow rate of 20 mL/min. Solvent was evaporated to give 240 mgs (82% yield) of 5-((5-((3-(benzofuran-5-yl)-2-methylbenzyl) oxy)-4-chloro-2-formylphenoxy)methyl)nicotinonitrile.

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

Analysis condition 1: Retention time=2.41 min; ESI-MS (+) m/z=509.0 (M+H)

Analysis condition 2: Retention time=3.21 min; ESI-MS (+) m/z=509.2 (M+H)

¹H NMR (500 MHz, DMSO-d₆) δ 10.25 (s, 1H), 9.08-8.91 (m, 2H), 8.57 (s, 1H), 8.06 (d, J=2.0 Hz, 1H), 7.75 (s, 1H), 7.68 (d, J=8.5 Hz, 1H), 7.62-7.57 (m, 1H), 7.54 (d, J=7.1 Hz, 1H), 7.41-7.22 (m, 4H), 7.01 (d, J=1.4 Hz, 1H), 5.51 (s, 2H), 5.45 (s, 2H), 2.26 (s, 3H).

Example 1013: (R)-2-((4-((3-(benzofuran-5-yl)-2-methylbenzyl)oxy)-5-chloro-2-((5-cyanopyridin-3-yl)methoxy) benzyl)amino)-3-hydroxy-2-methylpropanoic acid

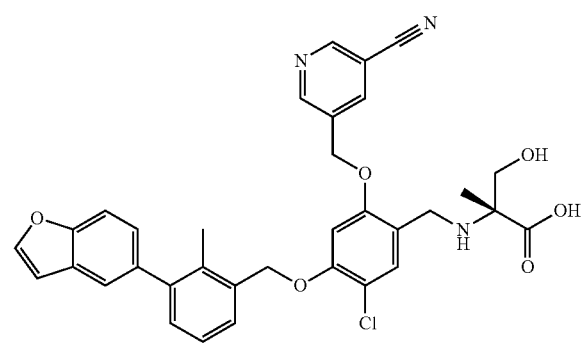 [SMILES: Cc1c(COc2cc(OCc3cncc(C#N)c3)c(CN[C@](C)(CO)C(=O)O)cc2Cl)cccc1-c1ccc2occc2c1]

The crude material was purified via preparative LC/MS using the following conditions: Waters XBridge 5 µm C18, 19×200 mm where mobile phase A was 5:95 acetonitrile:water with 10 mM ammonium acetate and mobile phase B was 95:5 acetonitrile: water with 10 mM ammonium acetate at a gradient of 45-85% B over 15 minutes with a 5-minute hold at 100% B at a flow rate of 20 mL/minute. Fractions containing the desired product were combined and dried via centrifugal evaporation. The yield of the product was 10 mg (28% yield), and its estimated purity by LCMS analysis was 100%. ¹H NMR (500 MHz, DMSO-d₆) δ 9.03 (m, 2H), 8.52 (s, 1H), 8.05 (s, 1H), 7.67 (d, J=7.3 Hz, 1H), 7.57 (m, 2H), 7.48 (m, 1H), 7.26 (m, 3H), 7.14 (s, 1H), 7.01 (s, 1H), 5.43-5.25 (m, 4H), 4.04-3.87 (m, 2H), 3.71-3.51 (m, 2H), 2.24 (s, 3H), 1.24 (s, 3H).

Two analytical LC/MS injections were used to determine the final purity.

Injection 1 conditions: Waters Acquity UPLC BEH 1.7 µm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 µm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.88 min; ESI-MS (+) m/z=612.9 (M+H).

Analysis condition 2: Retention time=3.35 min; ESI-MS (+) m/z=612.0 (M+H).

Example 1014: (S)-2-((4-((3-(benzofuran-5-yl)-2-methylbenzyl)oxy)-5-chloro-2-((5-cyanopyridin-3-yl)methoxy) benzyl)amino)-5-guanidinopentanoic acid

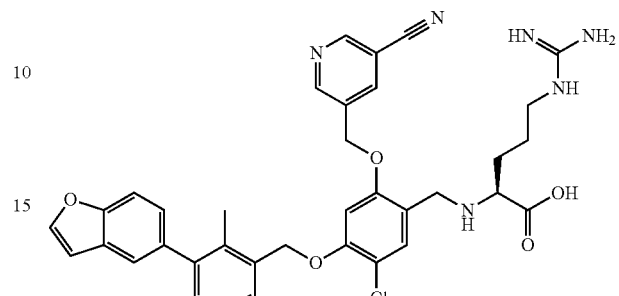

The crude material was purified via preparative LC/MS using the following conditions: Waters XBridge 5 µm C18, 19×200 mm where mobile phase A was 5:95 acetonitrile:water with 10 mM ammonium acetate and mobile phase B was 95:5 acetonitrile: water with 10 mM ammonium acetate at a gradient of 25-65% B over 15 minutes with a 5-minute hold at 100% B at a flow rate of 20 mL/minute. Fractions containing the desired product were combined and dried via centrifugal evaporation. The yield of the product was 24 mg (58% yield), and its estimated purity by LCMS analysis was 96%. ¹H NMR (500 MHz, DMSO-d₆) δ 9.05-8.95 (m, J=8.1 Hz, 2H), 8.46 (s, 1H), 8.05 (s, 1H), 7.66 (d, J=8.4 Hz, 1H), 7.58 (s, 1H), 7.49 (d, J=7.0 Hz, 1H), 7.39 (s, 1H), 7.32-7.19 (m, 3H), 7.10 (s, 1H), 7.01 (s, 1H), 5.33 (s, 2H), 5.26 (s, 2H), 3.73 (d, J=13.6 Hz, 1H), 3.66-3.58 (m, 1H), 3.16-3.03 (m, 1H), 3.03-2.94 (m, 1H), 2.94-2.85 (m, 1H), 2.24 (s, 3H), 1.62-1.40 (m, 4H).

Two analytical LC/MS injections were used to determine the final purity.

Injection 1 conditions: Waters Acquity UPLC BEH 1.7 µm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 µm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.73 min; ESI-MS (+) m/z=668.0 (M+H).

Analysis condition 2: Retention time=3.29 min; ESI-MS (+) m/z=668.1 (M+H).

Example 1015: 2-((4-((3-(benzofuran-5-yl)-2-methylbenzyl)oxy)-5-chloro-2-((5-cyanopyridin-3-yl)methoxy)benzyl) amino)-2-methylpropanoic acid

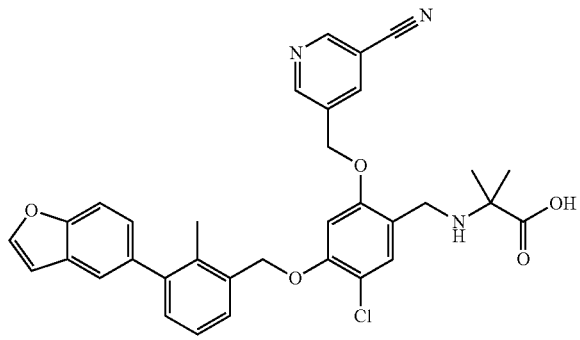

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile: water with 10 mM ammonium acetate at a gradient of 45-85% B over 15 minutes with a 5-minute hold at 100% B at a flow rate of 20 mL/minute. Fractions containing the desired product were combined and dried via centrifugal evaporation. The yield of the product was 11.5 mg (33% yield), and its estimated purity by LCMS analysis was 100%. $^1$H NMR (500 MHz, DMSO-$d_6$) δ 9.04 (m, 2H), 8.53 (s, 1H), 8.06 (s, 1H), 7.67 (d, J=8.4 Hz, 1H), 7.58 (m, 2H), 7.50 (d, J=7.0 Hz, 1H), 7.32-7.21 (m, 3H), 7.15 (s, 1H), 7.01 (s, 1H), 5.35 (s, 2H), 5.33 (s, 2H), 3.90 (s, 2H), 2.25 (s, 3H), 1.28 (m, 6H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3.5 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3.5 minutes with a 0.75-minute hold at 100% B at a flow rate of 1.0 mL/minute at a UV wavelength of 220 nm.

Analysis condition 1: Retention time=1.90 min; ESI-MS (+) m/z=596.0 (M+H), ESI-MS(−) m/z=594.2 (M−H).

Analysis condition 2: Retention time=3.35 min; ESI-MS (+) m/z=596.0 (M+H), ESI-MS(−) m/z=594.2 (M−H).

Intermediate: (3-(benzo[d]oxazol-6-yl)-2-methylphenyl)methanol

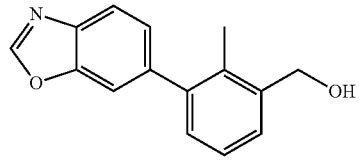 [SMILES: Cc1c(CO)cccc1-c1ccc2ncoc2c1]

The crude product was purified on silica gel using 10-60% ethylacetate/hexane to give 0.470 g of (3-(benzo[d]oxazol-6-yl)-2-methylphenyl)methanol (55% yield) as an orange solid. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute. LCMS Rt=0.987 min., m/z 240.1 (M+H). $^1$H NMR (400 MHz, CDCl$_3$) δ 8.15 (s, 1H), 7.82 (d, J=8.1 Hz, 1H), 7.52 (d, J=1.2 Hz, 1H), 7.47-7.42 (m, 1H), 7.34-7.28 (m, 2H), 7.25 (d, J=1.2 Hz, 1H), 4.80 (s, 2H), 2.25 (s, 3H).

Intermediate: 4-((3-(benzo[d]oxazol-6-yl)-2-methylbenzyl)oxy)-5-chloro-2-hydroxybenzaldehyde

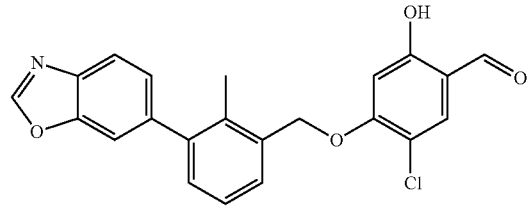 [SMILES: Cc1c(COc2cc(O)c(C=O)cc2Cl)cccc1-c1ccc2ncoc2c1]

The crude product was purified on silica gel using 0-50% ethylacetate/hexane to give 0.190 g of 4-((3-(benzo[d]oxazol-6-yl)-2-methylbenzyl)oxy)-5-chloro-2-hydroxybenzaldehyde (34% yield) as a white solid. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.973 min., m/z 394.3 (M−H). $^1$H NMR (400 MHz, DMSO-$d_6$) δ 11.18 (br. s., 1H), 10.05 (s, 1H), 8.81 (s, 1H), 7.88 (d, J=8.1 Hz, 1H), 7.75 (d, J=1.0 Hz, 1H), 7.72 (s, 1H), 7.55 (d, J=6.1 Hz, 1H), 7.40-7.29 (m, 3H), 6.89 (s, 1H), 5.35 (s, 2H), 2.24 (s, 3H).

Intermediate: 5-((5-((3-(benzo[d]oxazol-6-yl)-2-methylbenzyl)oxy)-4-chloro-2-formylphenoxy)methyl)nicotinonitrile

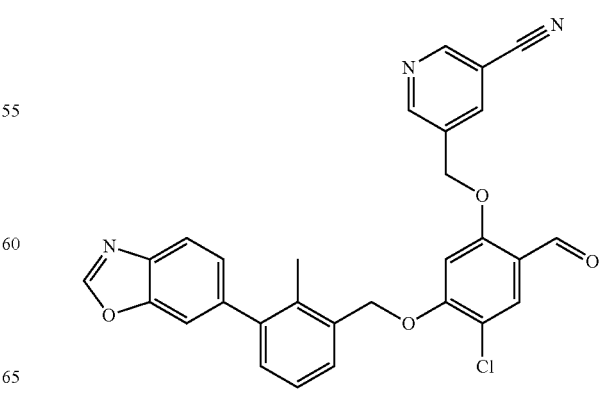

The crude material was purified via preparative LC/MS employing the following conditions: Waters XBridge 5 μm C18, 19×200 mm column with Mobile Phase A, 5:95 methanol/water with 10 mM ammonium acetate and Mobile Phase B, 95:5 methanol/water with 10 mM ammonium acetate at a gradient of 60-100% B over 15 minutes with a 10-minute hold at 100% B at a flow rate of 20 mL/min. Solvent was evaporated to give 271 mgs (72% yield) of 5-((5-((3-(benzo[d]oxazol-6-yl)-2-methylbenzyl)oxy)-4-chloro-2-formylphenoxy)methyl)nicotinonitrile.

Two analytical LC/MS injections were used to determine the final purity.

Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

Analysis condition 1: Retention time=2.12 min; ESI-MS (+) m/z=510.1 (M+H)

Analysis condition 2: Retention time=2.98 min; ESI-MS (+) m/z=510.1 (M+H)

$^1$H NMR (500 MHz, DMSO-$d_6$) δ 10.25 (s, 1H), 9.04 (m, 2H), 8.80 (s, 1H), 8.56 (s, 1H), 7.88 (d, J=8.2 Hz, 1H), 7.78-7.73 (m, 2H), 7.57 (dd, J=7.2, 1.5 Hz, 1H), 7.40-7.28 (m, 4H), 5.51 (s, 2H), 5.45 (s, 2H), 2.27 (s, 3H).

Example 1016: 2-((4-((3-(benzo[d]oxazol-6-yl)-2-methylbenzyl)oxy)-5-chloro-2-((5-cyanopyridin-3-yl)methoxy) benzyl)amino)-2-methylpropanoic acid

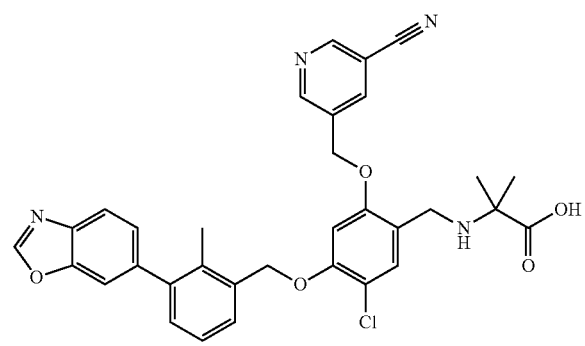

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile: water with 10 mM ammonium acetate at a gradient of 25-65% B over 15 minutes with a 5-minute hold at 100% B at a flow rate of 20 mL/minute. Fractions containing the desired product were combined and dried via centrifugal evaporation. The yield of the product was 12.4 mg (36% yield), and its estimated purity by LCMS analysis was 100%. $^1$H NMR (500 MHz, DMSO-$d_6$) δ 9.03 (m, 2H), 8.80 (s, 1H), 8.53 (s, 1H), 7.88 (d, J=8.1 Hz, 1H), 7.75 (s, 1H), 7.58 (s, 1H), 7.53 (d, J=7.0 Hz, 1H), 7.41-7.26 (m, 3H), 7.15 (s, 1H), 5.34 (m, 4H), 3.88 (s, 2H), 2.26 (s, 3H), 1.27 (s, 6H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.54 min; ESI-MS (+) m/z=597.2 (M+H), ESI-MS(−) m/z=595.2 (M−H).

Analysis condition 2: Retention time=2.57 min; ESI-MS (+) m/z=597.2 (M+H), ESI-MS(−) m/z=595.3 (M−H).

Example 1017: (R)-2-((4-((3-(benzo[d]oxazol-6-yl)-2-methylbenzyl)oxy)-5-chloro-2-((5-cyanopyridin-3-yl)methoxy) benzyl)amino)-3-hydroxy-2-methylpropanoic acid

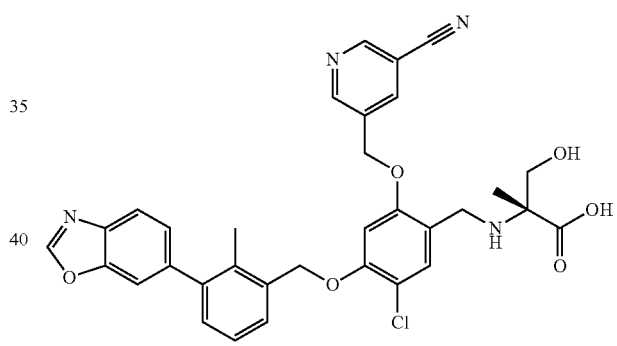

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile: water with 10 mM ammonium acetate at a gradient of 10-100% B over 20 minutes with a 5-minute hold at 100% B at a flow rate of 20 mL/minute. Fractions containing the desired product were combined and dried via centrifugal evaporation. The yield of the product was 20.3 mg (61% yield), and its estimated purity by LCMS analysis was 100%. $^1$H NMR (500 MHz, DMSO-$d_6$) δ 9.03 (s, 1H), 8.99 (s, 1H), 8.76 (s, 1H), 8.49 (s, 1H), 7.87 (d, J=8.1 Hz, 1H), 7.72 (s, 1H), 7.57 (s, 1H), 7.50 (d, J=7.0 Hz, 1H), 7.38-7.26 (m, 3H), 7.12 (s, 1H), 5.37 (s, 2H), 5.31 (s, 2H), 4.02 (s, 2H), 3.68 (m, 1H), 3.54 (m, 1H), 2.24 (s, 3H), 1.26 (s, 3H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3.5 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3.5 minutes with a 0.75-minute hold at 100% B at a flow rate of 1.0 mL/minute at a UV wavelength of 220 nm.

Analysis condition 1: Retention time=1.70 min; ESI-MS (+) m/z=613.1 (M+H), ESI-MS(−) m/z=611.1 (M−H).

Analysis condition 2: Retention time=3.27 min; ESI-MS (+) m/z=613.2 (M+H), ESI-MS(−) m/z=611.0 (M−H).

Intermediate: (3-(benzofuran-6-yl)-2-methylphenyl)methanol

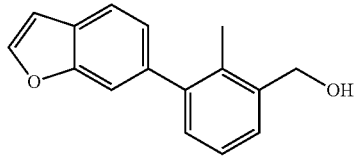 [SMILES: Cc1c(CO)cccc1-c1ccc2ccoc2c1]

The crude product was purified on silica gel using 10-60% ethylacetate/hexane to give 0.486 g of (3-(benzofuran-6-yl)-2-methylphenyl)methanol (56% yield) as a white foam. $^1$H NMR (400 MHz, CDCl$_3$) δ 7.67 (d, J=2.2 Hz, 1H), 7.63 (d, J=8.1 Hz, 1H), 7.45 (s, 1H), 7.44-7.40 (m, 1H), 7.33-7.28 (m, 1H), 7.25 (s, 1H), 7.19 (dd, J=7.9, 1.3 Hz, 1H), 6.83 (dd, J=2.1, 0.9 Hz, 1H), 4.80 (br. s., 2H), 2.27 (s, 3H).

Intermediate: 4-((3-(benzofuran-6-yl)-2-methylbenzyl)oxy)-5-chloro-2-hydroxybenzaldehyde

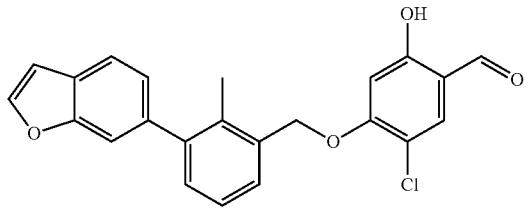 [SMILES: Cc1c(COc2cc(O)c(C=O)cc2Cl)cccc1-c1ccc2ccoc2c1]

The crude product was purified on silica gel using 10-60% ethylacetate/hexane to give 0.603 g of 4-((3-(benzofuran-6-yl)-2-methylbenzyl)oxy)-5-chloro-2-hydroxybenzaldehyde (60% yield) as a white solid. $^1$H NMR (500 MHz, DMSO-d$_6$) δ 10.05 (s, 1H), 8.05 (d, J=2.2 Hz, 1H), 7.74-7.71 (m, 2H), 7.57-7.51 (m, 2H), 7.37-7.28 (m, 2H), 7.22 (m, 1H), 7.03 (dd, J=2.2, 0.9 Hz, 1H), 6.91-6.86 (m, 1H), 5.34 (s, 2H), 2.25 (s, 3H).

Intermediate: 5-((5-((3-(benzofuran-6-yl)-2-methylbenzyl)oxy)-4-chloro-2-formylphenoxy)methyl)nicotinonitrile

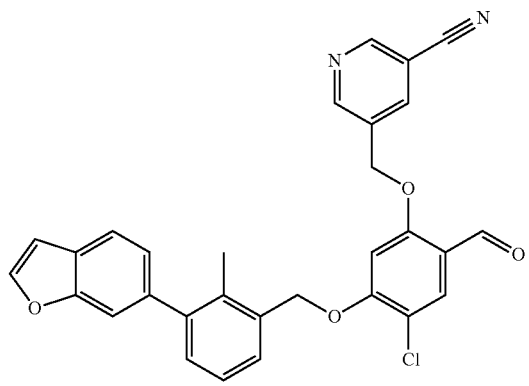 [SMILES: Cc1c(COc2cc(OCc3cncc(C#N)c3)c(C=O)cc2Cl)cccc1-c1ccc2ccoc2c1]

493 mgs of 5-((5-((3-(benzofuran-6-yl)-2-methylbenzyl)oxy)-4-chloro-2-formylphenoxy)methyl) nicotinonitrile was obtained (75% yield) as a yellow powder. The LC/MS data was obtained on a Shimadzu analytical LC/Micromass Platform LC (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute. LCMS Rt=1.509 min., m/z 509.15 (M+H). $^1$H NMR (500 MHz, DMSO-d$_6$) δ 10.25 (s, 1H), 9.09-8.97 (m, 2H), 8.56 (t, J=2.0 Hz, 1H), 8.05 (d, J=2.2 Hz, 1H), 7.81-7.70 (m, 2H), 7.60-7.51 (m, 2H), 7.37-7.29 (m, 3H), 7.22 (dd, J=7.9, 1.4 Hz, 1H), 7.03 (dd, J=2.2, 0.9 Hz, 1H), 5.51 (s, 2H), 5.41 (s, 2H), 2.27 (s, 3H).

Example 1018: 2-((4-((3-(benzofuran-6-yl)-2-methylbenzyl)oxy)-5-chloro-2-((5-cyanopyridin-3-yl)methoxy)benzyl) amino)-2-methylpropanoic acid

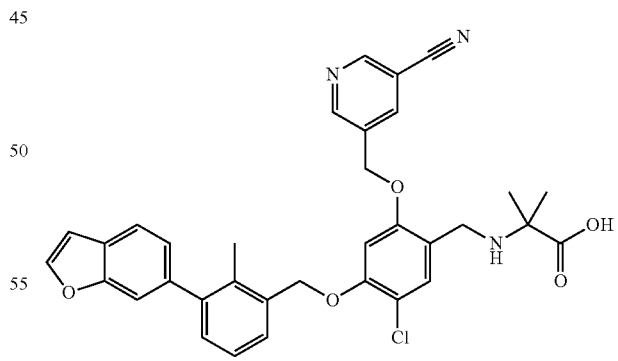

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile: water with 10 mM ammonium acetate at a gradient of 20-60% B over 15 minutes with a 5-minute hold at 100% B at a flow rate of 20 mL/minute. Fractions containing the desired product were combined and dried via centrifugal evaporation. The yield of the product was 4.9 mg (11% yield), and its estimated purity by LCMS analysis was 98%. $^1$H NMR (500 MHz, DMSO-6) δ 9.02 (d, J=15.4 Hz, 2H), 8.51 (br. s., 1H), 8.02 (br. s., 1H), 7.73 (d, J=7.7 Hz, 1H), 7.58 (s, 1H), 7.53 (br. s., 1H), 7.48 (m, 1H), 7.32-7.24 (m, 2H), 7.20 (d, J=7.7 Hz, 1H), 7.13 (br. s., 1H), 7.02 (br. s., 1H), 5.33 (m, 4H), 3.92 (s, 2H), 2.25 (s, 3H), 1.27 (s, 6H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.85 min; ESI-MS (+) m/z=596.5 (M+H), ESI-MS(−) m/z=594.6 (M−H).

Analysis condition 2: Retention time=2.86 min; ESI-MS (+) m/z=596.5 (M+H), ESI-MS(−) m/z=594.6 (M−H).

Example 1019: (R)-2-((4-((3-(benzofuran-6-yl)-2-methylbenzyl)oxy)-5-chloro-2-((5-cyanopyridin-3-yl)methoxy) benzyl)amino)-3-hydroxy-2-methylpropanoic acid

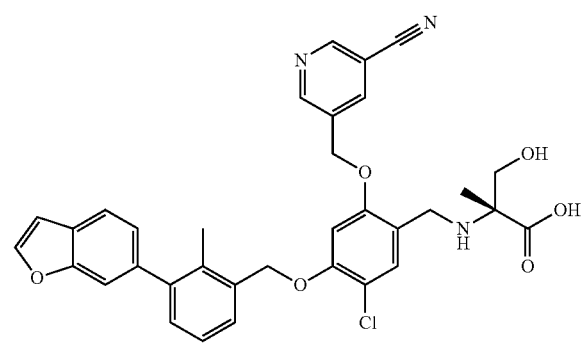 [SMILES: Cc1c(COc2cc(OCc3cncc(C#N)c3)c(CN[C@](C)(CO)C(=O)O)cc2Cl)cccc1-c1ccc2ccoc2c1]

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 10-50% B over 15 minutes with a 5-minute hold at 100% B at a flow rate of 20 mL/minute. The material was further purified via preparative LC/MS using the following conditions: Waters XBridge 5 μm C18, 19×200 mm where mobile phase A was 5:95 methanol: water with 10 mM ammonium acetate and mobile phase B was 95:5 methanol: water with 10 mM ammonium acetate at a gradient of 45-85% B over 15 minutes with a 5-minute hold at 100% B at a flow rate of 20 mL/minute. Fractions containing the desired product were combined and dried via centrifugal evaporation. The yield of the product was 8.2 mg (18% yield), and its estimated purity by LCMS analysis was 98%. $^1$H NMR (500 MHz, DMSO-d$_6$) δ 9.03 (s, 1H), 8.98 (s, 1H), 8.50 (s, 1H), 8.01 (s, 1H), 7.72 (d, J=7.9 Hz, 1H), 7.55 (s, 1H), 7.51 (s, 1H), 7.47 (d, J=6.1 Hz, 1H), 7.32-7.22 (m, 2H), 7.18 (d, J=7.9 Hz, 1H), 7.12 (s, 1H), 7.00 (s, 1H), 5.36 (s, 2H), 5.29 (s, 2H), 3.99 (br. s., 2H), 3.88 (m, 1H), 3.56 (m, 1H), 2.24 (s, 3H), 1.24 (s, 3H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.81 min; ESI-MS (+) m/z=612.6 (M+H), ESI-MS(−) m/z=610.6 (M−H).

Analysis condition 2: Retention time=2.85 min; ESI-MS (+) m/z=612.5 (M+H), ESI-MS(−) m/z=610.5 (M−H).

Example 1020: (S)-1-(4-((3-(benzofuran-6-yl)-2-methylbenzyl)oxy)-5-chloro-2-((5-cyanopyridin-3-yl)methoxy) benzyl)-2-methylpyrrolidine-2-carboxylic acid

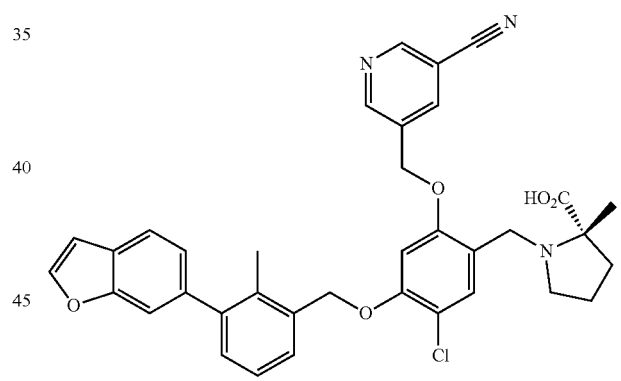

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 20-60% B over 15 minutes with a 5-minute hold at 100% B at a flow rate of 20 mL/minute. The material was further purified via preparative LC/MS using the following conditions: Waters XBridge 5 μm C18, 19×200 mm where mobile phase A was 5:95 methanol: water with 10 mM ammonium acetate and mobile phase B was 95:5 methanol: water with 10 mM ammonium acetate at a gradient of 40-80% B over 15 minutes with a 5-minute hold at 100% B at a flow rate of 20 mL/minute. Fractions containing the desired product were combined and dried via centrifugal evaporation. The yield of the product was 7.3 mg (15% yield), and its estimated purity by LCMS analysis was 96%. $^1$H NMR (500 MHz, DMSO-d$_6$) δ 9.03-8.95 (m, 2H), 8.45

(s, 1H), 8.01 (s, 1H), 7.72 (d, J=8.1 Hz, 1H), 7.52 (s, 1H), 7.48 (d, J=6.2 Hz, 1H), 7.42 (s, 1H), 7.32-7.23 (m, 2H), 7.19 (d, J=7.7 Hz, 1H), 7.12 (s, 1H), 7.00 (s, 1H), 5.38 (s, 2H), 5.27 (s, 2H), 3.82 (br. s., 2H), 2.90-2.77 (m, 2H), 2.25 (s, 3H), 2.16 (m, 1H), 1.79-1.59 (m, 3H), 1.30 (s, 3H).

Two analytical LC/MS injections were used to determine the final purity.

Injection 1 conditions: Waters Acquity UPLC BEH 1.7 µm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 µm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.95 min; ESI-MS (+) m/z=622.6 (M+H).

Analysis condition 2: Retention time=2.90 min; ESI-MS (+) m/z=622.6 (M+H).

Intermediate: (3-(benzo[d]thiazol-5-yl)-2-methylphenyl)methanol

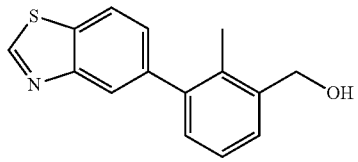

The crude product was purified on silica gel using 10-60% ethylacetate/hexane to give 0.71 g of (3-(benzo[d]thiazol-5-yl)-2-methylphenyl)methanol (98% yield) as a white solid.

$^1$H NMR (400 MHz, CDCl$_3$) δ 9.06 (s, 1H), 8.07 (d, J=1.2 Hz, 1H), 8.01 (d, J=8.3 Hz, 1H), 7.45 (dd, J=7.1, 1.5 Hz, 1H), 7.41 (dd, J=8.3, 1.7 Hz, 1H), 7.34-7.28 (m, 2H), 4.81 (d, J=5.6 Hz, 2H), 2.31-2.25 (s, 3H).

Intermediate: 4-((3-(benzo[d]thiazol-5-yl)-2-methylbenzyl)oxy)-5-chloro-2-hydroxybenzaldehyde

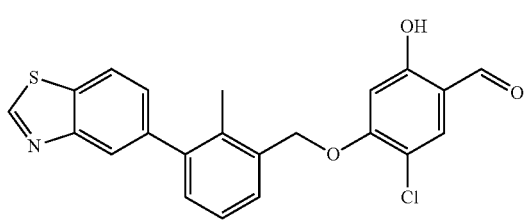 [SMILES: Cc1c(COc2cc(O)c(C=O)cc2Cl)cccc1-c1ccc2scnc2c1]

The crude product was purified on silica gel using 0-60% ethylacetate/hexane to give 0.234 g of 4-((3-(benzo[d]thiazol-5-yl)-2-methylbenzyl)oxy)-5-chloro-2-hydroxybenzaldehyde (21% yield) as a yellow powder. The LC/MS data was obtained on a Shimadzu analytical LC/Micromass Platform LC (ESI+) at 220 nm using the following set of conditions: Phenomenex Luna 3 □m C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

LCMS Rt=2.053 min., m/z 410.3 (M+H). $^1$H NMR (500 MHz, DMSO-d$_6$) δ 10.05 (s, 1H), 9.47 (s, 1H), 8.26 (d, J=8.4 Hz, 1H), 8.01 (d, J=1.4 Hz, 1H), 7.73 (s, 1H), 7.55 (dd, J=7.2, 1.7 Hz, 1H), 7.45 (dd, J=8.3, 1.7 Hz, 1H), 7.40-7.31 (m, 2H), 6.89 (s, 1H), 5.36 (s, 2H), 2.26 (s, 3H).

Intermediate: 5-((5-((3-(benzo[d]thiazol-5-yl)-2-methylbenzyl)oxy)-4-chloro-2-formylphenoxy)methyl)nicotinonitrile

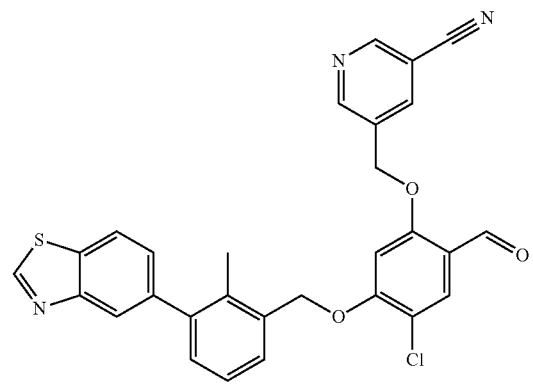 [SMILES: Cc1c(COc2cc(OCc3cncc(C#N)c3)c(C=O)cc2Cl)cccc1-c1ccc2scnc2c1]

231 mgs of 5-((5-((3-(benzo[d]thiazol-5-yl)-2-methylbenzyl)oxy)-4-chloro-2-formylphenoxy) methyl)nicotinonitrile was obtained (81% yield) as a yellow solid. The LC/MS data was obtained on a Shimadzu analytical LC/Micromass Platform LC (ESI+) at 220 nm using the following set of conditions: Phenomenex Luna 3 □m C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=2.037 min., m/z 526.3 (M+H). $^1$H NMR (500 MHz, DMSO-d$_6$) δ 10.25 (s, 1H), 9.47 (s, 1H), 9.05 (m, 2H), 8.57 (t, J=2.0 Hz, 1H), 8.26 (d, J=8.4 Hz, 1H), 8.02 (d, J=1.3 Hz, 1H), 7.75 (s, 1H), 7.62-7.54 (m, 1H), 7.47 (dd, J=8.3, 1.7 Hz, 1H), 7.38-7.35 (m, 2H), 7.30 (s, 1H), 5.51 (s, 2H), 5.46 (s, 2H), 2.29 (s, 3H).

Example 1021: (R)-2-((4-((3-(benzo[d]thiazol-5-yl)-2-methylbenzyl)oxy)-5-chloro-2-((5-cyanopyridin-3-yl)methoxy) benzyl)amino)-3-hydroxy-2-methylpropanoic acid

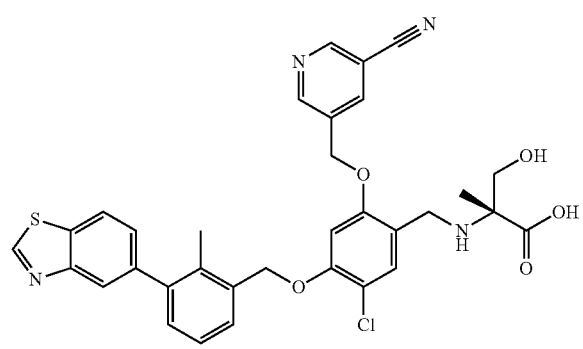

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 20-60% B over 15 minutes with a 5-minute hold at 100% B at a flow rate of 20 mL/minute. Fractions containing the desired product were combined and dried via centrifugal evaporation. The yield of the product was 5.8 mg (12% yield), and its estimated purity by LCMS analysis was 99%. $^1$H NMR (500 MHz, DMSO-$d_6$) δ 9.45 (s, 1H), 9.04 (s, 1H), 8.99 (s, 1H), 8.51 (s, 1H), 8.24 (d, J=8.1 Hz, 1H), 8.00 (s, 1H), 7.56-7.49 (m, 2H), 7.44 (d, J=8.1 Hz, 1H), 7.31 (m, 2H), 7.13 (s, 1H), 5.37 (s, 2H), 5.31 (s, 2H), 3.97 (s, 2H), 3.62 (m, 1H), 3.54 (m, 1H), 2.26 (s, 3H), 1.24 (s, 3H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.62 min; ESI-MS (+) m/z=629.5 (M+H), ESI-MS(−) m/z=627.5 (M−H).

Analysis condition 2: Retention time=2.65 min; ESI-MS (+) m/z=629.5 (M+H), ESI-MS(−) m/z=627.5 (M−H).

Example 1022: 2-((4-((3-(benzo[d]thiazol-5-yl)-2-methylbenzyl)oxy)-5-chloro-2-((5-cyanopyridin-3-yl)methoxy) benzyl)amino)-2-methylpropanoic acid

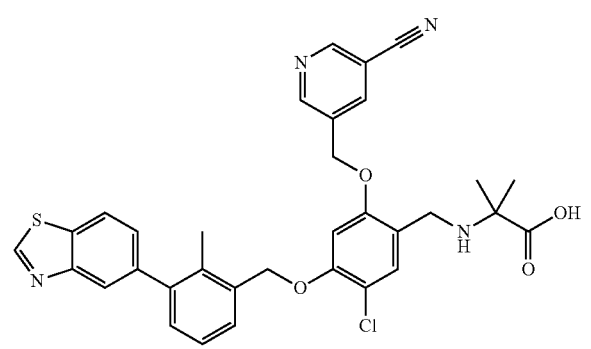 [SMILES: Cc1c(COc2cc(OCc3cncc(C#N)c3)c(CNC(C)(C)C(=O)O)cc2Cl)cccc1-c1ccc2scnc2c1]

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 30-70% B over 15 minutes with a 5-minute hold at 100% B at a flow rate of 20 mL/minute. Fractions containing the desired product were combined and dried via centrifugal evaporation. The yield of the product was 3.8 mg (8% yield), and its estimated purity by LCMS analysis was 100%. $^1$H NMR (500 MHz, DMSO-$d_6$) δ 9.46 (s, 1H), 9.04 (s, 1H), 9.01 (s, 1H), 8.53 (s, 1H), 8.25 (d, J=8.1 Hz, 1H), 8.00 (s, 1H), 7.58 (s, 1H), 7.56-7.49 (m, 1H), 7.44 (d, J=8.4 Hz, 1H), 7.32 (m, 2H), 7.14 (s, 1H), 5.34 (m, 4H), 3.90 (s, 2H), 2.27 (s, 3H), 1.27 (s, 6H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.65 min; ESI-MS (+) m/z=613.5 (M+H), ESI-MS(−) m/z=611.5 (M−H).

Analysis condition 2: Retention time=2.65 min; ESI-MS (+) m/z=613.5 (M+H), ESI-MS(−) m/z=611.5 (M−H).

Example 1023: (S)-1-(4-((3-(benzo[d]thiazol-5-yl)-2-methylbenzyl)oxy)-5-chloro-2-((5-cyanopyridin-3-yl)methoxy) benzyl)-2-methylpyrrolidine-2-carboxylic acid

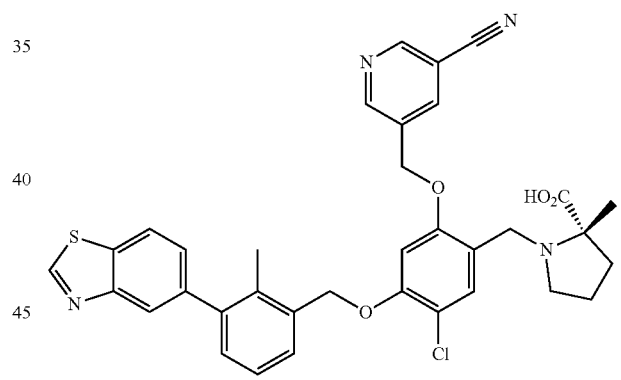

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 25-65% B over 15 minutes with a 5-minute hold at 100% B at a flow rate of 20 mL/minute. Fractions containing the desired product were combined and dried via centrifugal evaporation. The yield of the product was 9.7 mg (20% yield), and its estimated purity by LCMS analysis was 100%. $^1$H NMR (500 MHz, DMSO-$d_6$) δ 9.45 (s, 1H), 9.00 (m, 2H), 8.45 (s, 1H), 8.24 (d, J=8.4 Hz, 1H), 8.00 (s, 1H), 7.56-7.48 (m, 1H), 7.44 (d, J=8.1 Hz, 1H), 7.41 (s, 1H), 7.33-7.28 (m, 2H), 7.13 (s, 1H), 5.38 (s, 2H), 5.28 (s, 2H), 3.85-3.74 (m, 2H), 2.82 (m, 2H), 2.26 (s, 3H), 2.21-2.12 (m, 1H), 1.79-1.60 (m, 3H), 1.29 (s, 3H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.78 min; ESI-MS (+) m/z=639.6 (M+H), ESI-MS(−) m/z=637.6 (M−H).

Analysis condition 2: Retention time=2.68 min; ESI-MS (+) m/z=639.6 (M+H), ESI-MS(−) m/z=637.5 (M−H).

Intermediate: 5-((5-((3-(1H-benzo[d]imidazol-5-yl)-2-methylbenzyl)oxy)-4-chloro-2-formylphenoxy)methyl) nicotinonitrile

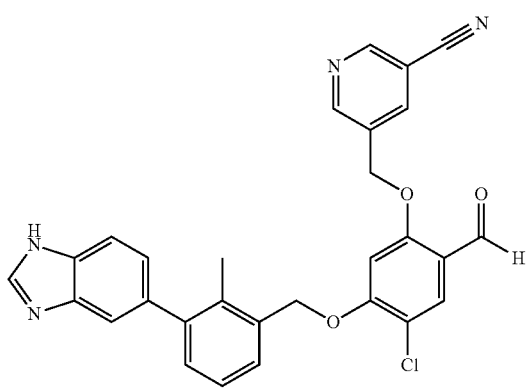 [SMILES: Cc1c(COc2cc(OCc3cncc(C#N)c3)c(C=O)cc2Cl)cccc1-c1ccc2[nH]cnc2c1]

To a small sealed tube was added 5-bromo-1H-benzimidazole (22.79 mg, 0.116 mmol), dioxane (1446 μl), water (482 μl), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (50 mg, 0.096 mmol), cesium carbonate (94 mg, 0.289 mmol), and [1,1'-bis(diphenylphosphino)ferrocene]dichloropalladium(II) (2.82 mg, 3.86 μmol). The vial was sealed and the mixture was de-gassed/flushed with nitrogen ×3. The mixture was heated at 90° C. overnight. The mixture was cooled and concentrated to near dryness, taken up in 4 mL of acetonitrile and purified using a Shimadzu preparative HPLC employing acetonitrile/water/0.1% trifluoroacetic acid where solvent A was 10% acetonitrile/90% water/0.1% trifluoroacetic acid and solvent B was 10% water/90% acetonitrile/0.1% trifluoroacetic acid with a XTERRA 5μ C18 19×100 mm column at a gradient of 30-100% B and a flow rate of 25 mL/min. over 15 minutes with a 10 minute hold to give 21.4 mgs (36% yield) of 5-((5-((3-(1H-benzo[d]imidazol-5-yl)-2-methylbenzyl)oxy)-4-chloro-2-formylphenoxy)methyl)nicotinonitrile, TFA salt. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.472 min., m/z 509.4 (M+H).

Example 1024: (R)-2-((4-((3-(1H-benzo[d]imidazol-5-yl)-2-methylbenzyl)oxy)-5-chloro-2-((5-cyanopyridin-3-yl) methoxy)benzyl)amino)-3-hydroxy-2-methylpropanoic acid

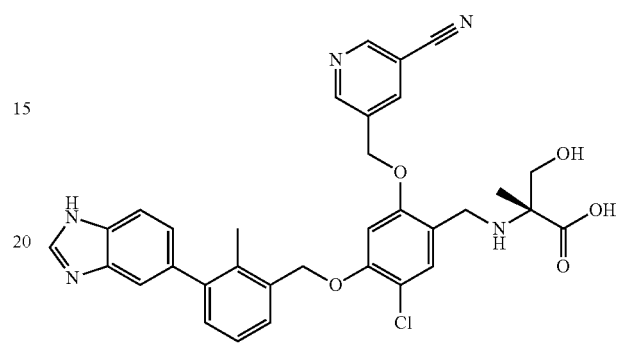

To a vial was added DMF (1 mL), acetic acid (0.111 mL), 5-((5-((3-(1H-benzo[d]imidazol-5-yl)-2-methylbenzyl)oxy)-4-chloro-2-formylphenoxy)methyl)nicotinonitrile, TFA (21.4 mg, 0.034 mmol), 2-methyl-D-serine (12.28 mg, 0.103 mmol), and borane-2-picoline complex (5.51 mg, 0.052 mmol). The vial was capped and the mixture shaken overnight at room temperature. The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile:water with 10 mM ammonium acetate at a gradient of 15-55% B over 15 minutes with a 5-minute hold at 100% B at a flow rate of 20 mL/minute. Fractions containing the desired product were combined and dried via centrifugal evaporation. The yield of the product was 7 mg (33% yield), and its estimated purity by LCMS analysis was 98%. $^1$H NMR (500 MHz, DMSO-$d_6$) δ 9.04 (s, 1H), 9.00 (s, 1H), 8.52 (s, 1H), 8.26 (s, 1H), 7.66 (d, J=8.1 Hz, 1H), 7.56 (s, 1H), 7.53-7.43 (m, 2H), 7.27 (m, 2H), 7.18-7.09 (m, 2H), 5.37 (s, 2H), 5.31 (s, 2H), 3.99 (s, 2H), 3.64 (m, 1H), 3.57 (m, 1H), 2.25 (s, 3H), 1.25 (s, 3H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.31 min; ESI-MS (+) m/z=612.6 (M+H), ESI-MS(−) m/z=610.6 (M−H).

Analysis condition 2: Retention time=2.32 min; ESI-MS (+) m/z=612.5 (M+H), ESI-MS(−) m/z=610.5 (M−H).

Intermediate: 2-(5-bromo-1H-benzo[d]imidazol-1-yl)-N,N-dimethylethanamine and 2-(6-bromo-1H-benzo[d]imidazol-1-yl)-N,N-dimethylethanamine

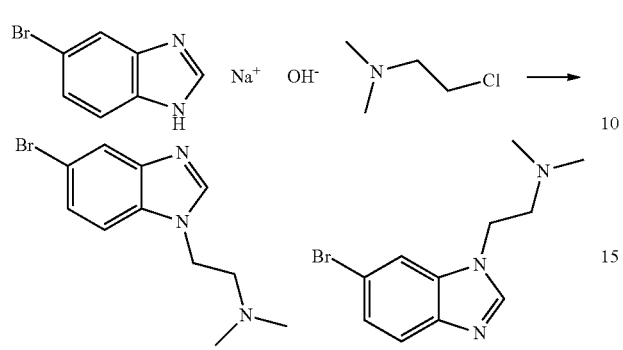

To a RBF was added DMSO (3 mL), 2-chloro-N,N-dimethylethanamine HCl salt (219 mg, 1.523 mmol), and 5-bromo-1H-benzimidazole (250 mg, 1.269 mmol). The mixture was cooled to 0° C. and powdered anhydrous sodium hydroxide (228 mg, 5.71 mmol) was added. The RBF was sealed and the mixture was allowed to warm to room temperature and stirred overnight. The crude mixture was diluted with 10 mL water and pushed through a 6 g Waters HLB cartridge. The cartridge was flushed with 30 mL×2 of additional water. The product was eluted with 60 mL of methanol then evaporated to give 351.6 mgs (93% yield) of a 1:1 mixture of 2-(5-bromo-1H-benzo[d]imidazol-1-yl)-N,N-dimethylethanamine and 2-(6-bromo-1H-benzo[d]imidazol-1-yl)-N,N-dimethylethanamine. The LC/MS data was obtained on a Shimadzu analytical LC/Micromass Platform LC (ESI+) at 220 nm using the following set of conditions: Waters Aquity BEH 1.7 µm C18, 2×50 mm column, with a gradient of 2-98% B (B=1000% HPLC grade acetonitrile/0.05% trifluoroacetic acid), (A=100% HPLC grade water/0.05% trifluoroacetic acid), in 1.5 minutes with a 1 minute hold at a rate of 0.8 mL/minute. LCMS Rt=0.694 min., m/z 267.9 & 269.9 (M+H). $^1$H NMR (500 MHz, CDCl$_3$) δ 7.98 (m, 1H), 7.94 (d, J=1.7 Hz, 0.5H), 7.66 (m, 0.5H), 7.56 (d, J=1.7 Hz, 0.5H), 7.42-7.35 (m, 1H), 7.27 (m, 0.5H), 4.21 (m, 2H), 2.71 (m, 2H), 2.33-2.25 (m, 6H).

Intermediate: 5-((4-chloro-5-((3-(1-(2-(dimethylamino)ethyl)-1H-benzo[d]imidazol-6-yl)-2-methylbenzyl)oxy)-2-formylphenoxy)methyl)nicotinonitrile and 5-((4-chloro-5-((3-(1-(2-(dimethylamino)ethyl)-1H-benzo[d]imidazol-5-yl)-2-methylbenzyl)oxy)-2-formylphenoxy)methyl) nicotinonitrile

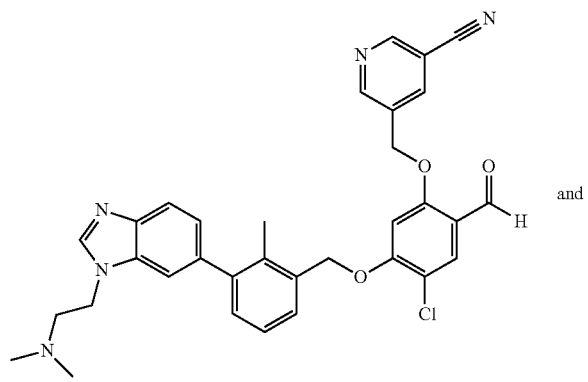 and 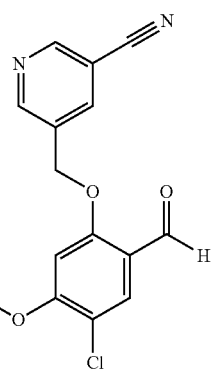

To a sealed tube was added THF (3614 µl), water (1205 µl), a 1:1 mixture of 2-(5-bromo-1H-benzo[d]imidazol-1-yl)-N,N-dimethylethanamine and 2-(6-bromo-1H-benzo[d]imidazol-1-yl)-N,N-dimethylethanamine (110 mg, 0.370 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (120 mg, 0.231 mmol), potassium phosphate (147 mg, 0.694 mmol), and Second Generation Xphos precatalyst (14.56 mgs, 0.019 mmol). The vessel was sealed, the mixture de-gassed/flushed with nitrogen and then heated overnight at 75° C. The crude reaction mixture was taken up in 8 mL of 1:1 DMF/methanol and purified using a Shimadzu preparative HPLC employing acetonitrile/water/0.1% trifluoroacetic acid where solvent A was 10% acetonitrile/90% water/0.1% trifluoroacetic acid and solvent B was 10% water/90% acetonitrile/0.1% trifluoroacetic acid with a XTERRA 5µ C18 30×100 mm column at a gradient of 20-100% B and a flow rate of 40 mL/min. over 15 minutes with a 10 minute hold to give 98.7 mgs of a 1:1 mixture of 5-((4-chloro-5-((3-(1-(2-(dimethylamino)ethyl)-1H-benzo[d]imidazol-6-yl)-2-methylbenzyl)oxy)-2-formylphenoxy)methyl)nicotinonitrile, 2TFA and 5-((4-chloro-5-((3-(1-(2-(dimethylamino)ethyl)-1H-benzo[d]imidazol-5-yl)-2-methylbenzyl)oxy)-2-formylphenoxy)methyl) nicotinonitrile, 2TFA. The LC/MS data was obtained on a Shimadzu analytical LC/Micromass Platform LC (ESI+) at 220 nm using the following set of conditions: Waters Aquity BEH 1.7 µm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 1.5 minutes with a 0.5 minute hold at a rate of 0.8 mL/minute.

LCMS Rt=0.964 min., m/z 580.30 (M+H).

Example 1025: (R)-2-((5-chloro-2-((5-cyanopyridin-3-yl)methoxy)-4-((3-(1-(2-(dimethylamino)ethyl)-1H-benzo[d]imidazol-6-yl)-2-methylbenzyl)oxy)benzyl)amino)-3-hydroxypropanoic acid and (R)-2-((5-chloro-2-((5-cyanopyridin-3-yl)methoxy)-4-((3-(1-(2-(dimethylamino)ethyl)-1H-benzo[d]imidazol-5-yl)-2-methylbenzyl)oxy)benzyl)amino)-3-hydroxypropanoic acid

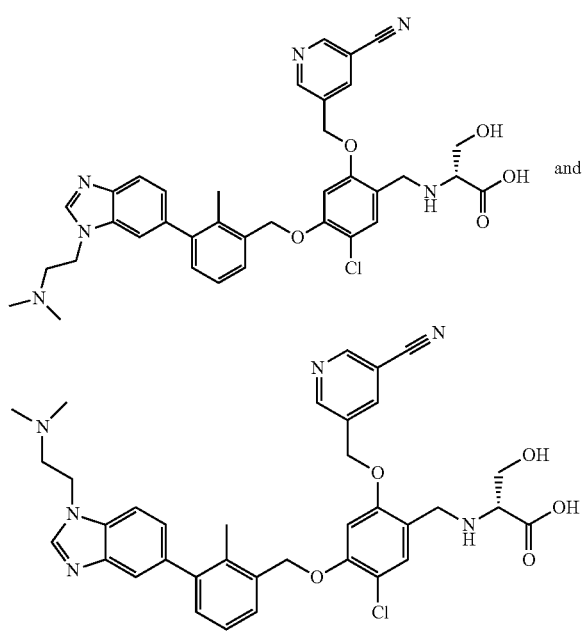

To a vial was added DMF (1 mL), acetic acid (0.100 mL), borane-2-picoline complex (3.97 mg, 0.037 mmol), D-serine (7.80 mg, 0.074 mmol), and a 1:1 mixture of 5-((4-chloro-5-((3-(1-(2-(dimethylamino)ethyl)-1H-benzo[d]imidazol-6-yl)-2-methylbenzyl)oxy)-2-formylphenoxy)methyl) nicotinonitrile, 2 TFA and 5-((4-chloro-5-((3-(1-(2-(dimethylamino)ethyl)-1H-benzo[d]imidazol-5-yl)-2-methylbenzyl)oxy)-2-formylphenoxy)methyl) nicotinonitrile, 2 TFA. The vial was capped and the mixture shaken overnight at room temperature. The crude material was purified via preparative LC/MS using the following conditions: Waters XBridge 5 μm C18, 19×200 mm where mobile phase A was 5:95 methanol: water with 10 mM ammonium acetate and mobile phase B was 95:5 methanol: water with 10 mM ammonium acetate at a gradient of 45-85% B over 20 minutes with a 5-minute hold at 100% B at a flow rate of 20 mL/minute. Fractions containing the desired product were combined and dried via centrifugal evaporation to give 5.3 mgs (31% yield, 98% purity) of a 1:1 mixture of regioisomers. $^1$H NMR (500 MHz, DMSO-d$_6$) δ 9.02 (m, 2H), 8.52 (br. s., 1H), 8.30-8.23 (m, 1H), 7.73-7.65 (m, 1H), 7.58-7.52 (m, 1H), 7.50 (m, 2H), 7.35-7.25 (m, 2H), 7.20 (d, J=7.3 Hz, 0.5H), 7.15 (m, 1.5H), 5.42-5.33 (m, 2H), 5.29 (br. s., 2H), 4.36 (m, 2H), 4.02-3.89 (m, 2H), 3.63 (m, 2H), 3.07 (m, 1H), 2.71-2.62 (m, 2H), 2.31-2.12 (m, 9H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3.5 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3.5 minutes with a 0.75-minute hold at 100% B at a flow rate of 1.0 mL/minute at a UV wavelength of 220 nm.

Analysis condition 1: Retention time=1.30 min; ESI-MS (+) m/z=669.1 (M+H), ESI-MS(−) m/z=667.2 (M−H).

Analysis condition 2: Retention time=2.89 min; ESI-MS (+) m/z=669.1 (M+H), ESI-MS(−) m/z=667.2 (M−H).

Example 1026: 2-((5-chloro-2-((5-cyanopyridin-3-yl)methoxy)-4-((3-(1-(2-(dimethylamino)ethyl)-1H-benzo[d]imidazol-6-yl)-2-methylbenzyl)oxy)benzyl)amino)-2-methylpropanoic acid and 2-((5-chloro-2-((5-cyanopyridin-3-yl)methoxy)-4-((3-(1-(2-(dimethylamino)ethyl)-1H-benzo[d]imidazol-5-yl)-2-methylbenzyl)oxy)benzyl)amino)-2-methylpropanoic acid

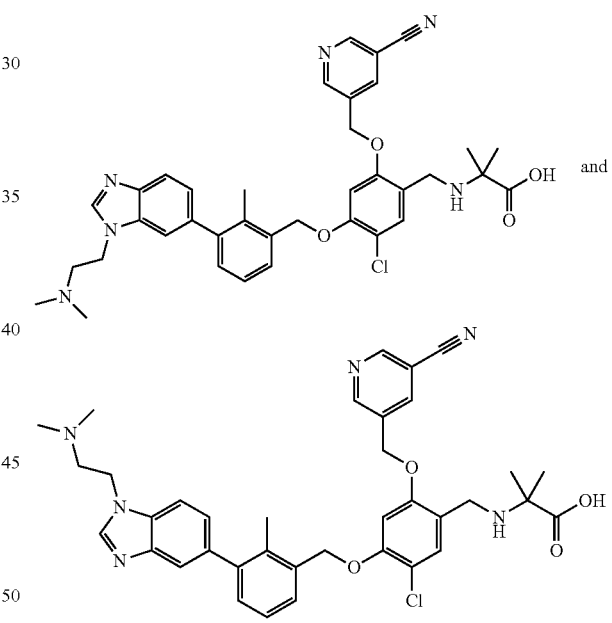

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 10-50% B over 25 minutes with a 5-minute hold at 100% B at a flow rate of 20 mL/minute. Fractions containing the desired product were combined and dried via centrifugal evaporation to give 4.2 mgs (25% yield, 97% purity) of a 1:1 mixture of regioisomers. $^1$H NMR (500 MHz, DMSO-d$_6$) δ 9.03 (m, 2H), 8.53 (s, 1H), 8.30-8.23 (m, 1H), 7.73-7.66 (m, 1H), 7.61-7.52 (m, 2H), 7.49 (m, 1H), 7.35-7.26 (m, 2H), 7.22-7.11 (m, 2H), 5.34 (m, 4H), 4.41-4.32 (m, 2H), 3.88 (s, 2H), 2.73-2.62 (m, 2H), 2.36-2.05 (m, 9H), 1.26 (s, 6H).

Two analytical LC/MS injections were used to determine the final purity.

Injection 1 conditions: Waters Acquity UPLC BEH 1.7 µm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3.5 minutes with a 0.75-minute hold at 100% B at a flow rate of 1.0 mL/minute at a UV wavelength of 220 nm.

Injection 2 conditions: Waters Acquity UPLC BEH 1.7 µm C18, 2.1×50 mm where mobile phase A was 5:95 methanol:water with 10 mM ammonium acetate; mobile phase B was 95:5 methanol:water with 10 mM ammonium acetate at a temperature of 50° C. at a gradient of 0-100% B over 3.5 minutes with a 0.75-minute hold at 100% B at a flow rate of 1.0 mL/minute at a UV wavelength of 220 nm.

Analysis condition 1: Retention time=1.49 min; ESI-MS (+) m/z=667.7 (M+H), ESI-MS(−) m/z=665.7 (M−H).

Analysis condition 2: Retention time=2.43 min; ESI-MS (+) m/z=667.8 (M+H), ESI-MS(−) m/z=665.3 (M−H).

Intermediate: (R)-1-(2-(5-bromobenzo[d]oxazol-2-yl)ethyl)pyrrolidin-3-ol acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.737 min., m/z 280.1 & 282.1 (M+H). $^1$H NMR (500 MHz, DMSO-d$_6$) δ 10.19 (br. s., 1H), 9.40 (s, 1H), 8.12 (d, J=2.2 Hz, 1H), 7.08 (dd, J=8.5, 2.2 Hz, 1H), 6.82 (d, J=8.5 Hz, 1H), 3.85 (t, J=6.2 Hz, 2H), 2.93 (t, J=6.2 Hz, 2H).

To a small sealed tube was added N-(5-bromo-2-hydroxyphenyl)-3-chloropropanamide (153 mg, 0.55 mmol), and polyphosphoric acid (5 mL). The tube was sealed and the mixture was heated for 4 hours at 130° C. The mixture was cooled to 0° C. and cold ammonium hydroxide was dripped in until pH 7. The product was diluted with 30 mL of ethyl acetate, extracted, washed with 15 mL of 1.5M potassium phosphate, water, brine, dried over magnesium sulfate and evaporated to give 100.6 mgs (70% yield) of a 1:1 mixture of 5-bromo-2-(2-chloroethyl)benzo[d]oxazole and 5-bromo-2-vinylbenzo[d]oxazole. The LC/MS data was obtained on a Shimadzu analytical LC/Micromass Platform LC (ESI+) at 220 nm using the following set of conditions: Phenomenex Luna 3 µm C18, 2×30 mm column, with a gradient of 0-100% B (B=90% HPLC grade acetonitrile/0.1% trifluo-

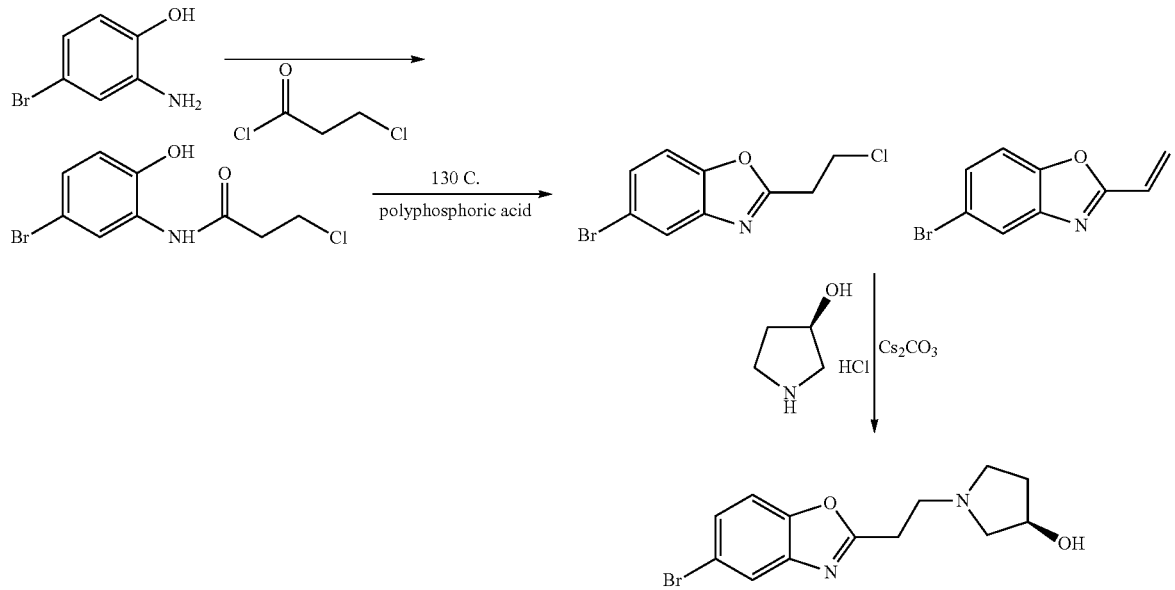

To 2-amino-4-bromophenol (980 mg, 5.21 mmol) in dichloromethane (DCM) (20 mL) was added, dropwise at room temperature, 3-chloropropionyl chloride (0.500 mL, 5.21 mmol). The pink mixture was stirred at room temperature for 1.5 hours. To the product mixture was added 5 mL of DCM and 0.5 eq (0.250 mL, 2.61 mmol) of 3-chloropropionyl chloride. Stirring was continued for 30 minutes. To the crude product was added, with stirring, 5 mL of saturated aqueous sodium bicarbonate. The mixture was stirred for 5 minutes then transferred to a separation funnel. The product was extracted, washed with brine, dried over magnesium sulfate, filtered and evaporated to give 1.46 g (99% yield) of N-(5-bromo-2-hydroxyphenyl)-3-chloropropanamide. The LC/MS data was obtained on a Shimadzu analytical LC/Micromass Platform LC (ESI+) at 220 nm using the following set of conditions: Phenomenex Luna 3 µm C18, 2×30 mm column, with a gradient of 0-100% B (B=90% HPLC grade roacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.750 min., m/z 259.9 & 261.9 (M+H) for the chloroethyl product. $^1$H NMR (500 MHz, CDCl$_3$) δ 7.85 (m, 1H), 7.46 (m, 1H), 7.40 (m, 1H), 6.75 (dd, J=17.5, 11.2 Hz, 0.5H), 6.50 (d, J=17.5 Hz, 0.5H), 5.91 (d, J=11.2 Hz, 0.5H), 4.01 (t, J=6.9 Hz, 1H), 3.42 (t, J=6.9 Hz, 1H).

To the 1:1 mixture of 5-bromo-2-(2-chloroethyl)benzo[d]oxazole (50 mgs, 0.192 mmol) and 5-bromo-2-vinylbenzo[d]oxazole (50 mgs, 0.223 mmol) was added DMF (5 mL), cesium carbonate (300 mg, 0.921 mmol), and (R)-pyrrolidin-3-ol hydrochloride (85 mg, 0.691 mmol). The mixture was stirred at 50° C. for 20 hrs. The mixture was cooled and transferred to a separation funnel. To the crude product was added 10 mL of water and 25 mL of ethyl acetate, the product extracted, washed with brine, dried over magnesium sulfate, filtered and evaporated to give 60.8 mgs (85% yield) of (R)-1-(2-(5-bromobenzo[d]oxazol-2-yl)ethyl)pyrrolidin-3-ol. The LC/MS data was obtained on a Shimadzu analytical LC/Micromass Platform LC (ESI+) at 220 nm using the following set of conditions: Phenomenex Luna 3 □m C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

LCMS Rt=1.218 min., m/z 312.1 (M+H). $^1$H NMR (500 MHz, CDCl$_3$) δ 7.73 (m, 1H), 7.40-7.34 (m, 1H), 7.34-7.29 (m, 1H), 4.30 (m, 1H), 3.08 (m, 2H), 2.97 (m, 2H), 2.77 (m, 1H), 2.71-2.57 (m, 2H), 2.37 (m, 1H), 2.10 (m, 1H), 1.70 (m, 1H).

Example 1027: (R)-5-((4-chloro-2-formyl-5-((3-(2-(2-(3-hydroxypyrrolidin-1-yl)ethyl)benzo[d]oxazol-5-yl)-2-methylbenzyl)oxy) phenoxy)methyl)nicotinonitrile

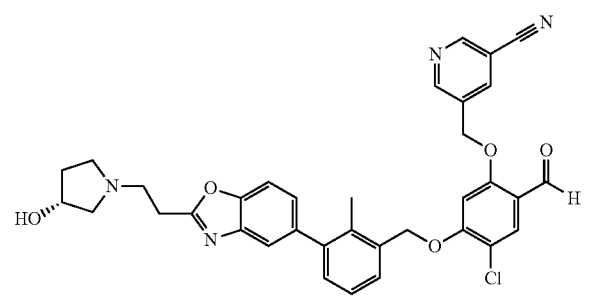 [SMILES: Cc1c(COc2cc(OCc3cncc(C#N)c3)c(C=O)cc2Cl)cccc1-c1ccc2oc(CCN3CC[C@@H](O)C3)nc2c1]

To a sealed tube was added 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (79 mg, 0.152 mmol), THF (4.5 mL), water (1.5 mL), (R)-1-(2-(5-bromobenzo[d]oxazol-2-yl)ethyl)pyrrolidin-3-ol (84 mg, 0.228 mmol), potassium phosphate tribasic (64.6 mg, 0.305 mmol), and 2nd Generation XPhos Precatalyst (5.99 mg, 7.61 μmol). The vessel was sealed, the mixture de-gassed/flushed with nitrogen then heated overnight at 75° C. The reaction mixture was cooled, concentrated to an oil, diluted with ethyl acetate, washed with water, brine, dried over sodium sulfate, filtered, and evaporated. The crude reaction mixture was taken up in 8 mL of 1:1 DMF/methanol and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters XTERRA 5 μm C18 30×100 mm column at a gradient of 20-100% B and a flow rate of 25 mL/min. over 10 minutes with a 10 minute hold to give 55.7 mgs (48% yield) of (R)-5-((4-chloro-2-formyl-5-((3-(2-(2-(3-hydroxypyrrolidin-1-yl)ethyl)benzo[d]oxazol-5-yl)-2-methylbenzyl)oxy) phenoxy)methyl)nicotinonitrile, TFA. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

LCMS rt=1.547 min., m/z 623.3 (M+H). $^1$H NMR (500 MHz, THF-d$_8$) δ 10.29 (m, 1H), 8.95 (s, 1H), 8.90 (s, 1H), 8.33 (s, 1H), 7.82 (m, 1H), 7.63-7.56 (m, 1H), 7.55-7.41 (m, 1H), 7.31-7.18 (m, 3H), 7.04 (m, 1H), 6.95-6.84 (m, 1H), 5.36 (m, 4H), 4.51-4.46 (m, 1H), 3.76 (m, 1H), 3.63-3.51 (m, 4H), 3.05 (t, J=7.2 Hz, 1H), 2.88 (s, 1H), 2.77 (s, 1H), 2.30 (m, 4H), 1.73 (m, 1H).

Example 1028: (R)-2-((5-chloro-2-((5-cyanopyridin-3-yl)methoxy)-4-((3-(2-(2-((R)-3-hydroxypyrrolidin-1-yl)ethyl)benzo[d]oxazol-5-yl)-2-methylbenzyl)oxy)benzyl)amino)-3-hydroxy-2-methylpropanoic acid

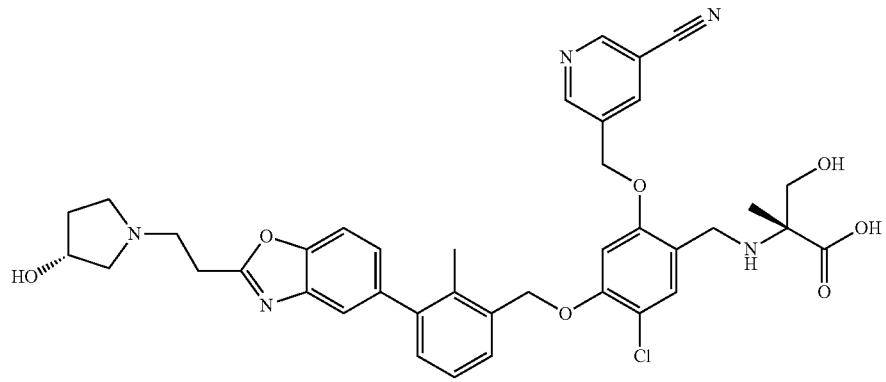 [SMILES: Cc1c(COc2cc(OCc3cncc(C#N)c3)c(CN[C@](C)(CO)C(=O)O)cc2Cl)cccc1-c1ccc2oc(CCN3CC[C@@H](O)C3)nc2c1]

To a vial was added DMF (1.3 mL), acetic acid (0.130 mL), (R)-5-((4-chloro-2-formyl-5-((3-(2-(2-(3-hydroxypyrrolidin-1-yl)ethyl)benzo[d]oxazol-5-yl)-2-methylbenzyl)oxy)phenoxy)methyl) nicotinonitrile, TFA (48.6 mg, 0.066 mmol), 2-Methyl-D-Serine (19.63 mg, 0.165 mmol), and borane-2-picoline complex (8.46 mg, 0.079 mmol). The vial was sealed and the mixture shaken at room temperature overnight. The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 20-60% B over 15 minutes with a 5-minute hold at 100% B at a flow rate of 20 mL/minute. Fractions containing the desired product were combined and dried via centrifugal evaporation. The yield of the product was 7.5 mg (16% yield), and its estimated purity by LCMS analysis was 100%. $^1$H NMR (500 MHz, DMSO-$d_6$) δ 9.03 (s, 1H), 9.00 (s, 1H), 8.50 (s, 1H), 7.73 (d, J=8.4 Hz, 1H), 7.58 (s, 1H), 7.55 (s, 1H), 7.49 (d, J=7.0 Hz, 1H), 7.33-7.23 (m, 3H), 7.13 (s, 1H), 5.36 (s, 2H), 5.30 (s, 2H), 4.22-4.13 (m, 1H), 3.94 (s, 2H), 3.61-3.58 (m, 1H), 3.52-3.50 (m, 1H), 3.16-3.08 (m, 2H), 2.96-2.87 (m, 2H), 2.80-2.73 (m, 1H), 2.62 (m, 1H), 2.50 (m, 1H), 2.36 (m, 1H), 2.23 (s, 3H), 2.00-1.91 (m, 1H), 1.51 (m, 1H), 1.22 (s, 3H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.43 min; ESI-MS (+) m/z=726.0 (M+H), ESI-MS(−) m/z=724.0 (M−H).

Analysis condition 2: Retention time=1.33 min; ESI-MS (+) m/z=725.9 (M+H), ESI-MS(−) m/z=724.0 (M−H).

Example 1029: (S)-1-(5-chloro-2-((5-cyanopyridin-3-yl)methoxy)-4-((3-(2-(2-((R)-3-hydroxypyrrolidin-1-yl)ethyl)benzo[d]oxazol-5-yl)-2-methylbenzyl)oxy)benzyl)piperidine-2-carboxylic acid acetonitrile: water with 0.1% trifluoroacetic acid acetonitrile: water with 0.1% TFA at a gradient of 15-55% B over 20 minutes with a 5-minute hold at 100% B at a flow rate of 20 mL/minute. Fractions containing the desired product were combined and dried via centrifugal evaporation. The yield of the product was 3.2 mg as a 2TFA salt, and its estimated purity by LCMS analysis was 96%. $^1$H NMR (500 MHz, DMSO-$d_6$) δ 9.01 (m, 2H), 8.46 (s, 1H), 7.74 (d, J=8.2 Hz, 1H), 7.60 (d, J=1.2 Hz, 1H), 7.52 (d, J=7.3 Hz, 1H), 7.44 (s, 1H), 7.34-7.25 (m, 3H), 7.14 (s, 1H), 5.35 (s, 2H), 5.28 (s, 2H), 4.18 (br. s., 1H), 3.80 (d, J=14.0 Hz, 1H), 3.63 (d, J=14.0 Hz, 1H), 3.13 (m, 4H), 2.98-2.87 (m, 3H), 2.79 (dd, J=9.8, 6.1 Hz, 1H), 2.65 (m, 1H), 2.38 (dd, J=9.5, 3.7 Hz, 1H), 2.33-2.27 (m, 1H), 2.25 (s, 3H), 1.95 (m, 1H), 1.86-1.68 (m, 2H), 1.50 (m, 4H), 1.41-1.34 (m, 1H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.468 min; ESI-MS (+) m/z=736.1 (M+H)

Analysis condition 2: Retention time=1.398 min; ESI-MS (+) m/z=736.1 (M+H)

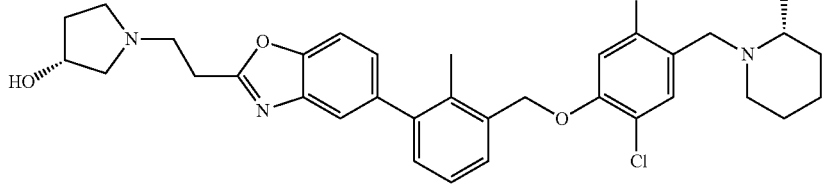

Example 1029 was prepared in a similar manner as Example 1028. The crude material was purified via preparative LC/MS using the following conditions: Waters XBridge 5 μm C18, 19×200 mm column where mobile phase A was 5:95 acetonitrile: water with 10 mM ammonium acetate and mobile phase B was 95:5 acetonitrile: water with 10 mM ammonium acetate at a gradient of 15-65% B over 25 minutes with a 5 minute hold at 100% B at a flow rate of 20 mL/minute. The material was further purified using the following conditions: Waters XBridge 5 μm C18, 19×200 mm where mobile phase A was 5:95 acetonitrile: water with 0.1% trifluoroacetic acid and mobile phase B was 95:5

Intermediate:
3-((6-bromopyridin-2-yl)oxy)propan-1-ol

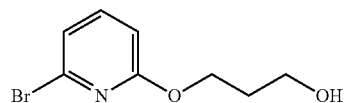 [SMILES: OCCCOc1cccc(Br)n1]

To a solution of 2,6-dibromopyridine (4.27 g, 18.03 mmol) and 5 eq. of 1,3-propanediol (6.47 mL, 90 mmol) in DMF (30 mL), at 0° C., was added portion-wise 60% sodium hydride in mineral oil (1.081 g, 27.0 mmol). The reaction was stirred for 10 minutes at 0° C., the ice bath was removed, and the mixture stirred for 2 hours at room temperature. The reaction mixture was re-cooled to 0° C. then quenched with 5 mL of brine. The product was extracted with ethyl acetate (50 mL×3), pushed through a plug of celite/sodium sulfate and evaporated overnight under a stream of nitrogen. The product was purified on silica gel using 0-70% ethyl acetate in hexanes to give 2.13 g of 3-((6-bromopyridin-2-yl)oxy)propan-1-ol (38% yield) as a colorless oil. The LC/MS data was obtained on a Shimadzu analytical LCMS (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.219 min., m/z 233.95 (M+H), 95% purity. ¹H NMR (400 MHz, CDCl₃) δ 7.43 (t, J=8.2 Hz, 1H), 7.07 (dd, J=8.2, 0.6 Hz, 1H), 6.69 (dd, J=8.2, 0.6 Hz, 1H), 4.49 (t, J=6.0 Hz, 2H), 3.76 (q, J=5.9 Hz, 2H), 2.11-1.92 (m, 2H).

Intermediate: (R)-1-(3-((6-bromopyridin-2-yl)oxy)propyl)pyrrolidin-3-ol

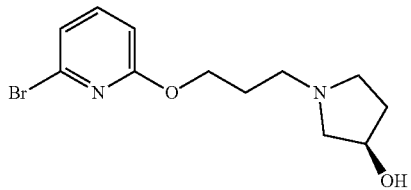 [SMILES: O[C@@H]1CCN(CCCOc2cccc(Br)n2)C1]

To a scintillation vial was added 3-((6-bromopyridin-2-yl)oxy)propan-1-ol (100 mg, 0.431 mmol), DCM (2 mL), and triethylamine (0.066 mL, 0.474 mmol). The solution was cooled to 0° C. and methanesulfonyl chloride (0.033 mL, 0.431 mmol) was added. The vial was capped, the ice-bath was removed, and the mixture stirred overnight at room temperature. The vial was transferred to a Buchi rotovap, solvent was removed, and the crude product, 3-((6-bromopyridin-2-yl)oxy)propyl methanesulfonate was obtained as a tan oil. To the isolated tan oil was added DMF (10 mL), 6 eq. of (R)-pyrrolidin-3-ol hydrochloride (320 mg, 2.59 mmol), 5 eq. sodium iodide (323 mg, 2.155 mmol), and 10 eq. potassium carbonate (596 mg, 4.31 mmol). The vial was capped and the mixture stirred for 7 hrs at 55° C. The mixture was cooled to room temperature, diluted with 10 mL water and pushed through a Waters 6 g HLB extraction cartridge. The cartridge was flushed with 20 mL of additional water, the product eluted with 20 mL of methanol. The methanol solution was then pushed through a Biotage 5 g SCX-2 cartridge. The SCX cartridge was flushed with 20 mL of methanol. The desired product was eluted with 50 mL of 2M ammonia in methanol. Volatiles were evaporated under a stream of nitrogen to give 60 mgs of (R)-1-(3-((6-bromopyridin-2-yl)oxy)propyl)pyrrolidin-3-ol (44% yield) as a light yellow oil. The LC/MS data was obtained on a Shimadzu analytical LCMS (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.059 min., m/z 302.95 (M+H), 90% purity. ¹H NMR (500 MHz, CDCl₃) δ 7.41 (t, J=7.6 Hz, 1H), 7.04 (d, J=7.6 Hz, 1H), 6.67 (d, J=7.6 Hz, 1H), 4.41-4.30 (m, 3H), 2.93 (m, 1H), 2.73 (d, J=10.1 Hz, 1H), 2.65-2.59 (m, 2H), 2.52 (dd, J=10.0, 5.1 Hz, 1H), 2.33-2.25 (m, 1H), 2.20 (m, 1H), 2.02-1.92 (m, 2H), 1.80-1.70 (m, 1H).

Intermediate: (R)-5-((4-chloro-2-formyl-5-((3-(6-(3-(3-hydroxypyrrolidin-1-yl)propoxy)pyridin-2-yl)-2-methylbenzyl)oxy)phenoxy)methyl)nicotinonitrile

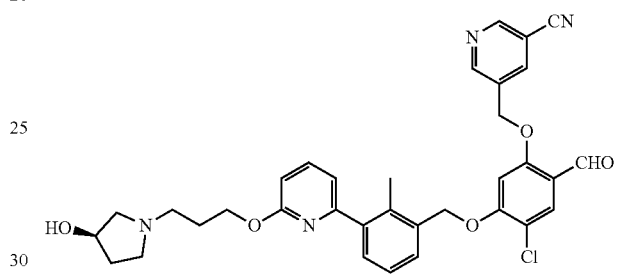

To a sealed tube was added 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (52.5 mg, 0.101 mmol), THF (6 mL), water (2.000 mL), (R)-1-(3-((6-bromopyridin-2-yl)oxy)propyl)pyrrolidin-3-ol (27.7 mg, 0.092 mmol), potassium phosphate, tribasic (48.8 mg, 0.230 mmol), and second generation X-Phos precatalyst (3.62 mg, 4.60 μmol). The vessel was sealed, the mixture de-gassed/flushed with nitrogen, then heated overnight at 80° C. The mixture was cooled and volatiles were removed under a stream of nitrogen. The resulting oily solid was taken up in DCM, washed with water, brine, dried over sodium sulfate, filtered, and evaporated under nitrogen to give 66.6 mgs of (R)-5-((4-chloro-2-formyl-5-((3-(6-(3-(3-hydroxypyrrolidin-1-yl)propoxy)pyridin-2-yl)-2-methylbenzyl)oxy)phenoxy)methyl)nicotinonitrile as a yellow solid (83%).

The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.480 min., m/z 614.25 (M+H). ¹H NMR (500 MHz, CDCl₃) δ 10.29 (s, 1H), 8.91 (m, 2H), 8.09 (m, 1H), 7.94 (s, 1H), 7.66 (dd, J=8.4, 7.3 Hz, 1H), 7.50-7.39 (m, 2H), 7.33 (m, 1H), 6.97 (m, 1H), 6.73 (dd, J=8.3, 0.7 Hz, 1H), 6.65 (s, 1H), 5.29-5.22 (m, 4H), 4.39 (t, J=6.5 Hz, 2H), 4.32 (m, 1H), 2.93 (m, 1H), 2.73 (m, 1H), 2.64 (t, J=7.3 Hz, 2H), 2.50 (m, 1H), 2.40 (s, 3H), 2.28 (m, 1H), 2.23-2.12 (m, 1H), 2.04-1.94 (m, 2H), 1.73 (m, 1H).

Example 1030: (S)-1-(5-chloro-2-((5-cyanopyridin-3-yl)methoxy)-4-((3-(6-(3-((R)-3-hydroxypyrrolidin-1-yl) propoxy)pyridin-2-yl)-2-methylbenzyl)oxy) benzyl)piperidine-2-carboxylic acid

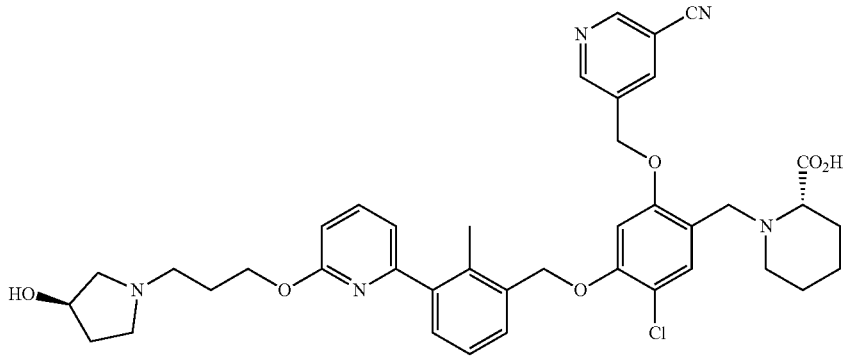 [SMILES: Cc1c(COc2cc(OCc3cncc(C#N)c3)c(CN3CCCC[C@H]3C(=O)O)cc2Cl)cccc1-c1cccc(OCCCN2CC[C@@H](O)C2)n1]

To a vial was added (R)-5-((4-chloro-2-formyl-5-((3-(6-(3-(3-hydroxypyrrolidin-1-yl)propoxy)pyridin-2-yl)-2-methylbenzyl)oxy)phenoxy)methyl)nicotinonitrile (34 mg, 0.055 mmol), L-pipecolic acid (10.74 mg, 0.083 mmol), DMF (1 mL), AcOH (0.111 mL), and borane-2-picoline complex (11.86 mg, 0.111 mmol). The vial was capped and the mixture shaken overnight at room temperature. The crude product was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 20-75% B over 30 minutes with a 5-minute hold at a flow rate of 20 mL/minute. Fractions containing the desired product were combined and dried via centrifugal evaporation. The yield of the product, (S)-1-(5-chloro-2-((5-cyanopyridin-3-yl)methoxy)-4-((3-(6-(3-((R)-3-hydroxypyrrolidin-1-yl)propoxy)pyridin-2-yl)-2-methylbenzyl)oxy)benzyl)piperidine-2-carboxylic acid, was 4.4 mg (10.4%), and its estimated purity by LCMS analysis was 95.5%. $^1$H NMR (500 MHz, DMSO-d$_6$) δ 9.00 (m, 2H), 8.46 (s, 1H), 7.79 (t, J=7.8 Hz, 1H), 7.54 (d, J=7.3 Hz, 1H), 7.44 (s, 1H), 7.40-7.35 (m, 1H), 7.34-7.27 (m, 1H), 7.12 (s, 1H), 7.06 (d, J=7.3 Hz, 1H), 6.79 (d, J=8.2 Hz, 1H), 5.34 (s, 2H), 5.28 (s, 2H), 4.29 (t, J=6.7 Hz, 2H), 4.21-4.10 (m, 1H), 3.77 (d, J=13.7 Hz, 1H), 3.06 (m, 1H), 2.87 (m, 1H), 2.69 (m, 1H), 2.48 (m, 1H), 2.33 (s, 3H), 2.29 (m, 2H), 2.22 (m, 1H), 2.03-1.89 (m, 2H), 1.89-1.82 (m, 6H), 1.49 (m, 4H), 1.34 (m, 1H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.358 min; ESI-MS (+) m/z=727.1 (M+H)

Analysis condition 2: Retention time=1.383 min; ESI-MS (+) m/z=727.1 (M+H)

Example 1031: (R)-5-((4-chloro-2-(hydroxymethyl)-5-((3-(6-(3-(3-hydroxypyrrolidin-1-yl)propoxy)pyridin-2-yl)-2-methylbenzyl)oxy)phenoxy)methyl)nicotinonitrile

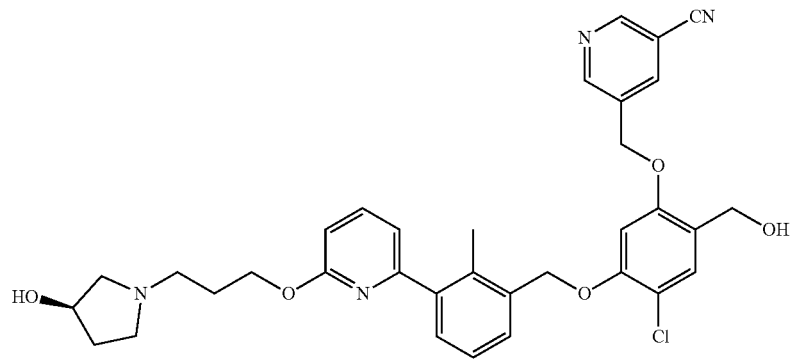 [SMILES: Cc1c(COc2cc(OCc3cncc(C#N)c3)c(CO)cc2Cl)cccc1-c1cccc(OCCCN2CC[C@@H](O)C2)n1]

Example 1031 was isolated from the reaction mixture for Example 1030. The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water with 10 mM ammonium acetate at a gradient of 20-75% B over 30 minutes with a 5-minute hold at a flow rate of 20 mL/minute. Fractions containing the desired product were combined and dried via centrifugal evaporation. The yield of the product was 4.6 mg (11% yield), and its estimated purity by LCMS analysis was 95%. $^1$H NMR (500 MHz, DMSO-$d_6$) δ 8.96 (m, 2H), 8.38 (s, 1H), 7.85-7.69 (m, 1H), 7.49 (d, J=7.0 Hz, 1H), 7.42-7.30 (m, 2H), 7.30-7.21 (m, 1H), 7.11-6.97 (m, 2H), 6.78 (d, J=7.9 Hz, 1H), 5.32 (s, 2H), 5.25 (s, 2H), 4.47 (s, 2H), 4.27 (m, 2H), 3.88 (m, 1H), 2.70 (m, 1H), 2.43 (m, 1H), 2.31 (m 4H), 1.95 (m 1H), 1.86 (m, 5H), 1.51 (m, 1H).

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.599 min; ESI-MS (+) m/z=616.1 (M+H)

Analysis condition 2: Retention time=1.598 min; ESI-MS (+) m/z=616.1 (M+H)

Intermediate: (2-methyl-3-(quinoxalin-6-yl)phenyl)methanol

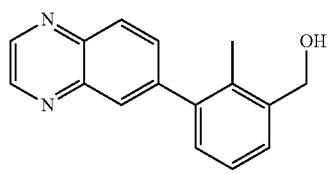 [SMILES: Cc1c(CO)cccc1-c1ccc2nccnc2c1]

(2-Methyl-3-(quinoxalin-6-yl)phenyl)methanol was obtained from the coupling between 6-(4,4,5,5-tetramethyl-1,3,2-dioxaborolan-2-yl)quinoxaline and (3-bromo-2-methylphenyl)methanol at room temperature by using the 2nd generation XPhos precatalyst and 0.5 M aqueous potassium phosphate, tribasic in THF.

$^1$H NMR (400 MHz, CHLOROFORM-d) δ 8.93-8.89 (m, 2H), 8.18 (d, J=8.5 Hz, 1H), 8.07 (d, J=2.0 Hz, 1H), 7.78 (dd, J=8.7, 1.9 Hz, 1H), 7.51 (dd, J=7.2, 1.6 Hz, 1H), 7.39-7.31 (m, 2H), 4.85 (d, J=5.5 Hz, 2H), 2.33 (s, 3H), 1.72 (t, J=5.6 Hz, 1H).

Intermediate: 5-chloro-2-hydroxy-4-((2-methyl-3-(quinoxalin-6-yl)benzyl)oxy)benzaldehyde

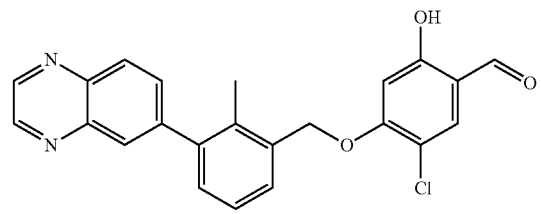 [SMILES: Cc1c(COc2cc(O)c(C=O)cc2Cl)cccc1-c1ccc2nccnc2c1]

5-Chloro-2-hydroxy-4-((2-methyl-3-(quinoxalin-6-yl)benzyl)oxy)benzaldehyde was obtained from the reaction between (2-methyl-3-(quinoxalin-6-yl)phenyl)methanol and 5-chloro-2,4-dihydroxybenzaldehyde using diisopropyl azodicarboxylate and triphenylphosphine in THF. $^1$H NMR (400 MHz, CHLOROFORM-d) δ 11.47 (s, 1H), 9.77-9.71 (m, 1H), 8.95-8.88 (m, 2H), 8.20 (d, J=8.5 Hz, 1H), 8.09 (d, J=1.8 Hz, 1H), 7.80 (dd, J=8.7, 1.9 Hz, 1H), 7.62-7.55 (m, 2H), 7.44-7.35 (m, 2H), 6.68 (s, 1H), 5.27 (m, 2H), 2.34 (s, 3H).

Intermediate: 5-((4-chloro-2-formyl-5-((2-methyl-3-(quinoxalin-6-yl)benzyl)oxy)phenoxy)methyl)nicotinonitrile

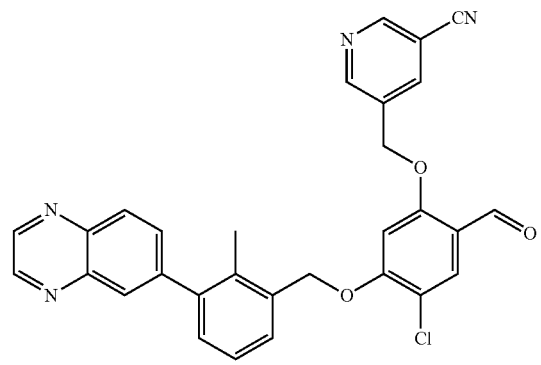 [SMILES: Cc1c(COc2cc(OCc3cncc(C#N)c3)c(C=O)cc2Cl)cccc1-c1ccc2nccnc2c1]

5-((4-Chloro-2-formyl-5-((2-methyl-3-(quinoxalin-6-yl)benzyl)oxy)phenoxy)methyl)nicotinonitrile was obtained from the reaction between 5-chloro-2-hydroxy-4-((2-methyl-3-(quinoxalin-6-yl)benzyl)oxy)benzaldehyde and 5-(chloromethyl)nicotinonitrile using cesium carbonate in DMF.

Example 1032: (S)-1-(5-chloro-2-((5-cyanopyridin-3-yl)methoxy)-4-((2-methyl-3-(quinoxalin-6-yl)benzyl)oxy)benzyl)piperidine-2-carboxylic acid

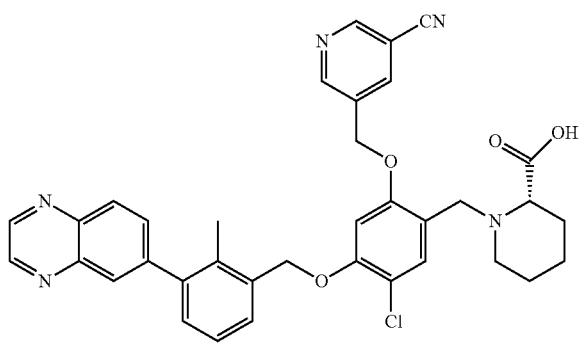 [SMILES: Cc1c(COc2cc(OCc3cncc(C#N)c3)c(CN3CCCC[C@H]3C(=O)O)cc2Cl)cccc1-c1ccc2nccnc2c1]

(S)-1-(5-Chloro-2-((5-cyanopyridin-3-yl)methoxy)-4-((2-methyl-3-(quinoxalin-6-yl)benzyl)oxy)benzyl)piperidine-2-carboxylic acid was obtained from the reaction between 5-((4-chloro-2-formyl-5-((2-methyl-3-(quinoxalin-6-yl)benzyl)oxy)phenoxy)methyl)nicotinonitrile and (S)-piperidine-2-carboxylic acid using TFA and sodium triacetoxyborohydride in DMF. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 15 minutes, then a 5-minute hold at 100% B; Flow: 20 mL/min. Fractions containing the desired product were combined and dried via centrifugal evaporation.

$^1$H NMR (500 MHz, DMSO-$d_6$) δ 9.01 (d, J=2.7 Hz, 4H), 8.47 (s, 1H), 8.19 (d, J=8.5 Hz, 1H), 8.03 (d, J=1.2 Hz, 1H), 7.87 (dd, J=8.5, 1.5 Hz, 1H), 7.62-7.57 (m, 1H), 7.44 (s, 1H), 7.41-7.35 (m, 2H), 7.15 (s, 1H), 5.40-5.34 (m, 2H), 5.32 (s, 2H), 3.79 (d, J=13.7 Hz, 1H), 3.62 (d, J=14.0 Hz, 1H), 3.14 (dd, J=7.3, 4.3 Hz, 1H), 2.93-2.85 (m, 1H) 2.34-2.24 (m, 4H), 1.84-1.68 (m, 2H), 1.49 (br. s., 3H), 1.37 (br. s., 1H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 condition: acetonitrile:water with 10 mM ammonium acetate) Rt (Retention time)=1.65 min, ESI m/z 634 (M+1), 632 (M−1).

LCMS (Injection 2 condition: methanol:water with 10 mM ammonium acetate) Rt=2.52 min, ESI m/z 634 (M+1), 632 (M−1).

Example 1033: (R)-1-(5-chloro-2-((5-cyanopyridin-3-yl)methoxy)-4-((2-methyl-3-(quinoxalin-6-yl)benzyl)oxy)benzyl)piperidine-2-carboxylic acid

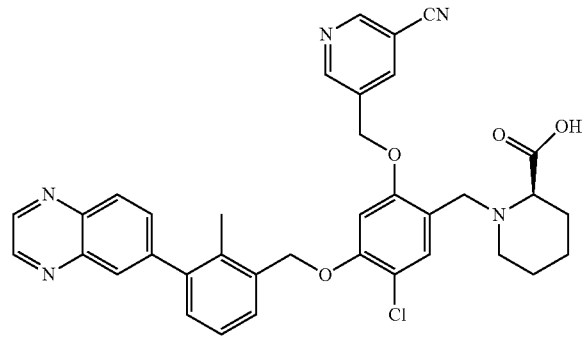 [SMILES: Cc1c(COc2cc(OCc3cncc(C#N)c3)c(CN3CCCC[C@@H]3C(=O)O)cc2Cl)cccc1-c1ccc2nccnc2c1]

(R)-1-(5-Chloro-2-((5-cyanopyridin-3-yl)methoxy)-4-((2-methyl-3-(quinoxalin-6-yl)benzyl)oxy)benzyl)piperidine-2-carboxylic acid was obtained from 5-((4-chloro-2-formyl-5-((2-methyl-3-(quinoxalin-6-yl)benzyl)oxy)phenoxy)methyl)nicotinonitrile and (R)-piperidine-2-carboxylic acid in a similar manner as Example 1001. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.01 (d, J=2.7 Hz, 4H), 8.47 (s, 1H), 8.19 (d, J=8.9 Hz, 1H), 8.02 (s, 1H), 7.87 (d, J=8.5 Hz, 1H), 7.61-7.57 (m, 1H), 7.44 (s, 1H), 7.42-7.35 (m, 2H), 7.15 (s, 1H), 5.40-5.30 (m, 4H), 3.79 (d, J=13.7 Hz, 1H), 3.62 (d, J=13.7 Hz, 1H), 3.14 (dd, J=7.3, 4.0 Hz, 1H), 2.93-2.85 (m, 1H), 2.34-2.25 (m, 4H), 1.85-1.68 (m, 2H), 1.49 (br. s., 3H), 1.37 (br. s., 1H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 condition: acetonitrile:water with 10 mM ammonium acetate) Rt=1.60 min, ESI m/z 634 (M+1), 632 (M−1).

LCMS (Injection 2 condition: methanol:water with 10 mM ammonium acetate) Rt=2.52 min, ESI m/z 634 (M+1), 632 (M−1).

Example 1034: (R)-2-((5-chloro-2-((5-cyanopyridin-3-yl)methoxy)-4-((2-methyl-3-(quinoxalin-6-yl)benzyl)oxy)benzyl)amino)-3-hydroxypropanoic acid

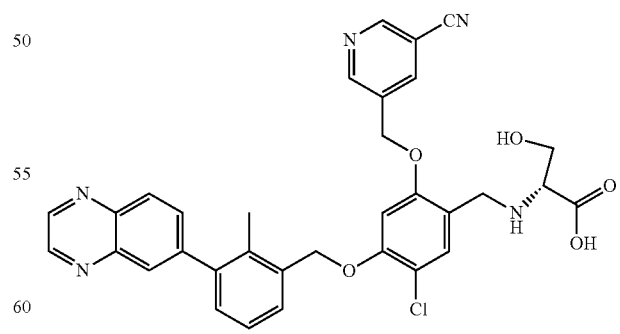

(R)-2-((5-Chloro-2-((5-cyanopyridin-3-yl)methoxy)-4-((2-methyl-3-(quinoxalin-6-yl)benzyl)oxy)benzyl)amino)-3-hydroxypropanoic acid was obtained from 5-((4-chloro-2-formyl-5-((2-methyl-3-(quinoxalin-6-yl)benzyl)oxy)phenoxy)methyl)nicotinonitrile and (R)-2-amino-3- hydroxypropanoic acid in a similar manner as Example 1001. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 15 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.07-8.99 (m, 4H), 8.54 (s, 1H), 8.20 (d, J=8.5 Hz, 1H), 8.03 (d, J=1.5 Hz, 1H), 7.87 (dd, J=8.5, 1.8 Hz, 1H), 7.59 (d, J=6.7 Hz, 1H), 7.55 (s, 1H), 7.42-7.35 (m, 2H), 7.18 (s, 1H), 5.43-5.33 (m, 4H), 4.07-3.98 (m, 2H), 3.74 (dd, J=11.3, 4.3 Hz, 1H), 3.67-3.61 (m, 1H), 3.22-3.17 (m, 1H), 2.32 (s, 3H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 condition: acetonitrile:water with 10 mM ammonium acetate) Rt=1.73 min, ESI m/z 610 (M+1), 608 (M−1).

LCMS (Injection 2 condition: methanol:water with 10 mM ammonium acetate) Rt=2.47 min, ESI m/z 610 (M+1), 608 (M−1).

Example 1035: (R)-2-((5-chloro-2-((5-cyanopyridin-3-yl)methoxy)-4-((2-methyl-3-(quinoxalin-6-yl)benzyl)oxy)benzyl)amino)-3-hydroxy-2-methylpropanoic acid

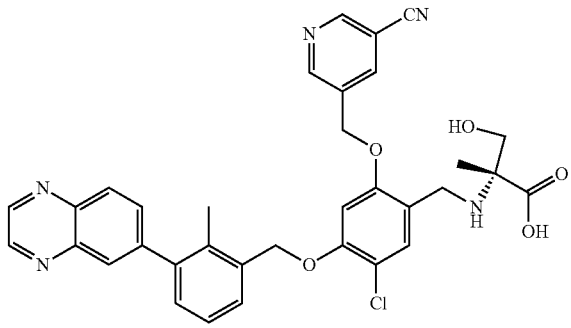 [SMILES: Cc1c(COc2cc(OCc3cncc(C#N)c3)c(CN[C@](C)(CO)C(=O)O)cc2Cl)cccc1-c1ccc2nccnc2c1]

(R)-2-((5-Chloro-2-((5-cyanopyridin-3-yl)methoxy)-4-((2-methyl-3-(quinoxalin-6-yl)benzyl)oxy)benzyl)amino)-3-hydroxy-2-methylpropanoic acid was obtained from 5-((4-chloro-2-formyl-5-((2-methyl-3-(quinoxalin-6-yl)benzyl)oxy)phenoxy)methyl)nicotinonitrile and (R)-2-amino-3-hydroxy-2-methylpropanoic acid in a similar manner as Example 1001. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 15 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.04 (d, J=1.5 Hz, 1H), 9.03-8.98 (m, 3H), 8.52 (s, 1H), 8.19 (d, J=8.8 Hz, 1H), 8.02 (d, J=1.2 Hz, 1H), 7.86 (dd, J=8.5, 1.5 Hz, 1H), 7.60-7.54 (m, 2H), 7.42-7.34 (m, 2H), 7.16 (s, 1H), 5.36 (d, J=11.6 Hz, 4H), 3.95 (s, 2H), 3.63-3.58 (m, 1H), 3.53 (d, J=11.3 Hz, 1H), 2.31 (s, 3H), 1.23 (s, 3H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 condition: acetonitrile:water with 10 mM ammonium acetate) Rt=1.54 min, ESI m/z 624 (M+1), 622 (M−1).

LCMS (Injection 2 condition: methanol:water with 10 mM ammonium acetate) Rt=2.50 min, ESI m/z 624 (M+1), 622 (M−1).

Example 1036: (S)-2-((5-chloro-2-((5-cyanopyridin-3-yl)methoxy)-4-((2-methyl-3-(quinoxalin-6-yl)benzyl)oxy)benzyl)amino)-3-hydroxy-2-methylpropanoic acid

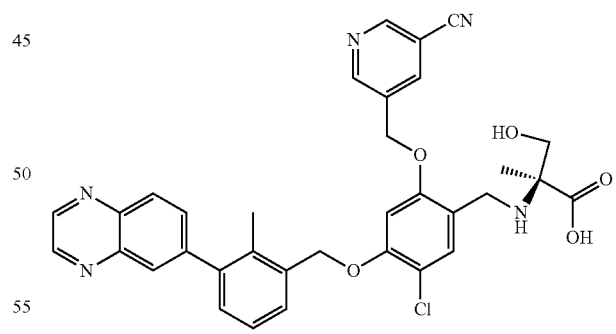

(S)-2-((5-Chloro-2-((5-cyanopyridin-3-yl)methoxy)-4-((2-methyl-3-(quinoxalin-6-yl)benzyl)oxy)benzyl)amino)-3-hydroxy-2-methylpropanoic acid was obtained from 5-((4-chloro-2-formyl-5-((2-methyl-3-(quinoxalin-6-yl)benzyl)oxy)phenoxy)methyl)nicotinonitrile and (S)-2-amino-3-hydroxy-2-methylpropanoic acid in a similar manner as Example 1001. The crude material was purified via preparative LC/MS with the following conditions: Column: XBridge C18, 19×200 mm, 5-μm particles; Mobile Phase A: 5:95 acetonitrile: water with 10-mM ammonium acetate;

Mobile Phase B: 95:5 acetonitrile: water with 10-mM ammonium acetate; Gradient: 15-55% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.04 (d, J=1.5 Hz, 1H), 9.03-8.99 (m, 3H), 8.52 (s, 1H), 8.19 (d, J=8.5 Hz, 1H), 8.02 (d, J=1.5 Hz, 1H), 7.86 (dd, J=8.5, 1.5 Hz, 1H), 7.59-7.55 (m, 2H), 7.41-7.34 (m, 2H), 7.16 (s, 1H), 5.36 (d, J=11.6 Hz, 4H), 3.95 (s, 2H), 3.63-3.59 (m, 1H), 3.53 (d, J=11.3 Hz, 1H), 2.31 (s, 3H), 1.24 (s, 3H).

Two analytical LC/MS injections were used to determine the final purity.

Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

LCMS (Injection 1 condition: acetonitrile:water with 10 mM ammonium acetate) Rt=1.62 min, ESI m/z 624 (M+1), 622 (M−1).

LCMS (Injection 2 condition: methanol:water with 10 mM ammonium acetate) Rt=2.50 min, ESI m/z 624 (M+1), 622 (M−1).

Intermediate: 3-bromo-1-(3-chloropropyl)pyridin-2 (1H)-one and 3-bromo-1-(3-bromopropyl)pyridin-2 (1H)-one

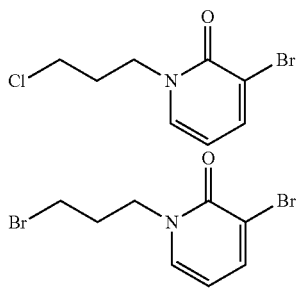

To a solution of 3-bromopyridin-2(1H)-one (500 mg, 2.87 mmol) in DMF (13 mL) was added $K_2CO_3$ (794 mg, 5.75 mmol). The reaction mixture was stirred at room temperature for 1 hr, then 1-bromo-3-chloropropane (0.283 mL, 2.87 mmol) was added and the reaction mixture was stirred at 50° C. for 19 hrs. The solvent was removed. The residue was dissolved in DCM. The organic layer was washed with water, brine and dried over $MgSO_4$, and then concentrated. The crude product was purified by column chromatography on silica gel eluting with a gradient of EtOAc in DCM (from 0-50%) to afford the mixture of target compound (352 mg, 49%). $^1$H NMR (500 MHz, CHLOROFORM-d) δ 7.77 (dd, J=7.3, 1.9 Hz, 1H), 7.39-7.35 (m, 1H), 6.11 (t, J=6.9 Hz, 1H), 4.22-4.15 (m, 2H), 3.61-3.54 (m, 1.5H), 3.42 (t, J=6.1 Hz, 0.5H), 2.41-2.35 (m, 0.5H), 2.30 (dt, J=12.4, 6.4 Hz, 1.5H). Based on the $^1$H NMR spectrum: 3-bromo-1-(3-chloropropyl)pyridin-2(1H)-one was 75% and 3-bromo-1-(3-bromopropyl)pyridin-2(1H)-one (76) was 25%.

Intermediate: 5-((4-chloro-5-((3-(1-(3-chloropropyl)-2-oxo-1,2-dihydropyridin-3-yl)-2-methylbenzyl)oxy)-2-formylphenoxy)methyl)nicotinonitrile

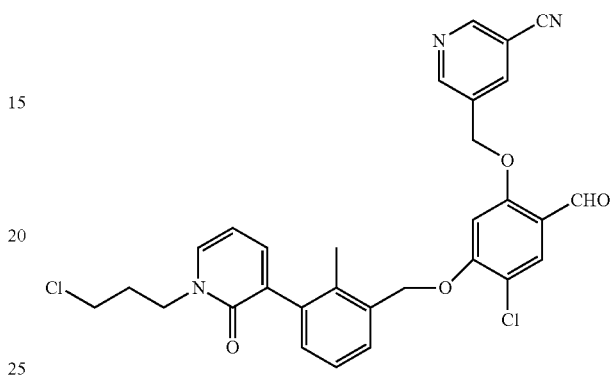

5-((4-Chloro-5-((3-(1-(3-chloropropyl)-2-oxo-1,2-dihydropyridin-3-yl)-2-methylbenzyl)oxy)-2-formylphenoxy) methyl)nicotinonitrile was obtained from the coupling of the mixture of 3-bromo-1-(3-chloropropyl)pyridin-2(1H)-one and 3-bromo-1-(3-bromopropyl)pyridin-2(1H)-one with 5-((4-chloro-2-formyl-5-((2-methyl-3-(4,4,5,5-tetramethyl-1,3,2-dioxaborolan-2-yl)benzyl)oxy)phenoxy)methyl)nicotinonitrile using 2nd generation XPhos precatalyst and 0.5 M aqueous potassium phosphate, tribasic in THF. $^1$H NMR (500 MHz, CHLOROFORM-d) δ 10.32-10.27 (m, 1H), 8.97 (d, J=2.0 Hz, 1H), 8.88 (d, J=1.9 Hz, 1H), 8.19 (t, J=2.0 Hz, 1H), 7.92 (s, 1H), 7.46 (dd, J=6.8, 2.0 Hz, 1H), 7.40 (dd, J=6.8, 2.0 Hz, 1H), 7.38-7.35 (m, 1H), 7.27-7.22 (m, 1H), 7.22-7.18 (m, 1H), 6.45 (s, 1H), 6.34 (t, J=6.8 Hz, 1H), 5.27 (d, J=6.0 Hz, 2H), 5.17 (s, 2H), 4.24-4.17 (m, 2H), 3.61 (t, J=6.1 Hz, 2H), 2.33-2.25 (m, 5H).

Intermediate: (R)-5-((4-chloro-2-formyl-5-((3-(1-(3-(3-hydroxypyrrolidin-1-yl)propyl)-2-oxo-1,2-dihydropyridin-3-yl)-2-methylbenzyl)oxy)phenoxy) methyl)nicotinonitrile

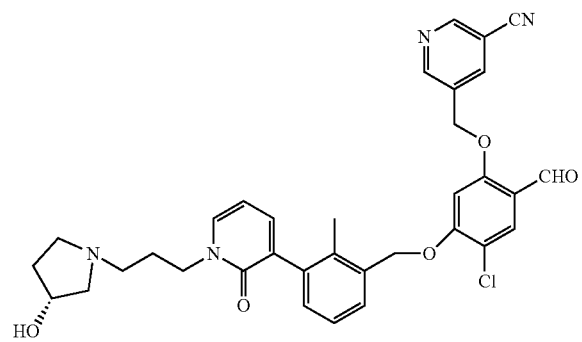 [SMILES: Cc1c(COc2cc(OCc3cncc(C#N)c3)c(C=O)cc2Cl)cccc1-c1cccn(CCCN2CC[C@@H](O)C2)c1=O]

A stirred mixture of 5-((4-chloro-5-((3-(1-(3-chloropropyl)-2-oxo-1,2-dihydropyridin-3-yl)-2-methylbenzyl)oxy)-2-formylphenoxy)methyl)nicotinonitrile (304 mg, 0.540 mmol) (77), (R)-pyrrolidin-3-ol, HCl (100 mg, 0.811 mmol) and K$_2$CO$_3$ (112 mg, 0.811 mmol), sodium iodide (81 mg, 0.540 mmol) in DMF (8 mL) was heated at 60° C. for 6 hrs. The solvent was removed. The residue was partitioned between EtOAc and water. The aqueous phase was extracted once with ethyl acetate. The organic extracts were combined and washed with brine and then dried over sodium sulfate. The drying agent was removed by filtration and solvent removed in vacuo. The resulting residue was purified by column chromatography on silica gel (Biotage 25s, 0-20% MeOH/DCM) to obtain 145 mg of target compound. $^1$H NMR (500 MHz, CHLOROFORM-d) δ 10.29 (s, 1H), 8.98 (d, J=2.0 Hz, 1H), 8.87 (d, J=1.9 Hz, 1H), 8.22 (t, J=2.0 Hz, 1H), 7.91 (s, 1H), 7.47-7.46 (m, 1H), 7.39-7.34 (m, 2H), 7.26-7.17 (m, 2H), 6.46-6.44 (m, 1H), 6.32-6.28 (m, 1H), 5.37 (br, s 2H), 5.16 (s, 2H), 4.34 (ddt, J=7.0, 4.7, 2.1 Hz, 1H), 4.12 (t, J=6.9 Hz, 2H), 2.91 (td, J=8.6, 4.8 Hz, 1H), 2.72 (d, J=9.9 Hz, 1H), 2.55-2.47 (m, 3H), 2.31-2.24 (m, 4H), 2.22-2.14 (m, 1H), 2.05-1.96 (m, 2H), 1.75 (dt, J=13.5, 6.7 Hz, 1H).

Example 1037: (S)-2-((5-chloro-2-((5-cyanopyridin-3-yl)methoxy)-4-((3-(1-(3-((R)-3-hydroxypyrrolidin-1-yl)propyl)-2-oxo-1,2-dihydropyridin-3-yl)-2-methylbenzyl)oxy)benzyl)amino)-3-hydroxy-2-methylpropanoic acid 2-((5-Chloro-2-((5-cyanopyridin-3-yl)methoxy)-4-((3-(1-(3-((R)-3-hydroxypyrrolidin-1-yl)propyl)-2-oxo-1,2-dihydropyridin-3-yl)-2-methylbenzyl)oxy)benzyl)amino)-3-hydroxy-2-methylpropanoic acid was obtained from the coupling of (R)-5-((4-chloro-2-formyl-5-((3-(1-(3-(3-hydroxypyrrolidin-1-yl)propyl)-2-oxo-1,2-dihydropyridin-3-yl)-2-methylbenzyl)oxy)phenoxy)methyl)nicotinonitrile and (S)-2-amino-3-hydroxy-2-methylpropanoic acid using borane-2-picoline complex and acetic acid in MeOH. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 5-45% B over 20 minutes, then a 5-minute hold at 100% B; Flow: 20 mL/min. Fractions containing the desired product were combined and dried via centrifugal evaporation. $^1$H NMR (500 MHz, DMSO-d$_6$) δ 9.04 (d, J=1.8 Hz, 1H), 9.00 (d, J=1.8 Hz, 1H), 8.51 (s, 1H), 7.73 (dd, J=6.8, 2.0 Hz, 1H), 7.54 (s, 1H), 7.43 (d, J=7.3 Hz, 1H), 7.35 (dd, J=6.6, 1.8 Hz, 1H), 7.22 (t, J=7.7 Hz, 1H), 7.13 (d, J=8.1 Hz, 1H), 7.07 (s, 1H), 6.32 (t, J=6.8 Hz, 1H), 5.34 (s, 2H), 5.28 (s, 2H), 4.17 (br. s., 1H), 4.01-3.94 (m, 4H), 2.72-2.65 (m, 1H), 2.57-2.53 (m, 2H), 2.45-2.35 (m, 3H), 2.29 (dd, J=9.5, 3.3 Hz, 1H), 2.16-212 (m, 1H), 2.14 (s, 3H), 2.00-1.92 (m, 1H), 1.85-1.75 (m, 2H), 1.53 (dd, J=8.4, 4.8 Hz, 1H), 1.23 (s, 3H).

Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 condition: acetonitrile:water with 10 mM ammonium acetate) Rt=1.185 min, ESI m/z 716 (M+1), 714 (M−1).

LCMS (Injection 2 condition: acetonitrile:water with 0.1% trifluoroacetic acid)

Rt=1.182 min, ESI m/z 716 (M+1), 714 (M−1).

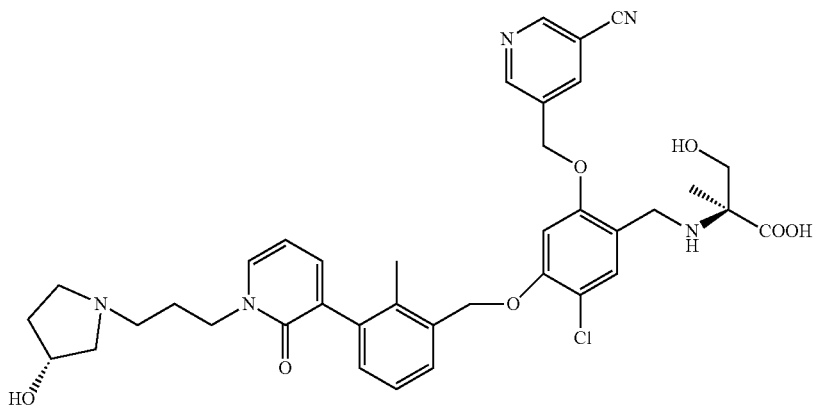 [SMILES: Cc1c(COc2cc(OCc3cncc(C#N)c3)c(CN[C@@](C)(CO)C(=O)O)cc2Cl)cccc1-c1cccn(CCCN2CC[C@@H](O)C2)c1=O]

Example 1038: (R)-2-((5-chloro-2-((5-cyanopyridin-3-yl)methoxy)-4-((3-(1-(3-((R)-3-hydroxypyrrolidin-1-yl)propyl)-2-oxo-1,2-dihydropyridin-3-yl)-2-methylbenzyl)oxy)benzyl)amino)-3-hydroxy-2-methylpropanoic acid

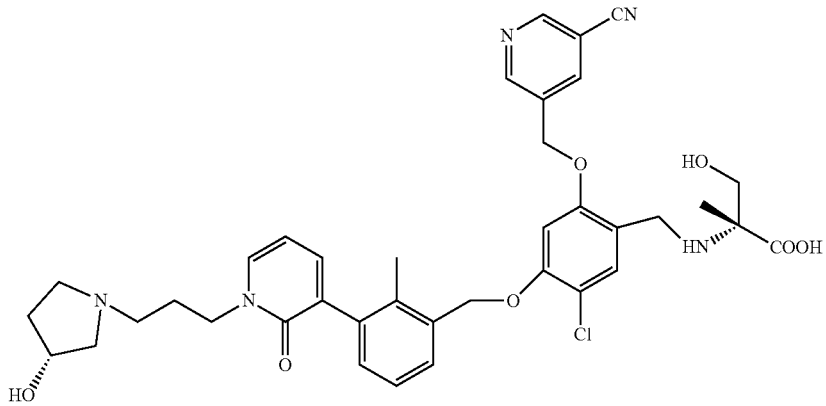 [SMILES: Cc1c(COc2cc(OCc3cncc(C#N)c3)c(CN[C@](C)(CO)C(=O)O)cc2Cl)cccc1-c1cccn(CCCN2CC[C@@H](O)C2)c1=O]

(R)-2-((5-Chloro-2-((5-cyanopyridin-3-yl)methoxy)-4-((3-(1-(3-((R)-3-hydroxypyrrolidin-1-yl)propyl)-2-oxo-1,2-dihydropyridin-3-yl)-2-methylbenzyl)oxy)benzyl)amino)-3-hydroxy-2-methylpropanoic acid was obtained from the reaction between (R)-5-((4-chloro-2-formyl-5-((3-(1-(3-(3-hydroxypyrrolidin-1-yl)propyl)-2-oxo-1,2-dihydropyridin-3-yl)-2-methylbenzyl)oxy)phenoxy)methyl)nicotinonitrile and (R)-2-amino-3-hydroxy-2-methylpropanoic acid in a similar manner as Example 1006. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 5-45% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.04 (d, J=1.8 Hz, 1H), 9.00 (d, J=1.8 Hz, 1H), 8.50 (s, 1H), 7.73 (dd, J=6.8, 2.0 Hz, 1H), 7.54 (s, 1H), 7.43 (d, J=7.0 Hz, 1H), 7.35 (dd, J=6.6, 2.2 Hz, 1H), 7.22 (t, J=7.7 Hz, 1H), 7.12 (d, J=8.1 Hz, 1H), 7.07 (s, 1H), 6.32 (t, J=6.8 Hz, 1H), 5.34 (s, 2H), 5.28 (s, 2H), 4.17 (br. s., 1H), 4.01-3.94 (m, 4H), 2.69 (dd, J=9.5, 6.2 Hz, 1H), 2.56-2.53 (m, 2H), 2.43-2.36 (m, 3H), 2.28 (dd, J=9.5, 3.7 Hz, 1H), 2.16-2.11 (m, 1H), 2.14 (s, 3H), 2.01-1.93 (m, 1H), 1.85-1.75 (m, 2H), 1.58-1.49 (m, 1H), 1.23 (s, 3H).

Two analytical LC/MS injections were used to determine the final purity.

Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 condition: acetonitrile:water with 10 mM ammonium acetate) Rt=1.203 min, ESI m/z 716 (M+1), 714 (M−1).

LCMS (Injection 2 condition: acetonitrile:water with 0.1% trifluoroacetic acid) Rt=1.158 min, ESI m/z 716 (M+1), 714 (M−1).

Example 1039: (S)-1-(5-chloro-2-((5-cyanopyridin-3-yl)methoxy)-4-((3-(1-(3-((R)-3-hydroxypyrrolidin-1-yl)propyl)-2-oxo-1,2-dihydropyridin-3-yl)-2-methylbenzyl)oxy)benzyl)piperidine-2-carboxylic acid

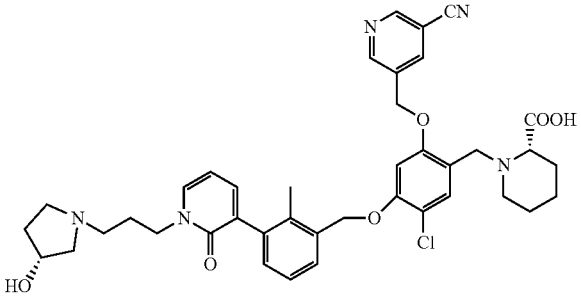 [SMILES: Cc1c(COc2cc(OCc3cncc(C#N)c3)c(CN3CCCC[C@H]3C(=O)O)cc2Cl)cccc1-c1cccn(CCCN2CC[C@@H](O)C2)c1=O]

(S)-1-(5-Chloro-2-((5-cyanopyridin-3-yl)methoxy)-4-((3-(1-(3-((R)-3-hydroxypyrrolidin-1-yl)propyl)-2-oxo-1,2-dihydropyridin-3-yl)-2-methylbenzyl)oxy)benzyl)piperidine-2-carboxylic acid was obtained from (R)-5-((4-chloro-2-formyl-5-((3-(1-(3-(3-hydroxypyrrolidin-1-yl)propyl)-2-oxo-1,2-dihydropyridin-3-yl)-2-methylbenzyl)oxy)phenoxy)methyl)nicotinonitrile and (S)-piperidine-2-carboxylic acid a similar manner as Example 1006. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.01 (s, 2H), 8.46 (s, 1H), 7.74 (d, J=4.8 Hz, 1H), 7.47-7.42 (m, 2H), 7.37-7.34 (m, 1H), 7.23 (t, J=7.5 Hz, 1H), 7.13 (d, J=7.3 Hz, 1H), 7.07 (s, 1H), 6.32 (t, J=6.8 Hz, 1H), 5.33 (s, 2H), 5.25 (s, 2H), 4.17 (br. s., 1H), 4.02-3.95 (m, 2H), 3.85 (d, J=13.6 Hz, 1H), 3.68 (d, J=13.6 Hz, 1H), 3.19-3.11 (m, 1H), 2.95-2.87 (m, 1H), 2.69 (dd, J=9.7, 6.4 Hz, 1H), 2.55 (m, 2H), 2.45-2.36 (m, 3H), 2.32-2.26 (m, 1H), 2.14 (s, 3H), 2.01-1.93 (m, 1H), 1.82 (t, J=6.6 Hz, 3H), 1.75-1.64 (m, 1H), 1.50 (br. s., 4H), 1.37 (br. s., 1H).

Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 condition: acetonitrile:water with 10 mM ammonium acetate) Rt=1.218 min, ESI m/z 726 (M+1), 724 (M−1).

LCMS (Injection 2 condition: acetonitrile:water with 0.1% trifluoroacetic acid) Rt=1.218 min, ESI m/z 726 (M+1), 724 (M−1).

Example 1040: (S)-2-((5-chloro-2-((5-cyanopyridin-3-yl)methoxy)-4-((3-(1-(3-((R)-3-hydroxypyrrolidin-1-yl)propyl)-2-oxo-1,2-dihydropyridin-3-yl)-2-methylbenzyl)oxy)benzyl)amino)-3-hydroxypropanoic acid 3-hydroxypropanoic acid was obtained from (R)-5-((4-chloro-2-formyl-5-((3-(1-(3-(3-hydroxypyrrolidin-1-yl)propyl)-2-oxo-1,2-dihydropyridin-3-yl)-2-methylbenzyl)oxy) phenoxy)methyl)nicotinonitrile and (S)-2-amino-3-hydroxypropanoic acid a similar manner as Example 1006. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-50% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 9.04 (d, J=1.5 Hz, 1H), 9.01 (d, J=1.8 Hz, 1H), 8.51 (s, 1H), 7.73 (dd, J=6.6, 1.8 Hz, 1H), 7.51 (s, 1H), 7.43 (d, J=7.7 Hz, 1H), 7.35 (dd, J=6.8, 2.0 Hz, 1H), 7.23 (t, J=7.5 Hz, 1H), 7.13 (d, J=7.7 Hz, 1H), 7.08 (s, 1H), 6.32 (t, J=6.8 Hz, 1H), 5.34 (d, J=7.3 Hz, 2H), 5.27 (s, 2H), 4.17 (br. s., 1H), 4.05-3.94 (m, 4H), 3.73-3.67 (m, 1H), 3.64-3.58 (m, 1H), 3.17-3.12 (m, 1H), 2.75-2.67 (m, 1H), 2.59-2.53 (m, 1H), 2.46-2.38 (m, 3H), 2.30 (dd, J=9.5, 3.7 Hz, 1H), 2.14 (s, 3H), 2.00-1.92 (m, 1H), 1.82 (t, J=7.2 Hz, 2H), 1.58-1.50 (br, s, H).

Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 condition: acetonitrile:water with 10 mM ammonium acetate) Rt=1.161 min, ESI m/z 702 (M+1), 700 (M−1).

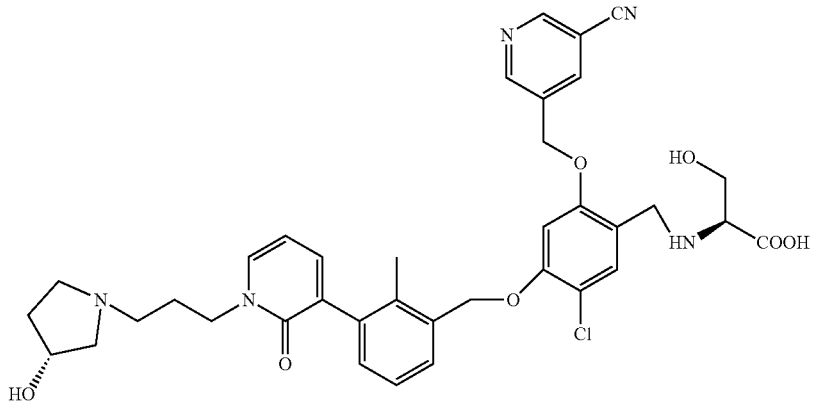 [SMILES: Cc1c(COc2cc(OCc3cncc(C#N)c3)c(CN[C@@H](CO)C(=O)O)cc2Cl)cccc1-c1cccn(CCCN2CC[C@@H](O)C2)c1=O]

(S)-2-((5-Chloro-2-((5-cyanopyridin-3-yl)methoxy)-4-((3-(1-(3-((R)-3-hydroxypyrrolidin-1-yl)propyl)-2-oxo-1,2-dihydropyridin-3-yl)-2-methylbenzyl)oxy)benzyl)amino)-

LCMS (Injection 2 condition: acetonitrile:water with 0.1% trifluoroacetic acid) Rt=1.158 min, ESI m/z 702 (M+1), 700 (M−1).

Example 1041: (S)-1-(4-((3-(benzo[d]oxazol-5-yl)-2-methylbenzyl)oxy)-5-chloro-2-((5-cyanopyridin-3-yl) methoxy)benzyl)piperidine-2-carboxylic acid

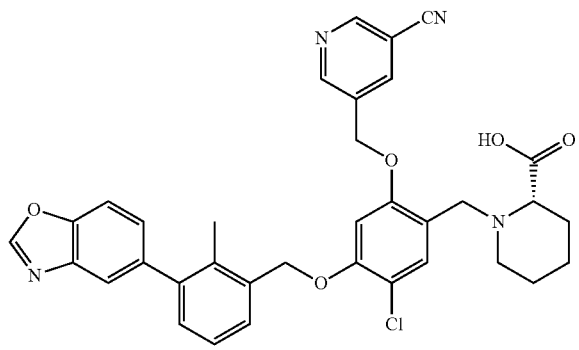 [SMILES: Cc1c(COc2cc(OCc3cncc(C#N)c3)c(CN3CCCC[C@H]3C(=O)O)cc2Cl)cccc1-c1ccc2ocnc2c1]

To a small sealed tube was added THF (2 mL), water (0.667 mL), 5-bromobenzoxazole (13.16 mg, 0.066 mmol), (S)-1-(5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)piperidine-2-carboxylic acid (35 mg, 0.055 mmol), potassium phosphate, tribasic (23.51 mg, 0.111 mmol), and second generation XPhos precatalyst (2.179 mg, 2.77 µmol). The vessel was sealed, the mixture de-gassed/flushed with nitrogen and then heated overnight at 75° C.

The crude material was purified via preparative LC/MS using the following conditions: Waters XBridge 5 µm C18, 19×200 mm where mobile phase A was 5:95 acetonitrile: water with 10 mM ammonium acetate and mobile phase B was 95:5 acetonitrile: water with 10 mM ammonium acetate at a gradient of 25-65% B over 15 minutes then a 5-minute hold at 100% B at a flow rate of 20 mL/minute. Fractions containing the desired product were combined and dried via centrifugal evaporation. The material was further purified via preparative LC/MS using the following conditions: Waters XBridge 5 µm C18, 19×200 mm where mobile phase A was 5:95 acetonitrile: water with 10 mM ammonium acetate and mobile phase B was 95:5 acetonitrile: water with 10 mM ammonium acetate at a gradient of 25-65% B over 15 minutes then a 5-minute hold at 100% B at a flow rate of 20 mL/minute. Fractions containing the desired product were combined and dried via centrifugal evaporation. The yield of the product was 4.2 mg (12% yield), and its estimated purity by LCMS analysis was 95%. $^1$H NMR (500 MHz, DMSO-$d_6$) δ 8.93 (m, 2H), 8.71 (s, 1H), 8.37 (s, 1H), 7.78 (m, 1H), 7.73 (s, 1H), 7.51-7.46 (m, 1H), 7.44-7.32 (m, 1H), 7.30-7.11 (m, 2H), 7.03 (m, 1H), 6.54 (m, 1H), 5.28 (m, 2H), 5.17 (m, 2H), 3.71 (d, J=13.7 Hz, 1H), 3.49 (d, J=13.7 Hz, 1H), 3.04-2.97 (m, 1H), 2.89-2.80 (m, 1H), 2.25-2.18 (m, 4H), 1.70 (m, 2H), 1.43 (m, 3H), 1.34-1.23 (m, 1H).

Two analytical LC/MS injections were used to determine the final purity.

Injection 1 conditions: Waters Acquity UPLC BEH 1.7 µm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 µm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.696 min; ESI-MS (+) m/z=623.0 (M+H)

Analysis condition 2: Retention time=1.874 min; ESI-MS (+) m/z=623.1 (M+H)

Examples 2001 to 2016 were prepared as described below, and the HPLC LC/MS conditions employed for these examples were listed below:

LC/MS Condition A:
Column=Waters Aquity UPLC BEH C18, 2.1×50 mm, 1.7 µm
Start % B=2; Final % B=98
Gradient time=1.5 min; Stop time=2 or 2.5 min
Flow Rate=0.8 mL/min; Wavelength=220 nm or 254 nm
Solvent A=100% water/0.05% TFA
Solvent B=100% ACN/0.05% TFA, (ACN=acetonitrile)
Oven temp.=40° C.

LC/MS Condition B:
Column=Phenomenex-Luna C18, 2.0×50 mm, 3 µm
Start % B=0; Final % B=100
Gradient time=4 min; Stop time=5 or 6 min
Flow Rate=0.8 mL/min; Wavelength=220 nm or 254 nm
Solvent A=5% ACN/95% water/10 mM NH$_4$OAc
Solvent B=95% ACN/5% water/10 mM NH$_4$OAc
Oven temp.=40° C.

LC/MS Condition C:
Column=ACQUITY UPLC BEH, C18 2.1×50 mm, 1.70
Start % B=0; Final % B=100
Gradient time=2 min; Stop time=3 min
Flow Rate=0.8 mL/min; Wavelength=220 nm or 254 nm
Solvent A=10% MeOH/90% H2O/0.1% TFA
Solvent B=90% MeOH/10% H2O/0.1% TFA
Oven temp.=40° C.

LC/MS Condition D:
Column=Waters Aquity UPLC BEH C18, 2.1×50 mm, 1.7 µm
Start % B=2; Final % B=98
Gradient time=1.5 min; Stop time=1.6 min
Flow Rate=0.8 mL/min; Wavelength=220 nm or 254 nm
Solvent A=100% water/0.05% TFA
Solvent B=100% ACN/0.05% TFA
Oven temp.=50° C.

LC/MS Condition E:
Column=Waters Acquity UPLC BEH C18, 2.1×50 mm, 1.7-µm
Start % B=0; Final % B=100
Gradient time=3 min; Stop time=3.75 min
Flow rate=1.0 mL/min; Wavelength=220 nm
Solvent A=5% ACN/95% water/10 mM NH$_4$OAc
Solvent B=95% ACN/5% water/10 mM NH$_4$OAc
Oven temp.=50° C.

LC/MS Condition F:
Column=Waters Acquity UPLC BEH C18, 2.1×50 mm, 1.7-µm
Start % B=0; Final % B=100
Gradient time=3 min; Stop time=3.75 min
Flow rate=1.0 mL/min; Wavelength=220 nm
Solvent A=5% ACN/95% water/0.1% TFA
Solvent B=95% ACN/5% water/0.1% TFA
Oven temp.=50° C.

Intermediate: 5-chloro-2-hydroxy-4-((2-methyl-3-(4,4,5,5-tetramethyl-1,3,2-dioxaborolan-2-yl)benzyl)oxy)benzaldehyde

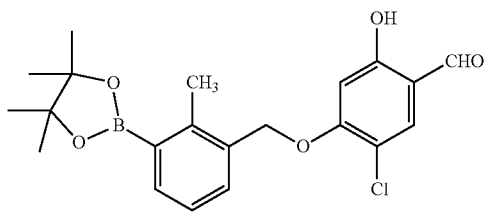 [SMILES: Cc1c(COc2cc(O)c(C=O)cc2Cl)cccc1B1OC(C)(C)C(C)(C)O1]

A magnetically stirred solution of (2-methyl-3-(4,4,5,5-tetramethyl-1,3,2-dioxaborolan-2-yl)phenyl)methanol (8.0 g, 32.2 mmol), 5-chloro-2,4-dihydroxybenzaldehyde (5.56 g, 32.2 mmol), and triphenylphosphine (11.4 g, 43.5 mmol) in freshly distilled anhydrous THF (250 mL) is cooled in an ice/water bath and slowly (over 30 min) treated with DIAD (diisopropyl azodicarboxylate, 8.0 mL, 41.1 mmol). The reaction is flushed with argon, sealed, and allowed to stir overnight while slowly warming to room temp. The reaction is evaporated in vacuo to a thick oil and then applied in $CH_2Cl_2$/hex to the head of a 120 g Teledyne Isco Silica Flash Column and purified on Biotage using a gradient from 100% hexanes to 40% EtOAc in hexanes over 12 col vols (column volumes). The fractions containing the product were evaporated in vacuo and dried on high vacuum to give 5.5 g (42%) of the pure title compound as a white solid: $^1$H NMR (500 MHz, CHLOROFORM-d) δ 11.43 (s, 1H), 9.71 (s, 1H), 7.80 (d, J=7.5 Hz, 1H), 7.60-7.47 (m, 2H), 7.25 (t, J=7.5 Hz, 1H), 6.61 (s, 1H), 5.19 (s, 2H), 2.59 (s, 3H), 1.39 (s, 12H).

Intermediate: 5-((4-chloro-2-formyl-5-((2-methyl-3-(4,4,5,5-tetramethyl-1,3,2-dioxaborolan-2-yl)benzyl)oxy)phenoxy)methyl)nicotinonitrile

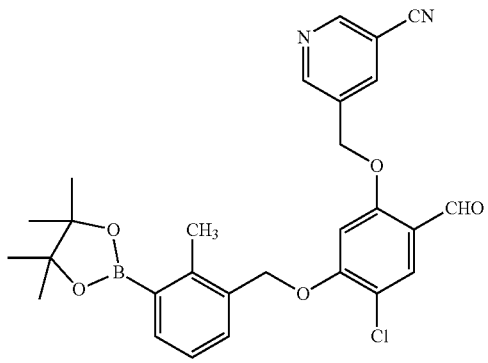 [SMILES: Cc1c(COc2cc(OCc3cncc(C#N)c3)c(C=O)cc2Cl)cccc1B1OC(C)(C)C(C)(C)O1]

To a magnetically stirred solution of 5-chloro-2-hydroxy-4-((2-methyl-3-(4,4,5,5-tetramethyl-1,3,2-dioxaborolan-2-yl)benzyl)oxy)benzaldehyde (2.76 g, 6.85 mmol) in anhydrous DMF (40 mL) is added 5-(chloromethyl)nicotinonitrile (1.26 g, 8.26 mmol), followed by cesium carbonate (3.35 g, 10.28 mmol). The reaction is flushed well with $N_2$, securely capped, and placed into a 75° C. oil bath. After 2.75 h, the reaction is cooled and partitioned with EtOAc (200 mL) and water (150 mL). The aqueous layer is extracted with additional EtOAc (200 mL). The combined the organic layers were washed with brine (2×50 mL), dried over $Na_2SO_4$, filtered, and evaporate in vacuo. The residue is dissolved in $CH_2Cl_2$ (15 mL), applied to the head of a 80 g Teledyne Isco Silica Flash Column and purified on Biotage using a gradient from 100% $CH_2Cl_2$ to 25% EtOAc/$CH_2Cl_2$ over 8 column volumes. The fractions containing the product were evaporated in vacuo then dried on high vacuum to give 1.92 g (54%) of the pure title compound as an off-white solid: $^1$H NMR (500 MHz, CHLOROFORM-d) δ 10.29 (s, 1H), 8.91 (dd, J=11.7, 2.1 Hz, 2H), 8.07 (t, J=2.1 Hz, 1H), 7.93 (s, 1H), 7.81 (dd, J=7.5, 1.2 Hz, 1H), 7.47 (d, J=6.6 Hz, 1H), 7.24 (t, J=7.6 Hz, 1H), 6.57 (s, 1H), 5.24 (s, 2H), 5.19 (s, 2H), 2.60 (s, 3H), 1.39 (s, 12H).

Intermediate: 4-bromo-3-chloro-2-(3-(piperidin-1-yl)propoxy)pyridine

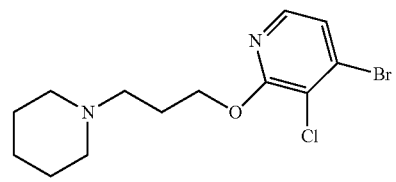 [SMILES: Clc1c(Br)ccnc1OCCCN1CCCCC1]

To a suspension of sodium hydride (74.1 mg, 3.09 mmol) in anhydrous DMF (5 mL) under a continuous argon flush was slowly added 3-(piperidin-1-yl)propan-1-ol (440 mg, 3.07 mmol). The reaction was stirred for 10 min, then treated with solid 4-bromo-2,3-dichloropyridine (655 mg, 2.89 mmol) in portions over 1 min. The reaction was allowed to stir at room temp for 3 h, filtered through a 0.45 uM frit, and purified via reverse phase Prep HPLC using a Sunfire C18 10 uM 50×300 mm column with from 10% Solvent B to 100% Solvent B over 30 min at 150 mL/min with detection at 220 nM (solvent A is 10% MeOH/90% water with 0.1% TFA and Solvent B is 90% MeOH and 10% water with 0.1% TFA) to give the pure title compound as a TFA salt (151.5 mg, 9%); $^1$H NMR (500 MHz, CHLOROFORM-d) δ 7.86 (d, J=5.3 Hz, 1H), 7.21 (d, J=5.3 Hz, 1H), 4.47 (t, J=5.7 Hz, 2H), 3.79 (br d, J=11.7 Hz, 2H), 3.37-3.25 (m, 2H), 2.83-2.67 (m, 2H), 2.39-2.25 (m, 2H), 2.04-1.89 (m, 5H), 1.56-1.40 (m, 1H)

Intermediate: 5-((4-chloro-5-((3-(3-chloro-2-(3-(piperidin-1-yl)propoxy)pyridin-4-yl)-2-methylbenzyl)oxy)-2-formylphenoxy)methyl)nicotinonitrile

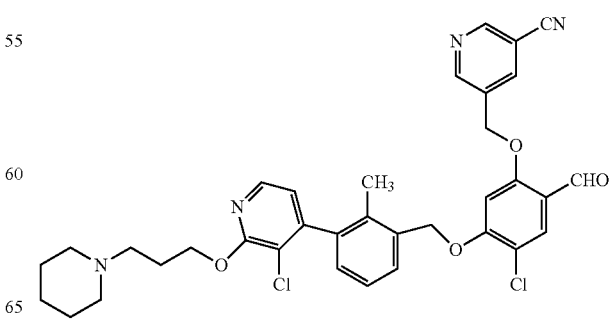

To a solution of 4-bromo-3-chloro-2-(3-(piperidin-1-yl)propoxy)pyridine, 2 TFA (86.3 mg, 0.154 mmol) and 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (90 mg, 0.173 mmol) in anhydrous THF (7 mL) is added potassium phosphate tribasic, 0.5 M in water (0.8 mL, 0.400 mmol). The reaction is flushed well with argon and then treated with 2$^{nd}$ generation X-phos precatalyst (17 mg, 0.022 mmol). The resulting mixture was again flushed with argon, securely capped, and allowed to stir at room temp for 3.5 days. The solvent was removed under a gentle stream of N$_2$ and the residue partitioned with water (100 mL) and EtOAc (75 mL). The organic layer was extracted with brine (40 mL) dried over Na$_2$SO$_4$ filtered and the solvent remoned in vacuo to give the title compound that was used crude. LC/MS Condition A: ret time 1.104 min; m/e=645, (ret time=retention time).

Intermediate:
3-((2,3-dichloropyridin-4-yl)oxy)propan-1-ol

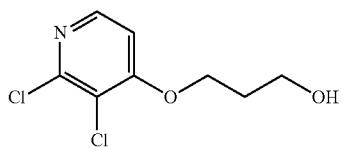 [SMILES: OCCCOc1ccnc(Cl)c1Cl]

To neat propane-1,3-diol (4 g, 52.6 mmol) under argon is added sodium hydride (68 mg, 2.75 mmol). The reaction (very warm) is flushed under N$_2$, then treated with 4-bromo-2,3-dichloropyridine (500 mg, 2.204 mmol) followed by anhydrous THF (5 mL). The reaction is flushed with argon, securely capped and allowed to stir at room temp for 2 days. The reaction poured into water (150 mL containing 1 N HCl (1 mL) and partitioned with EtOAc (200 mL). The layers were separated and the organic layer is washed with water (23×70 mL), brine (75 mL), dried over Na$_2$SO$_4$ and the solvent is removed in vacuo. The crude material is applied in CH$_2$Cl$_2$ to the head of a 80 g Teledyne Isco Silica Flash Column and purified on Biotage using a gradient from 100% CH$_2$Cl$_2$ to 100% EtOAc in hexanes over 9 column volumes. The fractions containing the product were combined, evaporated in vacuo and dried under high vacuum to give the pure title compound (210 mg, 43%) as a white solid LC/MS Condition A: ret time 0.860 min; m/e=222; $^1$H NMR (500 MHz, CHLOROFORM-d) δ 8.17 (d, J=5.5 Hz, 1H), 6.84 (d, J=5.6 Hz, 1H), 4.29 (t, J=6.0 Hz, 2H), 3.92 (t, J=5.8 Hz, 2H), 2.14 (quin, J=5.9 Hz, 2H)

Intermediate: 5-((4-chloro-5-((3-(3-chloro-4-(3-hydroxypropoxy)pyridin-2-yl)-2-methylbenzyl)oxy)-2-formylphenoxy)methyl)nicotinonitrile

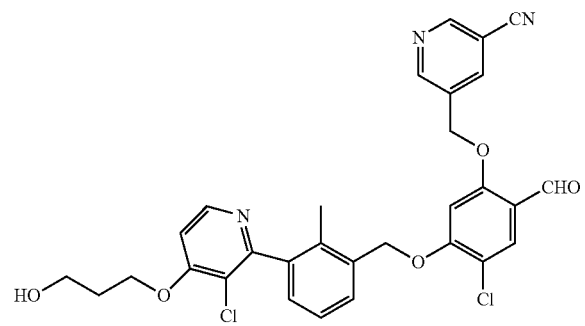 [SMILES: Cc1c(COc2cc(OCc3cncc(C#N)c3)c(C=O)cc2Cl)cccc1-c1nccc(OCCCO)c1Cl]

To a solution of 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (400 mg, 0.771 mmol) and 3-((2,3-dichloropyridin-4-yl)oxy)propan-1-ol (175 mg, 0.788 mmol) in anhydrous THF (30 mL) is added potassium phosphate tribasic, 0.5 M in water (3.9 mL, 1.950 mmol). The reaction is flushed with argon and then treated with 2$^{nd}$ generation X-phos precatalyst (60 mg, 0.076 mmol). The resulting mixture was again flushed well with argon, securely capped and placed in a 65 C oil bath for 18 h. The solvent was mostly removed under a gentle stream of N2 and the residue was partitioned with EtOAc (100 mL) and water (40 mL). The aqueous layer was extracted with EtOAc (50 mL) and the organic layers were combined, washed with brine (15 mL), dried over Na$_2$SO$_4$, filtered and the solvent removed in vacuo The crude material is applied in CH$_2$Cl$_2$ to the head of a 40 g Teledyne Isco Silica Flash Column and purified on Biotage using a gradient from 100% CH$_2$Cl$_2$ to 100% EtOAc over 8 column volumes, followed by a gradient from 100% EtOAc to 20% MeOH/EtOAc over 5 column volumes. The fractions containing the product were combined, evaporated in vacuo and dried under high vacuum to give the pure title compound (300 mg, 67%). LC/MS Condition A: ret time 1.002 min; m/e=578; $^1$H NMR (500 MHz, CHLOROFORM-d) δ 10.29 (s, 1H), 8.92 (d, J=1.5 Hz, 2H), 8.47 (d, J=5.6 Hz, 1H), 8.11 (t, J=1.8 Hz, 1H), 7.93 (s, 1H), 7.49 (d, J=7.3 Hz, 1H), 7.40-7.32 (m, 1H), 7.30 (s, 1H), 6.95 (d, J=5.6 Hz, 1H), 6.55 (s, 1H), 5.33 (s, 2H), 5.15 (s, 2H), 4.35 (br t, J=4.9 Hz, 2H), 3.95 (br s, 2H), 2.23-2.15 (m, 5H)

Intermediate: 5-((5-((3-(4-(3-bromopropoxy)-3-chloropyridin-2-yl)-2-methylbenzyl)oxy)-4-chloro-2-formylphenoxy)methyl)nicotinonitrile

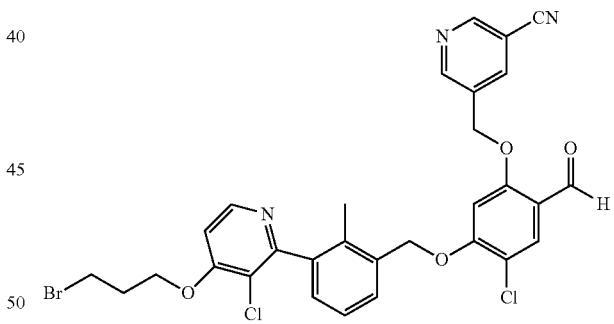

To a magnetically stirred solution of 5-((4-chloro-5-((3-(3-chloro-4-(3-hydroxypropoxy)pyridin-2-yl)-2-methylbenzyl)oxy)-2-formylphenoxy)methyl)nicotinonitrile (182 mg, 0.315 mmol) and triphenylphosphine (98.3 mg, 0.375 mmol) in CH$_2$Cl$_2$ (5 mL) is under argon a continuous argon flush is added solid carbon tetrabromide (123 mg, 0.371 mmol). The reaction is flushed well with argon, securely capped and stirred at room temp 4 h. The reaction is applied directly to the head of a 40 g Teledyne Isco Silica Flash Column and purified on Biotage using a gradient from 100% CH$_2$Cl$_2$ to 100% EtOAc over 11 col vols. The fractions containing the product were combined, evaporated in vacuo and dried under high vacuum to give the pure title compound (88.5 mg, 44%). LC/MS Condition B: ret time 3.68 min; m/e=640

¹H NMR (500 MHz, CHLOROFORM-d) δ 10.29 (s, 1H), 8.93 (m, 2H), 8.48 (d, J=5.5 Hz, 1H), 8.11 (t, J=2.1 Hz, 1H), 7.94 (s, 1H), 7.51-7.46 (m, 1H), 7.37-7.33 (m, 1H), 7.31-7.29 (m, 1H), 6.95 (d, J=5.6 Hz, 1H), 6.56 (s, 1H), 5.33 (s, 2H), 5.16 (s, 2H), 4.34 (t, J=5.6 Hz, 2H), 3.69 (t, J=6.3 Hz, 2H), 2.47 (quin, J=6.0 Hz, 2H), 2.19 (s, 3H).

Intermediate: (R)-2-((5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)amino)-3-hydroxy-2-methylpropanoic acid

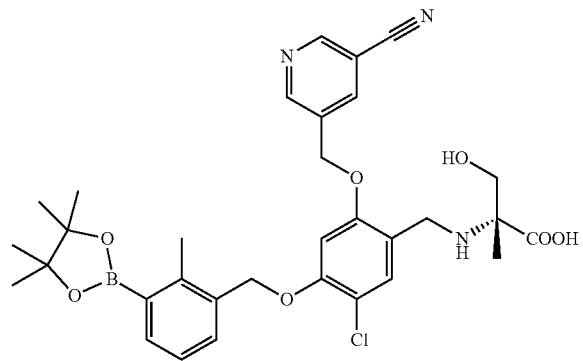 [SMILES: Cc1c(COc2cc(OCc3cncc(C#N)c3)c(CN[C@](C)(CO)C(=O)O)cc2Cl)cccc1B1OC(C)(C)C(C)(C)O1]

To a mixture of 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (1.2 g, 2.313 mmol) and (R)-2-amino-3-hydroxy-2-methylpropanoic acid (0.551 g, 4.63 mmol) in a mixture of DCE (15 mL) and EtOH (15 mL) was added acetic acid (0.265 mL, 4.63 mmol) and 4 A molecular sieves (100 mg). The resulting mixture was stirred at rt for 5 h, then treated dropwise with sodium cyanoborohydride (4.63 mL, 4.63 mmol) over 40 h. The reaction mixture was filtered, the filtrate was concentrated (<20° C. bath) and the residue was purified by reverse phase Prep HPLC using a Sunfire C₁₈ 10 uM 50×100 mm column with from 15% Solvent B to 100% Solvent B over 30 min at 150 mL/min with detection at 220 nM (solvent A is 5% CH₃CN/95% water with 10 mM NH₄OAc and Solvent B is 95% CH₃CN/5% water with 10 mM NH4Oac), to give the pure title compound (220 mg, 15%). LC/MS Condition C: ret time 2.120 min, m/e=622; ¹H NMR (400 MHz, METHANOL-d₄) δ 8.96 (d, J=6.3 Hz, 1H), 8.89 (d, J=6.0 Hz, 1H), 8.39 (d, J=12.5 Hz, 1H), 7.69 (dd, J=7.5, 1.3 Hz, 1H), 7.55 (d, J=1.0 Hz, 1H), 7.49-7.38 (m, 1H), 7.30-7.24 (m, 1H), 7.18 (dt, J=14.9, 7.5 Hz, 1H), 7.03-6.90 (m, 1H), 5.35 (d, J=2.3 Hz, 2H), 5.26 (s, 2H), 4.22 (s, 2H), 3.92 (d, J=11.8 Hz, 1H), 3.72 (d, J=12.0 Hz, 1H), 2.61-2.32 (m, 3H), 1.44 (s, 3H), 1.38 (s, 6H).

Intermediate: 2-bromo-1,3-dimethyl-5,6,7,8-tetrahydropyrazolo[1,2-a]pyridazin-4-ium bromide

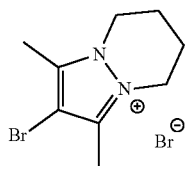

To a 150 mL pressure bottle is added 4-bromo-3,5-dimethyl-1H-pyrazole (2.29 g, 13.08 mmol), potassium carbonate (4 g, 28.9 mmol) and anhydrous acetonitrile (70 mL). The reaction is flushed with N₂, and then treated with 1,4-dibromobutane (22 g, 102 mmol). The reaction is capped and stirred at room temp for 18 h. The reaction was then heated to 50-55 C for 5 h, cooled to room temp, filtered and the solvent was evaporated off under a gentle stream of N₂. The residue is triturated with CH₂Cl₂ (40 mL) and the solid is collected by filtration to give the pure title compound (2.6 g, 64%) as a white solid ¹H NMR (500 MHz, CHLOROFORM-d) δ 4.60 (br s, 4H), 2.54 (s, 6H), 2.39 (dt, J=6.4, 3.0 Hz, 4H) Intermediate: (R)-1-(4-(4-bromo-3,5-dimethyl-1H-pyrazol-1-yl)butyl)pyrrolidin-3-ol

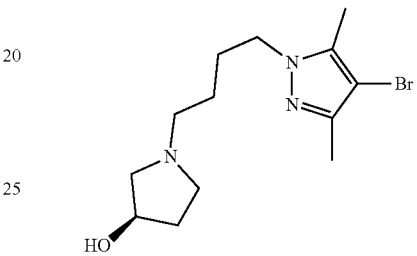

To a dry reaction vial under N₂ is added 2-bromo-1,3-dimethyl-5,6,7,8-tetrahydropyrazolo[1,2-a]pyridazin-4-ium bromide (400 mg, 1.290 mmol), (R)-pyrrolidin-3-ol, HCl (200 mg, 1.618 mmol), anhydrous DMSO (2 mL), and N,N-diisopropylethylamine (530 µl, 3.03 mmol). The reaction is flushed with Ar, securely capped and placed in a 135 C oil bath for 10.5 h. The reaction is diluted with methanol (2 mL) and purified by reverse phase Prep HPLC using a Sunfire C18 10 uM 50×300 mm column with from 10% Solvent B to 100% Solvent B over 30 min at 150 mL/min with detection at 220 nM (solvent A is 5% CH₃CN/95% water with 10 mM NH₄OAc and solvent B is 95% CH₃CN and 5% water with 10 mM NH₄OAc) to give the pure title compound (140.5 mg, 33%) as a tan solid. LC/MS Condition A: ret time 0.769 min, m/e=316

Intermediate: 4-((5-bromo-4-methylpyridin-3-yl)methoxy)-5-chloro-2-hydroxybenzaldehyde

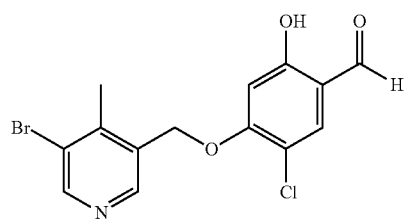 [SMILES: Cc1c(Br)cncc1COc1cc(O)c(C=O)cc1Cl]

To a mixture of (5-bromo-4-methylpyridin-3-yl)methanol (418 mg, 2.069 mmol), 5-chloro-2,4-dihydroxybenzaldehyde (400 mg, 2.318 mmol), and triphenylphosphine (600 mg, 2.288 mmol) in anhydrous THF (20 mL) under a continuous argon flush is added DIAD (450 µl, 2.314 mmol) via syringe over 5 min. The rxn is securely capped and stirred at room temp for 18 h. Evaporate off most of the solvent under a gentle stream of N₂. The residue is redissolved in a mixture of CH$_2$Cl$_2$ (25 mL) and water (30 mlit) and most of the solvent is removed under a gentle stream of N$_2$. The residue is triturated with cold MeOH (20 μL) and the solid is collected by filtration to give the title compound (263.2 mg, 36%) as a tan solid. LC/MS Condition A: ret time 1.144 min, m/e=356

$^1$H NMR (500 MHz, CHLOROFORM-d) δ 11.45 (s, 1H), 9.74 (s, 1H), 8.74 (s, 1H), 8.57 (s, 1H), 7.58 (s, 1H), 6.64 (s, 1H), 5.19 (s, 2H), 2.50 (s, 3H)

Intermediate: 5-((5-((5-bromo-4-methylpyridin-3-yl)methoxy)-4-chloro-2-formylphenoxy)methyl)nicotinonitrile

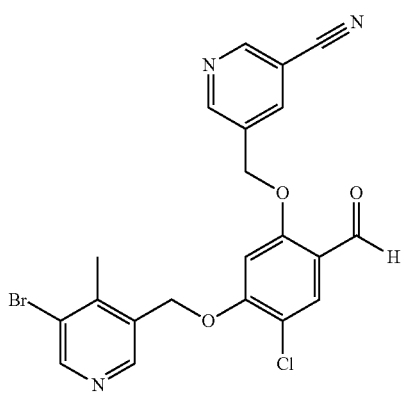 [SMILES: Cc1c(Br)cncc1COc1cc(OCc2cncc(C#N)c2)c(C=O)cc1Cl]

To a solution of 4-((5-bromo-4-methylpyridin-3-yl)methoxy)-5-chloro-2-hydroxybenzaldehyde (253 mg, 0.709 mmol) and 5-(chloromethyl)nicotinonitrile (130 mg, 0.852 mmol) in anhydrous DMF (1.1 mL) is added cesium carbonate (278 mg, 0.853 mmol). The reaction is flushed well with N$_2$, securely capped and placed in a 65° C. oil bath for 3 h. Added reaction via pipette to water (14 mL), filter off the solid, wash with Et$_2$O (10 mL) and dry under high vac to give the title compound (380 mg, quant) as a light brown solid. LC/MS Condition A: ret time 1.174 min, m/e=472; $^1$H NMR (500 MHz, DMSO-d$_6$) δ 10.24 (s, 1H), 9.04 (dd, J=6.2, 2.1 Hz, 2H), 8.74 (s, 1H), 8.62 (s, 1H), 8.56 (t, J=2.0 Hz, 1H), 7.75 (s, 1H), 7.31 (s, 1H), 5.49 (d, J=1.7 Hz, 4H), 2.46 (s, 3H)

Intermediate: 2-(3-(3-bromopropoxy)-2-methylphenyl)-4,4,5,5-tetramethyl-1,3,2-dioxaborolane

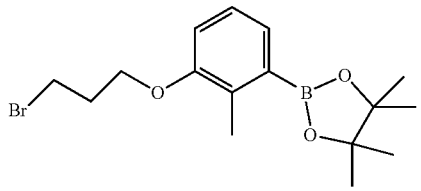 [SMILES: Cc1c(OCCCBr)cccc1B1OC(C)(C)C(C)(C)O1]

An oven dried 150 mL pressure bottle is charged with 2-(3-(3-bromopropoxy)-2-methylphenyl)-4,4,5,5-tetramethyl-1,3,2-dioxaborolane (5.30 g, 17.2 mmol), 4,4,4',4',5,5,5',5'-octamethyl-2,2'-bi(1,3,2-dioxaborolane) (7.3 g, 28.7 mmol), and potassium acetate (5.3 g, 54.0 mmol). Added dioxane (100 mL), bubbled in argon for 10 min, and added [1,1'-bis(diphenylphosphino)ferrocene]dichloropalladium (II) (825 mg, 1.128 mmol). The reaction was sealed and heated in a 80° C. oil bath for 21 h. The reaction was treated with water (300 mL) and EtOAc (250 L), and filtered through Celite to remove some dark solids. Washed Celite with ethyl acetate (300 mL). Partitioned layers. The organic layer was washed with brine, dried over sodium sulfate, evaporated to a dark oily solid. Applied in CH$_2$Cl$_2$/hexane to the head of a 330 g Teledyne Isco Silica Flash Column and purified on Biotage using a gradient from 100% hexanes to 100% CH$_2$Cl$_2$ over 11 col vols. The fractions containing the product were evaporated in vacuo and dried on hi vacuum to give 4.36 g (71%) of the pure title compound as a white solid.

$^1$H NMR (500 MHz, CHLOROFORM-d) δ 7.38 (d, J=7.3 Hz, 1H), 7.16 (t, J=7.8 Hz, 1H), 6.94 (d, J=8.1 Hz, 1H), 4.11 (t, J=5.7 Hz, 2H), 3.66 (t, J=6.5 Hz, 2H), 2.44 (s, 3H), 2.36 (quin, J=6.1 Hz, 2H), 1.37 (s, 12H).

Intermediate: 5-((5-((5-(3-(3-bromopropoxy)-2-methylphenyl)-4-methylpyridin-3-yl)methoxy)-4-chloro-2-formylphenoxy)methyl)nicotinonitrile

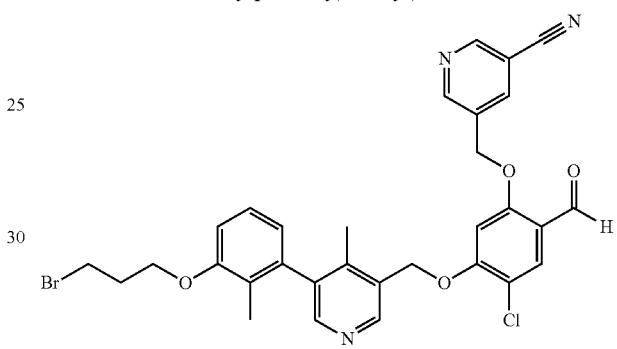

To a solution of 5-((5-((5-bromo-4-methylpyridin-3-yl)methoxy)-4-chloro-2-formylphenoxy)methyl)nicotinonitrile (335 mg, 0.709 mmol) and 2-(3-(3-bromopropoxy)-2-methylphenyl)-4,4,5,5-tetramethyl-1,3,2-dioxaborolane (275 mg, 0.774 mmol) in THF (30 mL) is added potassium phosphate tribasic (3.54 mL, 1.770 mmol). The reaction is flushed very well with argon, then treated with $2^{nd}$ generation X-Phos precatalyst (53 mg, 0.067 mmol). The reaction is again flushed very well with argon, securely capped and stirred at room temp for 2.5 h. The reaction is then placed in a 45° C. oil bath for 45 min, then allowed to stir overnight at room temp for 18 h. Added additional catalyst (12 mg, 0.015 mmol), flush well with argon and place in a 40° C. oil bath for 3.5 h. Dilute reaction with EtOAc (110 mL) and wash with water (1×15 mL), brine (1×15 mL), dry over Na$_2$SO$_4$, filter and evaporate off the solvent in vacuo to give the title compound (340 mg, 77%). LC/MS Condition A: ret time 1.155 min, m/e=620

Intermediate: 1-(3-(hydroxymethyl)-2-methylphenyl)-3,5-dimethyl-1H-pyrazole-4-carbaldehyde

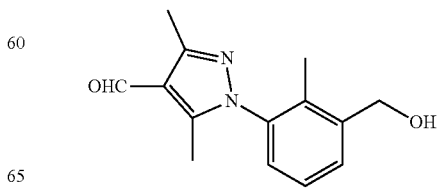

To a dry reaction vial is added (2-methyl-3-(4,4,5,5-tetramethyl-1,3,2-dioxaborolan-2-yl)phenyl)methanol (1.02 g, 4.11 mmol), 3,5-dimethyl-1H-pyrazole-4-carbaldehyde (510 mg, 4.11 mmol), copper (II) acetate (0.747 g, 4.11 mmol) and Pyridine (3 mL). The reaction is flushed with air, securely capped and placed in a 60 C sand bath with shaking for 42 h The solvent is mostly removed under a gentle stream of $N_2$ and $CH_2Cl_2$ (10 mL) is added to the resulting residue. The reaction is again flushed with air, capped and stirred at room temp for 7 days. The solid precipitate was filtered off and the filtrate was applied to the head of a 80 g Teledyne Isco Silica Flash Column and purified on Biotage using a gradient from 100% hexanes to 70% EtOAc/hexanes over 10 column volumes. The fractions containing the product were combined and evaporated in vacuo to give the title compound (149 mg, 15%). LC/MS Condition A: ret time 0.744 min, m/e=245.

Intermediate: 1-(3-((2-chloro-4-formyl-5-hydroxy-phenoxy)methyl)-2-methylphenyl)-3,5-dimethyl-1H-pyrazole-4-carbaldehyde

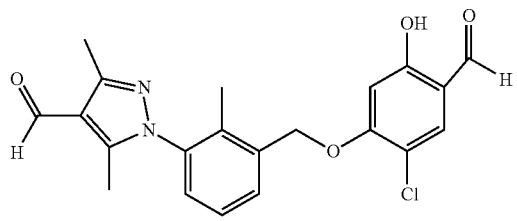 [SMILES: Cc1nn(-c2cccc(COc3cc(O)c(C=O)cc3Cl)c2C)c(C)c1C=O]

To a solution of 1-(3-(hydroxymethyl)-2-methylphenyl)-3,5-dimethyl-1H-pyrazole-4-carbaldehyde (149 mg, 0.610 mmol), 5-chloro-2,4-dihydroxybenzaldehyde (210 mg, 1.217 mmol) and triphenylphosphine (192 mg, 0.732 mmol) in THF (6 mL) under a continuous argon flow is added DIAD (0.192 mL, 0.989 mmol) over 4-5 min. After the addition was complete, the reaction was securely capped and allowed to stir at room temp for several hours. Evaporate off the solvent under a gentle stream of $N_2$. The residue is dissolved $CH_2Cl_2$ (7 mL), applied to the head of a 40 g Teledyne Isco Silica Flash Column and purified on Biotage using a linear gradient from 100% hexanes to 100% EtOAc over 15 column volumes. The fractions containing the product were combined and evaporated in vacuo to give the title compound (140 mg, 55%). LC/MS Condition A: ret time 1.189 min, m/e=399; $^1$H NMR (500 MHz, DMSO-$d_6$) δ 11.17 (s, 1H), 10.05 (s, 1H), 9.98 (s, 1H), 7.73 (s, 1H), 7.69 (d, J=7.6 Hz, 1H), 7.48-7.43 (m, 1H), 7.38 (d, J=7.6 Hz, 1H), 6.87 (s, 1H), 5.37 (s, 2H), 2.42 (s, 3H), 2.29 (s, 3H), 1.97 (s, 3H)

Intermediate: 5-((4-chloro-2-formyl-5-((3-(4-formyl-3,5-dimethyl-1H-pyrazol-1-yl)-2-methylbenzyl)oxy)phenoxy)methyl)nicotinonitrile

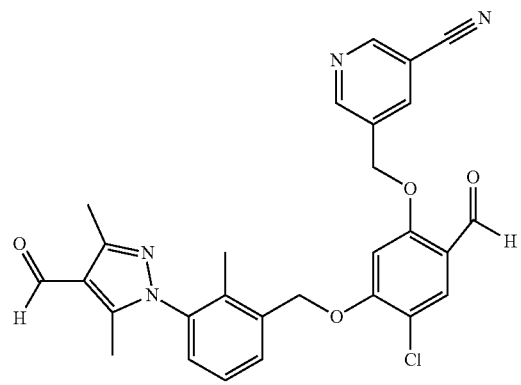 [SMILES: Cc1nn(-c2cccc(COc3cc(OCc4cncc(C#N)c4)c(C=O)cc3Cl)c2C)c(C)c1C=O]

To a solution of 1-(3-((2-chloro-4-formyl-5-hydroxyphenoxy)methyl)-2-methylphenyl)-3,5-dimethyl-1H-pyrazole-4-carbaldehyde (122 mg, 0.306 mmol) and 5-(chloromethyl) nicotinonitrile (56 mg, 0.367 mmol) in anhydrous DMF (550 μL) is added cesium carbonate (120 mg, 0.368 mmol) and sodium iodide (5 mg, 0.033 mmol). The reaction is flushed well with argon, securely capped and placed in a 65° C. oil bath for 3 h. Dilute reaction with EtOAc (125 mL) and extract the organic layer with water (3×20 mL), brine (1×20 mL), dry over Na2SO4, filter and evaporate off the solvent in vacuo to give the title compound (63.3 mg, 40%). LC/MS Condition A: ret time 1.195 min, m/e=515.

Intermediate: (R)-1-((3,5-dimethyl-1H-pyrazol-4-yl)methyl)pyrrolidin-3-ol

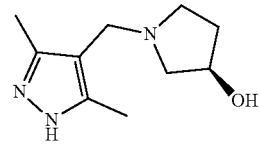

To a mixture of 3,5-dimethyl-1H-pyrazole-4-carbaldehyde (0.3 g, 2.417 mmol), and (R)-pyrrolidin-3-ol, HCl (0.597 g, 4.83 mmol) in EtOH (5 mL) was added acetic acid (0.277 mL, 4.83 mmol) and 4 A molecular sieves (100 mg). The reaction was flushed with $N_2$, securely capped and stirred at room temp for 2 h The reaction was then treated with sodium cyanoborohydride (4.83 mL, 4.83 mmol), flushed with $N_2$, capped and stirred at room temp for 6 h. The reaction was diluted with MeOH (100 mL), again flushed with $N_2$, capped and allowed to stir at room temp for 18 h. The reaction mixture was filtered and the filtrate was purified by reverse phase Prep HPLC using a Sunfire C18 10 uM 50×300 mm column with from 10% Solvent B to 100% Solvent B over 30 min at 150 mL/min with detection at 220 nM (solvent A is 5% $CH_3CN$/95% water with 10 mM $NH_4OAc$ and solvent B is 95% $CH_3CN$ and 5% water with 10 mM $NH_4OAc$) to give the pure title compound (280 mg, 33%) as a white solid. LC/MS Condition C: ret time 0.504 min, m/e=196. $^1$H NMR (500 MHz, CHLOROFORM-d) δ 4.46 (tt, J=5.6, 1.4 Hz, 1H), 3.90-3.78 (m, 2H), 3.41 (ddd, J=10.1, 8.4, 5.3 Hz, 1H), 3.23 (d, J=11.1 Hz, 1H), 2.82 (dd, J=11.2, 5.7 Hz, 1H), 2.71-2.63 (m, 1H), 2.30 (s, 6H), 2.06-1.98 (m, 2H).

Example 2001: 5-((4-chloro-5-((3-(3-chloro-2-(3-(piperidin-1-yl)propoxy)pyridin-4-yl)-2-methylbenzyl)oxy)-2-(((1,3-dihydroxy-2-methylpropan-2-yl)amino)methyl)phenoxy)methyl)nicotinonitrile

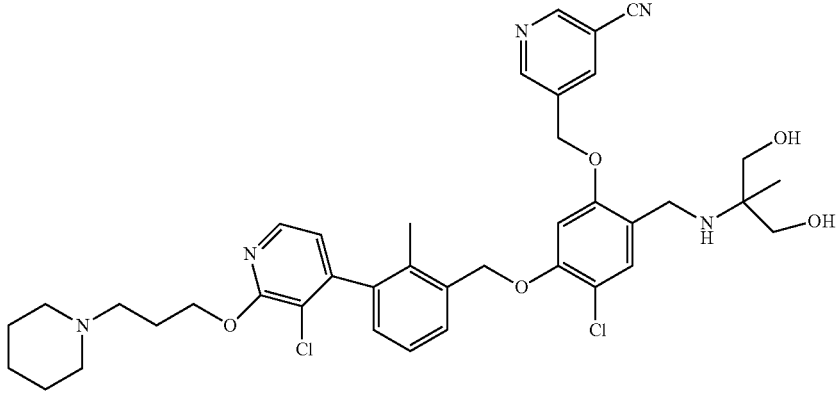 [SMILES: Cc1c(COc2cc(OCc3cncc(C#N)c3)c(CNC(C)(CO)CO)cc2Cl)cccc1-c1ccnc(OCCCN2CCCCC2)c1Cl]

To a solution of 5-((4-chloro-5-((3-(3-chloro-2-(3-(piperidin-1-yl)propoxy)pyridin-4-yl)-2-methylbenzyl)oxy)-2-formylphenoxy)methyl)nicotinonitrile (40 mg, 0.062 mmol) and 2-amino-2-methylpropane-1,3-diol (27 mg, 0.257 mmol) in DCE (0.8 mL) and Ethanol (0.7 mL) is added acetic acid (14 µl, 0.245 mmol) and activated 4 A mol. sieves. The reaction is flushed under argon, stirred room temp for 25 min, then treated with sodium cyanoborohydride, 1 M in THF (0.22 mL, 0.220 mmol) slowly via syringe over 3 h. After the addition is complete, the reaction is stirred at room temp for 3 h. The crude material was purified via preparative LC/MS with the following conditions: Column: XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 15-55% B over 20 minutes, then a 5-minute hold at 100% B; Flow: 20 mL/min. Fractions containing the desired product were combined and dried via centrifugal evaporation to give the pure title compound (21.6 mg, 46%).

LC/MS Condition E: ret time 1.59 min; m/e=734 (M+H)$^+$.
LC/MS Condition F: ret time 1.41 min; m/e=734 (M+H)$^+$.

Example 2002: (R)-5-((4-chloro-5-((3-(3-chloro-4-(3-(3-hydroxypyrrolidin-1-yl)propoxy)pyridin-2-yl)-2-methylbenzyl)oxy)-2-(((1,3-dihydroxy-2-methylpropan-2-yl)amino)methyl)phenoxy)methyl)nicotinonitrile To a solution of 5-((5-((3-(4-(3-bromopropoxy)-3-chloropyridin-2-yl)-2-methylbenzyl)oxy)-4-chloro-2-formylphenoxy)methyl)nicotinonitrile (46.5 mg, 0.073 mmol) and 2-amino-2-methylpropane-1,3-diol (25 mg, 0.238 mmol) in a mixture of DCE (0.8 mL) and Ethanol (0.7 mL) is added acetic acid (12 µl, 0.210 mmol) and activated 4 A mol. sieves. The reaction was flushed briefly under argon, stirred rt 25 min and then treated slowly over 3 h with sodium cyanoborohydride, 1.0 M in THF (220 µL, 0.220 mmol). After the addition is complete, the reaction was stirred rt for an additional 3 h. The solvent was mostly removed under a stream of N2 and the residue was redissolved in MeOH (1.5 mL). The resulting solution was treated with (R)-pyrrolidin-3-ol, HCl (120 mg, 0.971 mmol) and N,N-diisopropylethylamine (210 µL, 1.202 mmol) and placed in a 65 C sand bath with shaking for 18 h. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min to give the pure title compound (37.4 mg, 67%)

LC/MS Condition E: ret time 1.18 min; m/e=736 (M+H)$^+$.
LC/MS Condition F: ret time 1.15 min; m/e=736 (M+H)$^+$.

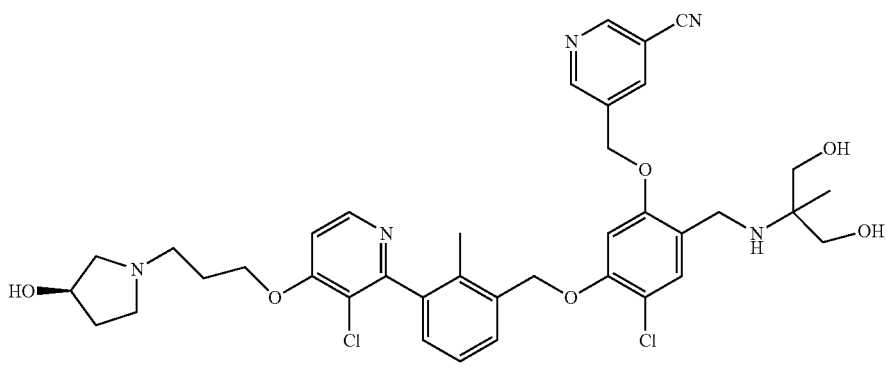 [SMILES: Cc1c(COc2cc(OCc3cncc(C#N)c3)c(CNC(C)(CO)CO)cc2Cl)cccc1-c1nccc(OCCCN2CC[C@@H](O)C2)c1Cl]

Example 2003: (R)-2-((5-chloro-2-((5-cyanopyridin-3-yl)methoxy)-4-((3-(1-(4-((S)-3-hydroxypyrrolidin-1-yl)butyl)-3,5-dimethyl-1H-pyrazol-4-yl)-2-methylbenzyl)oxy)benzyl)amino)-3-hydroxy-2-methylpropanoic acid

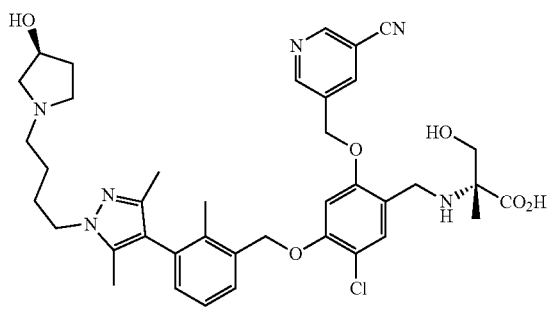 [SMILES: Cc1nn(CCCCN2CC[C@H](O)C2)c(C)c1-c1cccc(COc2cc(OCc3cncc(C#N)c3)c(CN[C@](C)(CO)C(=O)O)cc2Cl)c1C]

To a solution of (R)-2-((5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)amino)-3-hydroxy-2-methylpropanoic acid (35 mg, 0.056 mmol) and (R)-1-(4-(4-bromo-3,5-dimethyl-1H-pyrazol-1-yl)butyl)pyrrolidin-3-ol (20 mg, 0.063 mmol) in THF (6 mL) is added potassium phosphate tribasic 0.5 M in water (0.4 mL, 0.200 mmol). The reaction is flushed well with Ar, then treated with 2$^{nd}$ generation X-phos precatalyst (5 mg, 6.35 µmol) The reaction was again flushed well with argon, securely capped and placed in a 60 C oil bath with stirring for 65 h. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. to give the pure title compound (5.8 mg, 14%).

LC/MS Condition E: ret time 1.36 min; m/e=731 (M+H)$^+$.
LC/MS Condition F: ret time 1.23 min; m/e=731 (M+H)$^+$.

Example 2004: 5-((4-chloro-5-((3-(3-chloro-4-(3-hydroxypropoxy)pyridin-2-yl)-2-methylbenzyl)oxy)-2-(((1,3-dihydroxy-2-methylpropan-2-yl)amino)methyl)phenoxy)methyl)nicotinonitrile

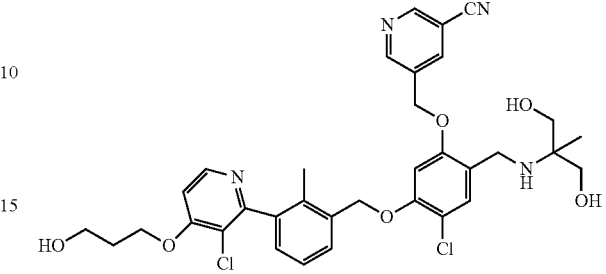

To a solution of 5-((4-chloro-5-((3-(3-chloro-4-(3-hydroxypropoxy)pyridin-2-yl)-2-methylbenzyl)oxy)-2-formylphenoxy)methyl)nicotinonitrile (23 mg, 0.040 mmol) and 2-amino-2-methylpropane-1,3-diol (25 mg, 0.238 mmol) in a mixture of DCE (0.8 mL) and EtOH (0.5 mL) is added acetic acid (10 µl, 0.175 mmol) and activated 4 A mol. sieves. The reaction is flushed briefly with argon, stirred at room temp for 20 min, then treated dropwise with sodium cyanoborohydride 1 M in THF (160 µl, 0.160 mmol over 2 h. After the addition was complete, the reaction was stirred at room temp for 18 h. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. to give the pure title compound (19.5 mg, 74%).

LC/MS Condition E: ret time 1.53 min; m/e=667 (M+H)$^+$.
LC/MS Condition F: ret time 1.32 min; m/e=667 (M+H)$^+$.

Example 2005: (S)-1-(5-chloro-2-((5-cyanopyridin-3-yl)methoxy)-4-((5-(3-(3-((R)-3-hydroxypyrrolidin-1-yl)propoxy)-2-methylphenyl)-4-methylpyridin-3-yl)methoxy)benzyl)piperidine-2-carboxylic acid

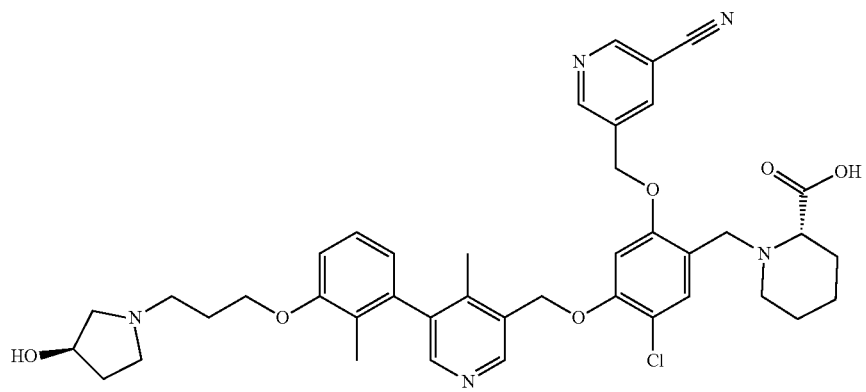 [SMILES: Cc1c(COc2cc(OCc3cncc(C#N)c3)c(CN3CCCC[C@H]3C(=O)O)cc2Cl)cncc1-c1cccc(OCCCN2CC[C@@H](O)C2)c1C]

To a solution of 5-((5-((5-(3-(3-bromopropoxy)-2-methylphenyl)-4-methylpyridin-3-yl)methoxy)-4-chloro-2-formylphenoxy)methyl)nicotinonitrile (52 mg, 0.084 mmol) and L-pipecolic acid (33 mg, 0.256 mmol), in a mixture of DCE (800 µL) and EtOH (500 µL), is added acetic acid (19 µL, 0.332 mmol) and 4 A mol sieves. The reaction is flushed briefly with N₂, capped stirred at room temp for 45 min, then treated dropwise with sodium cyanoborohydride, 1.0M in THF (250 µL, 0.250 mmol) over 2 h. After the addition is complete, the reaction is allowed to stir at room temp overnight. The solvent was mostly removed under a stream of N₂ and the residue was redissolved in MeOH (1.5 mL). The resulting solution was treated with (R)-3-hydroxypyrrolidine hydrochloride (155 mg, 1.254 mmol) and N,N-diisopropylethylamine (350 µL, 2.004 mmol) and placed in a 65 C sand bath with shaking for 3.5 h. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-50% B over 23 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-40% B over 20 minutes, then a 5-minute hold at 100% B; Flow: 20 mL/min. to give the pure title compound (14.2 mg, 14%) as a TFA salt.

LC/MS Condition E: ret time 1.24 min; m/e=740 (M+H)⁺.
LC/MS Condition F: ret time 1.08 min; m/e=740 (M+H)⁺.

Example 2006: 5-((4-chloro-2-(((2-((R)-3-hydroxypyrrolidin-1-yl)ethyl)amino)methyl)-5-((3-(4-(((2-((R)-3-hydroxypyrrolidin-1-yl)ethyl)amino)methyl)-3,5-dimethyl-1H-pyrazol-1-yl)-2-methylbenzyl)oxy)phenoxy)methyl)nicotinonitrile was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 5-35% B over 18 minutes, then a 3-minute hold at 100% B; Flow: 20 mL/min to give the pure title compound (2.9 mg, 8%).

LC/MS Condition E: ret time 1.18 min; m/e=743 (M+H)+.
LC/MS Condition F: ret time 0.907 min; m/e=743 (M+H)+.

Example 2007: 5-((4-chloro-2-(((R)-3-hydroxypyrrolidin-1-yl)methyl)-5-((3-(4-(((R)-3-hydroxypyrrolidin-1-yl)methyl)-3,5-dimethyl-1H-pyrazol-1-yl)-2-methylbenzyl)oxy)phenoxy)methyl)nicotinonitrile

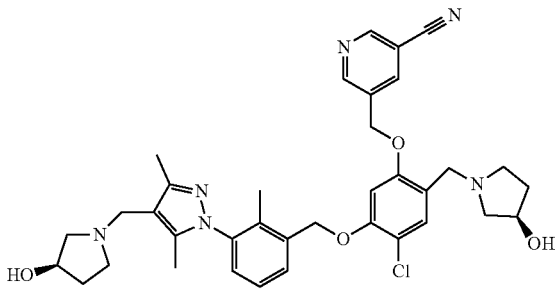 [SMILES: Cc1nn(-c2cccc(COc3cc(OCc4cncc(C#N)c4)c(CN4CC[C@@H](O)C4)cc3Cl)c2C)c(C)c1CN1CC[C@@H](O)C1]

To a solution of 5-((4-chloro-2-formyl-5-((3-(4-formyl-3,5-dimethyl-1H-pyrazol-1-yl)-2-methylbenzyl)oxy)phenoxy)methyl)nicotinonitrile (22.8 mg, 0.044 mmol) and (R)-3-hydroxypyrrolidine hydrochloride (40 mg, 0.324 mmol), in a mixture of DCE (900 µL) and EtOH (600 µL), is added acetic acid (5.2 µL, 0.091 mmol), N,N-diisopropylethylamine (13 µL, 0.074 mmol) and 4 A mol sieves. The reaction is flushed briefly with N₂, capped stirred at room temp for 2 h and then treated dropwise with sodium cyanoborohydride, 1.0M in THF (270 µL, 0.270 mmol) over 3.5 h. After the addition is complete, the reaction is stirred at

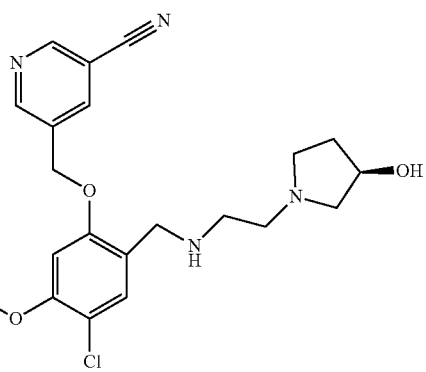

To a solution of 5-((4-chloro-2-formyl-5-((3-(4-formyl-3,5-dimethyl-1H-pyrazol-1-yl)-2-methylbenzyl)oxy)phenoxy)methyl)nicotinonitrile (22.8 mg, 0.044 mmol) in a mixture of DCE (900 µL) and EtOH (600 µL) is added (3R)-1-(2-aminoethyl)-3-pyrrolidinol (43 mg, 0.330 mmol), acetic acid (8 µL, 0.140 mmol) and 4 A mol sieves. The reaction is flushed briefly with N₂, securely capped stirred at room temp for 1 h, then treated dropwise with sodium cyanoborohydride, 1.0M in THF (270 µL, 0.270 mmol) over 5 h. After the addition was complete, the reaction was allowed to stir overnight at room temp. The crude material room temp overnight. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 8-48% B over 20 minutes, then a 5-minute hold at 100% B; Flow: 20 mL/min. to give the pure title compound (8.0 mg, 26%).

LC/MS Condition E: ret time 1.23 min; m/e=657 (M+H)⁺.
LC/MS Condition F: ret time 1.22 min; m/e=657 (M+H)⁺.

Example 2008: (R)-5-((4-chloro-2-(((1,3-dihydroxy-2-methylpropan-2-yl)amino)methyl)-5-((5-(3-(3-(3-hydroxypyrrolidin-1-yl)propoxy)-2-methylphenyl)-4-methylpyridin-3-yl)methoxy)phenoxy)methyl)nicotinonitrile

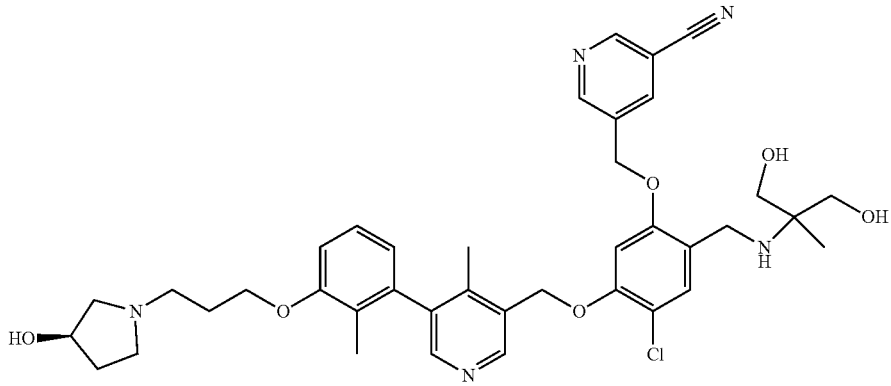 [SMILES: Cc1c(COc2cc(OCc3cncc(C#N)c3)c(CNC(C)(CO)CO)cc2Cl)cncc1-c1cccc(OCCCN2CC[C@@H](O)C2)c1C]

To a solution of 5-((5-((5-(3-(3-bromopropoxy)-2-methylphenyl)-4-methylpyridin-3-yl)methoxy)-4-chloro-2-formylphenoxy)methyl)nicotinonitrile (20.4 mg, 0.033 mmol) and 2-amino-2-methyl-1,3-propanediol (10.4 mg, 0.099 mmol) in a mixture of DCE (800 µL) and Ethanol (500 µL) is added acetic acid (7.5 µL, 0.131 mmol) and activated 4 Å mol sieves. The reaction is stirred at room temp for 30 min, then treated dropwise with sodium cyanoborohydride, 1.0M in THF (115 µL, 0.115 mmol) over 30 min. After the addition was complete, the reaction was stirred overnight at room temp. The solvent was mostly removed under a stream of N2 and the residue was redissolved in MeOH (1.5 mL). The resulting solution was treated with (R)-3-hydroxypyrrolidine hydrochloride (74 mg, 0.599 mmol) and N,N-diisopropylethylamine (185 µL, 1.059 mmol), flushed briefly with N₂, capped, placed in a 65° C. sand bath with shaking for 4.5 h then placed in a 45° C. sand bath for 36 h. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 5-55% B over 25 minutes, then a 5-minute hold at 100% B; Flow: 20 mL/min to give the title compound (7.2 mg, 29%).
LC/MS Condition E: ret time 1.31 min; m/e=716 (M+H)⁺.
LC/MS Condition F: ret time 1.18 min; m/e=716 (M+H)⁺.

Example 2009: (R)-2-((5-chloro-2-((5-cyanopyridin-3-yl)methoxy)-4-((3-(4-(((R)-3-hydroxypyrrolidin-1-yl)methyl)-3,5-dimethyl-1H-pyrazol-1-yl)-2-methylbenzyl)oxy)benzyl)amino)-3-hydroxy-2-methylpropanoic acid To a mixture of (R)-2-((5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)amino)-3-hydroxy-2-methylpropanoic acid (90 mg, 0.145 mmol), (R)-1-((3,5-dimethyl-1H-pyrazol-4-yl)methyl)pyrrolidin-3-ol, 2 AcOH (63 mg, 0.200 mmol), 2,2'-bipyridine (23 mg, 0.147 mmol), and copper (II) acetate (40 mg, 0.220 mmol) is added Pyridine (1 mL). The reaction is capped and stirred room temp in presence of air overnight. The crude material was purified via preparative LC/MS with the following conditions: Column: XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-45% B over 25 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-50% B over 15 minutes, then a 3-minute hold at 100% B; Flow: 20 mL/min to give the pure title compound (1.3 mg, 1.2%).
LC/MS Condition E: ret time 1.04 min; m/e=689 (M+H)⁺.
LC/MS Condition F: ret time 1.16 min; m/e=689 (M+H)⁺.

Example 2010: (R)-2-((5-chloro-2-((5-cyanopyridin-3-yl)methoxy)-4-((3-(4-formyl-3,5-dimethyl-1H-pyrazol-1-yl)-2-methylbenzyl)oxy)benzyl)amino)-3-hydroxy-2-methylpropanoic acid

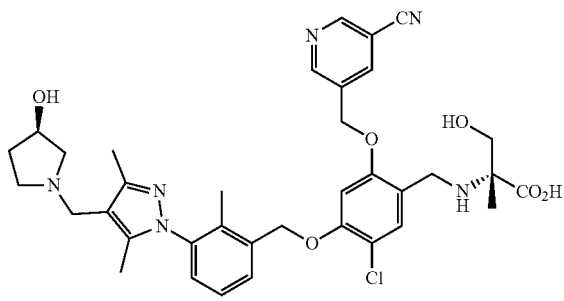 [SMILES: Cc1nn(-c2cccc(COc3cc(OCc4cncc(C#N)c4)c(CN[C@](C)(CO)C(=O)O)cc3Cl)c2C)c(C)c1CN1CC[C@@H](O)C1]

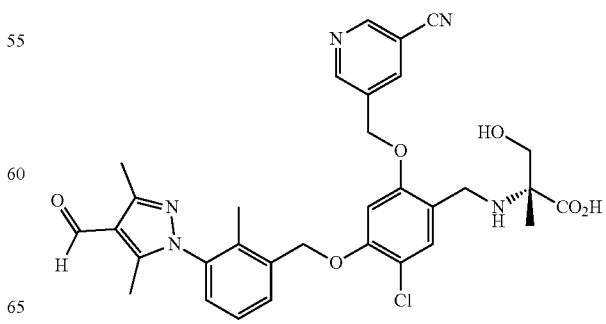

To a mixture of (R)-2-((5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)amino)-3-hydroxy-2-methylpropanoic acid (32.5 mg, 0.052 mmol), and 3,5-dimethyl-1H-pyrazole-4-carbaldehyde (11.9 mg, 0.096 mmol) in CH$_2$Cl$_2$ (2 mL) is added pyridine (32 μl, 0.396 mmol), followed by solid copper (II) acetate (16 mg, 0.088 mmol). The reaction is flushed with 02, sealed and stirred at room temp for 6 days. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min to give the title compound (1 mg, 2%). LC/MS Condition E: ret time 1.47 min; m/e=618 (M+H)$^+$.

LC/MS Condition F: ret time 1.57 min; m/e=618 (M+H)$^+$.

Intermediate: 4-((4-bromo-3-methylpyridin-2-yl)methoxy)-5-chloro-2-hydroxybenzaldehyde

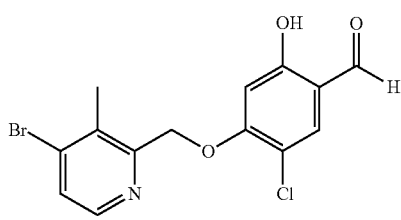 [SMILES: Cc1c(Br)ccnc1COc1cc(O)c(C=O)cc1Cl]

A mixture of (4-bromo-3-methylpyridin-2-yl)methanol (560 mg, 2.77 mmol), 5-chloro-2,4-dihydroxybenzaldehyde (478 mg, 2.77 mmol), and triphenylphosphine (800 mg, 3.05 mmol) in THF (20 mL) was cooled as a result of continuous N$_2$ flushing (a yellow cloudy mixture) while DIAD (450 μl, 2.314 mmol) was added via syringe over 2 min. The suspension became a clear orange solution as DIAD was added and after ~10 min, some precipitate was observed. The reaction was sealed under N$_2$ and stirred at rt overnight. The first crop of the product was collected by filtering the reaction mixture to give 0.277 g as a white solid. The filtrate was blown dry under N$_2$ and triturated with cold MeOH and was then filtered to give the 2nd crop of product in about-0.2 g as an off-white solid (Total 0.47 g, 45%). $^1$H NMR (400 MHz, CHLOROFORM-d) δ 11.37 (s, 1H), 9.69 (s, 1H), 8.24 (d, J=5.3 Hz, 1H), 7.53 (d, J=5.3 Hz, 1H), 7.52 (s, 1H), 6.76 (s, 1H), 5.38 (s, 2H), 2.54 (s, 3H). LC/MS Condition D: ret time 1.01 min, m/e=356 Intermediate: 5-((5-((4-bromo-3-methylpyridin-2-yl)methoxy)-4-chloro-2-formylphenoxy)methyl)nicotinonitrile

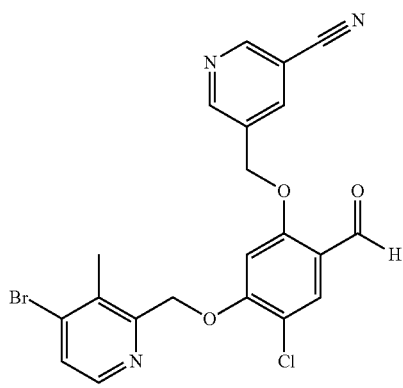 [SMILES: Cc1c(Br)ccnc1COc1cc(OCc2cncc(C#N)c2)c(C=O)cc1Cl]

A mixture of 4-((4-bromo-3-methylpyridin-2-yl)methoxy)-5-chloro-2-hydroxybenzaldehyde (0.277 g, 0.777 mmol), 5-(chloromethyl)nicotinonitrile (0.142 g, 0.932 mmol), sodium iodide (0.012 g, 0.078 mmol) and cesium carbonate (0.304 g, 0.932 mmol) in DMF (6 mL) was stirred at 75° C. under nitrogen for 3 h. The reaction mixture was cooled to rt and was poured into 50 ml ice-water. The mixture was then stirred for 2 h and filtered to collect the product 5-((5-((4-bromo-3-methylpyridin-2-yl)methoxy)-4-chloro-2-formylphenoxy)methyl)nicotinonitrile (0.3 g, 0.597 mmol, 77% yield) as an off-white solid.

$^1$H NMR (400 MHz, CHLOROFORM-d) δ 10.25 (s, 1H), 8.96 (d, J=2.0 Hz, 1H), 8.92 (d, J=1.8 Hz, 1H), 8.20 (d, J=5.3 Hz, 1H), 8.11 (t, J=2.0 Hz, 1H), 7.86 (s, 1H), 7.55 (d, J=5.3 Hz, 1H), 7.08 (s, 1H), 5.48 (s, 2H), 5.21 (s, 2H), 2.60 (s, 3H). LC/MS Condition D: ret time 1.07 min, m/e=472

Intermediate: 5-((5-((4-(3-(3-bromopropoxy)-2-methylphenyl)-3-methylpyridin-2-yl)methoxy)-4-chloro-2-formylphenoxy)methyl)nicotinonitrile

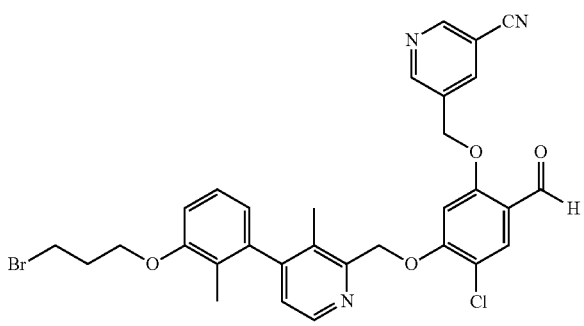 [SMILES: Cc1c(OCCCBr)cccc1-c1ccnc(COc2cc(OCc3cncc(C#N)c3)c(C=O)cc2Cl)c1C]

Chloro(2-dicyclohexylphosphino-2',4',6'-triisopropyl-1,1'-biphenyl)[2-(2'-amino-1,1'-biphenyl)]palladium(II) (0.025 g, 0.032 mmol) was added to a mixture of 2-(3-(3-bromopropoxy)-2-methylphenyl)-4,4,5,5-tetramethyl-1,3,2-dioxaborolane (0.225 g, 0.635 mmol) and potassium phosphate tribasic (3.17 mL, 1.587 mmol) in THF (15 mL) (flushed with N$_2$ for 10 min before the catalyst was added). The resulting mixture was stirred at rt for 18 h. The reaction mixture was partitioned between EtOAc/aqueous sodium bicarbonate. The aqueous layer was extracted with EtOAc (3×20 ml). The combined organic layers were washed with aqueous sodium bicarbonate (2×20 ml) and brine (20 ml), dried over magnesium sulfate, filtered and concentrated under vacuum to get 0.5 g of crude product, that was purified by silica gel chromatography (Biotage Horizon System; RediSepRf 40 g column; EtOAc/Hexane, Gradient: 0%-100%) to get 5-((5-((4-(3-(3-bromopropoxy)-2-methylphenyl)-3-methylpyridin-2-yl)methoxy)-4-chloro-2-formylphenoxy)methyl)nicotinonitrile (0.3 g, 0.459 mmol, 72.3% yield) as a white solid.

$^1$H NMR (400 MHz, CHLOROFORM-d) δ 10.27 (s, 1H), 8.99 (d, J=2.3 Hz, 1H), 8.92 (d, J=2.0 Hz, 1H), 8.44 (d, J=4.8 Hz, 1H), 8.15 (t, J=2.1 Hz, 1H), 7.86 (s, 1H), 7.27 (s, 1H), 7.24-7.18 (m, 1H), 7.11 (d, J=5.0 Hz, 1H), 6.91 (d, J=8.0 Hz, 1H), 6.67 (d, J=7.0 Hz, 1H), 5.60-5.45 (m, 2H), 5.27 (s, 2H), 4.17 (td, J=5.8, 3.3 Hz, 2H), 3.65 (t, J=6.4 Hz, 2H), 2.39 (dd, J=6.3, 5.8 Hz, 2H), 2.24 (s, 3H), 1.86 (s, 3H). LC/MS Condition D: ret time 1.08 min; m/e=620

Example 2011: (S)-1-(5-chloro-2-((5-cyanopyridin-3-yl)methoxy)-4-((4-(3-(3-((R)-3-hydroxypyrrolidin-1-yl)propoxy)-2-methylphenyl)-3-methylpyridin-2-yl)methoxy)benzyl)piperidine-2-carboxylic acid A mixture of 5-((5-((4-(3-(3-bromopropoxy)-2-methylphenyl)-3-methylpyridin-2-yl)methoxy)-4-chloro-2-formylphenoxy)methyl)nicotinonitrile (0.1 g, 0.161 mmol), (S)-piperidine-2-carboxylic acid (0.042 g, 0.322 mmol), acetic acid (0.018 mL, 0.322 mmol) and a few 4 A MS (molecular sieves) in ClCH$_2$CH$_2$Cl (5 mL) and EtOH (5 mL) was stirred at rt for 2 h. Sodium cyanoborohydride (1.0 M in THF) (0.322 mL, 0.322 mmol) was added and the resulting reaction mixture was stirred at rt for 1 day. The reaction mixture was flushed with N$_2$ overnight and pump dried for 2 h. The residue was dissolved in 4 ml of DMF, filtered and the filtrate was divided into 2 equal portions and one portion of them was subjected to the next step. The other portion was used to make Example 2014. To the solution of the intermediate was added (R)-pyrrolidin-3-ol, HCl (0.100 g, 0.805 mmol) and DIPEA (diisopropylethylamine, 0.141 mL, 0.805 mmol). The resulting reaction mixture was stirred at 60° C. for 6 h. The reaction mixture was filtered and the filtrate was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 10-50% B over 15 minutes, then a 3-minute hold at 100% B; Flow: 20 mL/min. Fractions containing the desired product were combined and dried via centrifugal evaporation to give (S)-1-(5-chloro-2-((5-cyanopyridin-3-yl)methoxy)-4-((4-(3-

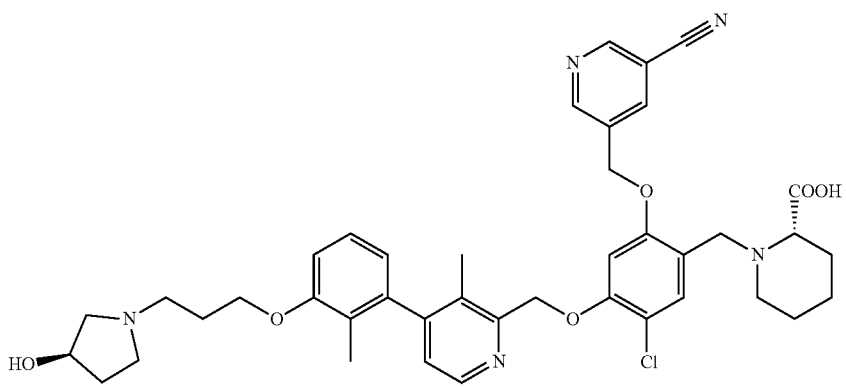 [SMILES: Cc1c(OCCCN2CC[C@@H](O)C2)cccc1-c1ccnc(COc2cc(OCc3cncc(C#N)c3)c(CN3CCCC[C@H]3C(=O)O)cc2Cl)c1C]

(3-((R)-3-hydroxypyrrolidin-1-yl)propoxy)-2-methylphenyl)-3-methylpyridin-2-yl)methoxy)benzyl)piperidine-2-carboxylic acid as TFA salt (6.6 mg, 5.4%)$^1$H NMR (500 MHz, DMSO-d$_6$) δ 8.99 (s, 2H), 8.46-8.37 (m, 2H), 7.39 (s, 1H), 7.28-7.18 (m, 1H), 7.12 (br. s., 2H), 7.01 (d, J=8.4 Hz, 1H), 6.68 (d, J=7.3 Hz, 1H), 5.40 (s, 2H), 5.29 (s, 2H), 4.20 (br. s., 1H), 4.13-4.00 (m, 2H), 3.74 (dd, J=14.3, 5.5 Hz, 1H), 3.57 (dd, J=14.1, 5.3 Hz, 1H), 3.13 (br. s., 1H), 2.88 (d, J=11.7 Hz, 1H), 2.78-2.69 (m, 1H), 2.66-2.56 (m, 3H), 2.46 (d, J=6.2 Hz, 1H), 2.40-2.33 (m, 1H), 2.30-2.19 (m, 1H), 2.11 (s, 3H), 2.02-1.93 (m, 1H), 1.92 (s, 5H), 1.81 (s, 3H), 1.78 (br. s., 2H), 1.60-1.32 (m, 5H). LC/MS Condition E ret time 1.25 min; m/e=740.1.

Example 2012: (S)-2-((5-chloro-2-((5-cyanopyridin-3-yl)methoxy)-4-((4-(3-(3-((R)-3-hydroxypyrrolidin-1-yl)propoxy)-2-methylphenyl)-3-methylpyridin-2-yl)methoxy)benzyl)amino)-3-hydroxy-2-methylpropanoic acid

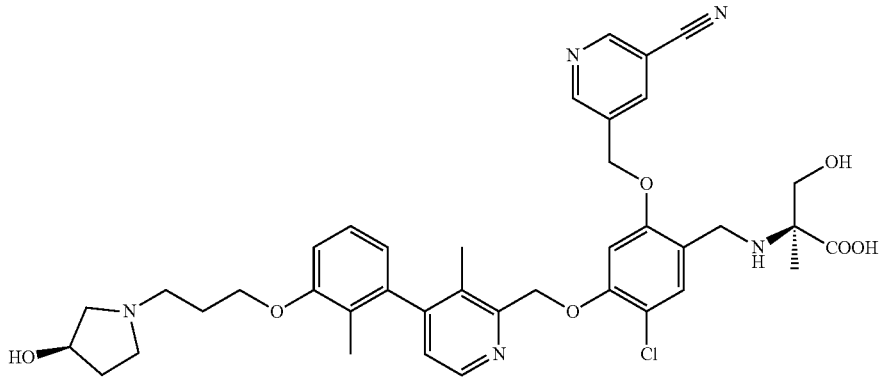 [SMILES: Cc1c(OCCCN2CC[C@@H](O)C2)cccc1-c1ccnc(COc2cc(OCc3cncc(C#N)c3)c(CN[C@@](C)(CO)C(=O)O)cc2Cl)c1C]

A mixture of 5-((5-((4-(3-(3-bromopropoxy)-2-methylphenyl)-3-methylpyridin-2-yl)methoxy)-4-chloro-2-formylphenoxy)methyl)nicotinonitrile (120 mg, 0.193 mmol), (S)-2-amino-3-hydroxy-2-methylpropanoic acid (46.0 mg, 0.387 mmol), acetic acid (0.022 mL, 0.387 mmol) and a few 4 A MS in ClCH$_2$CH$_2$Cl (2 mL) and EtOH (2 mL) was stirred at rt for 2 h. Sodium cyanoborohydride (0.322 mL, 0.322 mmol) was added and the resulting reaction mixture was stirred at rt for 3 days. The reaction mixture was filtered and the filtrate was concentrated and was pump dried for 2 h. The residue was dissolved in 4 ml of DMF. One half of the material was subjected to the next step. The other half portion was used for Example 2015. To the solution of the intermediate in 2 ml of DMF was added (R)-pyrrolidin-3-ol, HCl (47.8 mg, 0.387 mmol) and DIPEA (0.141 mL, 0.805 mmol). The resulting reaction mixture was stirred at 60° C. for 6 h. The reaction mixture was filtered and the filtrate was purified via preparative LC/MS with the following conditions: Column: waters xbridge c-18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 0-30% B over 15 minutes, then a 5-minute hold at 100% B; Flow: 20 mL/min. Fractions containing the desired product were combined and dried via centrifugal evaporation The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Fractions containing the desired product were combined and dried via centrifugal evaporation to give (S)-2-((5-chloro-2-((5-cyanopyridin-3-yl)methoxy)-4-((4-(3-(3-((R)-3-hydroxypyrrolidin-1-yl)propoxy)-2-methylphenyl)-3-methylpyridin-2-yl)methoxy)benzyl)amino)-3-hydroxy-2-methylpropanoic acid (4.9 mg, yield 3.4%). $^1$H NMR (500 MHz, DMSO-d$_6$) δ 9.05-8.97 (m, 1H), 8.48-8.37 (m, 1H), 7.48 (s, 1H), 7.28-7.22 (m, 1H), 7.17-7.10 (m, 2H), 7.02 (d, J=7.7 Hz, 1H), 6.68 (d, J=7.3 Hz, 1H), 5.41 (d, J=2.9 Hz, 2H), 5.32 (s, 2H), 4.20 (br. s., 1H), 4.13-4.02 (m, 3H), 3.85 (s, 3H), 3.59-3.44 (m, 3H), 2.80-2.68 (m, 1H), 2.66-2.56 (m, 3H), 2.37 (dd, J=9.5, 4.0 Hz, 3H), 2.11 (s, 3H), 2.03-1.93 (m, 2H), 1.83 (s, 3H), 1.57 (d, J=2.9 Hz, 1H), 1.22 (s, 3H). LC/MS Condition E: ret time 1.13 min; m/e=730.0.

Example 2013: (R)-5-((4-chloro-2-(((1-hydroxy-2-(hydroxymethyl)butan-2-yl)amino)methyl)-5-((4-(3-(3-(3-hydroxypyrrolidin-1-yl)propoxy)-2-methylphenyl)-3-methylpyridin-2-yl)methoxy)phenoxy)methyl)nicotinonitrile

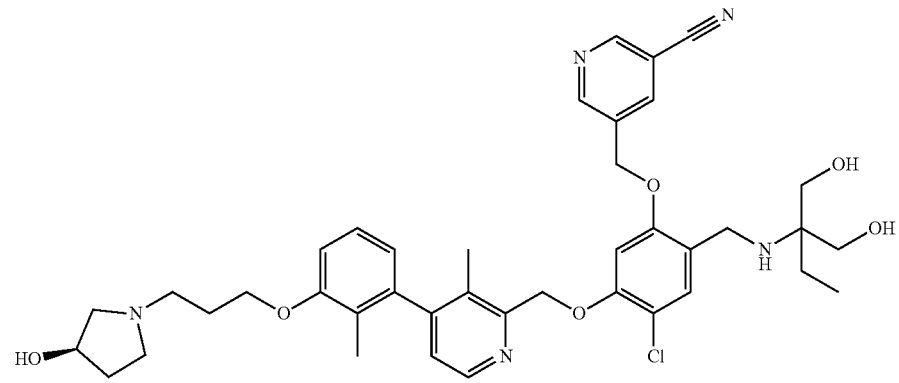 [SMILES: CCC(CO)(CO)NCc1cc(Cl)c(OCc2nccc(-c3cccc(OCCCN4CC[C@@H](O)C4)c3C)c2C)cc1OCc1cncc(C#N)c1]

A mixture of 5-((5-((4-(3-(3-bromopropoxy)-2-methylphenyl)-3-methylpyridin-2-yl)methoxy)-4-chloro-2-formylphenoxy)methyl)nicotinonitrile (80 mg, 0.129 mmol), 2-amino-2-ethylpropane-1,3-diol (30.7 mg, 0.258 mmol), acetic acid (0.015 mL, 0.258 mmol) and a few 4 A MS in ClCH$_2$CH$_2$Cl (2 mL) and EtOH (2 mL) was stirred at rt for 2 h. Sodium cyanoborohydride (0.322 mL, 0.322 mmol) was added and the resulting reaction mixture was stirred at rt for 24 h. The reaction mixture was flushed with N$_2$ overnight and pump dried for 2 h. The residue was dissolved in 4 ml of DMF, filtered and the filtrate was divided into two equal portions and one portion was subjected on the next step. The other portion was used for the synthesis of Example 2016. To the solution of the intermediate was added (R)-pyrrolidin-3-ol, HCl (0.100 g, 0.805 mmol) and DIPEA (0.141 mL, 0.805 mmol). The resulting reaction mixture was stirred at 60° C. for 6 h. The reaction mixture was filtered and the filtrate was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-40% B over 20 minutes, then a 5-minute hold at 100% B; Flow: 20 mL/min. Fractions containing the desired product were combined and dried via centrifugal evaporation to give (R)-5-((4-chloro-2-(((1-hydroxy-2-(hydroxymethyl)butan-2-yl)amino)methyl)-5-((4-(3-(3-(3-hydroxypyrrolidin-1-yl)propoxy)-2-methylphenyl)-3-methylpyridin-2-yl)methoxy)phenoxy)methyl)nicotinonitrile as TFA salt (15.2 mg, yield 15%). $^1$H NMR (500 MHz, DMSO-d$_6$) δ 8.99 (br. s., 2H), 8.47-8.34 (m, 2H), 7.39 (s, 1H), 7.25 (t, J=7.9 Hz, 1H), 7.16-7.09 (m, 2H), 7.01 (d, J=8.1 Hz, 1H), 6.68 (d, J=7.3 Hz, 1H), 5.39 (d, J=3.7 Hz, 2H), 5.30 (s, 2H), 4.20 (br. s., 1H), 4.12-3.97 (m, 2H), 3.61 (s, 1H), 2.79-2.56 (m, 4H), 2.49-2.31 (m, 2H), 2.11 (s, 3H), 2.04-1.94 (m, 1H), 1.83 (s, 3H), 1.57 (d, J=4.4 Hz, 1H), 1.36 (q, J=7.2 Hz, 2H), 0.77 (t, J=7.5 Hz, 3H). LC/MS Condition E: ret time 1.17 min; m/e=730.1.

Example 2014: (S)-1-(5-chloro-2-((5-cyanopyridin-3-yl)methoxy)-4-((3-methyl-4-(2-methyl-3-(3-(piperidin-1-yl)propoxy)phenyl)pyridin-2-yl)methoxy)benzyl)piperidine-2-carboxylic acid A mixture of (S)-1-(4-((4-(3-(3-bromopropoxy)-2-methylphenyl)-3-methylpyridin-2-yl)methoxy)-5-chloro-2-((5-cyanopyridin-3-yl)methoxy)benzyl)piperidine-2-carboxylic acid (the intermediate from Example 2011) (60 mg, 0.038 mmol), piperidine (32.0 mg, 0.376 mmol) and DIPEA (0.066 mL, 0.376 mmol) in DMF (2 mL) was stirred at 60° C. under nitrogen for 6 h. The reaction mixture was filtered and the filtrate was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 10-50% B over 15 minutes, then a 3-minute hold at 100% B; Flow: 20 mL/min. Fractions containing the desired product were combined and dried via centrifugal evaporation to give (S)-1-(5-chloro-2-((5-cyanopyridin-3-yl)methoxy)-4-((3-methyl-4-(2-methyl-3-(3-(piperidin-1-yl)propoxy)phenyl)pyridin-2-yl)methoxy)benzyl)piperidine-2-carboxylic acid as TFA salt (7.1 mg, yield 15%). $^1$H NMR (500 MHz, DMSO-d$_6$) δ 9.02 (s, 2H), 8.48-8.38 (m, 2H), 7.51 (s, 1H), 7.34-7.19 (m, 2H), 7.14 (d, J=4.8 Hz, 1H), 7.04 (d, J=8.4 Hz, 1H), 6.72 (d, J=7.7 Hz, 1H), 5.45 (d, J=4.0 Hz, 2H), 5.37 (br. s., 2H), 4.21 (br. s., 2H), 4.17-4.06 (m, 2H), 3.88 (br. s., 1H), 3.31-3.19 (m, 1H), 2.85 (br. s., 1H), 2.28-2.17 (m, 2H), 2.12 (s, 3H), 1.86 (d, J=4.4 Hz, 3H), 1.67 (br. s., 10H). LC/MS Condition E: ret time 1.12 min; m/e=738.3.

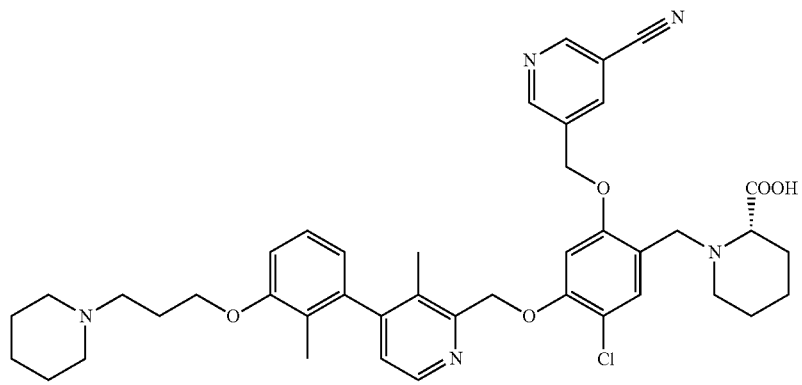 [SMILES: Cc1c(OCCCN2CCCCC2)cccc1-c1ccnc(COc2cc(OCc3cncc(C#N)c3)c(CN3CCCC[C@H]3C(=O)O)cc2Cl)c1C]

Example 2015: (S)-2-((5-chloro-2-((5-cyanopyridin-3-yl)methoxy)-4-((3-methyl-4-(2-methyl-3-(3-(piperidin-1-yl)propoxy)phenyl)pyridin-2-yl)methoxy)benzyl)amino)-3-hydroxy-2-methylpropanoic acid

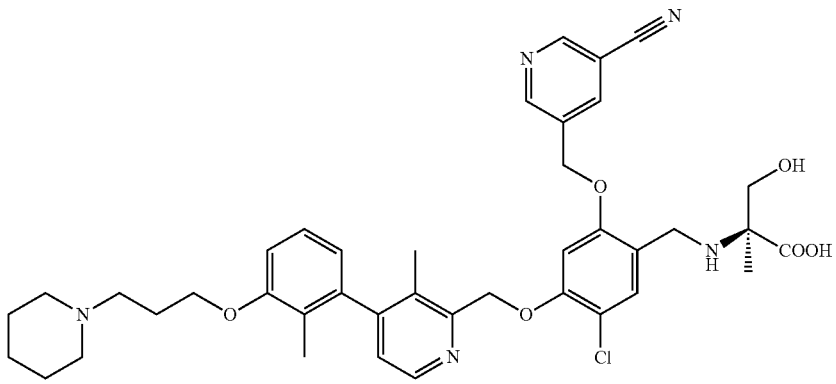 [SMILES: Cc1c(OCCCN2CCCCC2)cccc1-c1ccnc(COc2cc(OCc3cncc(C#N)c3)c(CN[C@@](C)(CO)C(=O)O)cc2Cl)c1C]

To the solution of (S)-2-((4-((4-(3-(3-bromopropoxy)-2-methylphenyl)-3-methylpyridin-2-yl)methoxy)-5-chloro-2-((5-cyanopyridin-3-yl)methoxy)benzyl)amino)-3-hydroxy-2-methylpropanoic acid (65 mg, 0.025 mmol) (the intermediate from Example 2012) in DMF (2 mL) was added piperidine (21.40 mg, 0.251 mmol). The resulting reaction mixture was stirred at 60° C. for 6 h. The reaction mixture was filtered and the filtrate was purified via preparative LC/MS with the following conditions: Column: waters xbridge c-18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 15 minutes, then a 5 minute hold at 100% B; Flow: 20 mL/min. Fractions containing the desired product were combined and dried via centrifugal evaporation to give (S)-2-((5-chloro-2-((5-cyanopyridin-3-yl)methoxy)-4-((3-methyl-4-(2-methyl-3-(3-(piperidin-1-yl)propoxy)phenyl)pyridin-2-yl)methoxy)benzyl)amino)-3-hydroxy-2-methylpropanoic acid (14.8 mg, yield 78%). $^1$H NMR (500 MHz, DMSO-$d_6$) δ 9.00 (d, J=14.3 Hz, 1H), 8.51-8.36 (m, 1H), 7.49 (s, 1H), 7.25 (t, J=7.9 Hz, 1H), 7.16 (s, 1H), 7.13 (d, J=4.8 Hz, 1H), 7.01 (d, J=8.1 Hz, 1H), 6.68 (d, J=7.3 Hz, 1H), 5.41 (br. s., 2H), 5.32 (s, 2H), 4.12-4.02 (m, 2H), 3.88 (br. s., 2H), 3.64-3.46 (m, 2H), 2.47 (t, J=7.2 Hz, 3H), 2.38 (d, J=5.1 Hz, 6H), 2.11 (s, 4H), 1.82 (s, 4H), 1.51 (d, J=4.8 Hz, 5H), 1.40 (d, J=4.8 Hz, 3H), 1.23 (s, 4H). LC/MS Condition E: ret time 1.10 min; m/e=728.1.

Example 2016: 5-((4-chloro-2-(((1-hydroxy-2-(hydroxymethyl)butan-2-yl)amino)methyl)-5-((3-methyl-4-(2-methyl-3-(3-(piperidin-1-yl)propoxy)phenyl)pyridin-2-yl)methoxy)phenoxy)methyl)nicotinonitrile

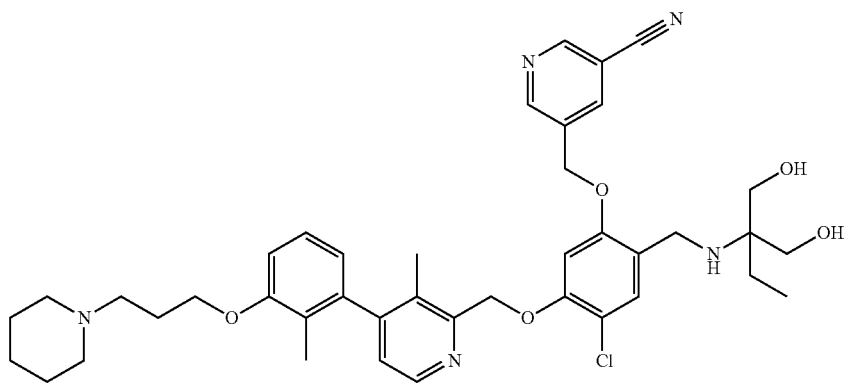 [SMILES: CCC(CO)(CO)NCc1cc(Cl)c(OCc2nccc(-c3cccc(OCCCN4CCCCC4)c3C)c2C)cc1OCc1cncc(C#N)c1]

A mixture of 5-((5-((4-(3-(3-bromopropoxy)-2-methylphenyl)-3-methylpyridin-2-yl)methoxy)-4-chloro-2-(((1-hydroxy-2-(hydroxymethyl)butan-2-yl)amino)methyl)phenoxy)methyl)nicotinonitrile (the intermediate from Example 2013) (42 mg, 0.022 mmol), piperidine (18.77 mg, 0.220 mmol) and DIPEA (0.038 mL, 0.220 mmol) in DMF (2 mL) was stirred at 60° C. under nitrogen for 4 h. LCMS showed the desired product. The reaction mixture was filtered and the filtrate was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Fractions containing the desired product were combined and dried via centrifugal evaporation to yield 5-((4-chloro-2-(((1-hydroxy-2-(hydroxymethyl)butan-2-yl)amino)methyl)-5-((3-methyl-4-(2-methyl-3-(3-(piperidin-1-yl)propoxy)phenyl)pyridin-2-yl)methoxy)phenoxy)methyl)nicotinonitrile (15.5 mg, yield 92%). $^1$H NMR (500 MHz, DMSO-$d_6$) δ 8.99 (br. s., 1H), 8.46-8.33 (m, 1H), 7.39 (s, 1H), 7.25 (t, J=7.9 Hz, 1H), 7.16-7.09 (m, 2H), 7.02 (d, J=8.4 Hz, 1H), 6.68 (d, J=7.7 Hz, 1H), 5.45-5.35 (m, 2H), 5.30 (s, 2H), 4.15-3.99 (m, 2H), 3.61 (s, 1H), 3.31 (s, 1H), 2.46 (t, J=7.0 Hz, 2H), 2.37 (br. s., 3H), 2.12 (s, 3H), 1.92 (s, 5H), 1.83 (s, 3H), 1.51 (d, J=5.1 Hz, 4H), 1.45-1.30 (m, 4H), 0.77 (t, J=7.5 Hz, 3H). LC/MS Condition E: ret time 1.11 min; m/e=728.2.

BIOLOGICAL ASSAY

The ability of the compounds of formula (I) to bind to PD-L1 was investigated using a PD-1/PD-L1 Homogenous Time-Resolved Fluorescence (HTRF) binding assay.

equilibrate for 30 minutes and the resulting signal (665 nm/620 nm ratio) was obtained using an EnVision fluorometer. Additional binding assays were established between the human proteins PD-1-Ig/PD-L2-His (20 & 5 nM, respectively) and CD80-His/PD-L1-Ig (100 & 10 nM, respectively).

Recombinant Proteins. Human PD-1 (25-167) with a C-terminal human Fc domain of immunoglobulin G (Ig) epitope tag [hPD-1 (25-167)-3S-IG] and human PD-L1 (18-239) with a C-terminal His epitope tag [hPD-L1(18-239)-TVMV-His] were expressed in HEK293T cells and purified sequentially by ProteinA affinity chromatography and size exclusion chromatography. Human PD-L2-His and CD80-His was obtained through commercial sources.

```
              Sequence of recombinant human PD-1-Ig hPD1 (25-167)-3S-IG
   1    LDSPDRPWNP PTFSPALLVV TEGDNATFTC SFSNTSESFV LNWYRMSPSN

51    QTDKLAAFPE DRSQPGQDCR FRVTQLPNGR DFHMSVVRAR RNDSGTYLCG

101    AISLAPKAQI KESLRAELRV TERRAEVPTA HPSPSPRPAG QFQGSPGGGG

151    GREPKSSDKT HTSPPSPAPE LLGGSSVFLF PPKPKDTLMI SRTPEVTCVV

201    VDVSHEDPEV KFNWYVDGVE VHNAKTKPRE EQYNSTYRVV SVLTVLHQDW

251    LNGKEYKCKV SNKALPAPIE KTISKAKGQP REPQVYTLPP SRDELTKNQV

301    SLTCLVKGFY PSDIAVEWES NGQPENNYKT TPPVLDSDGS FFLYSKLTVD

351    KSRWQQGNVF SCSVMHEALH NHYTQKSLSL SPGK (SEQ ID NO: 1)

Sequence of recombinant human PD-L1-His hPDL1 (18-239)-TVMV-His
   1    AFTVTVPKDL YVVEYGSNMT IECKFPVEKQ LDLAALIVYW EMEDKNIIQF

51    VHGEEDLKVQ HSSYRQRARL LKDQLSLGNA ALQITDVKLQ DAGVYRCMIS

101    YGGADYKRIT VKVNAPYNKI NQRILVVDPV TSEHELTCQA EGYPKAEVIW

151    TSSDHQVLSG KTTTTNSKRE EKLFNVTSTL RINTTTNEIF YCTFRRLDPE

201    ENHTAELVIP ELPLAHPPNE RTGSSETVRF QGHHHHHH (SEQ ID NO: 2)
```

Homogenous Time-Resolved Fluorescence (HTRF) Binding Assay.

The interaction of PD-1 and PD-L1 can be assessed using soluble, purified preparations of the extracellular domains of the two proteins. The PD-1 and PD-L1 protein extracellular domains were expressed as fusion proteins with detection tags, for PD-1, the tag was the Fc portion of Immunoglobulin (PD-1-Ig) and for PD-L1 it was the 6 histidine motif (PD-L1-His). All binding studies were performed in an HTRF assay buffer consisting of dPBS supplemented with 0.1% (with) bovine serum albumin and 0.05% (v/v) Tween-20. For the h/PD-L1-His binding assay, inhibitors were pre-incubated with PD-L1-His (10 nM final) for 15 m in 4 μl of assay buffer, followed by addition of PD-1-Ig (20 nM final) in 1 μl of assay buffer and further incubation for 15 m. HTRF detection was achieved using europium crypate-labeled anti-Ig (1 nM final) and allophycocyanin (APC) labeled anti-His (20 nM final). Antibodies were diluted in HTRF detection buffer and 5 μl was dispensed on top of the binding reaction. The reaction mixture was allowed to The table below lists the $IC_{50}$ values for representative compounds of this disclosure measured in the PD-1/PD-L1 Homogenous Time-Resolved Fluorescence (HTRF) binding assay. Ranges are as follows: A=0.001 to 0.010 micromolar; B=0.011 to 0.150 micromolar; C=0.151 to 10 micromolar.

| Example Number | Range or IC50 (μM) |
|---|---|
| 1001 | B |
| 1002 | C |
| 1003 | C |
| 1004 | C |
| 1005 | C |
| 1006 | 0.1185 |
| 1007 | C |
| 1008 | B |
| 1009 | B |
| 1010 | 1.57 |
| 1011 | B |
| 1012 | A |
| 1013 | B |

| Example Number | Range or IC50 (μM) |
|---|---|
| 1014 | C |
| 1015 | B |
| 1016 | A |
| 1017 | B |
| 1018 | B |
| 1019 | A |
| 1020 | A |
| 1021 | A |
| 1022 | B |
| 1023 | B |
| 1024 | 0.1354 |
| 1025 | C |
| 1026 | C |
| 1027 | C |
| 1028 | A |
| 1029 | A |
| 1030 | C |
| 1031 | C |
| 1032 | B |
| 1033 | B |
| 1034 | A |
| 1035 | A |
| 1036 | A |
| 1037 | C |
| 1038 | C |
| 1039 | C |
| 1040 | C |

| Example Number | Range or IC50 (μM) |
|---|---|
| 1041 | A |
| 2001 | A |
| 2002 | A |
| 2003 | C |
| 2004 | A |
| 2005 | A |
| 2006 | C |
| 2007 | C |
| 2008 | A |
| 2009 | C |
| 2010 | — |
| 2011 | B |
| 2012 | A |
| 2013 | A |
| 2014 | B |
| 2015 | A |
| 2016 | A |

The compounds of formula (I) possess activity as inhibitors of the PD-1/PD-L1 interaction, and therefore, may be used in the treatment of diseases or deficiencies associated with the PD-1/PD-L1 interaction. Via inhibition of the PD-1/PD-L1 interaction, the compounds of the present disclosure may be employed to treat infectious diseases such as HIV, Hepatitis A, B, C, or D and cancer.

What is claimed is:

1. A compound of formula (I):

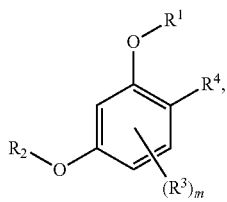

(I)

or a pharmaceutically acceptable salt thereof, wherein:

m is 0, 1, or 2;

$R^1$ is —$(CH_2)_n$Ar; wherein n is 1, 2, 3, or 4;

Ar is selected from benzodioxanyl, indazolyl, isoquinolinyl, isoxazolyl, naphthyl, oxadiazolyl, phenyl, pyridinyl, pyrimidinyl, and quinolinyl; wherein each ring is optionally substituted with 1, 2, 3, or 4 substituents independently selected from $C_1$-$C_4$alkoxy, $C_1$-$C_4$alkoxycarbonyl, $C_1$-$C_4$alkoxycarbonylamino, $C_1$-$C_4$alkyl, $C_1$-$C_4$alkylcarbonyl, $C_1$-$C_4$alkylsulfonyl, amido, amido$C_1$-$C_4$alkyl, —$(CH_2)_qCO_2C_1$-$C_4$alkyl, —$(CH_2)_q$OH, carboxy, cyano, formyl, halo, halo$C_1$-$C_4$alkyl, halo$C_1$-$C_4$alkoxy, nitro, phenyl optionally substituted with one cyano group, phenyloxy optionally substituted with one halo group, phenylcarbonyl, pyrrole, and tetrahydropyran, wherein q is 0, 1, 2, 3, or 4;

$R^2$ is selected from

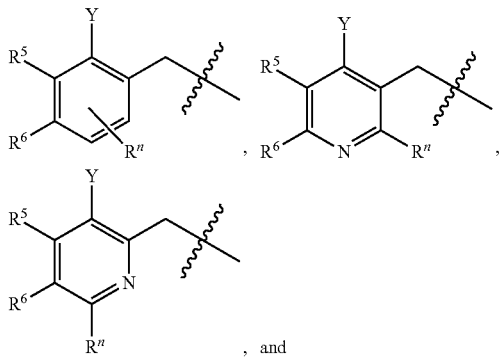

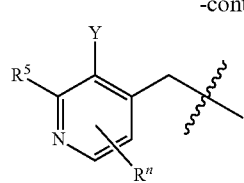

wherein $R^n$ is selected from hydrogen, $C_1$-$C_3$alkyl, halo, and halo$C_1$-$C_3$alkyl;

Y is selected from hydrogen, $C_1$-$C_3$alkoxy, $C_1$-$C_3$alkyl, cyano, and halo;

$R^5$ is phenyl or a monocyclic or bicyclic fully-unsaturated heterocycle containing five to ten atoms wherein one to four of those atoms are independently selected from nitrogen, oxygen and sulfur; and wherein the phenyl and the monocyclic or bicyclic group is optionally substituted with one, two, three, four, or five substituents independently selected from $C_1$-$C_3$alkyl, cyano, formyl, halo, halo$C_1$-$C_3$alkoxy, halo$C_1$-$C_3$alkyl, hydroxy, oxo, -L-$(CH_2)_m$N$R^cR^d$, -L-$(CH_2)_m$OH,

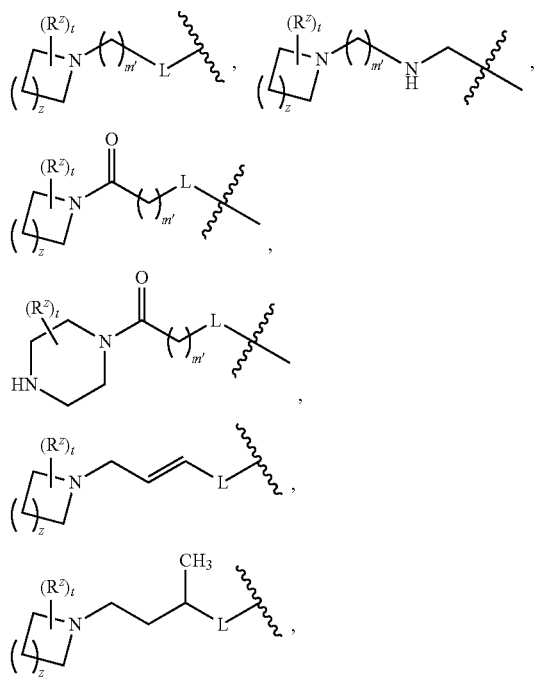

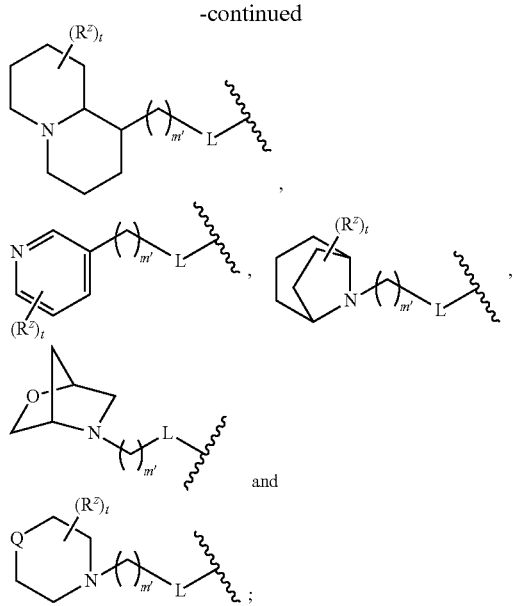

and

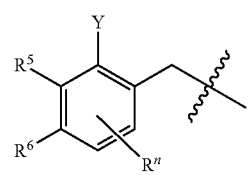

wherein
  L is selected from a bond, —CH$_2$, —NHC(O)—, —C(O)NH—, and —O—; provided that L is —CH$_2$— when it is attached to the parent molecular moiety through a nitrogen atom in the heterocycle;
  m' is 1, 2, 3, or 4; provided that when m' is 1, L is a bond that is attached to the parent molecular moiety through a carbon atom;
  t is 0, 1, 2, or 3;
  z is 1, 2, or 3;
  each R$^z$ is independently selected from C$_1$-C$_4$alkoxy, C$_1$-C$_4$alkoxycarbonyl, C$_1$-C$_4$alkoxycarbonylC$_1$-C$_4$alkyl, C$_1$-C$_4$alkyl, C$_1$-C$_4$alkylamido, C$_1$-C$_4$alkylamino, C$_1$-C$_4$alkylcarbonyl, amido, carboxy, carboxyC$_1$-C$_4$alkyl, cyano, di(C$_1$-C$_4$alkyl)amido, di(C$_1$-C$_4$alkyl)amino, halo, haloC$_1$-C$_4$alkoxy, haloC$_1$-C$_4$alkyl, hydroxy, hydroxyC$_1$-C$_4$alkyl, —NR$^c$R$^d$, (NR$^c$R$^d$)C$_1$-C$_4$alkyl, —NR$^e$R$^f$, (NR$^e$R$^f$)C$_1$-C$_4$alkyl, phenyl, and phenylC$_1$-C$_4$alkyl; wherein R$^e$ and R$^f$, together with the atom to which they are attached, form a ring selected from morpholine and

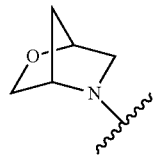

;

R$^c$ and R$^d$ are independently selected from hydrogen, C$_2$-C$_4$alkenylcarbonyl, C$_1$-C$_4$alkoxycarbonyl, C$_1$-C$_6$alkyl, C$_1$-C$_4$alkylcarbonyl, amidoC$_1$-C$_4$alkyl, aminoC$_1$-C$_4$alkyl, arylC$_1$-C$_4$alkyl, C$_3$-C$_{10}$cycloalkyl, (C$_3$-C$_{10}$cycloalkyl)C$_1$-C$_4$alkyl, haloC$_1$-C$_4$alkylcarbonyl, heteroarylC$_1$-C$_4$alkyl, and hydroxyC$_1$-C$_4$alkyl; wherein the alkyl part of the amidoC$_1$-C$_4$alkyl, the aminoC$_1$-C$_4$alkyl, the arylC$_1$-C$_4$alkyl, the (C$_3$-C$_{10}$cycloalkyl)C$_1$-C$_4$alkyl, and the heteroarylC$_1$-C$_4$alkyl is optionally substituted with one or two groups independently selected from carboxy and hydroxy; wherein the alkyl part of the hydroxyC$_1$-C$_4$alkyl is optionally substituted with one or two groups independently selected from carboxy and hydroxy; and wherein the aryl part of the arylC$_1$-C$_4$alkyl, the C$_3$-C$_{10}$cycloalkyl, the cycloalkyl part of the (C$_3$-C$_{10}$cycloalkyl)C$_1$-C$_4$alkyl and the heteroaryl part of the heteroarylC$_1$-C$_4$alkyl are each optionally substituted with one, two, or three groups independently selected from C$_1$-C$_4$alkoxycarbonyl, C$_1$-C$_4$alkyl, and halo;
  Q is selected from S, O, and —NR$^p$; wherein R$^p$ is selected from hydrogen, C$_1$-C$_4$alkyl, C$_1$-C$_4$alkylamidoC$_1$-C$_4$alkyl, C$_1$-C$_4$alkylaminoC$_1$-C$_4$alkyl, amidoC$_1$-C$_4$alkyl, aminoC$_1$-C$_4$alkyl, di(C$_1$-C$_4$alkyl)amidoC$_1$-C$_4$alkyl, di(C$_1$-C$_4$alkyl)aminoC$_1$-C$_3$alkyl, hydroxyC$_1$-C$_4$alkyl, pyridinyl, and phenyl optionally substituted with methoxy;
provided that when R$^2$ is

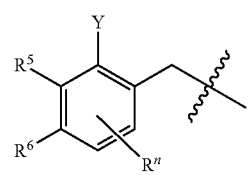

then R$^5$ is other than phenyl; and
  R$^6$ is hydrogen, or, R$^5$ and R$^6$, together with the atoms to which they are attached, form a five- or six-membered unsaturated ring containing one or two heteroatoms independently selected from nitrogen, oxygen, and sulfur; wherein the ring is optionally substituted with one or two substituents independently selected from C$_1$-C$_3$alkyl, cyano, formyl, halo, haloC$_1$-C$_3$alkyl, hydroxy, oxo, -L-(CH$_2$)$_n$NR$^c$R$^d$, -L-(CH$_2$)$_n$OH;
  each R$^3$ is independently selected from C$_2$-C$_4$alkenyl, C$_1$-C$_4$alkoxy, C$_1$-C$_4$alkyl, cyano, halo, and haloC$_1$-C$_4$alkyl; and
  R$^4$ is —(CH$_2$)$_n$NR$^q$R$^8$, wherein
  n' is 1, 2, 3, or 4;
  R$^q$ is selected from hydrogen, C$_1$-C$_4$alkyl, and benzyl; and
  R$^8$ is selected from

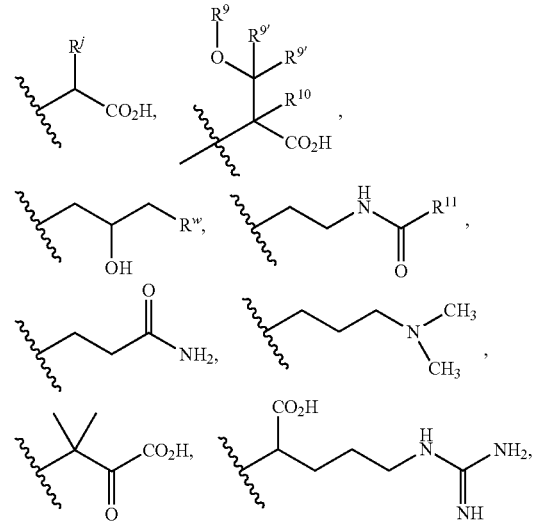

-continued

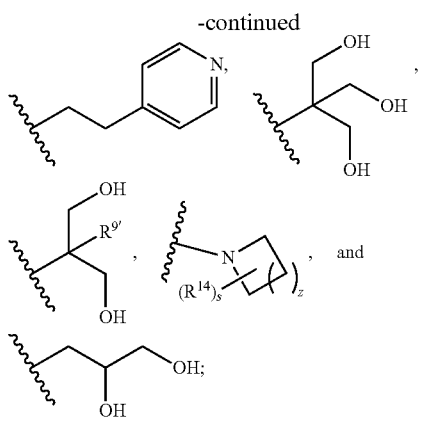

wherein
s is 0, 1, or 2;
z is 1, 2, or 3;
$R^j$ is selected from $C_1$-$C_3$alkyl, $C_1$-$C_3$alkylsulfonyl$C_1$-$C_3$alkyl, $C_1$-$C_3$alkylsulfoxyl$C_1$-$C_3$alkyl, and $C_1$-$C_3$alkylsulfanyl$C_1$-$C_3$alkyl;
$R^w$ is —$CO_2H$ or —$CONH_2$,
$R^9$ is selected from hydrogen, benzyl, and methyl;
each $R^{9'}$ is independently selected from hydrogen, ethyl, and methyl;
$R^{10}$ is selected from hydrogen, $C_1$-$C_3$alkyl, and benzyl; and
$R^{11}$ is selected from $C_2$-$C_4$alkenyl and $C_1$-$C_4$alkyl;
or
$R^8$ and $R^q$, together with the nitrogen atom to which they are attached, form a ring selected from

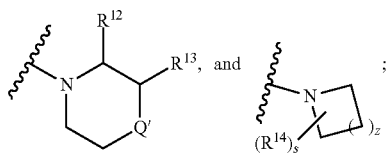

wherein
s is 0, 1, or 2;
z is 1, 2, or 3;
Q' is selected from $CHR^{13'}$, S, O, —$N(CH_2)_2OH$, and $NCH_3$;
$R^{12}$ is selected from hydrogen, —$CO_2H$, hydroxy$C_1$-$C_4$alkyl,
and —$C(O)NHSO_2R^{16}$; wherein $R^{16}$ is selected from trifluoromethyl, cyclopropyl, $C_1$-$C_4$alkyl, dimethylamino, 4-methylpiperazinyl, and imidazolyl substituted with a methyl group;
$R^{13}$ is selected from hydrogen, hydroxy$C_1$-$C_4$alkyl, and —$CO_2H$;
$R^{13'}$ is selected from hydrogen, hydroxy$C_1$-$C_3$alkyl, and —$CO_2H$; and
$R^{14}$ is selected from $C_1$-$C_4$alkoxycarbonyl, $C_1$-$C_3$alkyl, carboxy, halo, hydroxy, hydroxy$C_1$-$C_4$alkyl, and —$NR^{c1}R^{d1}$; wherein $R^{c1}$ and $R^{d1}$ are independently selected from hydrogen, $C_1$-$C_4$alkoxycarbonyl, and $C_1$-$C_4$alkylcarbonyl.

2. The compound of claim 1, or a pharmaceutically acceptable salt thereof, wherein $R^1$ is —$(CH_2)_nAr$ wherein n is 1 and Ar is pyridinyl optionally substituted with cyano.

3. The compound of claim 2, or a pharmaceutically acceptable salt thereof, wherein m is 1 and $R^3$ is halo.

4. The compound of claim 3, or a pharmaceutically acceptable salt thereof, wherein $R^2$ is selected from

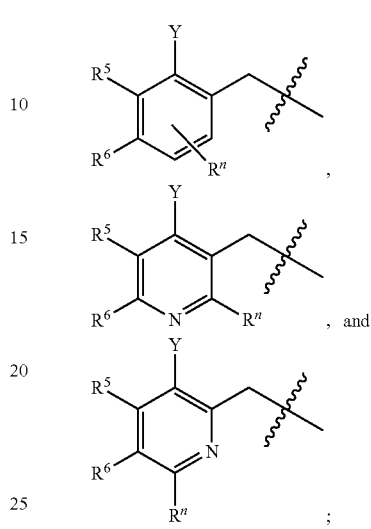

wherein
$R^n$ is hydrogen;
Y is methyl;
$R^5$ is phenyl or a monocyclic or bicyclic fully-unsaturated heterocycle containing five to ten atoms wherein one to four of those atoms are independently selected from nitrogen, oxygen and sulfur; and wherein the phenyl and the monocyclic or bicyclic group is optionally substituted with one, two, or three substituents independently selected from $C_1$-$C_3$alkyl, cyano, formyl, halo, halo$C_1$-$C_3$alkoxy, halo$C_1$-$C_3$alkyl, hydroxy, oxo, -L-$(CH_2)_mNR^cR^d$, -L-$(CH_2)_mOH$,

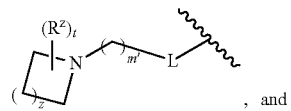

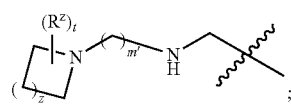

wherein L is selected from a bond, —$CH_2$—, and —O—;
m' is 1, 2, 3, or 4; provided that when m' is 1, L is a bond that is attached to the parent molecular moiety through a carbon atom;
t is 0 or 1;
z is 2 or 3;
$R^z$ is hydroxy;
$R^c$ and $R^d$ are each methyl; and
$R^6$ is hydrogen.

5. The compound of claim 3 wherein $R^4$ is $(CH_2)_{n'}NR^qR^8$, wherein
n' is 1;
$R^q$ is hydrogen; and
$R^8$ is selected from

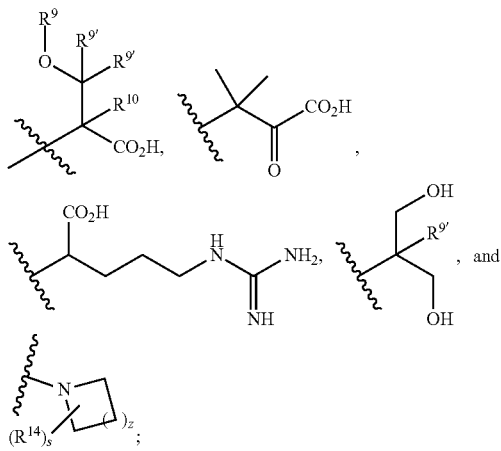

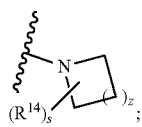

wherein
s is 1;
z is 2;
$R^9$ is selected from hydrogen, benzyl, and methyl;
each $R^{9'}$ is independently selected from hydrogen, ethyl, and methyl; and
$R^{10}$ is selected from hydrogen, $C_1$-$C_3$alkyl, and benzyl; or
$R^8$ and $R^q$, together with the nitrogen atom to which they are attached, form a ring which is:

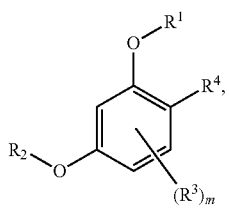

wherein
s is 0, 1, or 2;
z is 1, 2, or 3; and
$R^{14}$ is selected from $C_1$-$C_4$alkoxycarbonyl, $C_1$-$C_3$alkyl, carboxy, and hydroxy.

6. A compound of formula (I), (I)

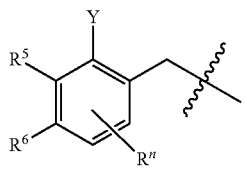

or a pharmaceutically acceptable salt thereof, wherein:
m is 1;
$R^1$ is —$(CH_2)_n$Ar; wherein
n is 1,
Ar is pyridinyl optionally substituted with cyano;

$R^2$ is selected from

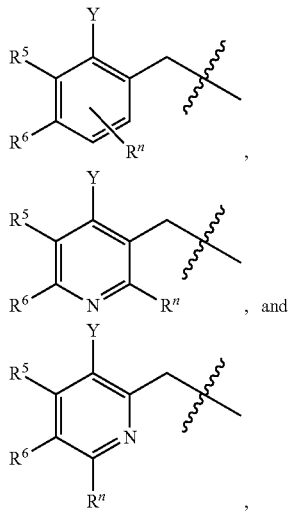

wherein
$R^n$ is hydrogen;
Y is $C_1$-$C_3$alkyl;
$R^5$ is phenyl or a monocyclic or bicyclic fully-unsaturated heterocycle containing five to ten atoms wherein one to four of those atoms are independently selected from nitrogen, oxygen and sulfur; and wherein the phenyl and the monocyclic or bicyclic group is optionally substituted with one, two, three, four, or five substituents independently selected from $C_1$-$C_3$alkyl, cyano, formyl, halo, halo$C_1$-$C_3$alkoxy, halo$C_1$-$C_3$alkyl, hydroxy, oxo, -L-$(CH_2)_m$OH,

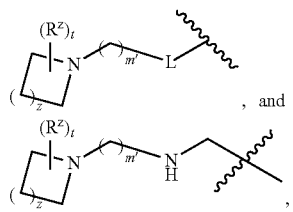

wherein
L is selected from a bond, —$CH_2$—, and —O—; provided that L is —$CH_2$— when it is attached to the parent molecular moiety through a nitrogen atom in the heterocycle;
m' is 1, 2, 3, or 4; provided that when m' is 1, L is a bond that is attached to the parent molecular moiety through a carbon atom;
t is 0, 1, 2, or 3;
z is 1, 2, or 3;
$R^z$ is hydroxy;
$R^c$ and $R^d$ are $C_1$-$C_6$alkyl;
provided that when $R^2$ is then $R^5$ is other than phenyl;
$R^6$ is hydrogen,
$R^3$ is halo; and
$R^4$ is $-(CH_2)_{n'}NR^qR^8$, wherein
n' is 1;
$R^q$ is hydrogen; and
$R^8$ is selected from

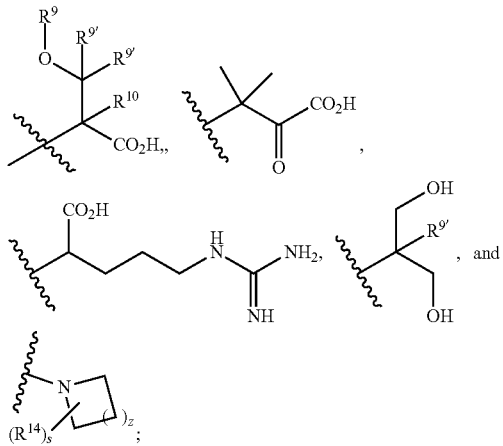

wherein
s is 1;
z is 2;
$R^9$ is selected from hydrogen, benzyl, and methyl;
each $R^{9'}$ is independently selected from hydrogen, ethyl, and methyl; and
$R^{10}$ is selected from hydrogen, $C_1$-$C_3$alkyl, and benzyl;
or
$R^8$ and $R^q$, together with the nitrogen atom to which they are attached, form a ring which is

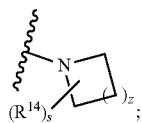

wherein
s is 1 or 2;
z is 2 or 3; and
$R^{14}$ is selected from $C_1$-$C_4$alkoxycarbonyl, $C_1$-$C_3$alkyl, carboxy, halo, and hydroxy.

7. A compound selected from
(R)-2-((5-chloro-2-((5-cyanopyridin-3-yl)methoxy)-4-((2-methyl-3-(quinolin-7-yl)benzyl)oxy)benzyl) amino)-3-hydroxy-2-methylpropanoic acid;
(R)-2-((5-chloro-2-((5-cyanopyridin-3-yl)methoxy)-4-((2-methyl-3-(quinolin-3-yl)benzyl)oxy)benzyl) amino)-3-hydroxy-2-methylpropanoic acid;
(S)-1-(5-chloro-2-((5-cyanopyridin-3-yl)methoxy)-4-((2-methyl-3-(quinolin-3-yl)benzyl)oxy)benzyl) piperidine-2-carboxylic acid;
(R)-2-((5-chloro-2-((5-cyanopyridin-3-yl)methoxy)-4-((2-methyl-3-(quinolin-2-yl)benzyl)oxy)benzyl) amino)-3-hydroxy-2-methylpropanoic acid;
(R)-2-((5-chloro-2-((5-cyanopyridin-3-yl)methoxy)-4-((2-methyl-3-(quinolin-6-yl)benzyl)oxy)benzyl) amino)-3-hydroxy-2-methylpropanoic acid;
(R)-2-((5-chloro-2-((5-cyanopyridin-3-yl)methoxy)-4-((2-methyl-3-(quinoxalin-2-yl)benzyl)oxy) benzyl) amino)-3-hydroxy-2-methylpropanoic acid;
(R)-2-((5-chloro-2-((5-cyanopyridin-3-yl)methoxy)-4-((3-(isoquinolin-3-yl)-2-methylbenzyl)oxy) benzyl) amino)-3-hydroxy-2-methylpropanoic acid;
(R)-2-((5-chloro-2-((5-cyanopyridin-3-yl)methoxy)-4-((3-(isoquinolin-7-yl)-2-methylbenzyl)oxy) benzyl) amino)-3-hydroxy-2-methylpropanoic acid;
(R)-2-((5-chloro-2-((5-cyanopyridin-3-yl)methoxy)-4-((3-(isoquinolin-6-yl)-2-methylbenzyl)oxy) benzyl) amino)-3-hydroxy-2-methylpropanoic acid;
(R)-2-((4-((3-(7-bromoquinoxalin-2-yl)-2-methylbenzyl)oxy)-5-chloro-2-((5-cyanopyridin-3-yl) methoxy)benzyl)amino)-3-hydroxy-2-methylpropanoic acid;
(R)-2-((4-((3-(benzo[d]thiazol-6-yl)-2-methylbenzyl)oxy)-5-chloro-2-((5-cyanopyridin-3-yl)methoxy) benzyl)amino)-3-hydroxy-2-methylpropanoic acid;
(R)-2-((4-((3-(benzo[d]oxazol-5-yl)-2-methylbenzyl)oxy)-5-chloro-2-((5-cyanopyridin-3-yl)methoxy) benzyl)amino)-3-hydroxy-2-methylpropanoic acid;
(R)-2-((4-((3-(benzofuran-5-yl)-2-methylbenzyl)oxy)-5-chloro-2-((5-cyanopyridin-3-yl)methoxy) benzyl) amino)-3-hydroxy-2-methylpropanoic acid;
(S)-2-((4-((3-(benzofuran-5-yl)-2-methylbenzyl)oxy)-5-chloro-2-((5-cyanopyridin-3-yl)methoxy) benzyl) amino)-5-guanidinopentanoic acid;
2-((4-((3-(benzofuran-5-yl)-2-methylbenzyl)oxy)-5-chloro-2-((5-cyanopyridin-3-yl)methoxy)benzyl) amino)-2-methylpropanoic acid;
2-((4-((3-(benzo[d]oxazol-6-yl)-2-methylbenzyl)oxy)-5-chloro-2-((5-cyanopyridin-3-yl)methoxy) benzyl) amino)-2-methylpropanoic acid;
(R)-2-((4-((3-(benzo[d]oxazol-6-yl)-2-methylbenzyl) oxy)-5-chloro-2-((5-cyanopyridin-3-yl)methoxy) benzyl)amino)-3-hydroxy-2-methylpropanoic acid;
2-((4-((3-(benzofuran-6-yl)-2-methylbenzyl)oxy)-5-chloro-2-((5-cyanopyridin-3-yl)methoxy)benzyl) amino)-2-methylpropanoic acid;
(R)-2-((4-((3-(benzofuran-6-yl)-2-methylbenzyl)oxy)-5-chloro-2-((5-cyanopyridin-3-yl)methoxy) benzyl) amino)-3-hydroxy-2-methylpropanoic acid;
(S)-1-(4-((3-(benzofuran-6-yl)-2-methylbenzyl)oxy)-5-chloro-2-((5-cyanopyridin-3-yl)methoxy) benzyl)-2-methylpyrrolidine-2-carboxylic acid;
(R)-2-((4-((3-(benzo[d]thiazol-5-yl)-2-methylbenzyl) oxy)-5-chloro-2-((5-cyanopyridin-3-yl)methoxy) benzyl)amino)-3-hydroxy-2-methylpropanoic acid;
2-((4-((3-(benzo[d]thiazol-5-yl)-2-methylbenzyl)oxy)-5-chloro-2-((5-cyanopyridin-3-yl)methoxy) benzyl) amino)-2-methylpropanoic acid;
(S)-1-(4-((3-(benzo[d]thiazol-5-yl)-2-methylbenzyl) oxy)-5-chloro-2-((5-cyanopyridin-3-yl)methoxy) benzyl)-2-methylpyrrolidine-2-carboxylic acid;
(R)-2-((4-((3-(1H-benzo[d]imidazol-5-yl)-2-methylbenzyl)oxy)-5-chloro-2-((5-cyanopyridin-3-yl) methoxy) benzyl)amino)-3-hydroxy-2-methylpropanoic acid;
(R)-2-((5-chloro-2-((5-cyanopyridin-3-yl)methoxy)-4-((3-(1-(2-(dimethylamino)ethyl)-1H-benzo[d]imidazol-6-yl)-2-methylbenzyl)oxy)benzyl)amino)-3-hydroxypropanoic acid;
(R)-2-((5-chloro-2-((5-cyanopyridin-3-yl)methoxy)-4-((3-(1-(2-(dimethylamino)ethyl)-1H-benzo[d]imidazol-5-yl)-2-methylbenzyl)oxy)benzyl)amino)-3-hydroxypropanoic acid;

2-((5-chloro-2-((5-cyanopyridin-3-yl)methoxy)-4-((3-(1-(2-(dimethylamino)ethyl)-1H-benzo[d]imidazol-6-yl)-2-methylbenzyl)oxy)benzyl)amino)-2-methylpropanoic acid;

2-((5-chloro-2-((5-cyanopyridin-3-yl)methoxy)-4-((3-(1-(2-(dimethylamino)ethyl)-1H-benzo[d]imidazol-5-yl)-2-methylbenzyl)oxy)benzyl)amino)-2-methylpropanoic acid;

(R)-5-((4-chloro-2-formyl-5-((3-(2-(2-(3-hydroxypyrrolidin-1-yl)ethyl)benzo[d]oxazol-5-yl)-2-methylbenzyl)oxy) phenoxy)methyl)nicotinonitrile;

(R)-2-((5-chloro-2-((5-cyanopyridin-3-yl)methoxy)-4-((3-(2-(2-((R)-3-hydroxypyrrolidin-1-yl)ethyl)benzo[d]oxazol-5-yl)-2-methylbenzyl)oxy)benzyl)amino)-3-hydroxy-2-methylpropanoic acid;

(S)-1-(5-chloro-2-((5-cyanopyridin-3-yl)methoxy)-4-((3-(2-(2-((R)-3-hydroxypyrrolidin-1-yl)ethyl)benzo[d]oxazol-5-yl)-2-methylbenzyl)oxy)benzyl)piperidine-2-carboxylic acid;

(S)-1-(5-chloro-2-((5-cyanopyridin-3-yl)methoxy)-4-((3-(6-(3-((R)-3-hydroxypyrrolidin-1-yl) propoxy)pyridin-2-yl)-2-methylbenzyl)oxy)benzyl)piperidine-2-carboxylic acid;

(R)-5-((4-chloro-2-(hydroxymethyl)-5-((3-(6-(3-(3-hydroxypyrrolidin-1-yl)propoxy)pyridin-2-yl)-2-methylbenzyl)oxy)phenoxy)methyl)nicotinonitrile;

(S)-1-(5-chloro-2-((5-cyanopyridin-3-yl)methoxy)-4-((2-methyl-3-(quinoxalin-6-yl)benzyl)oxy)benzyl)piperidine-2-carboxylic acid;

(R)-1-(5-chloro-2-((5-cyanopyridin-3-yl)methoxy)-4-((2-methyl-3-(quinoxalin-6-yl)benzyl)oxy)benzyl)piperidine-2-carboxylic acid;

(R)-2-((5-chloro-2-((5-cyanopyridin-3-yl)methoxy)-4-((2-methyl-3-(quinoxalin-6-yl)benzyl)oxy)benzyl)amino)-3-hydroxypropanoic acid;

(R)-2-((5-chloro-2-((5-cyanopyridin-3-yl)methoxy)-4-((2-methyl-3-(quinoxalin-6-yl)benzyl)oxy)benzyl)amino)-3-hydroxy-2-methylpropanoic acid;

(S)-2-((5-chloro-2-((5-cyanopyridin-3-yl)methoxy)-4-((2-methyl-3-(quinoxalin-6-yl)benzyl)oxy)benzyl)amino)-3-hydroxy-2-methylpropanoic acid;

(S)-2-((5-chloro-2-((5-cyanopyridin-3-yl)methoxy)-4-((3-(1-(3-((R)-3-hydroxypyrrolidin-1-yl)propyl)-2-oxo-1,2-dihydropyridin-3-yl)-2-methylbenzyl)oxy)benzyl)amino)-3-hydroxy-2-methylpropanoic acid;

(R)-2-((5-chloro-2-((5-cyanopyridin-3-yl)methoxy)-4-((3-(1-(3-((R)-3-hydroxypyrrolidin-1-yl)propyl)-2-oxo-1,2-dihydropyridin-3-yl)-2-methylbenzyl)oxy)benzyl)amino)-3-hydroxy-2-methylpropanoic acid;

(S)-1-(5-chloro-2-((5-cyanopyridin-3-yl)methoxy)-4-((3-(1-(3-((R)-3-hydroxypyrrolidin-1-yl)propyl)-2-oxo-1,2-dihydropyridin-3-yl)-2-methylbenzyl)oxy)benzyl)piperidine-2-carboxylic acid;

(S)-2-((5-chloro-2-((5-cyanopyridin-3-yl)methoxy)-4-((3-(1-(3-((R)-3-hydroxypyrrolidin-1-yl)propyl)-2-oxo-1,2-dihydropyridin-3-yl)-2-methylbenzyl)oxy)benzyl)amino)-3-hydroxypropanoic acid;

5-((4-chloro-5-((3-(3-chloro-2-(3-(piperidin-1-yl)propoxy)pyridin-4-yl)-2-methylbenzyl)oxy)-2-(((1,3-dihydroxy-2-methylpropan-2-yl)amino)methyl)phenoxy)methyl)nicotinonitrile;

(R)-5-((4-chloro-5-((3-(3-chloro-4-(3-(3-hydroxypyrrolidin-1-yl)propoxy)pyridin-2-yl)-2-methylbenzyl)oxy)-2-(((1,3-dihydroxy-2-methylpropan-2-yl)amino)methyl)phenoxy)methyl)nicotinonitrile;

(R)-2-((5-chloro-2-((5-cyanopyridin-3-yl)methoxy)-4-((3-(1-(4-((S)-3-hydroxypyrrolidin-1-yl)butyl)-3,5-dimethyl-1H-pyrazol-4-yl)-2-methylbenzyl)oxy)benzyl)amino)-3-hydroxy-2-methylpropanoic acid;

5-((4-chloro-5-((3-(3-chloro-4-(3-hydroxypropoxy)pyridin-2-yl)-2-methylbenzyl)oxy)-2-(((1,3-dihydroxy-2-methylpropan-2-yl)amino)methyl)phenoxy)methyl)nicotinonitrile;

(S)-1-(5-chloro-2-((5-cyanopyridin-3-yl)methoxy)-4-((5-(3-(3-((R)-3-hydroxypyrrolidin-1-yl)propoxy)-2-methylphenyl)-4-methylpyridin-3-yl)methoxy)benzyl)piperidine-2-carboxylic acid;

5-((4-chloro-2-(((2-((R)-3-hydroxypyrrolidin-1-yl)ethyl)amino)methyl)-5-((3-(4-(((2-((R)-3-hydroxypyrrolidin-1-yl)ethyl)amino)methyl)-3,5-dimethyl-1H-pyrazol-1-yl)-2-methylbenzyl)oxy)phenoxy)methyl)nicotinonitrile;

5-((4-chloro-2-(((R)-3-hydroxypyrrolidin-1-yl)methyl)-5-((3-(4-(((R)-3-hydroxypyrrolidin-1-yl)methyl)-3,5-dimethyl-1H-pyrazol-1-yl)-2-methylbenzyl)oxy)phenoxy)methyl)nicotinonitrile;

(R)-5-((4-chloro-2-(((1,3-dihydroxy-2-methylpropan-2-yl)amino)methyl)-5-((5-(3-(3-(3-hydroxypyrrolidin-1-yl)propoxy)-2-methylphenyl)-4-methylpyridin-3-yl)methoxy)phenoxy)methyl)nicotinonitrile;

(R)-2-((5-chloro-2-((5-cyanopyridin-3-yl)methoxy)-4-((3-(4-(((R)-3-hydroxypyrrolidin-1-yl)methyl)-3,5-dimethyl-1H-pyrazol-1-yl)-2-methylbenzyl)oxy)benzyl)amino)-3-hydroxy-2-methylpropanoic acid;

(R)-2-((5-chloro-2-((5-cyanopyridin-3-yl)methoxy)-4-((3-(4-formyl-3,5-dimethyl-1H-pyrazol-1-yl)-2-methylbenzyl)oxy)benzyl)amino)-3-hydroxy-2-methylpropanoic acid (S)-1-(5-chloro-2-((5-cyanopyridin-3-yl)methoxy)-4-((4-(3-(3-((R)-3-hydroxypyrrolidin-1-yl)propoxy)-2-methylphenyl)-3-methylpyridin-2-yl)methoxy)benzyl)piperidine-2-carboxylic acid;

(S)-2-((5-chloro-2-((5-cyanopyridin-3-yl)methoxy)-4-((4-(3-(3-((R)-3-hydroxypyrrolidin-1-yl)propoxy)-2-methylphenyl)-3-methylpyridin-2-yl)methoxy)benzyl)amino)-3-hydroxy-2-methylpropanoic acid;

(R)-5-((4-chloro-2-(((1-hydroxy-2-(hydroxymethyl)butan-2-yl)amino)methyl)-5-((4-(3-(3-(3-hydroxypyrrolidin-1-yl)propoxy)-2-methylphenyl)-3-methylpyridin-2-yl)methoxy)phenoxy)methyl)nicotinonitrile;

(S)-1-(5-chloro-2-((5-cyanopyridin-3-yl)methoxy)-4-((3-methyl-4-(2-methyl-3-(3-(piperidin-1-yl)propoxy)phenyl)pyridin-2-yl)methoxy)benzyl)piperidine-2-carboxylic acid;

(S)-1-(4-((3-(benzo[d]oxazol-5-yl)-2-methylbenzyl)oxy)-5-chloro-2-((5-cyanopyridin-3-yl) methoxy)benzyl)piperidine-2-carboxylic acid;

(S)-2-((5-chloro-2-((5-cyanopyridin-3-yl)methoxy)-4-((3-methyl-4-(2-methyl-3-(3-(piperidin-1-yl)propoxy)phenyl)pyridin-2-yl)methoxy)benzyl)amino)-3-hydroxy-2-methylpropanoic acid; and 5-((4-chloro-2-(((1-hydroxy-2-(hydroxymethyl)butan-2-yl)amino)methyl)-5-((3-methyl-4-(2-methyl-3-(3-(piperidin-1-yl)propoxy)phenyl)pyridin-2-yl)methoxy)phenoxy)methyl)nicotinonitrile;

or a pharmaceutically acceptable salt thereof.

8. A pharmaceutical composition comprising the compound of claim 1, or a pharmaceutically acceptable salt thereof, and a pharmaceutically acceptable carrier.

* * * * *